US007122373B1

(12) United States Patent
Williams et al.

(10) Patent No.: US 7,122,373 B1
(45) Date of Patent: Oct. 17, 2006

(54) HUMAN GENES AND GENE EXPRESSION PRODUCTS V

(75) Inventors: Lewis T. Williams, Tiburon, CA (US); Jaime Escobedo, Alamo, CA (US); Michael A. Innis, Moraga, CA (US); Pablo Dominguez Garcia, San Francisco, CA (US); Julie Sudduth-Klinger, Kensington, CA (US); Christoph Reinhard, Alameda, CA (US); Klaus Giese, Berlin (DE); Filippo Randazzo, San Francisco, CA (US); Giulia C. Kennedy, San Francisco, CA (US); David Pot, San Francisco, CA (US); Altaf Kassam, Oakland, CA (US); George Lamson, Moraga, CA (US); Radoje Drmanac, Palo Alto, CA (US); Radomir Crkvenjakov, Sunnyvale, CA (US); Mark Dickson, Hollister, CA (US); Snezana Drmanac, Palo Alto, CA (US); Ivan Labat, Sunnyvale, CA (US); Dena Leshkowitz, Sunnyvale, CA (US); David Kita, Foster City, CA (US); Veronica Garcia, Sunnyvale, CA (US); Lee William Jones, Sunnyvale, CA (US); Birgit Stache-Crain, Sunnyvale, CA (US)

(73) Assignee: Nuvelo, Inc., Sunnyvale, CA (US)

(*) Notice: Subject to any disclaimer, the term of this patent is extended or adjusted under 35 U.S.C. 154(b) by 809 days.

(21) Appl. No.: 09/313,292

(22) Filed: May 13, 1999

Related U.S. Application Data

(60) Provisional application No. 60/105,877, filed on Oct. 27, 1998, provisional application No. 60/105,234, filed on Oct. 21, 1998, provisional application No. 60/085,696, filed on May 15, 1998, provisional application No. 60/085,537, filed on May 15, 1998, provisional application No. 60/085,426, filed on May 14, 1998.

(51) Int. Cl.
*C12N 5/10* (2006.01)
*C12N 15/63* (2006.01)
*C12N 15/11* (2006.01)

(52) U.S. Cl. .................. 435/325; 435/320.1; 536/23.5

(58) Field of Classification Search ............... 435/69.1, 435/320.1; 536/23.5
See application file for complete search history.

(56) References Cited

OTHER PUBLICATIONS

Genbank Accession No. U58766 Nov. 1, 1996.*
Genbank Accession No. AA544005 Aug. 1, 1997.*
Genbank Accession No. M15796 Apr. 27, 1993.*
Genbank Accession No. M88458 Apr. 27, 1993.*
Genbank Accession No. AA068559 Feb. 6, 1997.*
Genbank Accession No. AA131908 May 14, 1997.*
Genbank Accession No. AA050390 Sep. 9, 1996.*
Genbank Accession No. W89528 Sep. 12, 1996.*
Genbank Accession No. H93085 Nov. 30, 1995.*
Genbank Accession No. S82472 Dec. 3, 1996.*
Yang et al Protein-peptide interactions analyzed with the yeast two-hybrid system Nucleic Acids Research 1995. vol. 23. No. 7. pp. 1152-1156.*
Clarke et al. Progression of human breast cancer cells from hormone-dependent to hormone-independent growth both in vitro and in vivo. Proc. Natl. Acad. Sci. USA vol. 86, pp. 3649-3653 (1989).*
Chandrasekaran et al. Glycosoaminoglycans of normal and malignant cultured human mammary cells. Cancer Research vol. 39, pp. 870-877 (1979).*
Brinkley et al. Variations in cell form and cytoskeleton in human breast carcinoma cells in vitro. Cancer Research vol. 40, pp. 3118-3129 (1980).*
Odum et al. Limitations of the MCF-7 Cell Proliferation Assay for Detecting Xenobiotic Oestrogens. Toxicology in Vitro vol. 12, pp. 273-278 (1998).*
Chabert et al. Cell culture of tumors alters endogenous poly(ADPR) polymerase expression and activity. Int. J. Cancer vol. 53 837-842 (1993).*
Dermer Another Anniversary for the War on Cancer. Bio/Technology vol. 12, p. 320 (1994).*
Carmeci et al. (Nov. 1997), "Identification of a Gene (GPR30) with Homology to the G-Protein-Coupled Receptor Superfamily Associated with Estrogen Receptor Expression in Breast Cancer," *Genomics*, vol. 45(3):607-617.
Morissey, J.H. (Feb. 20, 1989), "Human Tissue Factor Gene," *EMBL Databank*, ID HSTFPB.
Yeatman et al. (1995), "identification of a Differentially -Expressed Message Associated with Colon Cancer Liver Metastasis Using an Improved Method of Differential Display," *Nucleic Acids Research*, vol. 23(19):4007-4008.
Yeatman et al. (May 1996), "Identification of Genetic Alterations Associated with the Process of Human Experimental Colon Cancer Liver Metastasis in the Nude Mouse," *Clinical and Experimental Metastasis*, vol. 14(3):1996-2005.
Genbank Accession No. AF273437, deposited Aug. 17, 2000.
Genbank Accession No. AJ278133, deposited Mar. 19, 2001.
Genbank Accession No. AK001197, deposited Feb. 22, 2000.
Genbank Accession No. AK001402, deposited Feb. 22, 2000.

(Continued)

*Primary Examiner*—John S. Brusca
(74) *Attorney, Agent, or Firm*—Fish & Richardson P.C.

(57) ABSTRACT

This invention relates to novel human polynucleotides and variants thereof, their encoded polypeptides and variants thereof, to genes corresponding to these polynucleotides and to proteins expressed by the genes. The invention also relates to diagnostic and therapeutic agents employing such novel human polynucleotides, their corresponding genes or gene products, e.g., these genes and proteins, including probes, antisense constructs, and antibodies.

8 Claims, No Drawings

OTHER PUBLICATIONS

Genbank Accession No. AK001468, deposited Feb. 22, 2000.
Genbank Accession No. AK001472, deposited Feb. 22, 2000.
Genbank Accession No. AK003515, deposited Feb. 8, 2001.
Genbank Accession No. AK005163, deposited Feb. 8, 2001.
Genbank Accession No. AK007403, deposited Feb. 8, 2001.
Genbank Accession No. AK007686, deposited Feb. 8, 2001.
Genbank Accession No. AL117496, deposited Mar. 10, 2001.
Genbank Accession No. NM_006854, deposited Nov. 2, 2000.
Genbank Accession No. NM_016195, deposited Nov. 2, 2000.
Genbank Accession No. NM_018062, deposited Nov. 2, 2000.
Genbank Accession No. NM_018131, deposited Nov. 2, 2000.
Genbank Accession No. NM_025841, deposited Mar. 20, 2001.
Genbank Accession No. X63745, deposited Jul. 12, 1996.
Genbank Accession No. XM_002688, deposited Apr. 16, 2001.
Genbank Accession No. XM_004631, deposited Apr. 16, 2001.
Genbank Accession No. XM_004854, deposited Apr. 16, 2001.
Genbank Accession No. XM_005803, deposited Apr. 16, 2001.
Genbank Accession No. XM_005908, deposited Apr. 16, 2001.
Genbank Accession No. A42286, deposited Aug. 13, 1999.
Genbank Accession No. M88458, deposited Apr. 27, 1993.
Genbank Accession No. NM_002592, deposited Oct. 31, 2000.
Genbank Accession No. 2914385, deposited Oct. 14, 1997.

* cited by examiner

HUMAN GENES AND GENE EXPRESSION PRODUCTS V

CROSS-REFERENCE TO RELATED APPLICATIONS

This application claims the benefit of U.S. provisional patent application Ser. No. 60/085,426, filed May 14, 1998; and of U.S. provisional patent application Ser. No. 60/085,537, filed May 15, 1998; and of U.S. provisional patent application Ser. No. 60/085,696, filed May 15, 1998; and of U.S. provisional patent application Ser. No. 60/105,234, filed Oct. 21, 1998; and of U.S. provisional patent application Ser. No. 60/105,877 filed Oct. 27, 1998; each of which applications are incorporated herein by reference.

FIELD OF THE INVENTION

The present invention relates to polynucleotides of human origin and the encoded gene products.

BACKGROUND OF THE INVENTION

Identification of novel polynucleotides, particularly those that encode an expressed gene product, is important in the advancement of drug discovery, diagnostic technologies, and the understanding of the progression and nature of complex diseases such as cancer. Identification of genes expressed in different cell types isolated from sources that differ in disease state or stage, developmental stage, exposure to various environmental factors, the tissue of origin, the species from which the tissue was isolated, and the like is key to identifying the genetic factors that are responsible for the phenotypes associated with these various differences.

This invention provides novel human polynucleotides, the polypeptides encoded by these polynucleotides, and the genes and proteins corresponding to these novel polynucleotides.

SUMMARY OF THE INVENTION

This invention relates to novel human polynucleotides and variants thereof, their encoded polypeptides and variants thereof, to genes corresponding to these polynucleotides and to proteins expressed by the genes. The invention also relates to diagnostics and therapeutics comprising such novel human polynucleotides, their corresponding genes or gene products, including probes, antisense nucleotides, and antibodies. The polynucleotides of the invention correspond to a polynucleotide comprising the sequence information of at least one of SEQ ID NOS:1–2707.

Various aspects and embodiments of the invention will be readily apparent to the ordinarily skilled artisan upon reading the description provided herein.

DETAILED DESCRIPTION OF THE INVENTION

The invention relates to polynucleotides comprising the disclosed nucleotide sequences, to full length cDNA, mRNA genomic sequences, and genes corresponding to these sequences and degenerate variants thereof, and to polypeptides encoded by the polynucleotides of the invention and polypeptide variants. The following detailed description describes the polynucleotide compositions encompassed by the invention, methods for obtaining cDNA or genomic DNA encoding a full-length gene product, expression of these polynucleotides and genes, identification of structural motifs of the polynucleotides and genes, identification of the function of a gene product encoded by a gene corresponding to a polynucleotide of the invention, use of the provided polynucleotides as probes and in mapping and in tissue profiling, use of the corresponding polypeptides and other gene products to raise antibodies, and use of the polynucleotides and their encoded gene products for therapeutic and diagnostic purposes.

Polynucleotide Compositions

The scope of the invention with respect to polynucleotide compositions includes, but is not necessarily limited to, polynucleotides having a sequence set forth in any one of SEQ ID NOS:1–2707; polynucleotides obtained from the biological materials described herein or other biological sources (particularly human sources) by hybridization under stringent conditions (particularly conditions of high stringency); genes corresponding to the provided polynucleotides; variants of the provided polynucleotides and their corresponding genes, particularly those variants that retain a biological activity of the encoded gene product (e.g., a biological activity ascribed to a gene product corresponding to the provided polynucleotides as a result of the assignment of the gene product to a protein family(ies) and/or identification of a functional domain present in the gene product). Other nucleic acid compositions contemplated by and within the scope of the present invention will be readily apparent to one of ordinary skill in the art when provided with the disclosure here. "Polynucleotide" and "nucleic acid" as used herein with reference to nucleic acids of the composition is not intended to be limiting as to the length or structure of the nucleic acid unless specifically indicted.

The invention features polynucleotides that are expressed in human tissue, specifically human colon, breast, and/or lung tissue. Novel nucleic acid compositions of the invention of particular interest comprise a sequence set forth in any one of SEQ ID NOS:1–2707 or an identifying sequence thereof. An "identifying sequence" is a contiguous sequence of residues at least about 10 nt to about 20 nt in length, usually at least about 50 nt to about 100 nt in length, that uniquely identifies a polynucleotide sequence, e.g., exhibits less than 90%, usually less than about 80% to about 85% sequence identity to any contiguous nucleotide sequence of more than about 20 nt. Thus, the subject novel nucleic acid compositions include full length cDNAs or mRNAs that encompass an identifying sequence of contiguous nucleotides from any one of SEQ ID NOS: 1–2707.

The polynucleotides of the invention also include polynucleotides having sequence similarity or sequence identity. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided polynucleotide sequences, e.g. allelic variants, genetically altered versions of the gene, etc., bind to the provided polynucleotide sequences (SEQ ID NOS:1–2707) under stringent hybridization conditions. By using probes, particularly labeled probes of DNA sequences, one can isolate homologous or related genes. The source of homologous genes can be any species, e.g. primate species, particularly human; rodents, such as rats and mice; canines, felines, bovines, ovines, equines, yeast, nematodes, etc.

Preferably, hybridization is performed using at least 15 contiguous nucleotides (nt) of at least one of SEQ ID NOS:1–2707. That is, when at least 15 contiguous nt of one of the disclosed SEQ ID NOS. is used as a probe, the probe will preferentially hybridize with a nucleic acid comprising the complementary sequence, allowing the identification and retrieval of the nucleic acids that uniquely hybridize to the selected probe. Probes from more than one SEQ ID NO. can hybridize with the same nucleic acid if the cDNA from which they were derived corresponds to one mRNA. Probes of more than 15 nt can be used, e.g., probes of from about 18 nt to about 100 nt, but 15 nt represents sufficient sequence for unique identification.

The polynucleotides of the invention also include naturally occurring variants of the nucleotide sequences (e.g., degenerate variants, allelic variants, etc.). Variants of the polynucleotides of the invention are identified by hybridization of putative variants with nucleotide sequences disclosed herein, preferably by hybridization under stringent conditions. For example, by using appropriate wash conditions, variants of the polynucleotides of the invention can be identified where the allelic variant exhibits at most about 25–30% base pair (bp) mismatches relative to the selected polynucleotide probe. In general, allelic variants contain 15–25% bp mismatches, and can contain as little as even 5–15%, or 2–5%, or 1–2% bp mismatches, as well as a single bp mismatch.

The invention also encompasses homologs corresponding to the polynucleotides of SEQ ID NOS:1–2707, where the source of homologous genes can be any mammalian species, e.g., primate species, particularly human; rodents, such as rats; canines, felines, bovines, ovines, equines, yeast, nematodes, etc. Between mammalian species, e.g., human and mouse, homologs generally have substantial sequence similarity, e.g., at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared. Algorithms for sequence analysis are known in the art, such as gapped BLAST, described in Altschul, et al. *Nucleic Acids Res.* (1997) 25:3389–3402.

In general, variants of the invention have a sequence identity greater than at least about 65%, preferably at least about 75%, more preferably at least about 85%, and can be greater than at least about 90% or more as determined by the Smith-Waterman homology search algorithm as implemented in MPSRCH program (Oxford Molecular). For the purposes of this invention, a preferred method of calculating percent identity is the Smith-Waterman algorithm, using the following. Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

The subject nucleic acids can be cDNAs or genomic DNAs, as well as fragments thereof, particularly fragments that encode a biologically active gene product and/or are useful in the methods disclosed herein (e.g., in diagnosis, as a unique identifier of a differentially expressed gene of interest, etc.). The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' and 3' end of the transcribed region. The genomic DNA can be isolated as a fragment of 100 kbp or smaller; and substantially free of flanking chromosomal sequence. The genomic DNA flanking the coding region, either 3' and 5', or internal regulatory sequences as sometimes found in introns, contains sequences required for proper tissue, stage-specific, or disease-state specific expression.

The nucleic acid compositions of the subject invention can encode all or a part of the subject polypeptides. Double or single stranded fragments can be obtained from the DNA sequence by chemically synthesizing oligonucleotides in accordance with conventional methods, by restriction enzyme digestion, by PCR amplification, etc. Isolated polynucleotides and polynucleotide fragments of the invention comprise at least about 10, about 15, about 20, about 35, about 50, about 100, about 150 to about 200, about 250 to about 300, or about 350 contiguous nt selected from the polynucleotide sequences as shown in SEQ ID NOS:1–2707. For the most part, fragments will be of at least 15 nt, usually at least 18 nt or 25 nt, and up to at least about 50 contiguous nt in length or more. In a preferred embodiment, the polynucleotide molecules comprise a contiguous sequence of at least 12 nt selected from the group consisting of the polynucleotides shown in SEQ ID NOS:1–2707.

Probes specific to the polynucleotides of the invention can be generated using the polynucleotide sequences disclosed in SEQ ID NOS:1–2707. The probes are preferably at least about a 12, 15, 16, 18, 20, 22, 24, or 25 nt fragment of a corresponding contiguous sequence of SEQ ID NOS: 1–2707, and can be less than 2, 1, 0.5, 0.1, or 0.05 kb in length. The probes can be synthesized chemically or can be generated from longer polynucleotides using restriction enzymes. The probes can be labeled, for example, with a radioactive, biotinylated, or fluorescent tag. Preferably, probes are designed based upon an identifying sequence of a polynucleotide of one of SEQ ID NOS:1–2707. More preferably, probes are designed based on a contiguous sequence of one of the subject polynucleotides that remain unmasked following application of a masking program for masking low complexity (e.g., XBLAST) to the sequence., i.e., one would select an unmasked region, as indicated by the polynucleotides outside the poly-n stretches of the masked sequence produced by the masking program.

The polynucleotides of the subject invention are isolated and obtained in substantial purity, generally as other than an intact chromosome. Usually, the polynucleotides, either as DNA or RNA, will be obtained substantially free of other naturally-occurring nucleic acid sequences, generally being at least about 50%, usually at least about 90% pure and are typically "recombinant", e.g., flanked by one or more nucleotides with which it is not normally associated on a naturally occurring chromosome.

The polynucleotides of the invention can be provided as a linear molecule or within a circular molecule, and can be provided within autonomously replicating molecules (vectors) or within molecules without replication sequences. Expression of the polynucleotides can be regulated by their own or by other regulatory sequences known in the art. The polynucleotides of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

The subject nucleic acid compositions can be used to, for example, produce polypeptides, as probes for the detection of mRNA of the invention in biological samples (e.g., extracts of human cells) to generate additional copies of the polynucleotides, to generate ribozymes or antisense oligonucleotides, and as single stranded DNA probes or as triple-strand forming oligonucleotides. The probes described herein can be used to, for example, determine the presence or absence of the polynucleotide sequences as shown in SEQ ID NOS:1–2707 or variants thereof in a sample. These and other uses are described in more detail below.

Use of Polynucleotides to Obtain Full-Length cDNA, Gene, and Promoter Region

Full-length cDNA molecules comprising the disclosed polynucleotides are obtained as follows. A polynucleotide having a sequence of one of SEQ ID NOS:1–2707, or a portion thereof comprising at least 12, 15, 18, or 20 nt, is used as a hybridization probe to detect hybridizing members of a cDNA library using probe design methods, cloning methods, and clone selection techniques such as those described in U.S. Pat. No. 5,654,173. Libraries of cDNA are made from selected tissues, such as normal or tumor tissue, or from tissues of a mammal treated with, for example, a pharmaceutical agent. Preferably, the tissue is the same as the tissue from which the polynucleotides of the invention were isolated, as both the polynucleotides described herein and the cDNA represent expressed genes. Most preferably, the cDNA library is made from the biological material described herein in the Examples. The choice of cell type for library construction can be made after the identity of the protein encoded by the gene corresponding to the polynucleotide of the invention is known. This will indicate which tissue and cell types are likely to express the related gene, and thus represent a suitable source for the mRNA for generating the cDNA. Where the provided polynucleotides are isolated from cDNA libraries, the libraries are prepared from mRNA of human colon cells, more preferably, human colon cancer cells, even more preferably, from a highly metastatic colon cell, Km 12L4-A.

Techniques for producing and probing nucleic acid sequence libraries are described, for example, in Sambrook et al., *Molecular Cloning: A Laboratory Manual, 2nd Ed.*, (1989) Cold Spring Harbor Press, Cold Spring Harbor, N.Y. The cDNA can be prepared by using primers based on sequence from SEQ ID NOS:1–2707. In one embodiment, the cDNA library can be made from only poly-adenylated mRNA. Thus, poly-T primers can be used to prepare cDNA from the mRNA.

Members of the library that are larger than the provided polynucleotides, and preferably that encompass the complete coding sequence of the native message, are obtained. In order to confirm that the entire cDNA has been obtained, RNA protection experiments are performed as follows. Hybridization of a full-length cDNA to an mRNA will protect the RNA from RNase degradation. If the cDNA is not full length, then the portions of the mRNA that are not hybridized will be subject to RNase degradation. This is assayed, as is known in the art, by changes in electrophoretic mobility on polyacrylamide gels, or by detection of released monoribonucleotides. Sambrook et al., *Molecular Cloning: A Laboratory Manual, 2nd Ed.*, (1989) Cold Spring Harbor Press, Cold Spring Harbor, N.Y. In order to obtain additional sequences 5' to the end of a partial cDNA, 5' RACE (PCR *Protocols: A Guide to Methods and Applications*, (1990) Academic Press, Inc.) can be performed.

Genomic DNA is isolated using the provided polynucleotides in a manner similar to the isolation of full-length cDNAs. Briefly, the provided polynucleotides, or portions thereof, are used as probes to libraries of genomic DNA. Preferably, the library is obtained from the cell type that was used to generate the polynucleotides of the invention, but this is not essential. Most preferably, the genomic DNA is obtained from the biological material described herein in the Examples. Such libraries can be in vectors suitable for carrying large segments of a genome, such as P1 or YAC, as described in detail in Sambrook et al., 9.4–9.30. In addition, genomic sequences can be isolated from human BAC libraries, which are commercially available from Research Genetics, Inc., Huntsville, Ala., USA, for example. In order to obtain additional 5' or 3' sequences, chromosome walking is performed, as described in Sambrook et al., such that adjacent and overlapping fragments of genomic DNA are isolated. These are mapped and pieced together, as is known in the art, using restriction digestion enzymes and DNA ligase.

Using the polynucleotide sequences of the invention, corresponding full-length genes can be isolated using both classical and PCR methods to construct and probe cDNA libraries. Using either method, Northern blots, preferably, are performed on a number of cell types to determine which cell lines express the gene of interest at the highest level. Classical methods of constructing cDNA libraries are taught in Sambrook et al., supra. With these methods, cDNA can be produced from mRNA and inserted into viral or expression vectors. Typically, libraries of mRNA comprising poly(A) tails can be produced with poly(T) primers. Similarly, cDNA libraries can be produced using the instant sequences as primers.

PCR methods are used to amplify the members of a cDNA library that comprise the desired insert. In this case, the desired insert will contain sequence from the full length cDNA that corresponds to the instant polynucleotides. Such PCR methods include gene trapping and RACE methods. Gene trapping entails inserting a member of a cDNA library into a vector. The vector then is denatured to produce single stranded molecules. Next, a substrate-bound probe, such a biotinylated oligo, is used to trap cDNA inserts of interest. Biotinylated probes can be linked to an avidin-bound solid substrate. PCR methods can be used to amplify the trapped cDNA. To trap sequences corresponding to the full length genes, the labeled probe sequence is based on the polynucleotide sequences of the invention. Random primers or primers specific to the library vector can be used to amplify the trapped cDNA. Such gene trapping techniques are described in Gruber et al., WO 95/04745 and Gruber et al., U.S. Pat. No. 5,500,356. Kits are commercially available to perform gene trapping experiments from, for example, Life Technologies, Gaithersburg, Md., USA.

"Rapid amplification of cDNA ends," or RACE, is a PCR method of amplifying cDNAs from a number of different RNAs. The cDNAs are ligated to an oligonucleotide linker, and amplified by PCR using two primers. One primer is based on sequence from the instant polynucleotides, for which full length sequence is desired, and a second primer comprises sequence that hybridizes to the oligonucleotide linker to amplify the cDNA. A description of this methods is reported in WO 97/19110. In preferred embodiments of RACE, a common primer is designed to anneal to an arbitrary adaptor sequence ligated to cDNA ends (Apte and Siebert, *Biotechniques* (1993) 15:890–893; Edwards et al., *Nuc. Acids Res.* (1991) 19:5227–5232). When a single gene-specific RACE primer is paired with the common primer, preferential amplification of sequences between the single gene specific primer and the common primer occurs. Commercial cDNA pools modified for use in RACE are available.

Another PCR-based method generates full-length cDNA library with anchored ends without needing specific knowledge of the cDNA sequence. The method uses lock-docking primers (I–VI), where one primer, poly TV (I–III) locks over the polyA tail of eukaryotic mRNA producing first strand synthesis and a second primer, polyGH (IV–VI) locks onto the polyC tail added by terminal deoxynucleotidyl transferase (TdT)(see, e.g., WO 96/40998).

The promoter region of a gene generally is located 5' to the initiation site for RNA polymerase II. Hundreds of promoter regions contain the "TATA" box, a sequence such as TATTA or TATAA, which is sensitive to mutations. The promoter region can be obtained by performing 5' RACE using a primer from the coding region of the gene. Alternatively, the cDNA can be used as a probe for the genomic sequence, and the region 5' to the coding region is identified by "walking up." If the gene is highly expressed or differentially expressed, the promoter from the gene can be of use in a regulatory construct for a heterologous gene.

Once the full-length cDNA or gene is obtained, DNA encoding variants can be prepared by site-directed mutagenesis, described in detail in Sambrook et al., 15.3–15.63. The choice of codon or nucleotide to be replaced can be based on disclosure herein on optional changes in amino acids to achieve altered protein structure and/or function.

As an alternative method to obtaining DNA or RNA from a biological material, nucleic acid comprising nucleotides having the sequence of one or more polynucleotides of the invention can be synthesized. Thus, the invention encompasses nucleic acid molecules ranging in length from 15 nt (corresponding to at least 15 contiguous nt of one of SEQ ID NOS:1–2707) up to a maximum length suitable for one or more biological manipulations, including replication and expression, of the nucleic acid molecule. The invention includes but is not limited to (a) nucleic acid having the size of a full gene, and comprising at least one of SEQ ID NOS:1–2707; (b) the nucleic acid of (a) also comprising at least one additional gene, operably linked to permit expression of a fusion protein; (c) an expression vector comprising (a) or (b); (d) a plasmid comprising (a) or (b); and (e) a recombinant viral particle comprising (a) or (b). Once provided with the polynucleotides disclosed herein, construction or preparation of (a)–(e) are well within the skill in the art.

The sequence of a nucleic acid comprising at least 15 contiguous nt of at least any one of SEQ ID NOS:1–2707, preferably the entire sequence of at least any one of SEQ ID NOS:1–2707, is not limited and can be any sequence of A, T, G, and/or C (for DNA) and A, U, G, and/or C (for RNA) or modified bases thereof, including inosine and pseudouridine. The choice of sequence will depend on the desired function and can be dictated by coding regions desired, the intron-like regions desired, and the regulatory regions desired. Where the entire sequence of any one of SEQ ID NOS:1–2707 is within the nucleic acid, the nucleic acid obtained is referred to herein as a polynucleotide comprising the sequence of any one of SEQ ID NOS:1–2707.

Expression of Polypeptide Encoded by Full-Length cDNA or Full-Length Gene

The provided polynucleotides (e.g., a polynucleotide having a sequence of one of SEQ ID NOS:1–2707), the corresponding cDNA, or the full-length gene is used to express a partial or complete gene product. Constructs of polynucleotides having sequences of SEQ ID NOS:1–2707 can also be generated synthetically. Alternatively, single-step assembly of a gene and entire plasmid from large numbers of oligodeoxyribonucleotides is described by, e.g., Stemmer et al., *Gene (Amsterdam)* (1995) 164(1):49–53. In this method, assembly PCR (the synthesis of long DNA sequences from large numbers of oligodeoxyribonucleotides (oligos)) is described. The method is derived from DNA shuffling (Stemmer, *Nature* (1994) 370:389–391), and does not rely on DNA ligase, but instead relies on DNA polymerase to build increasingly longer DNA fragments during the assembly process.

Appropriate polynucleotide constructs are purified using standard recombinant DNA techniques as described in, for example, Sambrook et al., *Molecular Cloning: A Laboratory Manual, 2nd Ed.*, (1989) Cold Spring Harbor Press, Cold Spring Harbor, N.Y., and under current regulations described in United States Dept. of HHS, National Institute of Health (NIH) Guidelines for Recombinant DNA Research. The gene product encoded by a polynucleotide of the invention is expressed in any expression system, including, for example, bacterial, yeast, insect, amphibian and mammalian systems. Vectors, host cells and methods for obtaining expression in same are well known in the art. Suitable vectors and host cells are described in U.S. Pat. No. 5,654,173.

Polynucleotide molecules comprising a polynucleotide sequence provided herein are generally propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. Methods for preparation of vectors comprising a desired sequence are well known in the art.

The polynucleotides set forth in SEQ ID NOS:1–2707 or their corresponding full-length polynucleotides are linked to regulatory sequences as appropriate to obtain the desired expression properties. These can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated in the cell to which the gene is native. For example, an endogenous gene of a cell can be regulated by an exogenous regulatory sequence as disclosed in U.S. Pat. No. 5,641,670.

Identification of Functional and Structural Motifs of Novel Genes Screening Against Publicly Available Databases Translations of the nucleotide sequence of the provided polynucleotides, cDNAs or full genes can be aligned with individual known sequences. Similarity with individual sequences can be used to determine the activity of the polypeptides encoded by the polynucleotides of the invention. Also, sequences exhibiting similarity with more than one individual sequence can exhibit activities that are characteristic of either or both individual sequences.

The full length sequences and fragments of the polynucleotide sequences of the nearest neighbors can be used as probes and primers to identify and isolate the full length sequence corresponding to provided polynucleotides. The nearest neighbors can indicate a tissue or cell type to be used to construct a library for the full-length sequences corresponding to the provided polynucleotides.

Typically, a selected polynucleotide is translated in all six frames to determine the best alignment with the individual sequences. The sequences disclosed herein in the Sequence Listing are in a 5' to 3' orientation and translation in three frames can be sufficient (with a few specific exceptions as described in the Examples). These amino acid sequences are referred to, generally, as query sequences, which will be aligned with the individual sequences. Databases with individual sequences are described in "Computer Methods for Macromolecular Sequence Analysis" *Methods in Enzymology* (1996) 266, Doolittle, Academic Press, Inc., a division of Harcourt Brace & Co., San Diego, Calif., USA. Databases include GenBank, EMBL, and DNA Database of Japan (DDBJ).

Query and individual sequences can be aligned using the methods and computer programs described above, and include BLAST 2.0, available over the world wide web at ncbi.nlm.nih.gov/BLAST. See also Altschul, et al. *Nucleic Acids Res.* (1997) 25:3389–3402. Another alignment algorithm is Fasta, available in the Genetics Computing Group (GCG) package, Madison, Wis., USA, a wholly owned subsidiary of Oxford Molecular Group, Inc. Other techniques for alignment are described in Doolittle, supra. Preferably, an alignment program that permits gaps in the sequence is utilized to align the sequences. The Smith-Waterman is one type of algorithm that permits gaps in sequence alignments. See *Meth. Mol. Biol.* (1997) 70: 173–187. Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to identify sequences that are distantly related matches, and is especially tolerant of small gaps and nucleotide sequence errors. Amino acid sequences encoded by the provided polynucleotides can be used to search both protein and DNA databases. Incorporated herein by reference are all sequences that have been made public as of the filing date of this application by any of the DNA or protein sequence databases, including the patent databases (e.g., GeneSeq). Also incorporated by reference are those sequences that have been submitted to these databases as of the filing date of the present application but not made public until after the filing date of the present application.

Results of individual and query sequence alignments can be divided into three categories: high similarity, weak similarity, and no similarity. Individual alignment results ranging from high similarity to weak similarity provide a basis for determining polypeptide activity and/or structure. Parameters for categorizing individual results include: percentage of the alignment region length where the strongest alignment is found, percent sequence identity, and p value. The percentage of the alignment region length is calculated by counting the number of residues of the individual sequence found in the region of strongest alignment, e.g., contiguous region of the individual sequence that contains the greatest number of residues that are identical to the residues of the corresponding region of the aligned query sequence. This number is divided by the total residue length of the query sequence to calculate a percentage. For example, a query sequence of 20 amino acid residues might be aligned with a 20 amino acid region of an individual sequence. The individual sequence might be identical to amino acid residues 5, 9–15, and 17–19 of the query sequence. The region of strongest alignment is thus the region stretching from residue 9–19, an 11 amino acid stretch. The percentage of the alignment region length is: 11 (length of the region of strongest alignment) divided by (query sequence length) 20 or 55%.

Percent sequence identity is calculated by counting the number of amino acid matches between the query and individual sequence and dividing total number of matches by the number of residues of the individual sequences found in the region of strongest alignment. Thus, the percent identity in the example above would be 10 matches divided by 11 amino acids, or approximately, 90.9%

P value is the probability that the alignment was produced by chance. For a single alignment, the p value can be calculated according to Karlin et al., *Proc. Natl. Acad. Sci.* (1990) 87:2264 and Karlin et al., *Proc. Natl. Acad. Sci.* (1993) 90. The p value of multiple alignments using the same query sequence can be calculated using an heuristic approach described in Altschul et al., *Nat. Genet.* (1994) 6:119. Alignment programs such as BLAST program can calculate the p value. See also Altschul et al., *Nucleic Acids Res.* (1997) 25:3389–3402.

Another factor to consider for determining identity or similarity is the location of the similarity or identity. Strong local alignment can indicate similarity even if the length of alignment is short. Sequence identity scattered throughout the length of the query sequence also can indicate a similarity between the query and profile sequences. The boundaries of the region where the sequences align can be determined according to Doolittle, supra; BLAST 2.0 (see, e.g., Altschul, et al. *Nucleic Acids Res.* (1997) 25:3389–3402) or FAST programs; or by determining the area where sequence identity is highest.

High Similarity. In general, in alignment results considered to be of high similarity, the percent of the alignment region length is typically at least about 55% of total length query sequence; more typically, at least about 58%; even more typically; at least about 60% of the total residue length of the query sequence. Usually, percent length of the alignment region can be as much as about 62%; more usually, as much as about 64%; even more usually, as much as about 66%. Further, for high similarity, the region of alignment, typically, exhibits at least about 75% of sequence identity; more typically, at least about 78%; even more typically; at least about 80% sequence identity. Usually, percent sequence identity can be as much as about 82%; more usually, as much as about 84%; even more usually, as much as about 86%.

The p value is used in conjunction with these methods. If high similarity is found, the query sequence is considered to have high similarity with a profile sequence when the p value is less than or equal to about $10^{-2}$; more usually; less than or equal to about $10^{-3}$; even more usually; less than or equal to about $10^{-4}$ More typically, the p value is no more than about $10^{-5}$; more typically; no more than or equal to about $10^{-10}$; even more typically; no more than or equal to about $10^{-15}$ for the query sequence to be considered high similarity.

Weak Similarity. In general, where alignment results considered to be of weak similarity, there is no minimum percent length of the alignment region nor minimum length of alignment. A better showing of weak similarity is considered when the region of alignment is, typically, at least about 15 amino acid residues in length; more typically, at least about 20; even more typically; at least about 25 amino acid residues in length. Usually, length of the alignment region can be as much as about 30 amino acid residues; more usually, as much as about 40; even more usually, as much as about 60 amino acid residues. Further, for weak similarity, the region of alignment, typically, exhibits at least about 35% of sequence identity; more typically, at least about 40%; even more typically; at least about 45% sequence identity. Usually, percent sequence identity can be as much as about 50%; more usually, as much as about 55%; even more usually, as much as about 60%.

If low similarity is found, the query sequence is considered to have weak similarity with a profile sequence when the p value is usually less than or equal to about $10^{-2}$; more usually; less than or equal to about $10^{-3}$; even more usually; less than or equal to about $10^{-4}$. More typically, the p value is no more than about $10^{-5}$; more usually; no more than or equal to about $10^{-10}$; even more usually; no more than or equal to about $10^{-15}$ for the query sequence to be considered weak similarity.

Similarity Determined by Sequence Identity Alone. Sequence identity alone can be used to determine similarity of a query sequence to an individual sequence and can indicate the activity of the sequence. Such an alignment, preferably, permits gaps to align sequences. Typically, the query sequence is related to the profile sequence if the sequence identity over the entire query sequence is at least about 15%; more typically, at least about 20%; even more typically, at least about 25%; even more typically, at least about 50%. Sequence identity alone as a measure of similarity is most useful when the query sequence is usually, at least 80 residues in length; more usually, 90 residues; even more usually, at least 95 amino acid residues in length. More typically, similarity can be concluded based on sequence identity alone when the query sequence is preferably 100 residues in length; more preferably, 120 residues in length; even more preferably, 150 amino acid residues in length.

Alignments with Profile and Multiple Aligned Sequences. Translations of the provided polynucleotides can be aligned with amino acid profiles that define either protein families or common motifs. Also, translations of the provided polynucleotides can be aligned to multiple sequence alignments (MSA) comprising the polypeptide sequences of members of protein families or motifs. Similarity or identity with profile sequences or MSAs can be used to determine the activity of the gene products (e.g., polypeptides) encoded by the provided polynucleotides or corresponding cDNA or genes. For example, sequences that show an identity or similarity with a chemokine profile or MSA can exhibit chemokine activities.

Profiles can designed manually by (1) creating an MSA, which is an alignment of the amino acid sequence of members that belong to the family and (2) constructing a statistical representation of the alignment. Such methods are described, for example, in Birney et al., *Nucl. Acid Res.* (1996) 24(14): 2730–2739. MSAs of some protein families and motifs are publicly available. For example, genome.wustl.edu/Pfam includes MSAs of 547 different families and motifs. These MSAs are described also in Sonnhammer et al., *Proteins* (1997) 28: 405–420. Other sources over the world wide web include the site at embl-heidelberg.de/argos/ali/ali. A brief description of these MSAs is reported in Pascarella et al., *Prot. Eng.* (1996) 9(3):249–251. Techniques for building profiles from MSAs are described in Sonnhammer et al., supra; Birney et al., supra; and "Computer Methods for Macromolecular Sequence Analysis," *Methods in Enzymology* (1996) 266, Doolittle, Academic Press, Inc., San Diego, Calif., USA.

Similarity between a query sequence and a protein family or motif can be determined by (a) comparing the query sequence against the profile and/or (b) aligning the query sequence with the members of the family or motif. Typically, a program such as Searchwise is used to compare the query sequence to the statistical representation of the multiple alignment, also known as a profile (see Birney et al., supra). Other techniques to compare the sequence and profile are described in Sonnhammer et al., supra and Doolittle, supra.

Next, methods described by Feng et al., *J. Mol. Evol.* (1987) 25:351 and Higgins et al., *CABIOS* (1989) 5:151 can be used align the query sequence with the members of a family or motif, also known as a MSA. Sequence alignments can be generated using any of a variety of software tools. Examples include PileUp, which creates a multiple sequence alignment, and is described in Feng et al, *J. Mol. Evol.* (1987) 25:351. Another method, GAP, uses the alignment method of Needleman et al., *J. Mol. Biol.* (1970) 48:443. GAP is best suited for global alignment of sequences. A third method, BestFit, functions by inserting gaps to maximize the number of matches using the local homology algorithm of Smith et al., *Adv. Appl. Math.* (1981) 2:482. In general, the following factors are used to determine if a similarity between a query sequence and a profile or MSA exists: (1) number of conserved residues found in the query sequence, (2) percentage of conserved residues found in the query sequence, (3) number of frameshifts, and (4) spacing between conserved residues.

Some alignment programs that both translate and align sequences can make any number of frameshifts when translating the nucleotide sequence to produce the best alignment. The fewer frameshifts needed to produce an alignment, the stronger the similarity or identity between the query and profile or MSAs. For example, a weak similarity resulting from no frameshifts can be a better indication of activity or structure of a query sequence, than a strong similarity resulting from two frameshifts. Preferably, three or fewer frameshifts are found in an alignment; more preferably two or fewer frameshifts; even more preferably, one or fewer frameshifts; even more preferably, no frameshifts are found in an alignment of query and profile or MSAs.

Conserved residues are those amino acids found at a particular position in all or some of the family or motif members. Alternatively, a position is considered conserved if only a certain class of amino acids is found in a particular position in all or some of the family members. For example, the N-terminal position can contain a positively charged amino acid, such as lysine, arginine, or histidine.

Typically, a residue of a polypeptide is conserved when a class of amino acids or a single amino acid is found at a particular position in at least about 40% of all class members; more typically, at least about 50%; even more typically, at least about 60% of the members. Usually, a residue is conserved when a class or single amino acid is found in at least about 70% of the members of a family or motif; more usually, at least about 80%; even more usually, at least about 90%; even more usually, at least about 95%.

A residue is considered conserved when three unrelated amino acids are found at a particular position in the some or all of the members; more usually, two unrelated amino acids. These residues are conserved when the unrelated amino acids are found at particular positions in at least about 40% of all class member; more typically, at least about 50%; even more typically, at least about 60% of the members. Usually, a residue is conserved when a class or single amino acid is found in at least about 70% of the members of a family or motif; more usually, at least about 80%; even more usually, at least about 90%; even more usually, at least about 95%.

A query sequence has similarity to a profile or MSA when the query sequence comprises at least about 25% of the conserved residues of the profile or MSA; more usually, at least about 30%; even more usually; at least about 40%. Typically, the query sequence has a stronger similarity to a profile sequence or MSA when the query sequence comprises at least about 45% of the conserved residues of the profile or MSA; more typically, at least about 50%; even more typically; at least about 55%.

Identification of Secreted & Membrane-Bound Polypeptides

Both secreted and membrane-bound polypeptides of the present invention are of particular interest. For example, levels of secreted polypeptides can be assayed in body fluids that are convenient, such as blood, plasma, serum, and other body fluids such as urine, prostatic fluid and semen. Membrane-bound polypeptides are useful for constructing vaccine antigens or inducing an immune response. Such antigens would comprise all or part of the extracellular region of the membrane-bound polypeptides. Because both secreted and membrane-bound polypeptides comprise a fragment of contiguous hydrophobic amino acids, hydrophobicity predicting algorithms can be used to identify such polypeptides.

A signal sequence is usually encoded by both secreted and membrane-bound polypeptide genes to direct a polypeptide to the surface of the cell. The signal sequence usually comprises a stretch of hydrophobic residues. Such signal sequences can fold into helical structures. Membrane-bound polypeptides typically comprise at least one transmembrane region that possesses a stretch of hydrophobic amino acids that can transverse the membrane. Some transmembrane regions also exhibit a helical structure. Hydrophobic fragments within a polypeptide can be identified by using computer algorithms. Such algorithms include Hopp & Woods, *Proc. Natl. Acad. Sci. USA* (1981) 78:3824–3828; Kyte & Doolittle, *J. Mol. Biol.* (1982) 157:105–132; and RAOAR algorithm, Degli Esposti et al., *Eur. J. Biochem.* (1990) 190: 207–219.

Another method of identifying secreted and membrane-bound polypeptides is to translate the polynucleotides of the invention in all six frames and determine if at least 8 contiguous hydrophobic amino acids are present. Those translated polypeptides with at least 8; more typically, 10; even more typically, 12 contiguous hydrophobic amino acids are considered to be either a putative secreted or membrane bound polypeptide. Hydrophobic amino acids include alanine, glycine, histidine, isoleucine, leucine, lysine, methionine, phenylalanine, proline, threonine, tryptophan, tyrosine, and valine Identification of the Function of an Expression Product of a Full-Length Gene Ribozymes, antisense constructs, and dominant negative mutants can be used to determine function of the expression product of a gene corresponding to a polynucleotide provided herein. These methods and compositions are particularly useful where the provided novel polynucleotide exhibits no significant or substantial homology to a sequence encoding a gene of known function. Antisense molecules and ribozymes can be constructed from synthetic polynucleotides. Typically, the phosphoramidite method of oligonucleotide synthesis is used. See Beaucage et al., *Tet. Lett.* (1981) 22:1859 and U.S. Pat. No. 4,668,777. Automated devices for synthesis are available to create oligonucleotides using this chemistry. Examples of such devices include Biosearch 8600, Models 392 and 394 by Applied Biosystems, a division of Perkin-Elmer Corp., Foster City, Calif., USA; and Expedite by Perceptive Biosystems, Framingham, Mass., USA. Synthetic RNA, phosphate analog oligonucleotides, and chemically derivatized oligonucleotides can also be produced, and can be covalently attached to other molecules. RNA oligonucleotides can be synthesized, for example, using RNA phosphoramidites. This method can be performed on an automated synthesizer, such as Applied Biosystems, Models 392 and 394, Foster City, Calif., USA.

Phosphorothioate oligonucleotides can also be synthesized for antisense construction. A sulfurizing reagent, such as tetraethylthiruam disulfide (TETD) in acetonitrile can be used to convert the internucleotide cyanoethyl phosphite to the phosphorothioate triester within 15 minutes at room temperature. TETD replaces the iodine reagent, while all other reagents used for standard phosphoramidite chemistry remain the same. Such a synthesis method can be automated using Models 392 and 394 by Applied Biosystems, for example.

Oligonucleotides of up to 200 nt can be synthesized, more typically, 100 nt, more typically 50 nt; even more typically 30 to 40 nt. These synthetic fragments can be annealed and ligated together to construct larger fragments. See, for example, Sambrook et al., supra. Trans-cleaving catalytic RNAs (ribozymes) are RNA molecules possessing endoribonuclease activity. Ribozymes are specifically designed for a particular target, and the target message must contain a specific nucleotide sequence. They are engineered to cleave any RNA species site-specifically in the background of cellular RNA. The cleavage event renders the mRNA unstable and prevents protein expression. Importantly, ribozymes can be used to inhibit expression of a gene of unknown function for the purpose of determining its function in an in vitro or in vivo context, by detecting the phenotypic effect. One commonly used ribozyme motif is the hammerhead, for which the substrate sequence requirements are minimal. Design of the hammerhead ribozyme, as well as therapeutic uses of ribozymes, are disclosed in Usman et al., *Current Opin. Struct. Biol.* (1996) 6:527. Methods for production of ribozymes, including hairpin structure ribozyme fragments, methods of increasing ribozyme specificity, and the like are known in the art.

The hybridizing region of the ribozyme can be modified or can be prepared as a branched structure as described in Horn and Urdea, *Nucleic Acids Res.* (1989) 17:6959. The basic structure of the ribozymes can also be chemically altered in ways familiar to those skilled in the art, and chemically synthesized ribozymes can be administered as synthetic oligonucleotide derivatives modified by monomeric units. In a therapeutic context, liposome mediated delivery of ribozymes improves cellular uptake, as described in Birikh et al., *Eur. J. Biochem.* (1997) 245:1.

Antisense nucleic acids are designed to specifically bind to RNA, resulting in the formation of RNA-DNA or RNA-RNA hybrids, with an arrest of DNA replication, reverse transcription or messenger RNA translation. Antisense polynucleotides based on a selected polynucleotide sequence can interfere with expression of the corresponding gene. Antisense polynucleotides are typically generated within the cell by expression from antisense constructs that contain the antisense strand as the transcribed strand. Antisense polynucleotides based on the disclosed polynucleotides will bind and/or interfere with the translation of mRNA comprising a sequence complementary to the antisense polynucleotide. The expression products of control cells and cells treated with the antisense construct are compared to detect the protein product of the gene corresponding to the polynucleotide upon which the antisense construct is based. The protein is isolated and identified using routine biochemical methods.

Given the extensive background literature and clinical experience in antisense therapy, one skilled in the art can use selected polynucleotides of the invention as additional potential therapeutics. The choice of polynucleotide can be narrowed by first testing them for binding to "hot spot" regions of the genome of cancerous cells. If a polynucleotide is identified as binding to a "hot spot", testing the polynucleotide as an antisense compound in the corresponding cancer cells is warranted.

As an alternative method for identifying function of the gene corresponding to a polynucleotide disclosed herein, dominant negative mutations are readily generated for corresponding proteins that are active as homomultimers. A mutant polypeptide will interact with wild-type polypeptides (made from the other allele) and form a non-functional multimer. Thus, a mutation is in a substrate-binding domain, a catalytic domain, or a cellular localization domain. Preferably, the mutant polypeptide will be overproduced. Point mutations are made that have such an effect. In addition, fusion of different polypeptides of various lengths to the terminus of a protein can yield dominant negative mutants. General strategies are available for making dominant negative mutants (see, e.g., Herskowitz, *Nature* (1987) 329:219). Such techniques can be used to create loss of function mutations, which are useful for determining protein function.

Polypeptides and Variants Thereof

The polypeptides of the invention include those encoded by the disclosed polynucleotides, as well as nucleic acids that, by virtue of the degeneracy of the genetic code, are not identical in sequence to the disclosed polynucleotides. Thus, the invention includes within its scope a polypeptide encoded by a polynucleotide having the sequence of any one of SEQ ID NOS:1–2707 or a variant thereof.

In general, the term "polypeptide" as used herein refers to both the full length polypeptide encoded by the recited polynucleotide, the polypeptide encoded by the gene represented by the recited polynucleotide, as well as portions or fragments thereof. "Polypeptides" also includes variants of the naturally occurring proteins, where such variants are homologous or substantially similar to the naturally occurring protein, and can be of an origin of the same or different species as the naturally occurring protein (e.g., human, murine, or some other species that naturally expresses the recited polypeptide, usually a mammalian species). In general, variant polypeptides have a sequence that has at least about 80%, usually at least about 90%, and more usually at least about 98% sequence identity with a differentially expressed polypeptide of the invention, as measured by BLAST 2.0 using the parameters described above. The variant polypeptides can be naturally or non-naturally glycosylated, i.e., the polypeptide has a glycosylation pattern that differs from the glycosylation pattern found in the corresponding naturally occurring protein.

The invention also encompasses homologs of the disclosed polypeptides (or fragments thereof) where the homologs are isolated from other species, i.e. other animal or plant species, where such homologs, usually mammalian species, e.g. rodents, such as mice, rats; domestic animals, e.g., horse, cow, dog, cat; and humans. By "homolog" is meant a polypeptide having at least about 35%, usually at least about 40% and more usually at least about 60% amino acid sequence identity to a particular differentially expressed protein as identified above, where sequence identity is determined using the BLAST 2.0 algorithm, with the parameters described supra.

In general, the polypeptides of the subject invention are provided in a non-naturally occurring environment, e.g. are separated from their naturally occurring environment. In certain embodiments, the subject protein is present in a composition that is enriched for the protein as compared to a control. As such, purified polypeptide is provided, where by purified is meant that the protein is present in a composition that is substantially free of non-differentially expressed polypeptides, where by substantially free is meant that less than 90%, usually less than 60% and more usually less than 50% of the composition is made up of non-differentially expressed polypeptides.

Also within the scope of the invention are variants; variants of polypeptides include mutants, fragments, and fusions. Mutants can include amino acid substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Conservative amino acid substitutions are those that preserve the general charge, hydrophobicity/hydrophilicity, and/or steric bulk of the amino acid substituted. Variants can be designed so as to retain or have enhanced biological activity of a particular region of the protein (e.g., a functional domain and/or, where the polypeptide is a member of a protein family, a region associated with a consensus sequence). Selection of amino acid alterations for production of variants can be based upon the accessibility (interior vs. exterior) of the amino acid (see, e.g., Go et al, *Int. J. Peptide Protein Res.* (1980) 15:211), the thermostability of the variant polypeptide (see, e.g., Querol et al., *Prot.*

*Eng.* (1996) 9:265), desired glycosylation sites (see, e.g., Olsen and Thomsen, *J. Gen. Microbiol.* (1991) 137:579), desired disulfide bridges (see, e.g., Clarke et al., *Biochemistry* (1993) 32:4322; and Wakarchuk et al., *Protein Eng.* (1994) 7:1379), desired metal binding sites (see, e.g., Toma et al., *Biochemistry* (1991) 30:97, and Haezerbrouck et al., *Protein Eng.* (1993) 6:643), and desired substitutions with in proline loops (see, e.g., Masul et al., *Appl. Env. Microbiol.* (1994) 60:3579). Cysteine-depleted muteins can be produced as disclosed in U.S. Pat. No. 4,959,314.

Variants also include fragments of the polypeptides disclosed herein, particularly biologically active fragments and/or fragments corresponding to functional domains. Fragments of interest will typically be at least about 10 aa to at least about 15 aa in length, usually at least about 50 aa in length, and can be as long as 300 aa in length or longer, but will usually not exceed about 1000 aa in length, where the fragment will have a stretch of amino acids that is identical to a polypeptide encoded by a polynucleotide having a sequence of any SEQ ID NOS:1–2707, or a homolog thereof. The protein variants described herein are encoded by polynucleotides that are within the scope of the invention. The genetic code can be used to select the appropriate codons to construct the corresponding variants.

Computer-Related Embodiments

In general, a library of polynucleotides is a collection of sequence information, which information is provided in either biochemical form (e.g., as a collection of polynucleotide molecules), or in electronic form (e.g., as a collection of polynucleotide sequences stored in a computer-readable form, as in a computer system and/or as part of a computer program). The sequence information of the polynucleotides can be used in a variety of ways, e.g., as a resource for gene discovery, as a representation of sequences expressed in a selected cell type (e.g., cell type markers), and/or as markers of a given disease or disease state. In general, a disease marker is a representation of a gene product that is present in all cells affected by disease either at an increased or decreased level relative to a normal cell (e.g., a cell of the same or similar type that is not substantially affected by disease). For example, a polynucleotide sequence in a library can be a polynucleotide that represents an mRNA, polypeptide, or other gene product encoded by the polynucleotide, that is either overexpressed or underexpressed in a breast ductal cell affected by cancer relative to a normal (i.e., substantially disease-free) breast cell.

The nucleotide sequence information of the library can be embodied in any suitable form, e.g., electronic or biochemical forms. For example, a library of sequence information embodied in electronic form comprises an accessible computer data file (or, in biochemical form, a collection of nucleic acid molecules) that contains the representative nucleotide sequences of genes that are differentially expressed (e.g., overexpressed or underexpressed) as between, for example, i) a cancerous cell and a normal cell; ii) a cancerous cell and a dysplastic cell; iii) a cancerous cell and a cell affected by a disease or condition other than cancer; iv) a metastatic cancerous cell and a normal cell and/or non-metastatic cancerous cell; v) a malignant cancerous cell and a non-malignant cancerous cell (or a normal cell) and/or vi) a dysplastic cell relative to a normal cell. Other combinations and comparisons of cells affected by various diseases or stages of disease will be readily apparent to the ordinarily skilled artisan. Biochemical embodiments of the library include a collection of nucleic acids that have the sequences of the genes in the library, where the nucleic acids can correspond to the entire gene in the library or to a fragment thereof, as described in greater detail below.

The polynucleotide libraries of the subject invention generally comprise sequence information of a plurality of polynucleotide sequences, where at least one of the polynucleotides has a sequence of any of SEQ ID NOS:1–2707. By plurality is meant at least 2, usually at least 3 and can include up to all of SEQ ID NOS:1–2707. The length and number of polynucleotides in the library will vary with the nature of the library, e.g., if the library is an oligonucleotide array, a cDNA array, a computer database of the sequence information, etc.

Where the library is an electronic library, the nucleic acid sequence information can be present in a variety of media. "Media" refers to a manufacture, other than an isolated nucleic acid molecule, that contains the sequence information of the present invention. Such a manufacture provides the genome sequence or a subset thereof in a form that can be examined by means not directly applicable to the sequence as it exists in a nucleic acid. For example, the nucleotide sequence of the present invention, e.g. the nucleic acid sequences of any of the polynucleotides of SEQ ID NOS:1–2707, can be recorded on computer readable media, e.g. any medium that can be read and accessed directly by a computer. Such media include, but are not limited to: magnetic storage media, such as a floppy disc, a hard disc storage medium, and a magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present sequence information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc. In addition to the sequence information, electronic versions of the libraries of the invention can be provided in conjunction or connection with other computer-readable information and/or other types of computer-readable files (e.g., searchable files, executable files, etc, including, but not limited to, for example, search program software, etc.).

By providing the nucleotide sequence in computer readable form, the information can be accessed for a variety of purposes. Computer software to access sequence information is publicly available. For example, the gapped BLAST (Altschul et al. *Nucleic Acids Res*. (1997) 25:3389–3402) and BLAZE (Brutlag et al. *Comp. Chem.* (1993) 17:203) search algorithms on a Sybase system can be used to identify open reading frames (ORFs) within the genome that contain homology to ORFs from other organisms.

As used herein, "a computer-based system" refers to the hardware means, software means, and data storage means used to analyze the nucleotide sequence information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means can comprise any manufacture comprising a recording of the present sequence information as described above, or a memory access means that can access such a manufacture.

"Search means" refers to one or more programs implemented on the computer-based system, to compare a target sequence or target structural motif, or expression levels of a polynucleotide in a sample, with the stored sequence information. Search means can be used to identify fragments or regions of the genome that match a particular target sequence or target motif. A variety of known algorithms are publicly known and commercially available, e.g. MacPattern (EMBL), BLASTN and BLASTX (NCBI). A "target sequence" can be any polynucleotide or amino acid sequence of six or more contiguous nucleotides or two or more amino acids, preferably from about 10 to 100 amino acids or from about 30 to 300 nt A variety of comparing means can be used to accomplish comparison of sequence information from a sample (e.g., to analyze target sequences, target motifs, or relative expression levels) with the data storage means. A skilled artisan can readily recognize that any one of the publicly available homology search programs can be used as the search means for the computer based systems of the present invention to accomplish comparison of target sequences and motifs. Computer programs to analyze expression levels in a sample and in controls are also known in the art.

A "target structural motif," or "target motif," refers to any rationally selected sequence or combination of sequences in which the sequence(s) are chosen based on a three-dimensional configuration that is formed upon the folding of the target motif, or on consensus sequences of regulatory or active sites. There are a variety of target motifs known in the art. Protein target motifs include, but are not limited to, enzyme active sites and signal sequences. Nucleic acid target motifs include, but are not limited to, hairpin structures, promoter sequences and other expression elements such as binding sites for transcription factors.

A variety of structural formats for the input and output means can be used to input and output the information in the computer-based systems of the present invention. One format for an output means ranks the relative expression levels of different polynucleotides. Such presentation provides a skilled artisan with a ranking of relative expression levels to determine a gene expression profile.

As discussed above, the "library" of the invention also encompasses biochemical libraries of the polynucleotides of SEQ ID NOS:1–2707, e.g., collections of nucleic acids representing the provided polynucleotides. The biochemical libraries can take a variety of forms, e.g., a solution of cDNAs, a pattern of probe nucleic acids stably associated with a surface of a solid support (i.e., an array) and the like. Of particular interest are nucleic acid arrays in which one or more of SEQ ID NOS:1–2707 is represented on the array. By array is meant a an article of manufacture that has at least a substrate with at least two distinct nucleic acid targets on one of its surfaces, where the number of distinct nucleic acids can be considerably higher, typically being at least 10 nt, usually at least 20 nt and often at least 25 nt. A variety of different array formats have been developed and are known to those of skill in the art. The arrays of the subject invention find use in a variety of applications, including gene expression analysis, drug screening, mutation analysis and the like, as disclosed in the above-listed exemplary patent documents.

In addition to the above nucleic acid libraries, analogous libraries of polypeptides are also provided, where the where the polypeptides of the library will represent at least a portion of the polypeptides encoded by SEQ ID NOS: 1–2707.

Utilities

Use of Polynucleotide Probes in Mapping, and in Tissue Profiling

Polynucleotide probes, generally comprising at least 12 contiguous nt of a polynucleotide as shown in the Sequence Listing, are used for a variety of purposes, such as chromosome mapping of the polynucleotide and detection of transcription levels. Additional disclosure about preferred regions of the disclosed polynucleotide sequences is found in the Examples. A probe that hybridizes specifically to a polynucleotide disclosed herein should provide a detection signal at least 5-, 10-, or 20-fold higher than the background hybridization provided with other unrelated sequences.

Detection of Expression Levels. Nucleotide probes are used to detect expression of a gene corresponding to the provided polynucleotide. In Northern blots, mRNA is separated electrophoretically and contacted with a probe. A probe is detected as hybridizing to an mRNA species of a particular size. The amount of hybridization is quantitated to determine relative amounts of expression, for example under a particular condition. Probes are used for in situ hybridization to cells to detect expression. Probes can also be used in vivo for diagnostic detection of hybridizing sequences. Probes are typically labeled with a radioactive isotope. Other types of detectable labels can be used such as chromophores, fluors, and enzymes. Other examples of nucleotide hybridization assays are described in WO92/02526 and U.S. Pat. No. 5,124,246.

Alternatively, the Polymerase Chain Reaction (PCR) is another means for detecting small amounts of target nucleic acids (see, e.g., Mullis et al., *Meth. Enzymol.* (1987) 155: 335; U.S. Pat. No. 4,683,195; and U.S. Pat. No. 4,683,202). Two primer polynucleotides nucleotides that hybridize with the target nucleic acids are used to prime the reaction. The primers can be composed of sequence within or 3' and 5' to the polynucleotides of the Sequence Listing. Alternatively, if the primers are 3' and 5' to these polynucleotides, they need not hybridize to them or the complements. After amplification of the target with a thermostable polymerase, the amplified target nucleic acids can be detected by methods known in the art, e.g., Southern blot. mRNA or cDNA can also be detected by traditional blotting techniques (e.g., Southern blot, Northern blot, etc.) described in Sambrook et al., "Molecular Cloning: A Laboratory Manual" (New York, Cold Spring Harbor Laboratory, 1989) (e.g., without PCR amplification). In general, mRNA or cDNA generated from mRNA using a polymerase enzyme can be purified and separated using gel electrophoresis, and transferred to a solid support, such as nitrocellulose. The solid support is exposed to a labeled probe, washed to remove any unhybridized probe, and duplexes containing the labeled probe are detected.

Mapping. Polynucleotides of the present invention can be used to identify a chromosome on which the corresponding gene resides. Such mapping can be useful in identifying the function of the polynucleotide-related gene by its proximity to other genes with known function. Function can also be assigned to the polynucleotide-related gene when particular syndromes or diseases map to the same chromosome. For example, use of polynucleotide probes in identification and quantification of nucleic acid sequence aberrations is described in U.S. Pat. No. 5,783,387. An exemplary mapping method is fluorescence in situ hybridization (FISH), which facilitates comparative genomic hybridization to allow total genome assessment of changes in relative copy number of DNA sequences (see, e.g., Valdes et al, *Methods in Molecular Biology* (1997) 68:1). Polynucleotides can also be mapped to particular chromosomes using, for example, radiation hybrids or chromosome-specific hybrid panels. See Leach et al. *Advances in Genetics*, (1995) 33:63–99; Walter et al., *Nature Genetics* (1994) 7:22; Walter and Goodfellow, *Trends in Genetics* (1992) 9:352. Panels for radiation hybrid mapping are available from Research Genetics, Inc., Huntsville, Ala., USA. Databases for markers using various panels are available via the world wide web at shgc-www.stanford.edu; and www-genome.wi.mit.edu/cgi-bin/contig/rhmapper.pl. The statistical program RHMAP can be used to construct a map based on the data from radiation hybridization with a measure of the relative likelihood of one order versus another. RHMAP is available via the world wide web at http://www.sph.umich.edu/group/statgen/software. In addition, commercial programs are available for identifying regions of chromosomes commonly associated with disease, such as cancer.

Tissue Typing or Profiling. Expression of specific mRNA corresponding to the provided polynucleotides can vary in different cell types and can be tissue-specific. This variation of mRNA levels in different cell types can be exploited with nucleic acid probe assays to determine tissue types. For example, PCR, branched DNA probe assays, or blotting techniques utilizing nucleic acid probes substantially identical or complementary to polynucleotides listed in the Sequence Listing can determine the presence or absence of the corresponding cDNA or mRNA.

Tissue typing can be used to identify the developmental organ or tissue source of a metastatic lesion by identifying the expression of a particular marker of that organ or tissue. If a polynucleotide is expressed only in a specific tissue type, and a metastatic lesion is found to express that polynucleotide, then the developmental source of the lesion has been identified. Expression of a particular polynucleotide can be assayed by detection of either the corresponding mRNA or the protein product. As would be readily apparent to any forensic scientist, the sequences disclosed herein are useful in differentiating human tissue from non-human tissue. In particular, these sequences are useful to differentiate human tissue from bird, reptile, and amphibian tissue, for example.

Use of Polymorphisms. A polynucleotide of the invention can be used in forensics, genetic analysis, mapping, and diagnostic applications where the corresponding region of a gene is polymorphic in the human population. Any means for detecting a polymorphism in a gene can be used, including, but not limited to electrophoresis of protein polymorphic variants, differential sensitivity to restriction enzyme cleavage, and hybridization to allele-specific probes.

Antibody Production

Expression products of a polynucleotide of the invention, as well as the corresponding mRNA, cDNA, or complete gene, can be prepared and used for raising antibodies for experimental, diagnostic, and therapeutic purposes. For polynucleotides to which a corresponding gene has not been assigned, this provides an additional method of identifying the corresponding gene. The polynucleotide or related cDNA is expressed as described above, and antibodies are prepared. These antibodies are specific to an epitope on the polypeptide encoded by the polynucleotide, and can precipitate or bind to the corresponding native protein in a cell or tissue preparation or in a cell-free extract of an in vitro expression system.

Methods for production of antibodies that specifically bind a selected antigen are well known in the art. Immunogens for raising antibodies can be prepared by mixing a polynucleotide encoded by a polynucleotide of the invention with an adjuvant, and/or by making fusion proteins with larger immunogenic proteins. Polypeptides can also be covalently linked to other larger immunogenic proteins, such as keyhole limpet hemocyanin. Immunogens are typically administered intradermally, subcutaneously, or intramuscularly to experimental animals such as rabbits, sheep, and mice, to generate antibodies. Monoclonal antibodies can be Monoclonal antibodies can be generated by isolating spleen cells and fusing myeloma cells to form hybridomas. Alternatively, the selected polynucleotide is administered directly, such as by intramuscular injection, and expressed in vivo. The expressed protein generates a variety of protein-specific immune responses, including production of antibodies, comparable to administration of the protein.

Preparations of polyclonal and monoclonal antibodies specific for polypeptides encoded by a selected polynucleotide are made using standard methods known in the art. The antibodies specifically bind to epitopes present in the polypeptides encoded by polynucleotides disclosed in the Sequence Listing. Typically, at least 6, 8, 10, or 12 contiguous amino acids are required to form an epitope. Epitopes that involve non-contiguous amino acids may require a longer polypeptide, e.g., at least 15, 25, or 50 amino acids. Antibodies that specifically bind to human polypeptides encoded by the provided polypeptides should provide a detection signal at least 5-, 10-, or 20-fold higher than a detection signal provided with other proteins when used in Western blots or other immunochemical assays. Preferably, antibodies that specifically polypeptides of the invention do not bind to other proteins in immunochemical assays at detectable levels and can immunoprecipitate the specific polypeptide from solution.

The invention also contemplates naturally occurring antibodies specific for a polypeptide of the invention. For example, serum antibodies to a polypeptide of the invention in a human population can be purified by methods well known in the art, e.g., by passing antiserum over a column to which the corresponding selected polypeptide or fusion protein is bound. The bound antibodies can then be eluted from the column, for example using a buffer with a high salt concentration.

In addition to the antibodies discussed above, the invention also contemplates genetically engineered antibodies, antibody derivatives (e.g., single chain antibodies, antibody fragments (e.g., Fab, etc.)), according to methods well known in the art.

Polynucleotides or Arrays for Diagnostics

Polynucleotide arrays provide a high throughput technique that can assay a large number of polynucleotide sequences in a sample. This technology can be used as a diagnostic and as a tool to test for differential expression, e.g., to determine function of an encoded protein. Arrays can be created by spotting polynucleotide probes onto a substrate (e.g., glass, nitrocelllose, etc.) in a two-dimensional matrix or array having bound probes. The probes can be bound to the substrate by either covalent bonds or by non-specific interactions, such as hydrophobic interactions. Samples of polynucleotides can be detectably labeled (e.g., using radioactive or fluorescent labels) and then hybridized to the probes. Double stranded polynucleotides, comprising the labeled sample polynucleotides bound to probe polynucleotides, can be detected once the unbound portion of the sample is washed away. Techniques for constructing arrays and methods of using these arrays are described in EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734. Arrays can be used to, for example, examine differential expression of genes and can be used to determine gene function. For example, arrays can be used to detect differential expression of a polynucleotide between a test cell and control cell (e.g., cancer cells and normal cells). For example, high expression of a particular message in a cancer cell, which is not observed in a corresponding normal cell, can indicate a cancer specific gene product. Exemplary uses of arrays are further described in, for example, Pappalarado et al., Sem. Radiation Oncol. (1998) 8:217; and Ramsay Nature Biotechnol. (1998) 16:40.

Differential Expression in Diagnosis

The polynucleotides of the invention can also be used to detect differences in expression levels between two cells, e.g., as a method to identify abnormal or diseased tissue in a human. For polynucleotides corresponding to profiles of protein families, the choice of tissue can be selected according to the putative biological function. In general, the expression of a gene corresponding to a specific polynucleotide is compared between a first tissue that is suspected of being diseased and a second, normal tissue of the human. The tissue suspected of being abnormal or diseased can be derived from a different tissue type of the human, but preferably it is derived from the same tissue type; for example an intestinal polyp or other abnormal growth should be compared with normal intestinal tissue. The normal tissue can be the same tissue as that of the test sample, or any normal tissue of the patient, especially those that express the polynucleotide-related gene of interest (e.g., brain, thymus, testis, heart, prostate, placenta, spleen, small intestine, skeletal muscle, pancreas, and the mucosal lining of the colon). A difference between the polynucleotide-related gene, mRNA, or protein in the two tissues which are compared, for example in molecular weight, amino acid or nucleotide sequence, or relative abundance, indicates a change in the gene, or a gene which regulates it, in the tissue of the human that was suspected of being diseased. Examples of detection of differential expression and its use in diagnosis of cancer are described in U.S. Pat. Nos. 5,688,641 and 5,677,125.

A genetic predisposition to disease in a human can also be detected by comparing expression levels of an mRNA or protein corresponding to a polynucleotide of the invention in a fetal tissue with levels associated in normal fetal tissue. Fetal tissues that are used for this purpose include, but are not limited to, amniotic fluid, chorionic villi, blood, and the blastomere of an in vitro-fertilized embryo. The comparable normal polynucleotide-related gene is obtained from any tissue. The mRNA or protein is obtained from a normal tissue of a human in which the polynucleotide-related gene is expressed. Differences such as alterations in the nucleotide sequence or size of the same product of the fetal polynucleotide-related gene or mRNA, or alterations in the molecular weight, amino acid sequence, or relative abundance of fetal protein, can indicate a germline mutation in the polynucleotide-related gene of the fetus, which indicates a genetic predisposition to disease. In general, diagnostic, prognostic, and other methods of the invention based on differential expression involve detection of a level or amount of a gene product, particularly a differentially expressed gene product, in a test sample obtained from a patient suspected of having or being susceptible to a disease (e.g., breast cancer, lung cancer, colon cancer and/or metastatic forms thereof), and comparing the detected levels to those levels found in normal cells (e.g., cells substantially unaffected by cancer) and/or other control cells (e.g., to differentiate a cancerous cell from a cell affected by dysplasia). Furthermore, the severity of the disease can be assessed by comparing the detected levels of a differentially expressed gene product with those levels detected in samples representing the levels of differentially gene product associated with varying degrees of severity of disease. It should be noted that use of the term "diagnostic" herein is not necessarily meant to exclude "prognostic" or "prognosis," but rather is used as a matter of convenience.

The term "differentially expressed gene" is generally intended to encompass a polynucleotide that can, for example, include an open reading frame encoding a gene product (e.g., a polypeptide), and/or introns of such genes and adjacent 5' and 3' non-coding nucleotide sequences involved in the regulation of expression, up to about 20 kb beyond the coding region, but possibly further in either direction. The gene can be introduced into an appropriate vector for extrachromosomal maintenance or for integration into a host genome. In general, a difference in expression level associated with a decrease in expression level of at least about 25%, usually at least about 50% to 75%, more usually at least about 90% or more is indicative of a differentially expressed gene of interest, i.e., a gene that is underexpressed or down-regulated in the test sample relative to a control sample. Furthermore, a difference in expression level associated with an increase in expression of at least about 25%, usually at least about 50% to 75%, more usually at least about 90% and can be at least about 1½-fold, usually at least about 2-fold to about 10-fold, and can be about 100-fold to about 1,000-fold increase relative to a control sample is indicative of a differentially expressed gene of interest, i.e., an overexpressed or up-regulated gene.

"Differentially expressed polynucleotide" as used herein means a nucleic acid molecule (RNA or DNA) comprising a sequence that represents a differentially expressed gene, e.g., the differentially expressed polynucleotide comprises a sequence (e.g., an open reading frame encoding a gene product) that uniquely identifies a differentially expressed gene so that detection of the differentially expressed polynucleotide in a sample is correlated with the presence of a differentially expressed gene in a sample. "Differentially expressed polynucleotides" is also meant to encompass fragments of the disclosed polynucleotides, e.g., fragments retaining biological activity, as well as nucleic acids homologous, substantially similar, or substantially identical (e.g., having about 90% sequence identity) to the disclosed polynucleotides.

"Diagnosis" as used herein generally includes determination of a subject's susceptibility to a disease or disorder, determination as to whether a subject is presently affected by a disease or disorder, as well as to the prognosis of a subject affected by a disease or disorder (e.g., identification of pre-metastatic or metastatic cancerous states, stages of cancer, or responsiveness of cancer to therapy). The present invention particularly encompasses diagnosis of subjects in the context of breast cancer (e.g., carcinoma in situ (e.g., ductal carcinoma in situ), estrogen receptor (ER)-positive breast cancer, ER-negative breast cancer, or other forms and/or stages of breast cancer), lung cancer (e.g., small cell carcinoma, non-small cell carcinoma, mesothelioma, and other forms and/or stages of lung cancer), and colon cancer (e.g., adenomatous polyp, colorectal carcinoma, and other forms and/or stages of colon cancer).

"Sample" or "biological sample" as used throughout here are generally meant to refer to samples of biological fluids or tissues, particularly samples obtained from tissues, especially from cells of the type associated with the disease for which the diagnostic application is designed (e.g., ductal adenocarcinoma), and the like. "Samples" is also meant to encompass derivatives and fractions of such samples (e.g., cell lysates). Where the sample is solid tissue, the cells of the tissue can be dissociated or tissue sections can be analyzed.

Methods of the subject invention useful in diagnosis or prognosis typically involve comparison of the abundance of a selected differentially expressed gene product in a sample of interest with that of a control to determine any relative differences in the expression of the gene product, where the difference can be measured qualitatively and/or quantitatively. Quantitation can be accomplished, for example, by comparing the level of expression product detected in the sample with the amounts of product present in a standard curve. A comparison can be made visually; by using a technique such as densitometry, with or without computerized assistance; by preparing a representative library of cDNA clones of mRNA isolated from a test sample, sequencing the clones in the library to determine that number of cDNA clones corresponding to the same gene product, and analyzing the number of clones corresponding to that same gene product relative to the number of clones of the same gene product in a control sample; or by using an array to detect relative levels of hybridization to a selected sequence or set of sequences, and comparing the hybridization pattern to that of a control. The differences in expression are then correlated with the presence or absence of an abnormal expression pattern. A variety of different methods for determining the nucleic acid abundance in a sample are known to those of skill in the art (see, e.g., WO 97/27317). In general, diagnostic assays of the invention involve detection of a gene product of a the polynucleotide sequence (e.g., mRNA or polypeptide) that corresponds to a sequence of SEQ ID NOS:1–2707. The patient from whom the sample is obtained can be apparently healthy, susceptible to disease (e.g., as determined by family history or exposure to certain environmental factors), or can already be identified as having a condition in which altered expression of a gene product of the invention is implicated.

Diagnosis can be determined based on detected gene product expression levels of a gene product encoded by at least one, preferably at least two or more, at least 3 or more, or at least 4 or more of the polynucleotides having a sequence set forth in SEQ ID NOS:1–2707, and can involve detection of expression of genes corresponding to all of SEQ ID NOS:1–2707 and/or additional sequences that can serve as additional diagnostic markers and/or reference sequences. Where the diagnostic method is designed to detect the presence or susceptibility of a patient to cancer, the assay preferably involves detection of a gene product encoded by a gene corresponding to a polynucleotide that is differentially expressed in cancer. Examples of such differentially expressed polynucleotides are described in the Examples below. Given the provided polynucleotides and information regarding their relative expression levels provided herein, assays using such polynucleotides and detection of their expression levels in diagnosis and prognosis will be readily apparent to the ordinarily skilled artisan.

Any of a variety of detectable labels can be used in connection with the various embodiments of the diagnostic methods of the invention. Suitable detectable labels include fluorochromes, (e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA)), radioactive labels, (e.g. $^{32}$P, $^{35}$S, $^{3}$H, etc.), and the like. The detectable label can involve a two stage systems (e.g., biotin-avidin, hapten-anti-hapten antibody, etc.)

Reagents specific for the polynucleotides and polypeptides of the invention, such as antibodies and nucleotide probes, can be supplied in a kit for detecting the presence of an expression product in a biological sample. The kit can also contain buffers or labeling components, as well as instructions for using the reagents to detect and quantify expression products in the biological sample. Exemplary embodiments of the diagnostic methods of the invention are described below in more detail.

Polypeptide detection in diagnosis. In one embodiment, the test sample is assayed for the level of a differentially expressed polypeptide. Diagnosis can be accomplished using any of a number of methods to determine the absence or presence or altered amounts of the differentially expressed polypeptide in the test sample. For example, detection can utilize staining of cells or histological sections with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

mRNA detection. The diagnostic methods of the invention can also or alternatively involve detection of mRNA encoded by a gene corresponding to a differentially expressed polynucleotides of the invention. Any suitable qualitative or quantitative methods known in the art for detecting specific mRNAs can be used. mRNA can be detected by, for example, in situ hybridization in tissue sections, by reverse transcriptase-PCR, or in Northern blots containing poly A+ mRNA. One of skill in the art can readily use these methods to determine differences in the size or amount of mRNA transcripts between two samples. mRNA expression levels in a sample can also be determined by generation of a library of expressed sequence tags (ESTs) from the sample, where the EST library is representative of sequences present in the sample (Adams, et al., (1991) *Science* 252:1651). Enumeration of the relative representation of ESTs within the library can be used to approximate the relative representation of the gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein. Alternatively, gene expression in a test sample can be performed using serial analysis of gene expression (SAGE) methodology (e.g., Velculescu et al., *Science* (1995) 270:484) or differential display (DD) methodology (see, e.g., U.S. Pat. No. 5,776,683; and U.S. Pat. No. 5,807,680).

Alternatively, gene expression can be analyzed using hybridization analysis. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Use of a single gene in diagnostic applications. The diagnostic methods of the invention can focus on the expression of a single differentially expressed gene. For example, the diagnostic method can involve detecting a differentially expressed gene, or a polymorphism of such a gene (e.g., a polymorphism in an coding region or control region), that is associated with disease. Disease-associated polymorphisms can include deletion or truncation of the gene, mutations that alter expression level and/or affect activity of the encoded protein, etc.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express a differentially expressed genean be used as a source of mRNA, which can be assayed directly or reverse transcribed into cDNA for analysis. The nucleic acid can be amplified by conventional techniques, such as the polymerase chain reaction (PCR), to provide sufficient amounts for analysis, and a detectable label can be included in the amplification reaction (e.g., using a detectably labeled primer or detectably labeled oligonucleotides) to facilitate detection. Alternatively, various methods are also known in the art that utilize oligonucleotide ligation as a means of detecting polymorphisms, see e.g., Riley et al., *Nucl. Acids Res.* (1990) 18:2887; and Delahunty et al., *Am. J. Hum. Genet.* (1996) 58:1239.

The amplified or cloned sample nucleic acid can be analyzed by one of a number of methods known in the art. The nucleic acid can be sequenced by dideoxy or other methods, and the sequence of bases compared to a selected sequence, e.g., to a wild-type sequence. Hybridization with the polymorphic or variant sequence can also be used to determine its presence in a sample (e.g., by Southern blot, dot blot, etc.). The hybridization pattern of a polymorphic or variant sequence and a control sequence to an array of oligonucleotide probes immobilized on a solid support, as described in U.S. Pat. No. 5,445,934, or in WO 95/35505, can also be used as a means of identifying polymorphic or variant sequences associated with disease. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in a gene can be based on the functional or antigenic characteristics of the protein. Protein truncation assays are useful in detecting deletions that can affect the biological activity of the protein. Various immunoassays designed to detect polymorphisms in proteins can be used in screening. Where many diverse genetic mutations lead to a particular disease phenotype, functional protein assays have proven to be effective screening tools. The activity of the encoded protein can be determined by comparison with the wild-type protein.

Pattern matching in diagnosis using arrays. In another embodiment, the diagnostic and/or prognostic methods of the invention involve detection of expression of a selected set of genes in a test sample to produce a test expression pattern (TEP). The TEP is compared to a reference expression pattern (REP), which is generated by detection of expression of the selected set of genes in a reference sample (e.g., a positive or negative control sample). The selected set of genes includes at least one of the genes of the invention, which genes correspond to the polynucleotide sequences of SEQ ID NOS:1–2707. Of particular interest is a selected set of genes that includes gene differentially expressed in the disease for which the test sample is to be screened.

"Reference sequences" or "reference polynucleotides" as used herein in the context of differential gene expression analysis and diagnosis/prognosis refers to a selected set of polynucleotides, which selected set includes at least one or more of the differentially expressed polynucleotides described herein. A plurality of reference sequences, preferably comprising positive and negative control sequences, can be included as reference sequences. Additional suitable reference sequences are found in GenBank, Unigene, and other nucleotide sequence databases (including, e.g., expressed sequence tag (EST), partial, and full-length sequences).

"Reference array" means an array having reference sequences for use in hybridization with a sample, where the reference sequences include all, at least one of, or any subset of the differentially expressed polynucleotides described herein. Usually such an array will include at least 3 different reference sequences, and can include any one or all of the provided differentially expressed sequences. Arrays of interest can further comprise sequences, including polymorphisms, of other genetic sequences, particularly other sequences of interest for screening for a disease or disorder (e.g., cancer, dysplasia, or other related or unrelated diseases, disorders, or conditions). The oligonucleotide sequence on the array will usually be at least about 12 nt in length, and can be of about the length of the provided sequences, or can extend into the flanking regions to generate fragments of 100 nt to 200 nt in length or more. Reference arrays can be produced according to any suitable methods known in the art. For example, methods of producing large arrays of oligonucleotides are described in U.S. Pat. No. 5,134,854, and U.S. Pat. No. 5,445,934 using light-directed synthesis techniques. Using a computer controlled system, a heterogeneous array of monomers is converted, through simultaneous coupling at a number of reaction sites, into a heterogeneous array of polymers.

Alternatively, microarrays are generated by deposition of pre-synthesized oligonucleotides onto a solid substrate, for example as described in PCT published application no. WO 95/35505.

A "reference expression pattern" or "REP" as used herein refers to the relative levels of expression of a selected set of genes, particularly of differentially expressed genes, that is associated with a selected cell type, e.g., a normal cell, a cancerous cell, a cell exposed to an environmental stimulus, and the like. A "test expression pattern" or "TEP" refers to relative levels of expression of a selected set of genes, particularly of differentially expressed genes, in a test sample (e.g., a cell of unknown or suspected disease state, from which mRNA is isolated).

REPs can be generated in a variety of ways according to methods well known in the art. For example, REPs can be generated by hybridizing a control sample to an array having a selected set of polynucleotides (particularly a selected set of differentially expressed polynucleotides), acquiring the hybridization data from the array, and storing the data in a format that allows for ready comparison of the REP with a TEP. Alternatively, all expressed sequences in a control sample can be isolated and sequenced, e.g., by isolating mRNA from a control sample, converting the mRNA into cDNA, and sequencing the cDNA. The resulting sequence information roughly or precisely reflects the identity and relative number of expressed sequences in the sample. The sequence information can then be stored in a format (e.g., a computer-readable format) that allows for ready comparison of the REP with a TEP. The REP can be normalized prior to or after data storage, and/or can be processed to selectively remove sequences of expressed genes that are of less interest or that might complicate analysis (e.g., some or all of the sequences associated with housekeeping genes can be eliminated from REP data).

TEPs can be generated in a manner similar to REPs, e.g., by hybridizing a test sample to an array having a selected set of polynucleotides, particularly a selected set of differentially expressed polynucleotides, acquiring the hybridization data from the array, and storing the data in a format that allows for ready comparison of the TEP with a REP. The REP and TEP to be used in a comparison can be generated simultaneously, or the TEP can be compared to previously generated and stored REPs.

In one embodiment of the invention, comparison of a TEP with a REP involves hybridizing a test sample with a reference array, where the reference array has one or more reference sequences for use in hybridization with a sample. The reference sequences include all, at least one of, or any subset of the differentially expressed polynucleotides described herein. Hybridization data for the test sample is acquired, the data normalized, and the produced TEP compared with a REP generated using an array having the same or similar selected set of differentially expressed polynucleotides. Probes that correspond to sequences differentially expressed between the two samples will show decreased or increased hybridization efficiency for one of the samples relative to the other.

Methods for collection of data from hybridization of samples with a reference arrays are well known in the art. For example, the polynucleotides of the reference and test samples can be generated using a detectable fluorescent label, and hybridization of the polynucleotides in the samples detected by scanning the microarrays for the presence of the detectable label using, for example, a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., *Genome Res.* (1996) 6:639. A scan, using the appropriate excitation line, is performed for each fluorophore used. The digital images generated from the scan are then combined for subsequent analysis. For any particular array element, the ratio of the fluorescent signal from one sample (e.g., a test sample) is compared to the fluorescent signal from another sample (e.g., a reference sample), and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

In general, the test sample is classified as having a gene expression profile corresponding to that associated with a disease or non-disease state by comparing the TEP generated from the test sample to one or more REPs generated from reference samples (e.g., from samples associated with cancer or specific stages of cancer, dysplasia, samples affected by a disease other than cancer, normal samples, etc.). The criteria for a match or a substantial match between a TEP and a REP include expression of the same or substantially the same set of reference genes, as well as expression of these reference genes at substantially the same levels (e.g., no significant difference between the samples for a signal associated with a selected reference sequence after normalization of the samples, or at least no greater than about 25% to about 40% difference in signal strength for a given reference sequence. In general, a pattern match between a TEP and a REP includes a match in expression, preferably a match in qualitative or quantitative expression level, of at least one of, all or any subset of the differentially expressed genes of the invention.

Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800, 992.

Diagnosis Prognosis and Management of Cancer

The polynucleotides of the invention and their gene products are of particular interest as genetic or biochemical markers (e.g., in blood or tissues) that will detect the earliest changes along the carcinogenesis pathway and/or to monitor the efficacy of various therapies and preventive interventions. For example, the level of expression of certain polynucleotides can be indicative of a poorer prognosis, and therefore warrant more aggressive chemo- or radio-therapy for a patient or vice versa. The correlation of novel surrogate tumor specific features with response to treatment and outcome in patients can define prognostic indicators that allow the design of tailored therapy based on the molecular profile of the tumor. These therapies include antibody targeting and gene therapy. Determining expression of certain polynucleotides and comparison of a patients profile with known expression in normal tissue and variants of the disease allows a determination of the best possible treatment for a patient, both in terms of specificity of treatment and in terms of comfort level of the patient. Surrogate tumor markers, such as polynucleotide expression, can also be used to better classify, and thus diagnose and treat, different forms and disease states of cancer. Two classifications widely used in oncology that can benefit from identification of the expression levels of the polynucleotides of the invention are staging of the cancerous disorder, and grading the nature of the cancerous tissue.

The polynucleotides of the invention can be useful to monitor patients having or susceptible to cancer to detect potentially malignant events at a molecular level before they are detectable at a gross morphological level. Furthermore, a polynucleotide of the invention identified as important for one type of cancer can also have implications for development or risk of development of other types of cancer, e.g., where a polynucleotide is differentially expressed across various cancer types. Thus, for example, expression of a polynucleotide that has clinical implications for metastatic colon cancer can also have clinical implications for stomach cancer or endometrial cancer.

Staging. Staging is a process used by physicians to describe how advanced the cancerous state is in a patient. Staging assists the physician in determining a prognosis, planning treatment and evaluating the results of such treatment. Staging systems vary with the types of cancer, but generally involve the following "TNM" system: the type of tumor, indicated by T; whether the cancer has metastasized to nearby lymph nodes, indicated by N; and whether the cancer has metastasized to more distant parts of the body, indicated by M. Generally, if a cancer is only detectable in the area of the primary lesion without having spread to any lymph nodes it is called Stage I. If it has spread only to the closest lymph nodes, it is called Stage II. In Stage III, the cancer has generally spread to the lymph nodes in near proximity to the site of the primary lesion. Cancers that have spread to a distant part of the body, such as the liver, bone, brain or other site, are Stage IV, the most advanced stage.

The polynucleotides of the invention can facilitate fine-tuning of the staging process by identifying markers for the aggresivity of a cancer, e.g. the metastatic potential, as well as the presence in different areas of the body. Thus, a Stage II cancer with a polynucleotide signifying a high metastatic potential cancer can be used to change a borderline Stage II tumor to a Stage III tumor, justifying more aggressive therapy. Conversely, the presence of a polynucleotide signifying a lower metastatic potential allows more conservative staging of a tumor.

Grading of cancers. Grade is a term used to describe how closely a tumor resembles normal tissue of its same type. The microscopic appearance of a tumor is used to identify tumor grade based on parameters such as cell morphology, cellular organization, and other markers of differentiation. As a general rule, the grade of a tumor corresponds to its rate of growth or aggressiveness, with undifferentiated or high-grade tumors being more aggressive than well differentiated or low-grade tumors. The following guidelines are generally used for grading tumors: 1) GX Grade cannot be assessed; 2) G1 Well differentiated; G2 Moderately well differentiated; 3) G3 Poorly differentiated; 4) G4 Undifferentiated. The polynucleotides of the invention can be especially valuable in determining the grade of the tumor, as they not only can aid in determining the differentiation status of the cells of a tumor, they can also identify factors other than differentiation that are valuable in determining the aggressiveness of a tumor, such as metastatic potential.

Detection of lung cancer. The polynucleotides of the invention can be used to detect lung cancer in a subject. Although there are more than a dozen different kinds of lung cancer, the two main types of lung cancer are small cell and nonsmall cell, which encompass about 90% of all lung cancer cases. Small cell carcinoma (also called oat cell carcinoma) usually starts in one of the larger bronchial tubes, grows fairly rapidly, and is likely to be large by the time of diagnosis. Nonsmall cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and can vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

The polynucleotides of the invention, e.g., polynucleotides differentially expressed in normal cells versus cancerous lung cells (e.g., tumor cells of high or low metastatic potential) or between types of cancerous lung cells (e.g., high metastatic versus low metastatic), can be used to distinguish types of lung cancer as well as identifying traits specific to a certain patient's cancer and selecting an appropriate therapy. For example, if the patient's biopsy expresses a polynucleotide that is associated with a low metastatic potential, it may justify leaving a larger portion of the patient's lung in surgery to remove the lesion. Alternatively, a smaller lesion with expression of a polynucleotide that is associated with high metastatic potential may justify a more radical removal of lung tissue and/or the surrounding lymph nodes, even if no metastasis can be identified through pathological examination.

Detection of breast cancer. The majority of breast cancers are adenocarcinomas subtypes, which can be summarized as follows: 1) ductal carcinoma in situ (DCIS), including comedocarcinoma; 2) infiltrating (or invasive) ductal carcinoma (IDC); 3) lobular carcinoma in situ (LCIS); 4) infiltrating (or invasive) lobular carcinoma (ILC); 5) inflammatory breast cancer; 6) medullary carcinoma; 7) mucinous carcinoma; 8) Paget's disease of the nipple; 9) Phyllodes tumor; and 10) tubular carcinoma;

The expression of polynucleotides of the invention can be used in the diagnosis and management of breast cancer, as well as to distinguish between types of breast cancer. Detection of breast cancer can be determined using expression levels of any of the appropriate polynucleotides of the invention, either alone or in combination. Determination of the aggressive nature and/or the metastatic potential of a breast cancer can also be determined by comparing levels of one or more polynucleotides of the invention and comparing levels of another sequence known to vary in cancerous tissue, e.g. ER expression. In addition, development of breast cancer can be detected by examining the ratio of expression of a differentially expressed polynucleotide to the levels of steroid hormones (e.g., testosterone or estrogen) or to other hormones (e.g., growth hormone, insulin). Thus expression of specific marker polynucleotides can be used to discriminate between normal and cancerous breast tissue, to discriminate between breast cancers with different cells of origin, to discriminate between breast cancers with different potential metastatic rates, etc.

Detection of colon cancer. The polynucleotides of the invention exhibiting the appropriate expression pattern can be used to detect colon cancer in a subject. Colorectal cancer is one of the most common neoplasms in humans and perhaps the most frequent form of hereditary neoplasia. Prevention and early detection are key factors in controlling and curing colorectal cancer. Colorectal cancer begins as polyps, which are small, benign growths of cells that form on the inner lining of the colon. Over a period of several years, some of these polyps accumulate additional mutations and become cancerous. Multiple familial colorectal cancer disorders have been identified, which are summarized as follows: 1) Familial adenomatous polyposis (FAP); 2) Gardner's syndrome; 3) Hereditary nonpolyposis colon cancer (HNPCC); and 4) Familial colorectal cancer in Ashkenazi Jews. The expression of appropriate polynucleotides of the invention can be used in the diagnosis, prognosis and management of colorectal cancer. Detection of colon cancer can be determined using expression levels of any of these sequences alone or in combination with the levels of expression. Determination of the aggressive nature and/or the metastatic potential of a colon cancer can be determined by comparing levels of one or more polynucleotides of the invention and comparing total levels of another sequence known to vary in cancerous tissue, e.g., expression of p53, DCC ras, lor FAP (see, e.g., Fearon E R, et al., *Cell* (1990) 61(5):759; Hamilton S R et al., *Cancer* (1993) 72:957; Bodmer W, et al., *Nat Genet.* (1994) 4(3):217; Fearon E R, *Ann N Y Acad Sci.* (1995) 768:101). For example, development of colon cancer can be detected by examining the ratio of any of the polynucleotides of the invention to the levels of oncogenes (e.g. ras) or tumor suppressor genes (e.g. FAP or p53). Thus expression of specific marker polynucleotides can be used to discriminate between normal and cancerous colon tissue, to discriminate between colon cancers with different cells of origin, to discriminate between colon cancers with different potential metastatic rates, etc.

Use of Polynucleotides to Screen for Peptide Analogs and Antagonists

Polypeptides encoded by the instant polynucleotides and corresponding full length genes can be used to screen peptide libraries to identify binding partners, such as receptors, from among the encoded polypeptides. Peptide libraries can be synthesized according to methods known in the art (see, e.g., U.S. Pat. No. 5,010,175, and WO 91/17823). Agonists or antagonists of the polypeptides if the invention can be screened using any available method known in the art, such as signal transduction, antibody binding, receptor binding, mitogenic assays, chemotaxis assays, etc. The assay conditions ideally should resemble the conditions under which the native activity is exhibited in vivo, that is, under physiologic pH, temperature, and ionic strength. Suitable agonists or antagonists will exhibit strong inhibition or enhancement of the native activity at concentrations that do not cause toxic side effects in the subject. Agonists or antagonists that compete for binding to the native polypeptide can require concentrations equal to or greater than the native concentration, while inhibitors capable of binding irreversibly to the polypeptide can be added in concentrations on the order of the native concentration.

Such screening and experimentation can lead to identification of a novel polypeptide binding partner, such as a receptor, encoded by a gene or a cDNA corresponding to a polynucleotide of the invention, and at least one peptide agonist or antagonist of the novel binding partner. Such agonists and antagonists can be used to modulate, enhance, or inhibit receptor function in cells to which the receptor is native, or in cells that possess the receptor as a result of genetic engineering. Further, if the novel receptor shares biologically important characteristics with a known receptor, information about agonist/antagonist binding can facilitate development of improved agonists/antagonists of the known receptor.

Pharmaceutical Compositions and Therapeutic Uses

Pharmaceutical compositions of the invention can comprise polypeptides, antibodies, or polynucleotides (including antisense nucleotides and ribozymes) of the claimed invention in a therapeutically effective amount. The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation is determined by routine experimentation and is within the judgment of the clinician. For purposes of the present invention, an effective dose will generally be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g., mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in *Remington's Pharmaceutical Sciences* (Mack Pub. Co., N.J. 1991).

Delivery Methods. Once formulated, the compositions of the invention can be (1) administered directly to the subject (e.g., as polynucleotide or polypeptides); or (2) delivered ex vivo, to cells derived from the subject (e.g., as in ex vivo gene therapy). Direct delivery of the compositions will generally be accomplished by parenteral injection, e.g., subcutaneously, intraperitoneally, intravenously or intramuscularly, intratumoral or to the interstitial space of a tissue. Other modes of administration include oral and pulmonary administration, suppositories, and transdermal applications, needles, and gene guns or hyposprays. Dosage treatment can be a single dose schedule or a multiple dose schedule.

Methods for the ex vivo delivery and reimplantation of transformed cells into a subject are known in the art and described in e.g., International Publication No. WO 93/14778. Examples of cells useful in ex vivo applications include, for example, stem cells, particularly hematopoetic, lymph cells, macrophages, dendritic cells, or tumor cells. Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Once a gene corresponding to a polynucleotide of the invention has been found to correlate with a proliferative disorder, such as neoplasia, dysplasia, and hyperplasia, the disorder can be amenable to treatment by administration of a therapeutic agent based on the provided polynucleotide, corresponding polypeptide or other corresponding molecule (e.g., antisense, ribozyme, etc.).

The dose and the means of administration of the inventive pharmaceutical compositions are determined based on the specific qualities of the therapeutic composition, the condition, age, and weight of the patient, the progression of the disease, and other relevant factors. For example, administration of polynucleotide therapeutic compositions agents of the invention includes local or systemic administration, including injection, oral administration, particle gun or catheterized administration, and topical administration. Preferably, the therapeutic polynucleotide composition contains an expression construct comprising a promoter operably linked to a polynucleotide of at least 12, 22, 25, 30, or 35 contiguous nt of the polynucleotide disclosed herein. Various methods can be used to administer the therapeutic composition directly to a specific site in the body. For example, a small metastatic lesion is located and the therapeutic composition injected several times in several different locations within the body of tumor. Alternatively, arteries which serve a tumor are identified, and the therapeutic composition injected into such an artery, in order to deliver the composition directly into the tumor. A tumor that has a necrotic center is aspirated and the composition injected directly into the now empty center of the tumor. The antisense composition is directly administered to the surface of the tumor, for example, by topical application of the composition. X-ray imaging is used to assist in certain of the above delivery methods.

Receptor-mediated targeted delivery of therapeutic compositions containing an antisense polynucleotide, subgenomic polynucleotides, or antibodies to specific tissues can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci.* (*USA*) (1990) 87:3655; Wu et al., *J. Biol. Chem.* (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 g to about 2 mg, about 5 g to about 500 g, and about 20 g to about 100 g of DNA can also be used during a gene therapy protocol. Factors such as method of action (e.g., for enhancing or inhibiting levels of the encoded gene product) and efficacy of transformation and expression are considerations which will affect the dosage required for ultimate efficacy of the antisense subgenomic polynucleotides. Where greater expression is desired over a larger area of tissue, larger amounts of antisense subgenomic polynucleotides or the same amounts readministered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect. For polynucleotide-related genes encoding polypeptides or proteins with anti-inflammatory activity, suitable use, doses, and administration are described in U.S. Pat. No. 5,654,173.

The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532), and adeno-associated virus (AAV) vectors (see, e.g., WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* (1989) 264: 16985); eukaryotic cell delivery vehicles cells (see, e.g., U.S. Pat. No. 5,814,482; WO 95/07994; WO 96/17072; WO 95/30763; and WO 97/42338) and nucleic charge neutralization or fusion with cell membranes. Naked DNA can also be employed. Exemplary naked DNA introduction methods are described in WO 90/11092 and U.S. Pat. No. 5,580,859. Liposomes that can act as gene delivery vehicles are described in U.S. Pat. No. 5,422,120; WO 95/13796; WO 94/23697; WO 91/14445; and EP 0524968. Additional approaches are described in Philip, *Mol. Cell Biol.* (1994) 14:2411, and in Woffendin, *Proc. Natl. Acad. Sci.* (1994) 91:1581

Further non-viral delivery suitable for use includes mechanical delivery systems such as the approach described in Woffendin et al., *Proc. Natl. Acad. Sci. USA* (1994) 91(24):11581. Moreover, the coding sequence and the product of expression of such can be delivered through deposition of photopolymerized hydrogel materials or use of ionizing radiation (see, e.g., U.S. Pat. No. 5,206,152 and WO 92/11033). Other conventional methods for gene delivery that can be used for delivery of the coding sequence include, for example, use of hand-held gene transfer particle gun (see, e.g., U.S. Pat. No. 5,149,655); use of ionizing radiation for activating transferred gene (see, e.g., U.S. Pat. No. 5,206,152 and WO 92/11033).

The present invention will now be illustrated by reference to the following examples which set forth particularly advantageous embodiments. However, it should be noted that these embodiments are illustrative and are not to be construed as restricting the invention in any way.

EXAMPLES

Example 1

Source of Biological Materials and Overview of Novel Polynucleotides Expressed by the Biological Materials cDNA libraries were constructed from either human colon cancer cell line Km12L4-A (Morikawa, et al., *Cancer Research* (1988) 48:6863), KM12C (Morikawa et al. *Cancer Res*. (1988) 48:1943–1948), or MDA-MB-231 (Brinkley et al. *Cancer Res*. (1980) 40:3118–3129) was used to construct a cDNA library from mRNA isolated from the cells. Sequences expressed by these cell lines were isolated and analyzed; most sequences were about 275–300 nucleotides in length. The KM12L4-A cell line is derived from the KM12C cell line. The KM12C cell line, which is poorly metastatic (low metastatic) was established in culture from a Dukes' stage $B_2$ surgical specimen (Morikawa et al. *Cancer Res*. (1988) 48:6863). The KML4-A is a highly metastatic subline derived from KM12C (Yeatman et al. *Nucl. Acids. Res*. (1995) 23:4007; Bao-Ling et al. *Proc. Annu. Meet. Am. Assoc. Cancer. Res*. (1995) 21:3269). The KM12C and KM12C-derived cell lines (e.g., KM12L4, KM12L4-A, etc.) are well-recognized in the art as a model cell line for the study of colon cancer (see, e.g., Moriakawa et al., supra; Radinsky et al. *Clin. Cancer Res*. (1995) 1:19; Yeatman et al., (1995) supra; Yeatman et al. *Clin. Exp. Metastasis* (1996) 14:246). The MDA-MB-231 cell line was originally isolated from pleural effusions (Cailleau, *J. Natl. Cancer. Inst*. (1974) 53:661), is of high metastatic potential, and forms poorly differentiated adenocarcinoma grade II in nude mice consistent with breast carcinoma.

The sequences of the isolated polynucleotides were first masked to eliminate low complexity sequences using the XBLAST masking program (Claverie "Effective Large-Scale Sequence Similarity Searches," In: *Computer Methods for Macromolecular Sequence Analysis*, Doolittle, ed., *Meth. Enzymol.* 266:212–227 Academic Press, NY, N.Y. (1996); see particularly Claverie, in "Automated DNA Sequencing and Analysis Techniques" Adams et al., eds., Chap. 36, p. 267 Academic Press, San Diego, 1994 and Claverie et al. *Comput. Chem*. (1993) 17:191). Generally, masking does not influence the final search results, except to eliminate sequences of relative little interest due to their low complexity, and to eliminate multiple "hits" based on similarity to repetitive regions common to multiple sequences, e.g., Alu repeats. Masking resulted in the elimination of 43 sequences. The remaining sequences were then used in a BLASTN vs. GenBank search; sequences that exhibited greater than 70% overlap, 99% identity, and a p value of less than $1 \times 10^{-40}$ were discarded. Sequences from this search also were discarded if the inclusive parameters were met, but the sequence was ribosomal or vector-derived.

The resulting sequences from the previous search were classified into three groups (1, 2 and 3 below) and searched in a BLASTX vs. NRP (non-redundant proteins) database search: (1) unknown (no hits in the GenBank search), (2) weak similarity (greater than 45% identity and p value of less than $1 \times 10^{-5}$), and (3) high similarity (greater than 60% overlap, greater than 80% identity, and p value less than $1 \times 10^{-5}$). Sequences having greater than 70% overlap, greater than 99% identity, and p value of less than $1 \times 10^{-40}$ were discarded.

The remaining sequences were classified as unknown (no hits), weak similarity, and high similarity (parameters as above). Two searches were performed on these sequences. First, a BLAST vs. EST database search was performed and sequences with greater than 99% overlap, greater than 99% similarity and a p value of less than $1 \times 10^{-40}$ were discarded. Sequences with a p value of less than $1 \times 10^{-65}$ when compared to a database sequence of human origin were also excluded. Second, a BLASTN vs. Patent GeneSeq database was performed and sequences having greater than 99% identity, p value less than $1 \times 10^{-40}$, and greater than 99% overlap were discarded.

The remaining sequences were subjected to screening using other rules and redundancies in the dataset. Sequences with a p value of less than $1 \times 10^{-111}$ in relation to a database sequence of human origin were specifically excluded. The final result provided the 1,565 sequences listed as SEQ ID NOS:1–1565 in the accompanying Sequence Listing and summarized in Table 1A (inserted prior to claims). Each identified polynucleotide represents sequence from at least a partial mRNA transcript.

Table 1A provides: 1) the SEQ ID NO assigned to each sequence for use in the present specification; 2) the filing date of the U.S. priority application in which the sequence was first filed; 3) the attorney docket number assigned to the priority application (for internal use); 4) the SEQ ID NO assigned to the sequence in the priority application; 5) the sequence name used as an internal identifier of the sequence; and 6) the name assigned to the clone from which the sequence was isolated. Because the provided polynucleotides represent partial mRNA transcripts, two or more polynucleotides of the invention may represent different regions of the same mRNA transcript and the same gene. Thus, if two or more SEQ ID NOS: are identified as belonging to the same clone, then either sequence can be used to obtain the full-length mRNA or gene.

In order to confirm the sequences of SEQ ID NOS: 1–1565, the clones were retrieved from a library using a robotic retrieval system, and the inserts of the retrieved clones re-sequenced. These "validation" sequences are provided as SEQ ID NOS:1566–2610 in the Sequence Listing, and a summary of the "validation" sequences provided in Table 1B (inserted prior to claims). Table 1B provides: 1) the SEQ ID NO assigned to each sequence for use in the present specification; 2) the sequence name assigned to the "validation" sequence obtained; 3) whether the "validation" sequence contains sequence that overlaps with an original sequence of SEQ ID NOS:1–1565 (Validation Overlap (VO)), or whether the "validation" sequence does not substantially overlap with an original sequence of SEQ ID NOS:1–1565 (indicated by Validation Non-Overlap (VNO)); and 4) where the sequence is indicated as VO, the name of the clone that contains the indicated "validation" sequence. "Validation" sequences are indicated as "VO" where the "validation" sequence overlaps with an original sequence (e.g., one of SEQ ID NOS:1–1565), and/or the "validation" sequence belongs to the same cluster as the original sequence using the clustering technique described above. Because the inserts of the clones are generally longer than the original sequence and the validation sequence, it is possible that a "validation" sequence can be obtained from the same clone as an original sequence but yet not share any of the sequence of the original. Such validation sequences will, however, belong to the same cluster as the original sequence using the clustering technique described above. VO "validation" sequences are contained within the same clone as the original sequence (one of SEQ ID NOS: 1–1565). "Validation" sequences that provided overlapping sequence are indicating by "VO" can be correlated with the original sequences they validate by referring to Table 1A. Sequences indicated as VNO are treated as newly isolated sequences and may or may not be related to the sequences of SEQ ID NOS:1–1565. Because the "validation" sequences are often longer than the original polynucleotide sequences and thus provide additional sequence information. All validation sequences can be obtained either from an indicated clone (e.g., for VO sequences) or from a cDNA library described herein (e.g., using primers designed from the sequence provided in the sequence listing).

Example 2

Results of Public Database Search to Identify Function of Gene Products

SEQ ID NOS:1566–2610 were translated in all three reading frames, and the nucleotide sequences and translated amino acid sequences used as query sequences to search for homologous sequences in either the GenBank (nucleotide sequences) or Non-Redundant Protein (amino acid sequences) databases. Query and individual sequences were aligned using the BLAST 2.0 programs, available over the world wide web at ncbi.nlm.nih.gov/BLAST (see also Altschul, et al. *Nucleic Acids Res*. (1997) 25:3389–3402). The sequences were masked to various extents to prevent searching of repetitive sequences or poly-A sequences, using the XBLAST program for masking low complexity as described above in Example 1.

Tables 2A and 2B (inserted before the claims) provide the alignment summaries having a p value of $1 \times 10^{-2}$ or less indicating substantial homology between the sequences of the present invention and those of the indicated public databases. Table 2A provides the SEQ ID NO of the query sequence, the accession number of the GenBank database entry of the homologous sequence, and the p value of the alignment. Table 2A provides the SEQ ID NO of the query sequence, the accession number of the Non-Redundant Protein database entry of the homologous sequence, and the p value of the alignment. The alignments provided in Tables 2A and 2B are the best available alignment to a DNA or amino acid sequence at a time just prior to filing of the present specification. The activity of the polypeptide encoded by the SEQ ID NOS listed in Tables 2A and 2B can be extrapolated to be substantially the same or substantially similar to the activity of the reported nearest neighbor or closely related sequence. The accession number of the nearest neighbor is reported, providing a publicly available reference to the activities and functions exhibited by the nearest neighbor. The public information regarding the activities and functions of each of the nearest neighbor sequences is incorporated by reference in this application. Also incorporated by reference is all publicly available information regarding the sequence, as well as the putative and actual activities and functions of the nearest neighbor sequences listed in Table 2 and their related sequences. The search program and database used for the alignment, as well as the calculation of the p value are also indicated.

Full length sequences or fragments of the polynucleotide sequences of the nearest neighbors can be used as probes and primers to identify and isolate the full length sequence of the corresponding polynucleotide. The nearest neighbors can indicate a tissue or cell type to be used to construct a library for the full-length sequences of the corresponding polynucleotides.

Example 3

Members of Protein Families

SEQ ID NOS:1566–2601 were used to conduct a profile search as described in the specification above. Several of the polynucleotides of the invention were found to encode polypeptides having characteristics of a polypeptide belonging to a known protein family (and thus represent new members of these protein families) and/or comprising a known functional domain (Table 3A, inserted prior to claims). Table 3A provides the SEQ ID NO: of the query sequence, a brief description of the profile hit, the position of the query sequence within the individual sequence (indicated as "start" and "stop"), and the orientation (Direction) of the query sequence with respect to the individual sequence, where forward (for) indicates that the alignment is in the same direction (left to right) as the sequence provided in the Sequence Listing and reverse (rev) indicates that the alignment is with a sequence complementary to the sequence provided in the Sequence Listing.

Some polynucleotides exhibited multiple profile hits where the query sequence contains overlapping profile regions, and/or where the sequence contains two different functional domains. Each of the profile hits of Table 3A are described in more detail below. The acronyms for the profiles (provided in parentheses) are those used to identify the profile in the Pfam and Prosite databases. The Pfam database can be accessed through any of the following URLS: pfam.wustl.edu/index; sanger.ac.uk/Software/Pfam; and cgr.ki.se/Pfam. The Prosite database can be accessed at expasy.ch/prosite. The public information available on the Pfam and Prosite databases regarding the various profiles, including but not limited to the activities, function, and consensus sequences of various proteins families and protein domains, is incorporated herein by reference.

14-3-3 Family (14 3 3). SEQ ID NO:1967 corresponds to a sequence encoding a 14-3-3 protein family member. The 14-3-3 protein family includes a group of closely related acidic homodimeric proteins of about 30 kD first identified as very abundant in mammalian brain tissues and located preferentially in neurons (Aitken et al. *Trends Biochem. Sci*. (1995) 20:95–97; Morrison *Science* (1994) 266:56–57; and Xiao et al. *Nature* (1995) 376:188–191). The 14-3-3 proteins have multiple biological activities, including a key role in signal transduction pathways and the cell cycle. 14-3-3 proteins interact with kinases (e.g., PKC or Raf-1), and can also function as protein-kinase dependent activators of tyrosine and tryptophan hydroxylases. The 14-3-3 protein sequences are extremely well conserved, and include two highly conserved regions: the first is a peptide of 11 residues located in the N-terminal section; the second, a 20 amino acid region located in the C-terminal section. The consensus patterns are as follows: 1) R-N-L-[LIV]-S-[VG]-[GA]-Y-[KN]-N-[IVA]; 2) Y-K-[DE]-S-T-L-I-[IM]-Q-L-[LF]-[RHC]-D-N-[LF]-T-[LS]-W-[TAN]-[SAD].

3'5'-Cyclin Nucleotide Phosphodiesterases (PDEase). SEQ ID NO: 2366 represents a polynucleotide encoding a novel 3'5'-cyclic nucleotide phosphodiesterase. PDEases catalyze the hydrolysis of cAMP or cGMP to the corresponding nucleoside 5' monophosphates (Charbonneau et al, *Proc. Natl. Acad. Sci. U.S.A.* (1986) 83:9308). There are at least seven different subfamilies of PDEases (Beavo et al., *Trends Pharmacol. Sci.* (1990) 11:150; http://weber.u.washington.edu/~pde/: 1) Type 1, calmodulin/calcium-dependent PDEases; 2) Type 2, cGMP-stimulated PDEases; 3) Type 3, cGMP-inhibited PDEases; 4) Type 4, cAMP-specific PDEases.; 5) Type 5, cGMP-specific PDEases; 6) Type 6, rhodopsin-sensitive cGMP-specific PDEases; and 7) Type 7, High affinity cAMP-specific PDEases. All PDEase forms share a conserved domain of about 270 residues. The signature pattern is determined from a stretch of 12 residues that contains two conserved histidines: H-D-[LIVMFY]-x-H-x-[AG]-x(2)-[NQ]-x-[LIVMFY].

Four Transmembrane Integral Membrane Proteins (transmembrane4). SEQ ID NOS:1579 and 1978 sequences correspond to a sequence encoding a member of the four transmembrane segments integral membrane protein family (tm4 family). The tm4 family of proteins includes a number of evolutionarily-related eukaryotic cell surface antigens (Levy et al., *J. Biol. Chem.*, (1991) 266:14597; Tomlinson et al., *Eur. J. Immunol.* (1993) 23:136; Barclay et al. The leucocyte antigen factbooks. (1993) Academic Press, London/San Diego). The tm4 family members are type III membrane proteins, which are integral membrane proteins containing an N-terminal membrane-anchoring domain that functions both as a translocation signal and as a membrane anchor. The family members also contain three additional transmembrane regions, at least seven conserved cysteines residues, and are of approximately the same size (218 to 284 residues). The consensus pattern spans a conserved region including two cysteines located in a short cytoplasmic loop between two transmembrane domains: Consensus pattern: G-x(3)-[LIVMF]-x(2)-[GSA]-[LIVMF](2)-G-C-x-[GA]-[STA]-x(2)-[EG]-x(2)-[CWN]-[LIVM](2).

Seven Transmembrane Integral Membrane Proteins—Rhodopsin Family (7tm 1). SEQ ID NOS:1652, 1927, and 2068 correspond to a sequence encoding a member of the seven transmembrane (7tm) receptor rhodopsin family. G-protein coupled receptors of the (7tm) rhodopsin family include hormones, neurotransmitters, and light receptors that transduce extracellular signals by interaction with guanine nucleotide-binding (G) proteins (Strosberg *Eur. J. Biochem.* (1991) 196:1, Kerlavage *Curr. Opin. Struct. Biol.* (1991) 1:394, Probst, et al., *DNA Cell Biol.* (1992) 11:1, Savarese, et al., Biochem. J. (1992) 283:1, gcrdb.uthsc-sa.edu, swift.embl-heidelberg.de/7tm) The consensus pattern that contains the conserved triplet and that also spans the major part of the third transmembrane helix is used to detect this widespread family of proteins: [GSTALIVM-FYWC]-[GSTANCPDE]-{EDPKRH}-x(2)-[LIVMN-QGA]-x(2)-[LIVMFT]-[GSTANC]-[LIVMFYWSTAC]-[DENH]-R-[FYWCSH]-x(2)-[LIVM].

Seven Transmembrane Integral Membrane Proteins—Secretin Family (7tm 2). SEQ ID NOS:1598, 1719, 1911, 1927, 2068, and 2341 correspond to a sequence encoding a member of the seven transmembrane receptor (7tm) secretin family (Jueppner et al. *Science* (1991) 254:1024; Hamann et al. *Genomics* (1996) 32:144). The N-terminal extracellular domain of these receptors contains five conserved cysteines residues involved in disulfide bonds, with a consensus pattern in the region that spans the first three cysteines. One of the most highly conserved regions spans the C-terminal part of the last transmembrane region and the beginning of the adjacent intracellular region and is used as a second signature pattern. The two consensus patterns are: 1) C-x(3)-[FYWLIV]-D-x(3,4)-C-[FW]-x(2)-[STAGV]-x(8,9)-C-[PF]; and 2) Q-G-[LMFCA]-[LIVMFT]-[LIV]-x-[LIVFST]-[LIF]-[VFYH]-C-[LFY]-x-N-x(2)-V ATPases Associated with Various Cellular Activities (ATPases). Several of the polynucleotides of the invention correspond to a sequence that encodes a member of a family of ATPases Associated with diverse cellular Activities (AAA). The AAA protein family is composed of a large number of ATPases that share a conserved region of about 220 amino acids containing an ATP-binding site (Froehlich et al., *J. Cell Biol.* (1991) 114:443; Erdmann et al. *Cell* (1991) 64:499; Peters et al., *EMBO J.* (1990) 9:1757; Kunau et al., *Biochimie* (1993) 75:209–224; Confalonieri et al., *BioEssays* (1995) 17:639; http://yeamob.pci.chemie.uni-tuebingen.de/AAA/Description.html). The AAA domain, which can be present in one or two copies, acts as an ATP-dependent protein clamp (Confalonieri et al. (1995) *BioEssays* 17:639) and contains a highly conserved region located in the central part of the domain. The consensus pattern is: [LIVMT]-x-[LIVMT]-[LIVMF]-x-[GATMC]-[ST]-[NS]-x(4)-[LIVM]-D-x-A-[LIFA]-x-R.

Basic Region Plus Leucine Zipper Transcription Factors (BZIP). SEQ ID NO:1623 represents a polynucleotide encoding a novel member of the family of basic region plus leucine zipper transcription factors. The bZIP superfamily (Hurst, *Protein Prof.* (1995) 2:105; and Ellenberger, *Curr. Opin. Struct. Biol.* (1994) 4:12) of eukaryotic DNA-binding transcription factors encompasses proteins that contain a basic region mediating sequence-specific DNA-binding followed by a leucine zipper required for dimerization. The consensus pattern for this protein family is: [KR]-x(1,3)-[RKSAQ]-N-x(2)-[SAQ](2)-x-[RKTAENQ]-x-R-x-[RK].

C2 domain (C2). SEQ ID NOS: 1715 and 2426 correspond to a sequence encoding a C2 domain, which is involved in calcium-dependent phospholipid binding (Davletov *J. Biol. Chem.* (1993) 268:26386–26390) or, in proteins that do not bind calcium, the domain may facilitate binding to inositol-1,3,4,5-tetraphosphate (Fukuda et al. *J. Biol. Chem.* (1994) 269:29206–29211; Sutton et al. *Cell* (1995) 80:929–938). The consensus sequence is: [ACG]-x(2)-L-x(2,3)-D-x(1,2)-[NGSTLIF]-[GTMR]-x-[STAP]-D-[PA]-[FY].

Cysteine proteases (Cys-protease). SEQ ID NO:2238 represents a polynucleotide encoding a protein having a eukaryotic thiol (cysteine) protease active site. Cysteine proteases (Dufour *Biochimie* (1988) 70:1335) are a family of proteolytic enzymes that contain an active site cysteine. Catalysis proceeds through a thioester intermediate and is facilitated by a nearby histidine side chain; an asparagine completes the essential catalytic triad. The sequences around the three active site residues are well conserved and can be used as signature patterns: Q-x(3)-[GE]-x-C-[YW]-x(2)-[STAGC]-[STAGCV] (where C is the active site residue); 2) [LIVMGSTAN]-x-H-[GSACE]-[LIVM]-x-[LIVMAT](2)-G-x-[GSADNH] (where H is the active site residue); and 3) [FYCH]-[WI]-[LIVT]-x-[KRQAG]-N-[ST]-W-x(3)-[FYW]-G-x(2)-G-[LFYW]-[LIVMFYG]-x-[LIVMF] (where N is the active site residue).

DEAD and DEAH box families ATP-dependent helicases (Dead box helic). SEQ ID NOS:1630, 1865, and 2517 represent polynucleotides encoding a novel member of the DEAD and DEAH box families (Schmid et al., *Mol. Microbiol.* (1992) 6:283; Linder et al., *Nature* (1989) 337:121; Wassarman, et al., *Nature* (1991) 349:463). All members of these families are involved in ATP-dependent, nucleic-acid unwinding. All DEAD box family members share a number of conserved sequence motifs, some of which are specific to the DEAD family, with others shared by other ATP-binding proteins or by proteins belonging to the helicases 'superfamily' (Hodgman *Nature* (1988) 333:22 and *Nature* (1988) 333:578 (Errata); http://www.expasy.ch/www/linder/HELICASES_TEXT.html). One of these motifs, called the 'D-E-A-D-box', represents a special version of the B motif of ATP-binding proteins. Proteins that have His instead of the second Asp and are 'D-E-A-H-box' proteins (Wassarman et al., *Nature* (1991) 349:463; Harosh, et al., *Nucleic Acids Res.* (1991) 19:6331; Koonin, et al., *J. Gen. Virol.* (1992) 73:989; http://www.expasy.ch/www/linder/HELICASES_TEXT.html). The following signature patterns are used to identify member for both subfamilies: 1) [LIVMF](2)-D-E-A-D-[RKEN]-x-[LIVMFYGSTN]; and 2) [GSAH]-x-[LIVMF](3)-D-E-[ALIV]-H-[NECR].

Dual specificity phosphatase (DSPc). Dual specificity phosphatases (DSPs) are Ser/Thr and Tyr protein phosphatases that comprise a tertiary fold highly similar to that of tyrosine-specific phosphatases, except for a "recognition" region connecting helix alpha1 to strand beta1. This tertiary fold may determine differences in substrate specific between VH-1 related dual specificity phosphatase (VHR), the protein tyrosine phosphatases (PTPs), and other DSPs. Phosphatases are important in the control of cell growth, proliferation, differentiation and transformation.

EF Hand (EFhand). SEQ ID NO:1595 corresponds to a polynucleotide encoding a member of the EF-hand protein family, a calcium binding domain shared by many calcium-binding proteins belonging to the same evolutionary family (Kawasaki et al., *Protein. Prof.* (1995) 2:305–490). The domain is a twelve residue loop flanked on both sides by a twelve residue alpha-helical domain, with a calcium ion coordinated in a pentagonal bipyramidal configuration. The six residues involved in the binding are in positions 1, 3, 5, 7, 9 and 12; these residues are denoted by X, Y, Z, -Y, -X and -Z. The invariant Glu or Asp at position 12 provides two oxygens for liganding Ca (bidentate ligand). The consensus pattern includes the complete EF-hand loop as well as the first residue which follows the loop and which seem to always be hydrophobic: D-x-[DNS]-{ILVFYW}-[DEN-STG]-[DNQGHRK]-{GP}-[LIVMC]-[DENQSTAGC]-x(2)-[DE]-[LIVMFYW].

Eukaryotic Aspartyl Proteases (asp). Several of the polynucleotides of the invention correspond to a sequence encoding a novel eukaryotic aspartyl protease. Aspartyl proteases, known as acid proteases, (EC 3.4.23.) are a widely distributed family of proteolytic enzymes (Foltmann., *Essays Biochem.* (1981) 17:52; Davies, *Annu. Rev. Biophys. Chem.* (1990) 19:189; Rao, et al., *Biochemistry* (1991) 30:4663) known to exist in vertebrates, fungi, plants, retroviruses and some plant viruses. Aspartate proteases of eukaryotes are monomeric enzymes which consist of two domains. Each domain contains an active site centered on a catalytic aspartyl residue. The consensus pattern to identify eukaryotic aspartyl protease is: [LIVMFGAC]-[LIVMTADN]-[LIVFSA]-D-[ST]-G-[STAV]-[STAP-DENQ]-x-[LIVMFSTNC]-x-[LIVMFGTA], where D is the active site residue.

Fibronectin Type II collagen-binding domain (FntypeII). SEQ ID NO: 1968 corresponds to a polynucleotide encoding a polypeptide having a type II fibronectin collagen binding domain. Fibronectin is a plasma protein that binds cell surfaces and various compounds including collagen, fibrin, heparin, DNA, and actin. The major part of the sequence of fibronectin consists of the repetition of three types of domains, called type I, II, and III (Skorstengaardet al., *Eur. J. Biochem.* (1986) 161:441). The type II domain, which is duplicated in fibronectin, is approximately forty residues long, contains four conserved cysteines involved in disulfide bonds and is part of the collagen-binding region of fibronectin. The consensus pattern for identifying members of this family, which pattern spans this entire domain, is: C-x(2)-P-F-x-[FYWI]-x(7)-C-x(8,10)-W-C-x(4)-[DNSR]-[FYW]-x(3,5)-[FYW]-x-[FYWI]-C (where the four C's are involved in disulfide bonds).

G-Protein Alpha Subunit (G-alpha). SEQ ID NO: 1779 corresponds to a gene encoding a member of the G-protein alpha subunit family. G-proteins are a family of membrane-associated proteins that couple extracellularly-activated integral-membrane receptors to intracellular effectors, such as ion channels and enzymes that vary the concentration of second messenger molecules. G-proteins are composed of 3 subunits (alpha, beta and gamma) which, in the resting state, associate as a trimer at the inner face of the plasma membrane. The alpha subunit, which binds GTP and exhibits GTPase activity, is about 350–400 amino acids in length with a molecular weight in the range of 40–45 kDa. Seventeen distinct types of alpha subunit have been identified in mammals, and fall into 4 main groups on the basis of both sequence similarity and function: alpha-s, alpha-q, alpha-i and alpha-12 (Simon et al., *Science* (1993) 252:802). They are often N-terminally acylated, usually with myristate and/or palmitoylate, and these fatty acid modifications can be important for membrane association and high-affinity interactions with other proteins.

Helicases conserved C-terminal domain (helicase C). SEQ ID NOS: 1621 and 1652 represent polynucleotides encoding novel members of the DEAD/H helicase family. The DEAD and DEAH families are described above.

Helix-Loop-Helix (HLH) DNA Binding Domain (HLH). SEQ ID NO:2192 corresponds to a sequence encoding an HLH domain. The HLH domain, which normally spans about 40 to 50 amino acids, is present in a number of eukaryotic transcription factors. The HLH domain is formed of two amphipathic helices joined by a variable length linker region that forms a loop that mediates protein dimerization (Murre et al. *Cell* (1989) 56:777–783). Basic HLH proteins (bHLH), which have an extra basic region of about 15 amino acid residues adjacent the HLH domain and specifically bind to DNA, include two groups: class A (ubiquitous) and class B (tissue-specific). bHLH family members bind variations of the E-box motif (CANNTG). The homo- or heterodimerization mediated by the HLH domain is independent of, but necessary for DNA binding, as two basic regions are required for DNA binding activity. The HLH proteins lacking the basic domain function as negative regulators since they form heterodimers, but fail to bind DNA. Consensus pattern: [DENSTAP]-[KTR]-[LIVMAGSNT]-{FY-WCPHKR}-[LIVMT]-[LIVM]-x(2)-[STAV]-[LIVM-STACKR]-x-[VMFYH]-[LIVMTA]-{P}-{P}-[LIVM-RKHQ].

Kinase Domain of Tors. The TOR profile is directed towards a lipid kinase protein family. This family is composed of large proteins with a lipid and protein kinase domain and characterized through their sensitivity to rapamycin (an antifungal compound). TOR proteins are involved in signal transduction downstream of P13 kinase and many other signals. TOR (also called FRAP, RAFT) plays a role in regulating protein synthesis and cell growth., and in yeast controls translation initiation and early G1 progression. See, e.g., Barbet et al. *Mol Biol Cell*. (1996) 7(1):25–42; Helliwell et al. *Genetics* (1998) 148:99–112.

MAP kinase kinase (mkk). SEQ ID NOS: 1825,1876, 2039, and 2526 represent members of the MAP kinase kinase (mkk) family. MAP kinases (MAPK) are involved in signal transduction, and are important in cell cycle and cell growth controls. The MAP kinase kinases (MAPKK) are dual-specificity protein kinases which phosphorylate and activate MAP kinases. MAPKK homologues have been found in yeast, invertebrates, amphibians, and mammals. Moreover, the MAPKK/MAPK phosphorylation switch constitutes a basic module activated in distinct pathways in yeast and in vertebrates. MAPKKs are essential transducers through which signals must pass before reaching the nucleus. For review, see, e.g., Biologique *Biol Cell* (1993) 79:193–207; Nishida et al., *Trends Biochem Sci* (1993) 18:128–31; Ruderman *Curr Opin Cell Biol* (1993) 5:207–13; Dhanasekaran et al., *Oncogene* (1998) 17:1447–55; Kiefer et al., *Biochem Soc Trans* (1997) 25:491–8; and Hill, *Cell Signal* (1996) 8:533–44.

Neurotransmitter-Gated Ion-Channel (neur_chan). Several of the sequences correspond to a sequence encoding a neurotransmitter-gated ion channel. Neurotransmitter-gated ion-channels, which provide the molecular basis for rapid signal transmission at chemical synapses, are post-synaptic oligomeric transmembrane complexes that transiently form a ionic channel upon the binding of a specific neurotransmitter. Five types of neurotransmitter-gated receptors are known: 1) nicotinic acetylcholine receptor (AchR); 2) glycine receptor; 3) gamma-aminobutyric-acid (GABA) receptor; 4) serotonin 5HT3 receptor; and 5) glutamate receptor. All known sequences of subunits from neurotransmitter-gated ion-channels are structurally related, and are composed of a large extracellular glycosylated N-terminal ligand-binding domain, followed by three hydrophobic transmembrane regions that form the ionic channel, followed by an intracellular region of variable length. A fourth hydrophobic region is found at the C-terminal of the sequence. The consensus pattern is: C-x-[LIVMFQ]-x-[LIVMF]-x(2)-[FY]-P-x-D-x(3)-C, where the two C's are linked by a disulfide bond.

Protein Kinase (protkinase). Several sequences represent polynucleotides encoding protein kinases, which catalyze phosphorylation of proteins in a variety of pathways, and are implicated in cancer. Eukaryotic protein kinases (Hanks, et al., *FASEB J*. (1995) 9:576; Hunter, *Meth. Enzymol*. (1991) 200:3; Hanks, et al., *Meth. Enzymol*. (1991) 200:38; Hanks, *Curr. Opin. Struct. Biol*. (1991) 1:369; Hanks et al., *Science* (1988) 241:42) belong to a very extensive family of proteins that share a conserved catalytic core common to both serine/threonine and tyrosine protein kinases. There are a number of conserved regions in the catalytic domain of protein kinases. The first region, located in the N-terminal extremity of the catalytic domain, is a glycine-rich stretch of residues in the vicinity of a lysine residue, which has been shown to be involved in ATP binding. The second region, located in the central part of the catalytic domain, contains a conserved an aspartic acid residue that is important for the catalytic activity of the enzyme (Knighton, et al., *Science* (1991) 253:407).

The protein kinase profile includes two signature patterns for this second region: one specific for serine/threonine kinases and the other for tyrosine kinases. A third profile is based on the alignment in (Hanks, et al., *FASEB J*. (1995) 9:576) and covers the entire catalytic domain. The consensus patterns are as follows: 1) [LIV]-G-{P}-G-{P}-[FYWMG-STNH]-[SGA]-{PW}-[LIVCAT]-{PD}-x-[GSTA-CLIVMFY]-x(5,18)-[LIVMFYWCSTAR]-[AIVP]-[LIVM-FAGCKR]-K, where K binds ATP; 2) [LIVMFYC]-x-[HY]-x-D-[LIVMFY]-K-x(2)-N-[LIVMFYCT](3), where D is an active site residue; and 3) [LIVMFYC]-x-[HY]-x-D-[LIVMFY]-[RSTAC]-x(2)-N-[LIVMFYC], where D is an active site residue.

Protein Tyrosine Phosphatase (Y phosphatase) (PTPase). SEQ ID NOS:1719, 1769, 2062, 2197, and 2275 represent polynucleotides encoding a tyrosine-specific protein phosphatase, a kinase that catalyzes the removal of a phosphate groups attached to a tyrosine residue (EC 3.1.3.48) (PTPase) (Fischer et al., *Science* (1991) 253:401; Charbonneau et al., *Annu. Rev. Cell Biol*. (1992) 8:463; Trowbridge *Biol. Chem*. (1991) 266:23517; Tonks et al., *Trends Biochem. Sci*. (1989) 14:497; and Hunter, *Cell* (1989) 58:1013). PTPases are important in the control of cell growth, proliferation, differentiation and transformation. Multiple forms of PTPase have been characterized and can be classified into two categories: soluble PTPases and transmembrane receptor proteins that contain PTPase domain(s). Structurally, all known receptor PTPases are made up of a variable length extracellular domain, followed by a transmembrane region and a C-terminal catalytic cytoplasmic domain. PTPase domains consist of about 300 amino acids. Two conserved cysteines are absolutely required for activity, with a number of other conserved residues in the immediate vicinity also important for activity. The consensus pattern for PTPases is: [LIVMF]-H-C-x(2)-G-x(3)-[STC]-[STAGP]-x-[LIVMFY]; C is the active site residue.

RNA Recognition Motif (rrm). SEQ ID NOS: 1850 and 2194 correspond to sequence encoding an RNA recognition motif, also known as an RRM, RBD, or RNP domain. This domain, which is about 90 amino acids long, is contained in eukaryotic proteins that bind single-stranded RNA (Bandziulis et al. *Genes Dev*. (1989) 3:431–437; Dreyfuss et al. *Trends Biochem. Sci*. (1988) 13:86–91). Two regions within the RNA-binding domain are highly conserved: the first is a hydrophobic segment of six residues (which is called the RNP-2 motif), the second is an octapeptide motif (which is called RNP-1 or RNP-CS). The consensus pattern is: [RK]-G-{EDRKHPCG}-[AGSCI]-[FY]-[LIVA]-x-[FYLM].

SH2 Domain (SH2). SEQ ID NO: 2441 corresponds to a sequence encoding an SH2 domain. The Src homology 2 (SH2) domain includes an approximately 100 amino acid residue domain, which is conserved in the oncoproteins Src and Fps, as well as in many other intracellular signal-transducing proteins (Sadowski et al. *Mol Cell. Biol*. (1986) 6:4396–4408; Russel et al. *FEBS Lett*. (1992) 304:15–20). SH2 domains function as regulatory modules of intracellular signaling cascades by interacting with high affinity to phosphotyrosine-containing target peptides in a sequence-specific and strictly phosphorylation-dependent manner. The SH2 domain has a conserved 3D structure consisting of two alpha helices and six to seven beta-strands. The core of the domain is formed by a continuous beta-meander composed of two connected beta-sheets (Kuriyan et al. *Curr. Opin. Struct. Biol*. (1993) 3:828–837).

Thioredoxin family active site (Thioredox). SEQ ID NO: 1618 represents a polynucleotide encoding a protein of the thioredoxin family. Thioredoxins are small proteins of approximately one hundred amino acid residues that participate in various redox reactions via the reversible oxidation of an active center disulfide bond (Holmgren, *Annu. Rev. Biochem.* (1985) 54:237; Gleason, et al., *FEMS Microbiol. Rev.* (1988) 54:271; Holmgren A. *J. Biol. Chem.* (1989) 264:13963; Eklund, et al. *Proteins* (1991) 11:13). Thioredoxins exist in either reduced or oxidized forms where the two cysteine residues are linked in an intramolecular disulfide bond. The sequence around the redox-active disulfide bond is well conserved. The consensus pattern is: [LIVMF]-[LIVMSTA]-x-[LIVMFYC]-[FYWSTHE]-x(2)-[FY-WGTN]-C-[GATPLVE]-[PHYWSTA]-C-x(6)-[LIVM-FYWT] (where the two C's form the redox-active bond).

Trypsin (trypsin). SEQ ID NOS: 1579, 2290, 2341, 2421, 2430, and 2438 correspond to novel serine proteases of the trypsin family. The catalytic activity of the serine proteases from the trypsin family is provided by a charge relay system involving an aspartic acid residue hydrogen-bonded to a histidine, which itself is hydrogen-bonded to a serine. The sequences in the vicinity of the active site serine and histidine residues are well conserved (Brenner *Nature* (1988) 334:528). The consensus patterns for the trypsin protein family are: 1) [LIVM]-[ST]-A-[STAG]-H-C, where H is the active site residue; and 2) [DNSTAGC]-[GSTAPIMVQH]-x(2)-G-[DE]-S-G-[GS]-[SAP]-[LIVM-FYWH]-[LIVMFYSTANQH], where S is the active site residue. All sequences known to belong to this family are detected by the above consensus sequences, except for 18 different proteases which have lost the first conserved glycine. If a protein includes both the serine and the histidine active site signatures, the probability of it being a trypsin family serine protease is 100%.

WD Domain, G-Beta Repeats (WD domain). SEQ ID NO: 2281 represents a members of the WD domain/G-beta repeat family. Beta-transducin (G-beta) is one of the three subunits (alpha, beta, and gamma) of the guanine nucleotide-binding proteins (G proteins) which act as intermediaries in the transduction of signals generated by transmembrane receptors (Gilman, *Annu. Rev. Biochem.* (1987) 56:615). The alpha subunit binds to and hydrolyzes GTP; the beta and gamma subunits are required for the replacement of GDP by GTP as well as for membrane anchoring and receptor recognition. In higher eukaryotes, G-beta exists as a small multigene family of highly conserved proteins of about 340 amino acid residues. Structurally, G-beta has eight tandem repeats of about 40 residues, each containing a central Trp-Asp motif (this type of repeat is sometimes called a WD-40 repeat). The consensus pattern for the WD domain/G-Beta repeat family is: [LIVMSTAC]-[LIVMFY-WSTAGC]-[LIMSTAG]-[LIVMSTAGC]-x(2)-[DN]-x(2)-[LIVMWSTAC]-x-[LIVMFSTAG]-W-[DEN]-[LIVMF-STAGCN].

wnt Family of Developmental Signaling Proteins (Wnt dev sign). Several of the sequences correspond to novel members of the wnt family of developmental signaling proteins. Wnt-1 (previously known as int-1), the seminal member of this family, (Nusse, *Trends Genet.* (1988) 4:291) plays a role in intercellular communication and is important in central nervous system development. All wnt family proteins share the following features characteristic of secretory proteins: a signal peptide, several potential N-glycosylation sites and 22 conserved cysteines that may be involved in disulfide bonds. Wnt proteins generally adhere to the plasma membrane of secreting cells and are therefore likely to signal over only few cell diameters. The consensus pattern, which is based upon a highly conserved region including three cysteines, is as follows: C-K-C-H-G-[LIVMT]-S-G-x-C.

Zinc Finger, $C_2H_2$ Type (Zincfing $C_2H_2$). SEQ ID NOS: 1735, 1942, 2018, 2254, and 2515 correspond to polynucleotides encoding members of the $C_2H_2$ type zinc finger protein family, which contain zinc finger domains that facilitate nucleic acid binding (Klug et al., *Trends Biochem. Sci.* (1987) 12:464; Evans et al., *Cell* (1988) 52:1; Payre et al., *FEBS Lett.* (1988) 234:245; Miller et al., *EMBO J.* (1985) 4:1609; and Berg, *Proc. Natl. Acad. Sci. USA* (1988) 85:99). In addition to the conserved zinc ligand residues, a number of other positions are also important for the structural integrity of the $C_2H_2$ zinc fingers. (Rosenfeld et al., *J. Biomol. Struct. Dyn.* (1993) 11:557) The best conserved position, which is generally an aromatic or aliphatic residue, is located four residues after the second cysteine. The consensus pattern for $C_2H_2$ zinc fingers is: C-x(2,4)-C-x(3)-[LIVMFYWC]-x(8)-H-x(3,5)-H. The two C's and two H's are zinc ligands.

Example 4

Differential Expression of Polynucleotides of the Invention: Description of Libraries and Detection of Differential Expression The relative expression levels of the polynucleotides of the invention was assessed in several libraries prepared from various sources, including cell lines and patient tissue samples. Table 4 provides a summary of these libraries, including the shortened library name (used hereafter), the mRNA source used to prepared the cDNA library, the "nickname" of the library that is used in the tables below (in quotes), and the approximate number of clones in the library.

TABLE 4

Description of cDNA Libraries

| Library (lib #) | Description | Number of Clones in Cluster |
|---|---|---|
| 1 | Km12L4 Human Colon Cell Line, High Metastatic Potential (derived from Km12C); "High Met Colon" | 307133 |
| 2 | Km12C Human Colon Cell Line, Low Metastatic Potential; "Low Met Colon" | 284755 |
| 3 | MDA-MB-231 Human Breast Cancer Cell Line, High Metastatic Potential; micrometastases in lung; "High Met Breast" | 326937 |
| 4 | MCF7 Human Breast Cancer Cell, Non Metastatic; "Low Met Breast" | 318979 |
| 8 | MV-522 Human Lung Cancer Cell Line, High Metastatic Potential; "High Met Lung" | 223620 |
| 9 | UCP-3 Human Lung Cancer Cell Line, Low Metastatic Potential; "Low Met Lung" | 312503 |
| 12 | Human microvascular endothelial cells (HMEC) - Untreated PCR (OligodT) cDNA library; "HMEC" | 41938 |
| 13 | Human microvascular endothelial cells (HMEC) - Basic fibroblast growth factor (bFGF) treated PCR (OligodT) cDNA library; "HMEC-bFGF" | 42100 |
| 14 | Human microvascular endothelial cells (HMEC) - Vascular endothelial growth factor (VEGF) treated PCR (OligodT) cDNA library; "HMEC-VEGF" | 42825 |
| 15 | Normal Colon - UC#2 Patient PCR (OligodT) cDNA library; "Normal Colon Tissue" | 282722 |
| 16 | Colon Tumor - UC#2 Patient PCR (OligodT) cDNA library; "Normal Colon Tumor Tissue" | 298831 |

TABLE 4-continued

Description of cDNA Libraries

| Library (lib #) | Description | Number of Clones in Cluster |
|---|---|---|
| 17 | Liver Metastasis from Colon Tumor of UC#2 Patient PCR (OligodT) cDNA library; "High Met Colon Tissue" | 303467 |
| 18 | Normal Colon - UC#3 Patient PCR (OligodT) cDNA library; "Normal Colon Tissue" | 36216 |
| 19 | Colon Tumor - UC#3 Patient PCR (OligodT) cDNA library; "Colon Tumor Tissue" | 41388 |
| 20 | Liver Metastasis from Colon Tumor of UC#3 Patient PCR (OligodT) cDNA library; "High Met Colon Tissue" | 30956 |
| 21 | GRRpz Human Prostate Cell Line; "Normal Prostate" | 164801 |
| 22 | Woca Human Prostate Cancer Cell Line; "Prostate Cancer" | 162088 |

The KM12L4, KM12C, and MDA-MB-231 cell lines are described in Example 1 above. The MCF7 cell line was derived from a pleural effusion of a breast adenocarcinoma and is non-metastatic. The MV-522 cell line is derived from a human lung carcinoma and is of high metastatic potential. The UCP-3 cell line is a low metastatic human lung carcinoma cell line; the MV-522 is a high metastatic variant of UCP-3. These cell lines are well-recognized in the art as models for the study of human breast and lung cancer (see, e.g., Chandrasekaran et al., *Cancer Res.* (1979) 39:870 (MDA-MB-231 and MCF-7); Gastpar et al., *J Med Chem* (1998) 41:4965 (MDA-MB-231 and MCF-7); Ranson et al., *Br J Cancer* (1998) 77:1586 (MDA-MB-231 and MCF-7); Kuang et al., *Nucleic Acids Res* (1998)26:1116 (MDA-MB-231 and MCF-7); Varki et al., *Int J Cancer* (1987) 40:46 (UCP-3); Varki et al., *Tumour Biol.* (1990) 11:327; (MV-522 and UCP-3); Varki et al., *Anticancer Res.* (1990) 10:637; (MV-522); Kelner et al., *Anticancer Res* (1995) 15:867 (MV-522); and Zhang et al., *Anticancer Drugs* (1997) 8:696 (MV522)). The samples of libraries 15–20 are derived from two different patients (UC#2, and UC#3). The bFGF-treated HMEC were prepared by incubation with bFGF at 10 ng/ml for 2 hrs; the VEGF-treated HMEC were prepared by incubation with 20 ng/ml VEGF for 2 hrs. Following incubation with the respective growth factor, the cells were washed and lysis buffer added for RNA preparation. The GRRpz and WOca cell lines were provided by Dr. Donna M. Peehl, Department of Medicine, Stanford University School of Medicine. GRRpz was derived from normal prostate epithelium. The WOca cell line is a Gleason Grade 4 cell line.

Each of the libraries is composed of a collection of cDNA clones that in turn are representative of the mRNAs expressed in the indicated mRNA source. In order to facilitate the analysis of the millions of sequences in each library, the sequences were assigned to clusters. The concept of "cluster of clones" is derived from a sorting/grouping of cDNA clones based on their hybridization pattern to a panel of roughly 300 7 bp oligonucleotide probes (see Drmanac et al., *Genomics* (1996) 37(1):29). Random cDNA clones from a tissue library are hybridized at moderate stringency to 300 7 bp oligonucleotides. Each oligonucleotide has some measure of specific hybridization to that specific clone. The combination of 300 of these measures of hybridization for 300 probes equals the "hybridization signature" for a specific clone. Clones with similar sequence will have similar hybridization signatures. By developing a sorting/grouping algorithm to analyze these signatures, groups of clones in a library can be identified and brought together computationally. These groups of clones are termed "clusters". Depending on the stringency of the selection in the algorithm (similar to the stringency of hybridization in a classic library cDNA screening protocol), the "purity" of each cluster can be controlled. For example, artifacts of clustering may occur in computational clustering just as artifacts can occur in "wet-lab" screening of a cDNA library with 400 bp cDNA fragments, even at the highest stringency. The stringency used in the implementation of cluster herein provides groups of clones that are in general from the same cDNA or closely related cDNAs. Closely related clones can be a result of different length clones of the same cDNA, closely related clones from highly related gene families, or splice variants of the same cDNA.

Differential expression for a selected cluster was assessed by first determining the number of cDNA clones corresponding to the selected cluster in the first library (Clones in $1^{st}$), and the determining the number of cDNA clones corresponding to the selected cluster in the second library (Clones in $2^{nd}$). Differential expression of the selected cluster in the first library relative to the second library is expressed as a "ratio" of percent expression between the two libraries. In general, the "ratio" is calculated by: 1) calculating the percent expression of the selected cluster in the first library by dividing the number of clones corresponding to a selected cluster in the first library by the total number of clones analyzed from the first library; 2) calculating the percent expression of the selected cluster in the second library by dividing the number of clones corresponding to a selected cluster in a second library by the total number of clones analyzed from the second library; 3) dividing the calculated percent expression from the first library by the calculated percent expression from the second library. If the "number of clones" corresponding to a selected cluster in a library is zero, the value is set at 1 to aid in calculation. The formula used in calculating the ratio takes into account the "depth" of each of the libraries being compared, i.e., the total number of clones analyzed in each library.

In general, a polynucleotide is said to be significantly differentially expressed between two samples when the ratio value is greater than at least about 2, preferably greater than at least about 3, more preferably greater than at least about 5, where the ratio value is calculated using the method described above. The significance of differential expression is determined using a z score test (Zar, *Biostatistical Analysis*, Prentice Hall, Inc., USA, "Differences between Proportions," pp 296–298 (1974).

Examples 5–12

Differential Expression of Polynucleotides of the Invention

A number of polynucleotide sequences have been identified that are differentially expressed between, for example, cells derived from high metastatic potential cancer tissue and low metastatic cancer cells, and between cells derived from high metastatic potential cancer tissue and normal tissue. Evaluation of the levels of expression of the genes corresponding to these sequences can be valuable in diagnosis, prognosis, and/or treatment (e.g., to facilitate rationale design of therapy, monitoring during and after therapy, etc.). Moreover, the genes corresponding to differentially expressed sequences described herein can be therapeutic targets due to their involvement in regulation (e.g., inhibition or promotion) of development of, for example, the metastatic phenotype. For example, sequences that correspond to genes that are increased in expression in high metastatic potential cells relative to normal or non-metastatic tumor cells may encode genes or regulatory sequences involved in processes such as angiogenesis, differentiation, cell replication, and metastasis.

Detection of the relative expression levels of differentially expressed polynucleotides described herein can provide valuable information to guide the clinician in the choice of therapy. For example, a patient sample exhibiting an expression level of one or more of these polynucleotides that corresponds to a gene that is increased in expression in metastatic or high metastatic potential cells may warrant more aggressive treatment for the patient. In contrast, detection of expression levels of a polynucleotide sequence that corresponds to expression levels associated with that of low metastatic potential cells may warrant a more positive prognosis than the gross pathology would suggest.

A number of polynucleotide sequences of the present invention are differentially expressed between human microvascular endothelial cells (HMEC) that have been treated with growth factors relative to untreated HMEC. Sequences that are differentially expressed between growth factor-treated HMEC and untreated HMEC can represent sequences encoding gene products involved in angiogenesis, metastasis (cell migration), and other development and oncogenic processes. For example, sequences that are more highly expressed in HMEC treated with growth factors (such as bFGF or VEGF) relative to untreated HMEC can serve as markers of cancer cells of higher metastatic potential. Detection of expression of these sequences in colon cancer tissue can be valuable in determining diagnostic, prognostic and/or treatment information associated with the prevention of achieving the malignant state in these tissues, and can be important in risk assessment for a patient. A patient sample displaying an increased level of one or more of these polynucleotides may thus warrant closer attention or more frequent screening procedures to catch the malignant state as early as possible.

The differential expression of the polynucleotides described herein can thus be used as, for example, diagnostic markers, prognostic markers, for risk assessment, patient treatment and the like. These polynucleotide sequences can also be used in combination with other known molecular and/or biochemical markers. The following examples provide relative expression levels of polynucleotides from specified cell lines and patient tissue samples.

Example 5

High Metastatic Potential Breast Cancer Versus Low Metastatic Breast Cancer Cells The following tables summarize polynucleotides that represent genes that are differentially expressed between high metastatic potential and low metastatic potential breast cancer cells.

TABLE 5

High metastatic potential breast (lib3) > low metastatic potential (lib4) breast cancer cells

| SEQ ID NO: | Lib3 Clones | Lib4 Clones | Lib3/Lib4 |
|---|---|---|---|
| 1213 | 40 | 0 | 39 |
| 1538 | 60 | 3 | 20 |

TABLE 5-continued

High metastatic potential breast (lib3) > low metastatic potential (lib4) breast cancer cells

| SEQ ID NO: | Lib3 Clones | Lib4 Clones | Lib3/Lib4 |
|---|---|---|---|
| 1466 | 14 | 0 | 14 |
| 1356 | 10 | 0 | 10 |
| 1383 | 10 | 1 | 10 |
| 1158 | 10 | 1 | 10 |
| 441 | 10 | 1 | 10 |
| 1338 | 10 | 0 | 10 |
| 1426 | 19 | 2 | 9 |
| 1547 | 9 | 1 | 9 |
| 1313 | 8 | 1 | 8 |
| 841 | 8 | 1 | 8 |
| 1534 | 8 | 0 | 8 |
| 1503 | 8 | 0 | 8 |
| 829 | 8 | 1 | 8 |
| 1408 | 8 | 0 | 8 |
| 1447 | 7 | 0 | 7 |
| 1389 | 7 | 0 | 7 |
| 356 | 7 | 0 | 7 |
| 1492 | 7 | 0 | 7 |
| 1543 | 22 | 3 | 7 |
| 799 | 7 | 0 | 7 |
| 1437 | 6 | 0 | 6 |
| 1251 | 6 | 0 | 6 |
| 972 | 18 | 3 | 6 |
| 1482 | 6 | 0 | 6 |
| 1299 | 6 | 0 | 6 |
| 109 | 24 | 4 | 6 |
| 1558 | 6 | 0 | 6 |
| 1355 | 6 | 0 | 6 |
| 1548 | 11 | 2 | 5 |
| 250 | 10 | 2 | 5 |
| 919 | 26 | 6 | 4 |
| 358 | 36 | 12 | 3 |
| 1525 | 75 | 28 | 3 |
| 1157 | 49 | 17 | 3 |

TABLE 6

Low metastatic potential breast (lib4) > high metastatic potential breast cancer cells (lib3)

| SEQ ID NO: | Lib3 Clones | Lib4 Clones | Lib4/Lib3 |
|---|---|---|---|
| 248 | 0 | 58 | 59 |
| 726 | 1 | 23 | 24 |
| 14 | 1 | 19 | 19 |
| 699 | 0 | 14 | 14 |
| 763 | 1 | 14 | 14 |
| 20 | 1 | 13 | 13 |
| 79 | 1 | 13 | 13 |
| 715 | 0 | 10 | 10 |
| 991 | 0 | 8 | 8 |
| 1199 | 0 | 8 | 8 |
| 707 | 0 | 7 | 7 |
| 1128 | 4 | 26 | 7 |
| 891 | 0 | 6 | 6 |
| 1146 | 2 | 11 | 6 |
| 731 | 7 | 44 | 6 |
| 1518 | 3 | 15 | 5 |
| 340 | 3 | 13 | 4 |
| 949 | 4 | 13 | 3 |
| 1247 | 7 | 18 | 3 |
| 1185 | 497 | 1216 | 3 |

Example 6

High Metastatic Potential Lung Cancer Versus Low Metastatic Lung Cancer Cells

The following summarizes polynucleotides that represent genes differentially expressed between high metastatic potential lung cancer cells and low metastatic potential lung cancer cells:

TABLE 7

High metastatic potential lung (lib8) > low metastatic potential lung (lib9) lung cancer cells

| SEQ ID NO: | Lib8 Clones | Lib9 Clones | Lib8/Lib9 |
|---|---|---|---|
| 150 | 31 | 0 | 43 |
| 651 | 43 | 2 | 30 |
| 1298 | 14 | 1 | 20 |
| 57 | 11 | 0 | 15 |
| 625 | 7 | 0 | 10 |
| 1322 | 7 | 1 | 10 |
| 36 | 7 | 0 | 10 |
| 621 | 18 | 3 | 8 |
| 215 | 6 | 1 | 8 |
| 561 | 19 | 4 | 7 |
| 247 | 5 | 0 | 7 |
| 199 | 5 | 0 | 7 |
| 998 | 5 | 0 | 7 |
| 502 | 5 | 0 | 7 |
| 1382 | 8 | 2 | 6 |
| 1181 | 17 | 4 | 6 |
| 1309 | 8 | 2 | 6 |
| 1157 | 15 | 4 | 5 |
| 1260 | 14 | 5 | 4 |
| 1185 | 710 | 266 | 4 |
| 1525 | 21 | 10 | 3 |

TABLE 8

Low metastatic potential lung (lib9) > high metastatic potential lung (lib8) cancer cells

| SEQ ID NO: | Lib8 Clones | Lib9 Clones | Lib9/Lib8 |
|---|---|---|---|
| 924 | 1 | 13 | 9 |
| 822 | 1 | 13 | 9 |
| 728 | 1 | 12 | 9 |
| 341 | 1 | 12 | 9 |
| 1527 | 3 | 31 | 7 |
| 698 | 4 | 26 | 5 |
| 949 | 2 | 15 | 5 |
| 744 | 3 | 23 | 5 |
| 973 | 8 | 27 | 2 |

Example 7

High Metastatic Potential Colon Cancer Versus Low Metastatic Colon Cancer Cells

Tables 9 and 10 summarize polynucleotides that represent genes differentially expressed between high metastatic potential and low metastatic potential colon cancer cells:

TABLE 9

High metastatic potential (lib1) > low metastatic potential (lib2) colon cancer cells

| SEQ ID NO: | Lib1 Clones | Lib2 Clones | Lib1/Lib2 |
|---|---|---|---|
| 248 | 67 | 2 | 31 |
| 87 | 12 | 0 | 11 |
| 698 | 11 | 0 | 10 |
| 57 | 13 | 3 | 4 |
| 924 | 24 | 10 | 2 |
| 1249 | 24 | 9 | 2 |

TABLE 10

Low metastatic potential (lib2) > high metastatic potential colon cancer (lib1) cells

| SEQ ID NO: | Lib1 Clones | Lib2 Clones | Lib2/Lib1 |
|---|---|---|---|
| 1268 | 1 | 17 | 18 |
| 1114 | 0 | 15 | 16 |
| 1032 | 1 | 14 | 15 |
| 109 | 5 | 60 | 13 |
| 973 | 1 | 11 | 12 |
| 91 | 1 | 11 | 12 |
| 982 | 0 | 9 | 10 |
| 1267 | 3 | 28 | 10 |
| 93 | 1 | 8 | 9 |
| 1556 | 1 | 8 | 9 |
| 1251 | 0 | 8 | 9 |
| 1206 | 2 | 17 | 9 |
| 812 | 0 | 8 | 9 |
| 1254 | 0 | 7 | 8 |
| 1220 | 0 | 7 | 8 |
| 766 | 0 | 7 | 8 |
| 1156 | 0 | 7 | 8 |
| 1007 | 0 | 7 | 8 |
| 981 | 0 | 7 | 8 |
| 762 | 0 | 7 | 8 |
| 876 | 0 | 6 | 6 |
| 1234 | 2 | 11 | 6 |
| 1183 | 0 | 6 | 6 |
| 1044 | 2 | 12 | 6 |
| 785 | 0 | 6 | 6 |
| 1069 | 3 | 17 | 6 |
| 770 | 0 | 6 | 6 |
| 778 | 0 | 6 | 6 |
| 792 | 0 | 6 | 6 |
| 822 | 2 | 10 | 5 |
| 1258 | 7 | 23 | 4 |
| 1224 | 7 | 17 | 3 |
| 984 | 8 | 19 | 3 |
| 841 | 10 | 28 | 3 |
| 339 | 14 | 34 | 3 |
| 1213 | 11 | 29 | 3 |
| 1201 | 5 | 14 | 3 |
| 1192 | 22 | 48 | 2 |

Example 8

High Metastatic Potential Colon Cancer Patient Tissue Vs. Normal Patient Tissue

Tables 11 summarizes polynucleotides that represent genes differentially expressed between high metastatic potential colon cancer cells and normal colon cells of patient tissue.

TABLE 11

High metastatic potential colon tissue (lib17) vs. normal colon tissue (lib 15)

| SEQ ID NO: | Lib15 Clones | Lib17 Clones |
|---|---|---|
| | | Lib17/Lib15 |
| 1422 | 1 | 13 | 12 |
| 1132 | 1 | 10 | 9 |
| 730 | 1 | 9 | 8 |
| 1311 | 0 | 7 | 7 |
| 78 | 9 | 48 | 5 |
| 822 | 5 | 20 | 4 |
| | | | Lib15/Lib17 |
| 463 | 8 | 1 | 9 |

Example 9

High Tumor Potential Colon Tissue Vs. Metastasized Colon Cancer Tissue

The following table summarizes polynucleotides that represent genes differentially expressed between high tumor potential colon cancer cels and cells derived from high metastatic potential colon cancer cells of a patient.

TABLE 12

High tumor potential colon tissue (lib16) vs. high metastatic colon tissue (lib 17)

| SEQ ID NO: | Lib16 Clones | Lib17 Clones | Lib16/Lib17 |
|---|---|---|---|
| 1185 | 14 | 4 | 4 |

| | | | Lib17/Lib16 |
|---|---|---|---|
| 822 | 2 | 20 | 10 |

Example 10

High Tumor Potential Colon Cancer Patient Tissue Versus Normal Patient Tissue Tables 13 and 14 summarize polynucleotides that represent genes differentially expressed between high metastatic potential colon cancer cells and normal colon cells in patient tissue:

TABLE 13

Higher expression in tumor potential colon tissue (lib16) vs. normal colon tissue (lib15)

| SEQ ID NO: | Lib15 Clones | Lib16 Clones | Lib16/Lib15 |
|---|---|---|---|
| 1311 | 0 | 8 | 8 |
| 78 | 9 | 28 | 3 |

TABLE 14

Higher expression in normal colon tissue (lib15) vs. tumor potential colon tissue (lib16)

| SEQ ID NO: | Lib15 Clones | Lib16 Clones | Lib15/Lib16 |
|---|---|---|---|
| 463 | 8 | 0 | 8 |
| 1099 | 12 | 3 | 4 |

Example 11

Growth Factor-Stimulated Human Microvascular Endothelial Cells (HMEC) Relative to Untreated HMEC The following tables summarize polynucleotides that represent genes differentially expressed between growth factor-treated and untreated HMEC.

TABLE 15

Higher expression in bFGF treated HMEC (lib13) vs. untreated HMEC (lib12)

| SEQ ID NO: | Lib12 Clones | Lib13 Clones | Lib13/Lib12 |
|---|---|---|---|
| 1520 | 9 | 23 | 3 |
| 1538 | 17 | 35 | 2 |

TABLE 16

Higher expression in VEGF treated HMEC (lib14) vs. untreated HMEC (lib12)

| SEQ ID NO: | Lib12 Clones | Lib14 Clones | Lib14/Lib12 |
|---|---|---|---|
| 1154 | 2 | 12 | 6 |
| 1226 | 2 | 10 | 5 |
| 1538 | 17 | 38 | 2 |

Example 12

Polynucleotides Differentially Expressed in Human Prostate Cancer Cells Relative to Normal Human Prostate Cells The following tables summarize identified polynucleotides that represent genes differentially expressed between prostate cancer cells and normal prostate cells:

TABLE 17

Higher expression in normal prostate cells (lib21) relative to prostate cancer cells (lib22)

| SEQ ID NO: | Lib21 Clones | Lib22 Clones | Lib21/Lib22 |
|---|---|---|---|
| 1525 | 6 | 0 | 6 |
| 248 | 116 | 51 | 2 |
| 1203 | 22 | 9 | 2 |

TABLE 18

Higher expression in prostate cancer cells (lib22) relative to normal prostate cells (lib21)

| SEQ ID NO: | Lib21 Clones | Lib22 Clones | Lib22/Lib21 |
|---|---|---|---|
| 1213 | 0 | 34 | 35 |
| 340 | 1 | 12 | 12 |
| 699 | 0 | 11 | 11 |

Example 13

Differential Expression Across Multiple Libraries

A number of polynucleotide sequences have been identified that represent genes that are differentially expressed across multiple libraries. Expression of these sequences in a tissue or any origin can be valuable in determining diagnostic, prognostic and/or treatment information associated with the prevention of achieving the malignant state in these tissues, and can be important in risk assessment for a patient. These polynucleotides can also serve as non-tissue specific markers of, for example, risk of metastasis of a tumor. Table 19 summarizes this data.

TABLE 19

Genes Differentially Expressed Across Multiple Library Comparisons

| SEQ ID NO: | Cell or Tissue Sample and Cancer State Compared | Ratio |
|---|---|---|
| 57 | High Met Lung (lib8) > Low Met Lung (lib9) | 15 |
| 57 | High Met Colon (lib1) > Low Met Colon (lib2) | 4 |
| 78 | High Met Colon Tissue (lib17) > Normal Colon Tissue (lib15) | 5 |
| 78 | Normal Colon Tumor Tissue (lib16) > Normal Colon Tissue (lib15) | 3 |
| 109 | High Met Breast (lib3) > Low Met Breast (lib4) | 6 |
| 109 | Low Met Colon (lib2) > High Met Colon (lib1) | 13 |
| 248 | High Met Colon (lib1) > Low Met Colon (lib2) | 31 |
| 248 | Normal Prostate (lib21) > Prostate Cancer (lib22) | 2 |
| 248 | Low Met Breast (lib4) > High Met Breast (lib3) | 59 |
| 340 | Prostate Cancer (lib22) > Normal Prostate (lib21) | 12 |
| 340 | Low Met Breast (lib4) > High Met Breast (lib3) | 4 |
| 463 | Normal Colon Tissue (lib15) > High Met Colon Tissue (lib17) | 9 |
| 463 | Normal Colon Tissue (lib15) > Normal Colon Tumor Tissue (lib16) | 8 |
| 698 | High Met Colon (lib1) > Low Met Colon (lib2) | 10 |
| 698 | Low Met Lung (lib9) > High Met Lung (lib8) | 5 |
| 699 | Low Met Breast (lib4) > High Met Breast (lib3) | 14 |
| 699 | Prostate Cancer (lib22) > Normal Prostate (lib21) | 11 |
| 822 | High Met Colon Tissue (lib17) > Normal Colon Tumor Tissue (lib16) | 10 |
| 822 | Low Met Lung (lib9) > High Met Lung (lib8) | 9 |
| 822 | Low Met Colon (lib2) > High Met Colon (lib1) | 5 |
| 822 | High Met Colon Tissue (lib17) > Normal Colon Tissue (lib15) | 4 |
| 841 | High Met Breast (lib3) > Low Met Breast (lib4) | 8 |
| 841 | Low Met Colon (lib2) > High Met Colon (lib1) | 3 |
| 924 | High Met Colon (lib1) > Low Met Colon (lib2) | 2 |
| 924 | Low Met Lung (lib9) > High Met Lung (lib8) | 9 |
| 949 | Low Met Lung (lib9) > High Met Lung (lib8) | 5 |
| 949 | Low Met Breast (lib4) > High Met Breast (lib3) | 3 |
| 973 | Low Met Colon (lib2) > High Met Colon (lib1) | 12 |
| 973 | Low Met Lung (lib9) > High Met Lung (lib8) | 2 |
| 1157 | High Met Lung (lib8) > Low Met Lung (lib9) | 5 |
| 1157 | High Met Breast (lib3) > Low Met Breast (lib4) | 3 |
| 1185 | Normal Colon Tumor Tissue (lib16) > High Met Colon Tissue (lib17) | 4 |
| 1185 | High Met Lung (lib8) > Low Met Lung (lib9) | 4 |
| 1185 | Low Met Breast (lib4) > High Met Breast (lib3) | 3 |
| 1213 | High Met Breast (lib3) > Low Met Breast (lib4) | 39 |
| 1213 | Prostate Cancer (lib22) > Normal Prostate (lib21) | 35 |
| 1213 | Low Met Colon (lib2) > High Met Colon (lib1) | 3 |
| 1251 | High Met Breast (lib3) > Low Met Breast (lib4) | 6 |
| 1251 | Low Met Colon (lib2) > High Met Colon (lib1) | 9 |
| 1311 | Normal Colon Tumor Tissue (lib16) > Normal Colon Tissue (lib15) | 8 |
| 1311 | High Met Colon Tissue (lib17) > Normal Colon Tissue (lib15) | 7 |
| 1525 | Normal Prostate (lib21) > Prostate Cancer (lib22) | 6 |
| 1525 | High Met Lung (lib8) > Low Met Lung (lib9) | 3 |
| 1525 | High Met Breast (lib3) > Low Met Breast (lib4) | 3 |
| 1538 | High Met Breast (lib3) > Low Met Breast (lib4) | 20 |
| 1538 | HMEC-VEGF (lib14) > HMEC (lib12) | 2 |
| 1538 | HMEC-bFGF (lib13) > HMEC (lib12) | 2 |

Key for Table 19:
High Met = high metastatic potential;
Low Met = low metastatic potential;
met = metastasized;
tumor = non-metastasized tumor;
HMEC = human microvascular endothelial cell;
bFGF = bFGF treated;
VEGF = VEGF treated.

Example 14

Identification of Contiguous Sequences Having a Polynucleotide of the Invention

The novel polynucleotides were used to screen publicly available and proprietary databases to determine if any of the polynucleotides of SEQ ID NOS:2611–2707 would facilitate identification of a contiguous sequence, e.g., the polynucleotides would provide sequence that would result in 5' extension of another DNA sequence, resulting in production of a longer contiguous sequence composed of the provided polynucleotide and the other DNA sequence(s). Contiging was performed using the Gelmerge application (default settings) of GCG from the Univ. of Wisconsin.

Using these parameters, 97 contiged sequences were generated. These contiged sequences are provided as SEQ ID NOS:2611–2707 (see Table 1C). Table 1C provides the SEQ ID NO of the contig sequence, the name of the sequence used to create the contig, and the accession number of the publicly available tentative human consensus (THC) sequence used with the sequence of the corresponding sequence name to provide the contig. The sequence name of Table 1C can be correlated with the SEQ ID NO: of the polynucleotide of the invention using Tables 1A and 1B.

The contiged sequences (SEQ ID NOS:2611–2707) thus represent longer sequences that encompass a polynucleotide sequence of the invention. The contiged sequences were then translated in all three reading frames to determine the best alignment with individual sequences using the BLAST programs as described above. The sequences were masked using the XBLAST program for masking low complexity as described above in Example 1. Several of the contiged sequences were found to encode polypeptides having characteristics of a polypeptide belonging to a known protein families (and thus represent new members of these protein families) and/or comprising a known functional domain (Table 3B, inserted prior to claims). Thus the invention encompasses fragments, fusions, and variants of such polynucleotides that retain biological activity associated with the protein family and/or functional domain identified herein.

Descriptions of the profiles for the indicated protein families and functional domains are provided in Example 3 above. A description of the profile for PR55 is provided below.

Protein Phosphatase 2A Regulatory Subunit PR55 (PR55). Several of the contigs correspond to a sequence encoding a protein comprising a protein phosphatase 2A (PP2A) regulatory subunit PR55. PP2A is a serine/threonine phosphatase involved in many aspects of cellular function including the regulation of metabolic enzymes and proteins involved in signal transduction. PP2A is a trimeric enzyme comprising a core composed of a catalytic subunit associated with a 65 Kd regulatory subunit (PR65, also called subunit A). This complex associates with a third variable subunit (subunit B), which confers distinct properties to the holoenzyme (Mayer-Jaekel et al. Trends Cell Biol. (1994) 4:287–291). One of the forms of the variable subunit is a 55 Kd protein (PR55) which is highly conserved in mammals and may facilitate substrate recognition or targeting the enzyme complex to the appropriate subcellular compartment. The PR55 subunit comprises two conserved sequences of 15 residues; one located in the N-terminal region, the other in the center of the protein. The consensus patterns are: E-F-D-Y-L-K-S-L-E-I-E-E-K-I-N; and N-[AG]-H-[TA]-Y-H-I-N-S-I-S-[LIVM]-N-S-D.

Those skilled in the art will recognize, or be able to ascertain, using not more than routine experimentation, many equivalents to the specific embodiments of the invention described herein. Such specific embodiments and equivalents are intended to be encompassed by the following claims.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Deposit Information. The following materials were deposited with the American Type Culture Collection (CMCC= Chiron Master Culture Collection).

TABLE 20

Cell Lines Deposited with ATCC

| Cell Line | Deposit Date | ATCC Accession No. | CMCC Accession No. |
|---|---|---|---|
| KM12L4-A | Mar. 19, 1998 | CRL-12496 | 11606 |
| Km12C | May 15, 1998 | CRL-12533 | 11611 |
| MDA-MB-231 | May 15, 1998 | CRL-12532 | 10583 |
| MCF-7 | Oct. 9, 1998 | CRL-12584 | 10377 |

In addition, pools of selected clones, as well as libraries containing specific clones, were assigned an "ES" number (internal reference) and deposited with the ATCC. Table 21 below provides the ATCC Accession Nos. of the ES deposits, all of which were deposited on or before May 13, 1999. The names of the clones contained within each of these deposits are provided in the tables numbered 22 and greater (inserted before the claims).

TABLE 21

Pools of Clones and Libraries Deposited with ATCC on or before May 13, 1999

| ES # | ATCC Accession # | ES # | ATCC Accession # | ES # | ATCC Accession # |
|---|---|---|---|---|---|
| 34 | PTA-47 | 41 | PTA-52 | 48 | PTA-49 |
| 35 | PTA-57 | 42 | PTA-53 | 49 | PTA-66 |
| 36 | PTA-54 | 43 | PTA-62 | 50 | PTA-50 |

TABLE 21-continued

Pools of Clones and Libraries Deposited with ATCC on or before May 13, 1999

| ES # | ATCC Accession # | ES # | ATCC Accession # | ES # | ATCC Accession # |
|---|---|---|---|---|---|
| 37 | PTA-58 | 44 | PTA-55 | 51 | PTA-65 |
| 38 | PTA-48 | 45 | PTA-61 | 52 | PTA-46 |
| 39 | PTA-60 | 46 | PTA-64 | 53 | PTA-51 |
| 40 | PTA-63 | 47 | PTA-56 | 54 | PTA-59 |

The deposits described herein are provided merely as convenience to those of skill in the art, and is not an admission that a deposit is required under 35 U.S.C. § 112. The sequence of the polynucleotides contained within the deposited material, as well as the amino acid sequence of the polypeptides encoded thereby, are incorporated herein by reference and are controlling in the event of any conflict with the written description of sequences herein. A license may be required to make, use, or sell the deposited material, and no such license is granted hereby.

Retrieval of Individual Clones from Deposit of Pooled Clones. Where the ATCC deposit is composed of a pool of cDNA clones or a library of cDNA clones, the deposit was prepared by first transfecting each of the clones into separate bacterial cells. The clones in the pool or library were then deposited as a pool of equal mixtures in the composite deposit. Particular clones can be obtained from the composite deposit using methods well known in the art. For example, a bacterial cell containing a particular clone can be identified by isolating single colonies, and identifying colonies containing the specific clone through standard colony hybridization techniques, using an oligonucleotide probe or probes designed to specifically hybridize to a sequence of the clone insert (e.g., a probe based upon unmasked sequence of the encoded polynucleotide having the indicated SEQ ID NO). The probe should be designed to have a $T_m$ of approximately 80° C. (assuming 2° C. for each A or T and 4° C. for each G or C). Positive colonies can then be picked, grown in culture, and the recombinant clone isolated. Alternatively, probes designed in this manner can be used to PCR to isolate a nucleic acid molecule from the pooled clones according to methods well known in the art, e.g., by purifying the cDNA from the deposited culture pool, and using the probes in PCR reactions to produce an amplified product having the corresponding desired polynucleotide sequence.

TABLE 1A

Priority Appln Information

| SEQ ID NO: | Filed | Dkt No. | SEQ ID NO: | Sequence Name | Clone Name |
|---|---|---|---|---|---|
| 1 | May 14, 1998 | 1487 | 1 | RTA00000608F.d.17.1 | M00003981C:E04 |
| 2 | May 14, 1998 | 1487 | 2 | RTA00000589F.n.08.1 | M00004182D:H03 |
| 3 | May 14, 1998 | 1487 | 3 | RTA00000589F.p.06.1 | M00004223D:D07 |
| 4 | May 14, 1998 | 1487 | 4 | RTA00000597F.b.03.4 | M00003770D:C07 |
| 5 | May 14, 1998 | 1487 | 5 | RTA00000608F.k.12.1 | M00004029A:E01 |
| 6 | May 14, 1998 | 1487 | 6 | RTA00000585F.h.08.2 | M00001432B:H08 |
| 7 | May 14, 1998 | 1487 | 7 | RTA00000585F.h.14.2 | M00001433A:C07 |
| 8 | May 14, 1998 | 1487 | 8 | RTA00000609F.f.01.3 | M00004060C:A02 |
| 9 | May 14, 1998 | 1487 | 9 | RTA00000588F.j.01.3 | M00003835A:E03 |
| 10 | May 14, 1998 | 1487 | 10 | RTA00000596F.b.19.1 | M00001663C:C03 |
| 11 | May 14, 1998 | 1487 | 11 | RTA00000585F.m.18.1 | M00001444A:A09 |
| 12 | May 14, 1998 | 1487 | 12 | RTA00000596F.m.11.1 | M00003753C:B01 |
| 13 | May 14, 1998 | 1487 | 13 | RTA00000589F.k.05.1 | M00004133C:B02 |

TABLE 1A-continued

Priority Appln Information

| SEQ ID NO: | Filed | Dkt No. | SEQ ID NO: | Sequence Name | Clone Name |
|---|---|---|---|---|---|
| 14 | May 14, 1998 | 1487 | 14 | RTA00000589F.a.18.2 | M00003984C:F04 |
| 15 | May 14, 1998 | 1487 | 15 | RTA00000585F.g.19.2 | M00001431A:E05 |
| 16 | May 14, 1998 | 1487 | 16 | RTA00000595F.c 21.1 | M00001598C:D10 |
| 17 | May 14, 1998 | 1487 | 17 | RTA00000584F.n.20.1 | M00001406C:A11 |
| 18 | May 14, 1998 | 1487 | 18 | RTA00000611F.o.18.5 | M00004204A:D04 |
| 19 | May 14, 1998 | 1487 | 19 | RTA00000597F.f.23.1 | M00003787D:A06 |
| 20 | May 14, 1998 | 1487 | 20 | RTA00000585F.p.13.2 | M00001452B:H06 |
| 21 | May 14, 1998 | 1487 | 21 | RTA00000583F.f.06.1 | M00001348D:H08 |
| 22 | May 14, 1998 | 1487 | 22 | RTA00000585F.h.08.1 | M00001432B:H08 |
| 23 | May 14, 1998 | 1487 | 23 | RTA00000589F.n.10.1 | M00004184B:F11 |
| 24 | May 14, 1998 | 1487 | 24 | RTA00000614F.k.01.1 | M00004465C:B12 |
| 25 | May 14, 1998 | 1487 | 25 | RTA00000587F.p.24.1 | M00001584C:A03 |
| 26 | May 14, 1998 | 1487 | 26 | RTA00000587F.g.19.2 | M00001548C:A09 |
| 27 | May 14, 1998 | 1487 | 27 | RTA00000612F.c.12.2 | M00004222A:H10 |
| 28 | May 14, 1998 | 1487 | 28 | RTA00000589F.f.09.1 | M00004064A:B12 |
| 29 | May 14, 1998 | 1487 | 29 | RTA00000586F.k.02.1 | M00001490B:G04 |
| 30 | May 14, 1998 | 1487 | 30 | RTA00000609F.b.20.2 | M00004050A:F02 |
| 31 | May 14, 1998 | 1487 | 31 | RTA00000584F.m.13.1 | M00001402D:C07 |
| 32 | May 14, 1998 | 1487 | 32 | RTA00000614F.i.12.1 | M00004447D:D10 |
| 33 | May 14, 1998 | 1487 | 33 | RTA00000608F.m.14.1 | M00004035A:A10 |
| 34 | May 14, 1998 | 1487 | 34 | RTA00000608F.m.01.1 | M00004033C:D10 |
| 35 | May 14, 1998 | 1487 | 35 | RTA00000597F.o.18.1 | M00003819C:E04 |
| 36 | May 14, 1998 | 1487 | 36 | RTA00000584F.g.06.1 | M00001390A:C06 |
| 37 | May 14, 1998 | 1487 | 37 | RTA00000609F.a.07.2 | M00004046A:F04 |
| 38 | May 14, 1998 | 1487 | 38 | RTA00000607F.o.12.2 | M00003961C:G02 |
| 39 | May 14, 1998 | 1487 | 39 | RTA00000597F.p.17.1 | M00003821C:E04 |
| 40 | May 14, 1998 | 1487 | 40 | RTA00000609F.f.16.3 | M00004063C:B11 |
| 41 | May 14, 1998 | 1487 | 41 | RTA00000584F.o.04.1 | M00001407B:A08 |
| 42 | May 14, 1998 | 1487 | 42 | RTA00000608F.d.21.1 | M00003982A:G03 |
| 43 | May 14, 1998 | 1487 | 43 | RTA00000614F.b.23.1 | M00004389C:E01 |
| 44 | May 14, 1998 | 1487 | 44 | RTA00000612F.1.04.1 | M00004268C:F08 |
| 45 | May 14, 1998 | 1487 | 45 | RTA00000611F.n.20.3 | M00004200D:A07 |
| 46 | May 14, 1998 | 1487 | 46 | RTA00000608F.e.01.1 | M00003982B:C10 |
| 47 | May 14, 1998 | 1487 | 47 | RTA00000585F.k.21.1 | M00001439C:G06 |
| 48 | May 14, 1998 | 1487 | 48 | RTA00000589F.d.07.1 | M00004037B:A09 |
| 49 | May 14, 1998 | 1487 | 49 | RTA00000614F.j.07.1 | M00004460B:H09 |
| 50 | May 14, 1998 | 1487 | 50 | RTA00000614F.o.08.1 | M00004508B:G02 |
| 51 | May 14, 1998 | 1487 | 51 | RTA00000608F.e.11.1 | M00003983C:E07 |
| 52 | May 14, 1998 | 1487 | 52 | RTA00000589F.d.08.1 | M00004037B:B05 |
| 53 | May 14, 1998 | 1487 | 53 | RTA00000614F.1.09.1 | M00004491D:D07 |
| 54 | May 14, 1998 | 1487 | 54 | RTA00000607F.m.15.1 | M00003949B:D05 |
| 55 | May 14, 1998 | 1487 | 55 | RTA00000609F.p.17.1 | M00004093D:D09 |
| 56 | May 14, 1998 | 1487 | 56 | RTA00000583F.d.22.1 | M00001346B:G03 |
| 57 | May 14, 1998 | 1487 | 57 | RTA00000589F.h.07.1 | M00004081B:C11 |
| 58 | May 14, 1998 | 1487 | 58 | RTA00000611F.k.19.3 | M00004191B:G01 |
| 59 | May 14, 1998 | 1487 | 59 | RTA00000595F.p.10.1 | M00001654D:F06 |
| 60 | May 14, 1998 | 1487 | 60 | RTA00000609F.h.01.1 | M00004068D:B01 |
| 61 | May 14, 1998 | 1487 | 61 | RTA00000612F.g.24.2 | M00004244B:A02 |
| 62 | May 14, 1998 | 1487 | 62 | RTA00000608F.b.10.1 | M00003975B:H09 |
| 63 | May 14, 1998 | 1487 | 63 | RTA00000587F.j.12.1 | M00001555D:F11 |
| 64 | May 14, 1998 | 1487 | 64 | RTA00000610F.p.02.1 | M00004152C:E01 |
| 65 | May 14, 1998 | 1487 | 65 | RTA00000608F.f.15.2 | M00003987A:C07 |
| 66 | May 14, 1998 | 1487 | 66 | RTA00000614F.k.11.1 | M00004467D:F09 |
| 67 | May 14, 1998 | 1487 | 67 | RTA00000612F.b.10.2 | M00004216D:E10 |
| 68 | May 14, 1998 | 1487 | 68 | RTA00000606F.k.11.1 | M00003864B:A04 |
| 69 | May 14, 1998 | 1487 | 69 | RTA00000583F.g.18.1 | M00001352C:E01 |
| 70 | May 14, 1998 | 1487 | 70 | RTA00000585F.i.13.1 | M00001435A:F03 |
| 71 | May 14, 1998 | 1487 | 71 | RTA00000612F.g.11.2 | M00004240D:A07 |
| 72 | May 14, 1998 | 1487 | 72 | RTA00000607F.1.05.1 | M00003936C:F10 |
| 73 | May 14, 1998 | 1487 | 73 | RTA00000610F.a.11.1 | M00004097C:A03 |
| 74 | May 14, 1998 | 1487 | 74 | RTA00000596F.k.09.1 | M00003746B:E12 |
| 75 | May 14, 1998 | 1487 | 75 | RTA00000611F.d.11.1 | M00004169A:B11 |
| 76 | May 14, 1998 | 1487 | 76 | RTA00000588F.g.06.1 | M00003797D:E10 |
| 77 | May 14, 1998 | 1487 | 77 | RTA00000595F.n.15.1 | M00001648C:F06 |
| 78 | May 14, 1998 | 1487 | 78 | RTA00000584F.c.22.1 | M00001382C:C09 |
| 79 | May 14, 1998 | 1487 | 79 | RTA00000585F.1.17.1 | M00001441D:H05 |
| 80 | May 14, 1998 | 1487 | 80 | RTA00000608F.k.15.2 | M00004029C:B03 |
| 81 | May 14, 1998 | 1487 | 81 | RTA00000597F.g.14.1 | M00003789C:E03 |
| 82 | May 14, 1998 | 1487 | 82 | RTA00000588F.n.16.3 | M00003906C:H12 |
| 83 | May 14, 1998 | 1487 | 83 | RTA00000606F.o.14.1 | M00003886C:D10 |
| 84 | May 14, 1998 | 1487 | 84 | RTA00000608F.n.09.1 | M00004037A:A07 |
| 85 | May 14, 1998 | 1487 | 85 | RTA00000613F.h.06.1 | M00004329C:F11 |
| 86 | May 14, 1998 | 1487 | 86 | RTA00000587F.1.08.1 | M00001564C:D04 |

TABLE 1A-continued

Priority Appln Information

| SEQ ID NO: | Filed | Dkt No. | SEQ ID NO: | Sequence Name | Clone Name |
|---|---|---|---|---|---|
| 87 | May 14, 1998 | 1487 | 87 | RTA0000059OF.d.23.1 | M00004350B:F06 |
| 88 | May 14, 1998 | 1487 | 88 | RTA00000609F.i.24.2 | M00004073D:E01 |
| 89 | May 14, 1998 | 1487 | 89 | RTA00000614F.j.23.1 | M00004465C:B10 |
| 90 | May 14, 1998 | 1487 | 90 | RTA00000587F.p.15.1 | M00001582D:B10 |
| 91 | May 14, 1998 | 1487 | 91 | RTA00000640F.a.05.1 | M00004190A:A09 |
| 92 | May 14, 1998 | 1487 | 92 | RTA00000609F.k.01.2 | M00004077D:D10 |
| 93 | May 14, 1998 | 1487 | 93 | RTA00000589F.e.14.2 | M00004054D:D02 |
| 94 | May 14, 1998 | 1487 | 94 | RTA00000586F.a.13.1 | M00001455A:E09 |
| 95 | May 14, 1998 | 1487 | 95 | RTA00000590F.d.10.1 | M00004337D:G08 |
| 96 | May 14, 1998 | 1487 | 96 | RTA00000608F.i.18.1 | M00003998A:D03 |
| 97 | May 14, 1998 | 1487 | 97 | RTA00000608F.m.05.1 | M00004034A:E08 |
| 98 | May 14, 1998 | 1487 | 98 | RTA00000597F.p.10.1 | M00003820D:E02 |
| 99 | May 14, 1998 | 1487 | 99 | RTA00000585F.n.20.1 | M00001446D:B10 |
| 100 | May 14, 1998 | 1487 | 100 | RTA00000584F.a.14.1 | M00001377A:D03 |
| 101 | May 14, 1998 | 1487 | 101 | RTA00000609F.p.03.2 | M00004092A:C03 |
| 102 | May 14, 1998 | 1487 | 102 | RTA00000606F.f.06.1 | M00003841A:E09 |
| 103 | May 14, 1998 | 1487 | 103 | RTA00000609F.o.22.1 | M00004091D:D09 |
| 104 | May 14, 1998 | 1487 | 104 | RTA00000587F.d.02.1 | M00001537B:C12 |
| 105 | May 14, 1998 | 1487 | 105 | RTA00000612F.n.07.2 | M00004277C:H11 |
| 106 | May 14, 1998 | 1487 | 106 | RTA00000606F.p.03.1 | M00003888C:E01 |
| 107 | May 14, 1998 | 1487 | 107 | RTA00000589F.g.15.1 | M00004076D:B03 |
| 108 | May 14, 1998 | 1487 | 108 | RTA00000610F.b.09.1 | M00004102C:F07 |
| 109 | May 14, 1998 | 1487 | 109 | RTA00000603F.a.13.1 | M00003820C:A09 |
| 110 | May 14, 1998 | 1487 | 110 | RTA00000606F.o.01.1 | M00003883D:C03 |
| 111 | May 14, 1998 | 1487 | 111 | RTA00000589F.c.17.1 | M00004030B:C05 |
| 112 | May 14, 1998 | 1487 | 112 | RTA00000589F.k.22.1 | M00004140B:B01 |
| 113 | May 14, 1998 | 1487 | 113 | RTA00000585F.k.08.1 | M00001438C:H05 |
| 114 | May 14, 1998 | 1487 | 114 | RTA00000595F.a.09.1 | M00001586A:F09 |
| 115 | May 14, 1998 | 1487 | 115 | RTA00000597F.g.22.1 | M00003790B:F12 |
| 116 | May 14, 1998 | 1487 | 116 | RTA00000597F.c.02.3 | M00003773A:C09 |
| 117 | May 14, 1998 | 1487 | 117 | RTA00000587F.b.18.1 | M00001530A:D11 |
| 118 | May 14, 1998 | 1487 | 118 | RTA00000606F.a.18.1 | M00003824B:D06 |
| 119 | May 14, 1998 | 1487 | 119 | RTA00000612F.j.14.2 | M00004260A:B07 |
| 120 | May 14, 1998 | 1487 | 120 | RTA00000612F.g.23.3 | M00004243C:E10 |
| 121 | May 14, 1998 | 1487 | 121 | RTA00000583F.p.05.1 | M00001374C:C09 |
| 122 | May 14, 1998 | 1487 | 122 | RTA00000586F.a.12.1 | M00001455A:C03 |
| 123 | May 14, 1998 | 1487 | 123 | RTA00000613F.d.21.1 | M00004308A:E06 |
| 124 | May 14, 1998 | 1487 | 124 | RTA00000586F.e.02.2 | M00001466C:F02 |
| 125 | May 14, 1998 | 1487 | 125 | RTA00000595F.f.07.1 | M00001609A:B12 |
| 126 | May 14, 1998 | 1487 | 126 | RTA00000607F.o.13.2 | M00003962B:B09 |
| 127 | May 14, 1998 | 1487 | 127 | RTA00000595F.b.06.1 | M00001590D:A07 |
| 128 | May 14, 1998 | 1487 | 128 | RTA00000609F.l.04.2 | M00004081C:A01 |
| 129 | May 14, 1998 | 1487 | 129 | RTA00000610F.b.08.1 | M00004102B:B04 |
| 130 | May 14, 1998 | 1487 | 130 | RTA00000585F.k.06.1 | M00001438B:H06 |
| 131 | May 14, 1998 | 1487 | 131 | RTA00000611F.o.20.5 | M00004204B:A04 |
| 132 | May 14, 1998 | 1487 | 132 | RTA00000614F.g.09.1 | M00004421A:G04 |
| 133 | May 14, 1998 | 1487 | 133 | RTA00000597F.h.12.1 | M00003793C:D11 |
| 134 | May 14, 1998 | 1487 | 134 | RTA00000597F.p.21.1 | M00003822A:G05 |
| 135 | May 14, 1998 | 1487 | 135 | RTA00000595F.l.24.2 | M00001641B:G05 |
| 136 | May 14, 1998 | 1487 | 136 | RTA00000584F.l.05.1 | M00001399C:E10 |
| 137 | May 14, 1998 | 1487 | 137 | RTA00000586F.j.16.1 | M00001489B:F08 |
| 138 | May 14, 1998 | 1487 | 138 | RTA00000613F.h.20.1 | M00004332B:E11 |
| 139 | May 14, 1998 | 1487 | 139 | RTA00000606F.k.06.1 | M00003862C:H10 |
| 140 | May 14, 1998 | 1487 | 140 | RTA00000587F.j.01.1 | M00001557C:B08 |
| 141 | May 14, 1998 | 1487 | 141 | RTA00000610F.l.23.1 | M00004143A:H07 |
| 142 | May 14, 1998 | 1487 | 142 | RTA00000606F.j.21.1 | M00003860B:A07 |
| 143 | May 14, 1998 | 1487 | 143 | RTA00000608F.j.15.1 | M00003997D:D07 |
| 144 | May 14, 1998 | 1487 | 144 | RTA00000596F.o.21.1 | M00003763D:F06 |
| 145 | May 14, 1998 | 1487 | 145 | RTA00000597F.l.05.1 | M00003809B:D08 |
| 146 | May 14, 1998 | 1487 | 146 | RTA00000608F.h.04.1 | M00003992D:G01 |
| 147 | May 14, 1998 | 1487 | 147 | RTA00000585F.d.21.1 | M00001424A:H09 |
| 148 | May 14, 1998 | 1487 | 148 | RTA00000606F.k.15.1 | M00003864C:D09 |
| 149 | May 14, 1998 | 1487 | 149 | RTA00000612F.k.16.2 | M00004266A:F10 |
| 150 | May 14, 1998 | 1487 | 150 | RTA00000589F.b.14.1 | M00003991B:B05 |
| 151 | May 14, 1998 | 1487 | 151 | RTA00000597F.m.17.1 | M00003813D:A06 |
| 152 | May 14, 1998 | 1487 | 152 | RTA00000585F.k.14.1 | M00001439B:E02 |
| 153 | May 14, 1998 | 1487 | 153 | RTA00000584F.f.21.1 | M00001389B:B06 |
| 154 | May 14, 1998 | 1487 | 154 | RTA00000597F.i.09.1 | M00003796C:H03 |
| 155 | May 14, 1998 | 1487 | 155 | RTA00000597F.h.20.1 | M00003795A:B01 |
| 156 | May 14, 1998 | 1487 | 156 | RTA00000608F.k.24.1 | M00004030B:B02 |
| 157 | May 14, 1998 | 1487 | 157 | RTA00000586F.n.05.1 | M00001500B:H07 |
| 158 | May 14, 1998 | 1487 | 158 | RTA00000608F.n.02.1 | M00004035D:E04 |
| 159 | May 14, 1998 | 1487 | 159 | RTA00000585F.e.11.2 | M00001425C:E10 |

TABLE 1A-continued

Priority Appln Information

| SEQ ID NO: | Filed | Dkt No. | SEQ ID NO: | Sequence Name | Clone Name |
|---|---|---|---|---|---|
| 160 | May 14, 1998 | 1487 | 160 | RTA00000596F.k.08.1 | M00003746A:E01 |
| 161 | May 14, 1998 | 1487 | 161 | RTA00000611F.b.14.1 | M00004163A:D11 |
| 162 | May 14, 1998 | 1487 | 162 | RTA00000607F.m.10.1 | M00003948B:B03 |
| 163 | May 14, 1998 | 1487 | 163 | RTA00000586F.p.01.1 | M00001506A:F01 |
| 164 | May 14, 1998 | 1487 | 164 | RTA00000589F.g.08.1 | M00004075C:C09 |
| 165 | May 14, 1998 | 1487 | 165 | RTA00000608F.n.19.1 | M00004037D:B05 |
| 166 | May 14, 1998 | 1487 | 166 | RTA00000607F.c.16.2 | M00003905C:B01 |
| 167 | May 14, 1998 | 1487 | 167 | RTA00000595F.j.09.1 | M00001622C:F06 |
| 168 | May 14, 1998 | 1487 | 168 | RTA00000584F.j.10.1 | M00001397B:E02 |
| 169 | May 14, 1998 | 1487 | 169 | RTA00000589F.i.13.1 | M00004103B:C07 |
| 170 | May 14, 1998 | 1487 | 170 | RTA00000585F.f.04.2 | M00001427A:C05 |
| 171 | May 14, 1998 | 1487 | 171 | RTA00000606F.d.24.1 | M00003837C:F05 |
| 172 | May 14, 1998 | 1487 | 172 | RTA00000609F.n.22.1 | M00004088A:F12 |
| 173 | May 14, 1998 | 1487 | 173 | RTA00000610F.m.14.1 | M00004144D:B06 |
| 174 | May 14, 1998 | 1487 | 174 | RTA00000606F.k.17.1 | M00003864D:G05 |
| 175 | May 14, 1998 | 1487 | 175 | RTA00000583F.d.06.1 | M00001345A:A12 |
| 176 | May 14, 1998 | 1487 | 176 | RTA00000608F.m.09.1 | M00004034C:F05 |
| 177 | May 14, 1998 | 1487 | 177 | RTA00000608F.o.17.1 | M00004040D:B05 |
| 178 | May 14, 1998 | 1487 | 178 | RTA00000583F.k.15.3 | M00001362B:H09 |
| 179 | May 14, 1998 | 1487 | 179 | RTA00000610F.f.16.1 | M00004120A:C02 |
| 180 | May 14, 1998 | 1487 | 180 | RTA00000608F.h.19.2 | M00003994C:C11 |
| 181 | May 14, 1998 | 1487 | 181 | RTA00000584F.m.07.1 | M00001401D:D04 |
| 182 | May 14, 1998 | 1487 | 182 | RTA00000587F.h.20.2 | M00001552B:D01 |
| 183 | May 14, 1998 | 1487 | 183 | RTA00000596F.b.01.1 | M00001660A:F10 |
| 184 | May 14, 1998 | 1487 | 184 | RTA00000611F.n.13.2 | M00004199D:C02 |
| 185 | May 14, 1998 | 1487 | 185 | RTA00000597F.o.06.1 | M00003818A:F09 |
| 186 | May 14, 1998 | 1487 | 186 | RTA00000589F.n.03.1 | M00004178B:F06 |
| 187 | May 14, 1998 | 1487 | 187 | RTA00000597F.k.07.1 | M00003805A:G05 |
| 188 | May 14, 1998 | 1487 | 188 | RTA00000611F.c.19.2 | M00004166B:E10 |
| 189 | May 14, 1998 | 1487 | 189 | RTA00000606F.l.12.1 | M00003868D:F02 |
| 190 | May 14, 1998 | 1487 | 190 | RTA00000614F.d.22.1 | M00004407D:B09 |
| 191 | May 14, 1998 | 1487 | 191 | RTA00000608F.n.16.1 | M00004037C:D07 |
| 192 | May 14, 1998 | 1487 | 192 | RTA00000595F.l.20.2 | M00001640D:C10 |
| 193 | May 14, 1998 | 1487 | 193 | RTA00000608F.k.22.1 | M00004030A:E09 |
| 194 | May 14, 1998 | 1487 | 194 | RTA00000583F.h.23.1 | M00001355B:A01 |
| 195 | May 14, 1998 | 1487 | 195 | RTA00000608F.c.23.1 | M00003980C:A11 |
| 196 | May 14, 1998 | 1487 | 196 | RTA00000585F.n.01.1 | M00001444A:G12 |
| 197 | May 14, 1998 | 1487 | 197 | RTA00000596F.n.08.1 | M00003756C:C08 |
| 198 | May 14, 1998 | 1487 | 198 | RTA00000612F.d.16.2 | M00004229C:G11 |
| 199 | May 14, 1998 | 1487 | 199 | RTA00000589F.c.19.1 | M00004031A:B04 |
| 200 | May 14, 1998 | 1487 | 200 | RTA00000584F.j.08.1 | M00001397A:F10 |
| 201 | May 14, 1998 | 1487 | 201 | RTA00000583F.j.03.3 | M00001358D:D09 |
| 202 | May 14, 1998 | 1487 | 202 | RTA00000597F.j.09.1 | M00003801D:F05 |
| 203 | May 14, 1998 | 1487 | 203 | RTA00000614F.n.21.1 | M00004506C:H10 |
| 204 | May 14, 1998 | 1487 | 204 | RTA00000606F.d.05.1 | M00003833B:A11 |
| 205 | May 14, 1998 | 1487 | 205 | RTA00000589F.d.10.1 | M00004038C:D12 |
| 206 | May 14, 1998 | 1487 | 206 | RTA00000597F.p.01.1 | M00003820A:H04 |
| 207 | May 14, 1998 | 1487 | 207 | RTA00000586F.l.20.1 | M00001496A:B03 |
| 208 | May 14, 1998 | 1487 | 208 | RTA00000607F.c.07.2 | M00003903C:A12 |
| 209 | May 14, 1998 | 1487 | 209 | RTA00000595F.b.02.1 | M00001589C:D12 |
| 210 | May 14, 1998 | 1487 | 210 | RTA00000597F.n.18.1 | M00003816C:F10 |
| 211 | May 14, 1998 | 1487 | 211 | RTA00000612F.d.10.2 | M00004228C:D11 |
| 212 | May 14, 1998 | 1487 | 212 | RTA00000609F.n.13.1 | M00004086D:A07 |
| 213 | May 14, 1998 | 1487 | 213 | RTA00000610F.b.02.1 | M00004101D:A03 |
| 214 | May 14, 1998 | 1487 | 214 | RTA00000590F.a.17.1 | M00004249C:E12 |
| 215 | May 14, 1998 | 1487 | 215 | RTA00000587F.i.02.1 | M00001553D:B06 |
| 216 | May 14, 1998 | 1487 | 216 | RTA00000583F.p.22.1 | M00001376A:H02 |
| 217 | May 14, 1998 | 1487 | 217 | RTA00000609F.d.08.1 | M00004054D:A03 |
| 218 | May 14, 1998 | 1487 | 218 | RTA00000609F.k.06.2 | M00004078C:A08 |
| 219 | May 14, 1998 | 1487 | 219 | RTA00000585F.i.20.1 | M00001435B:G10 |
| 220 | May 14, 1998 | 1487 | 220 | RTA00000585F.e.15.2 | M00001426A:F09 |
| 221 | May 14, 1998 | 1487 | 221 | RTA00000595F.c.18.1 | M00001597C:B03 |
| 222 | May 14, 1998 | 1487 | 222 | RTA00000596F.p.18.1 | M00003766A:G09 |
| 223 | May 14, 1998 | 1487 | 223 | RTA00000611F.l.04.3 | M00004193A:C07 |
| 224 | May 14, 1998 | 1487 | 224 | RTA00000614F.o.06.1 | M00004508A:G12 |
| 225 | May 14, 1998 | 1487 | 225 | RTA00000586F.o.13.1 | M00001504D:D09 |
| 226 | May 14, 1998 | 1487 | 226 | RTA00000612F.o.21.1 | M00004283C:D03 |
| 227 | May 14, 1998 | 1487 | 227 | RTA00000585F.k.18.1 | M00001439C:A01 |
| 228 | May 14, 1998 | 1487 | 228 | RTA00000611F.o.19.5 | M00004204A:D10 |
| 229 | May 14, 1998 | 1487 | 229 | RTA00000611F.l.10.3 | M00004193C:H01 |
| 230 | May 14, 1998 | 1487 | 230 | RTA00000612F.b.22.2 | M00004217D:G10 |
| 231 | May 14, 1998 | 1487 | 231 | RTA00000583F.n.06.1 | M00001370B:B12 |
| 232 | May 14, 1998 | 1487 | 232 | RTA00000611F.p.08.3 | M00004206C:G11 |

TABLE 1A-continued

Priority Appln Information

| SEQ ID NO: | Filed | Dkt No. | SEQ ID NO: | Sequence Name | Clone Name |
|---|---|---|---|---|---|
| 233 | May 14, 1998 | 1487 | 233 | RTA00000607F.e.03.2 | M00003909D:G01 |
| 234 | May 14, 1998 | 1487 | 234 | RTA00000607F.b.09.2 | M00003896D:B01 |
| 235 | May 14, 1998 | 1487 | 235 | RTA00000585F.j.16.1 | M00001436D:C10 |
| 236 | May 14, 1998 | 1487 | 236 | RTA00000607F.g.05.2 | M00003915C:G01 |
| 237 | May 14, 1998 | 1487 | 237 | RTA00000586F.o.14.1 | M00001505A:E09 |
| 238 | May 14, 1998 | 1487 | 238 | RTA00000607F.h.15.1 | M00003920B:A10 |
| 239 | May 14, 1998 | 1487 | 239 | RTA00000586F.m.14.1 | M00001499B:H05 |
| 240 | May 14, 1998 | 1487 | 240 | RTA00000610F.p.17.1 | M00004154D:F11 |
| 241 | May 14, 1998 | 1487 | 241 | RTA00000584F.d.11.1 | M00001383C:C07 |
| 242 | May 14, 1998 | 1487 | 242 | RTA00000610F.e.07.1 | M00004114C:F02 |
| 243 | May 14, 1998 | 1487 | 243 | RTA00000610F.b.17.1 | M00004103B:C09 |
| 244 | May 14, 1998 | 1487 | 244 | RTA00000596F.c.05.1 | M00001669A:H11 |
| 245 | May 14, 1998 | 1487 | 245 | RTA00000586F.b.17.1 | M00001458B:F06 |
| 246 | May 14, 1998 | 1487 | 246 | RTA00000607F.l.16.1 | M00003939A:A02 |
| 247 | May 14, 1998 | 1487 | 247 | RTA00000590F.f.18.2 | M00004446A:G01 |
| 248 | May 14, 1998 | 1487 | 248 | RTA00000603F.b.07.1 | M00004242C:C01 |
| 249 | May 14, 1998 | 1487 | 249 | RTA00000589F.f.11.1 | M00004066A:E12 |
| 250 | May 14, 1998 | 1487 | 250 | RTA00000589F.j.09.1 | M00004115A:G09 |
| 251 | May 14, 1998 | 1487 | 251 | RTA00000583F.a.18.1 | M00001339B:E05 |
| 252 | May 14, 1998 | 1487 | 252 | RTA00000612F.f.23.3 | M00004239C:C09 |
| 253 | May 14, 1998 | 1487 | 253 | RTA00000597F.0.12.1 | M00003818C:E09 |
| 254 | May 14, 1998 | 1487 | 254 | RTA00000607F.b.05.2 | M00003896B:F08 |
| 255 | May 14, 1998 | 1487 | 255 | RTA00000607F.e.23.2 | M00003912C:C11 |
| 256 | May 14, 1998 | 1487 | 256 | RTA00000586F.m.11.1 | M00001499A:D05 |
| 257 | May 14, 1998 | 1487 | 257 | RTA00000585F.g.18.2 | M00001431A:C10 |
| 258 | May 14, 1998 | 1487 | 258 | RTA00000614F.d.07.1 | M00004403A:B05 |
| 259 | May 14, 1998 | 1487 | 259 | RTA00000606F.c.23.1 | M00003832B:G03 |
| 260 | May 14, 1998 | 1487 | 260 | RTA00000609F.d.13.1 | M00004055B:F06 |
| 261 | May 14, 1998 | 1487 | 261 | RTA00000606F.c.04.1 | M00003829A:E02 |
| 262 | May 14, 1998 | 1487 | 262 | RTA00000587F.f.02.1 | M00001542C:F06 |
| 263 | May 14, 1998 | 1487 | 263 | RTA00000585F.e.14.2 | M00001426A:C02 |
| 264 | May 14, 1998 | 1487 | 264 | RTA00000584F.o.03.2 | M00001406D:H01 |
| 265 | May 14, 1998 | 1487 | 265 | RTA00000614F.m.24.1 | M00004501A:G06 |
| 266 | May 14, 1998 | 1487 | 266 | RTA00000586F.j.21.1 | M00001489D:C08 |
| 267 | May 14, 1998 | 1487 | 267 | RTA00000585F.d.02.2 | M00001421C:A03 |
| 268 | May 14, 1998 | 1487 | 268 | RTA00000597F.o.19.1 | M00003819D:G09 |
| 269 | May 14, 1998 | 1487 | 269 | RTA00000613F.h.02.1 | M00004328A:H06 |
| 270 | May 14, 1998 | 1487 | 270 | RTA00000612F.m.08.2 | M00004273D:E11 |
| 271 | May 14, 1998 | 1487 | 271 | RTA00000606F.g.04.1 | M00003844C:H05 |
| 272 | May 14, 1998 | 1487 | 272 | RTA00000608F.h.04.2 | M00003992D:G01 |
| 273 | May 14, 1998 | 1487 | 273 | RTA00000609F.e.19.3 | M00004059A:G09 |
| 274 | May 14, 1998 | 1487 | 274 | RTA00000613F.c.10.1 | M00004297D:B08 |
| 275 | May 14, 1998 | 1487 | 275 | RTA00000587F.d.24.1 | M00001539B:B01 |
| 276 | May 14, 1998 | 1487 | 276 | RTA00000597F.a.22.5 | M00003769D:G12 |
| 277 | May 14, 1998 | 1487 | 277 | RTA00000595F.m.11.1 | M00001644D:F09 |
| 278 | May 14, 1998 | 1487 | 278 | RTA00000613F.k.05.1 | M00004346B:D06 |
| 279 | May 14, 1998 | 1487 | 279 | RTA00000611F.n.15.2 | M00004200A:G06 |
| 280 | May 14, 1998 | 1487 | 280 | RTA00000609F.m.20.2 | M00004085B:G06 |
| 281 | May 14, 1998 | 1487 | 281 | RTA00000609F.c.08.1 | M00004051C:D10 |
| 282 | May 14, 1998 | 1487 | 282 | RTA00000586F.k.13.1 | M00001491C:C01 |
| 283 | May 14, 1998 | 1487 | 283 | RTA00000595F.i.16.1 | M00001623D:A09 |
| 284 | May 14, 1998 | 1487 | 284 | RTA00000588F.j.17.3 | M00003839D:G06 |
| 285 | May 14, 1998 | 1487 | 285 | RTA00000610F.j.05.1 | M00004129A:H08 |
| 286 | May 14, 1998 | 1487 | 286 | RTA00000596F.o.14.1 | M00003762A:D11 |
| 287 | May 14, 1998 | 1487 | 287 | RTA00000583F.e.15.1 | M00001347B:H01 |
| 288 | May 14, 1998 | 1487 | 288 | RTA00000584F.a.01.2 | M00001376B:C11 |
| 289 | May 14, 1998 | 1487 | 289 | RTA00000597F.c.10.4 | M00003773D:C02 |
| 290 | May 14, 1998 | 1487 | 290 | RTA00000595F.d.20.1 | M00001604B:D09 |
| 291 | May 14, 1998 | 1487 | 291 | RTA00000609F.m.04.2 | M00004084A:D11 |
| 292 | May 14, 1998 | 1487 | 292 | RTA00000589F.b.08.1 | M00003988C:A06 |
| 293 | May 14, 1998 | 1487 | 293 | RTA00000583F.k.13.3 | M00001362B:A09 |
| 294 | May 14, 1998 | 1487 | 294 | RTA00000606F.b.07.1 | M00003825C:B02 |
| 295 | May 14, 1998 | 1487 | 295 | RTA00000583F.a.17.1 | M00001339B:A03 |
| 296 | May 14, 1998 | 1487 | 296 | RTA00000611F.o.09.5 | M00004201D:E12 |
| 297 | May 14, 1998 | 1487 | 297 | RTA00000610F.j.15.1 | M00004134C:B11 |
| 298 | May 14, 1998 | 1487 | 298 | RTA00000608F.e.21.1 | M00003985A:C01 |
| 299 | May 14, 1998 | 1487 | 299 | RTA00000614F.k.08.1 | M00004467A:F09 |
| 300 | May 14, 1998 | 1487 | 300 | RTA00000610F.p.11.1 | M00004153D:E06 |
| 301 | May 14, 1998 | 1487 | 301 | RTA00000595F.l.14.1 | M00001639A:A04 |
| 302 | May 14, 1998 | 1487 | 302 | RTA00000596F.m.03.1 | M00003752A:B06 |
| 303 | May 14, 1998 | 1487 | 303 | RTA00000595F.n.06.2 | M00001647C:C07 |
| 304 | May 14, 1998 | 1487 | 304 | RTA00000596F.e.22.2 | M00001679C:F03 |
| 305 | May 14, 1998 | 1487 | 305 | RTA00000607F.c.18.2 | M00003905C:E10 |

TABLE 1A-continued

Priority Appln Information

| SEQ ID NO: | Filed | Dkt No. | SEQ ID NO: | Sequence Name | Clone Name |
|---|---|---|---|---|---|
| 306 | May 14, 1998 | 1487 | 306 | RTA00000597F.o.15.1 | M00003819A:B09 |
| 307 | May 14, 1998 | 1487 | 307 | RTA00000584F.f.10.1 | M00001387D:C07 |
| 308 | May 14, 1998 | 1487 | 308 | RTA00000597F.b.07.5 | M00003771A:G09 |
| 309 | May 14, 1998 | 1487 | 309 | RTA00000584F.m.17.1 | M00001403B:A01 |
| 310 | May 14, 1998 | 1487 | 310 | RTA00000608F.g.08.2 | M00003989C:F01 |
| 311 | May 14, 1998 | 1487 | 311 | RTA00000587F.o.03.1 | M00001575A:H02 |
| 312 | May 14, 1998 | 1487 | 312 | RTA00000597F.m.10.1 | M00003812D:E08 |
| 313 | May 14, 1998 | 1487 | 313 | RTA00000596F.1.10.1 | M00003749D:G07 |
| 314 | May 14, 1998 | 1487 | 314 | RTA00000584F.h.08.1 | M00001391D:A07 |
| 315 | May 14, 1998 | 1487 | 315 | RTA00000587F.f.07.1 | M00001543A:F01 |
| 316 | May 14, 1998 | 1487 | 316 | RTA00000595F.b.04.1 | M00001589D:G10 |
| 317 | May 14, 1998 | 1487 | 317 | RTA00000590F.d.17.1 | M00004345A:H06 |
| 318 | May 14, 1998 | 1487 | 318 | RTA00000612F.1.07.2 | M00004268D:G07 |
| 319 | May 14, 1998 | 1487 | 319 | RTA00000607F.e.15.2 | M00003911C:G05 |
| 320 | May 14, 1998 | 1487 | 320 | RTA00000614F.i.23.1 | M00004449D:H01 |
| 321 | May 14, 1998 | 1487 | 321 | RTA00000612F.1.08.2 | M00004269A:B11 |
| 322 | May 14, 1998 | 1487 | 322 | RTA00000608F.n.23.1 | M00004038C:C05 |
| 323 | May 14, 1998 | 1487 | 323 | RTA00000583F.e.11.1 | M00001347A:G06 |
| 324 | May 14, 1998 | 1487 | 324 | RTA00000612F.e.10.3 | M00004234B:E03 |
| 325 | May 14, 1998 | 1487 | 325 | RTA00000609F.0.20.1 | M00004091C:F04 |
| 326 | May 14, 1998 | 1487 | 326 | RTA00000583F.d.19.1 | M00001346B:A07 |
| 327 | May 14, 1998 | 1487 | 327 | RTA00000609F.o.16.2 | M00004091B:C12 |
| 328 | May 14, 1998 | 1487 | 328 | RTA00000586F.a.23.1 | M00001456C:F02 |
| 329 | May 14, 1998 | 1487 | 329 | RTA00000583F.j.04.3 | M00001359A:B07 |
| 330 | May 14, 1998 | 1487 | 330 | RTA00000585F.a.02.3 | M00001412D:C03 |
| 331 | May 14, 1998 | 1487 | 331 | RTA00000606F.o.02.1 | M00003884B:E06 |
| 332 | May 14, 1998 | 1487 | 332 | RTA00000609F.m.09.2 | M00004084C:G04 |
| 333 | May 14, 1998 | 1487 | 333 | RTA00000606F.b.10.1 | M00003826B:D01 |
| 334 | May 14, 1998 | 1487 | 334 | RTA00000596F.k.19.1 | M00003748B:B06 |
| 335 | May 14, 1998 | 1487 | 335 | RTA00000596F.o.17.1 | M00003763B:D03 |
| 336 | May 14, 1998 | 1487 | 336 | RTA00000611F.g.23.1 | M00004180B:F04 |
| 337 | May 14, 1998 | 1487 | 337 | RTA00000586F.m.05.1 | M00001496D:D02 |
| 338 | May 14, 1998 | 1487 | 338 | RTA00000612F.n.03.2 | M00004277B:C06 |
| 339 | May 14, 1998 | 1487 | 339 | RTA00000585F.b.18.3 | M00001417B:E01 |
| 340 | May 14, 1998 | 1487 | 340 | RTA00000606F.b.03.1 | M00003825B:A05 |
| 341 | May 14, 1998 | 1487 | 341 | RTA00000583F.n.05.1 | M00001370B:B04 |
| 342 | May 14, 1998 | 1487 | 342 | RTA00000607F.o.10.2 | M00003961B:A12 |
| 343 | May 14, 1998 | 1487 | 343 | RTA00000613F.c.13.1 | M00004297D:E08 |
| 344 | May 14, 1998 | 1487 | 344 | RTA00000595F.f.14.1 | M00001610B:A01 |
| 345 | May 14, 1998 | 1487 | 345 | RTA00000608F.a.10.3 | M00003973A:C05 |
| 346 | May 14, 1998 | 1487 | 346 | RTA00000609F.j.05.3 | M00004075A:G10 |
| 347 | May 14, 1998 | 1487 | 347 | RTA00000586F.d.01.1 | M00001463C:A01 |
| 348 | May 14, 1998 | 1487 | 348 | RTA00000612F.h.03.3 | M00004245A:G09 |
| 349 | May 14, 1998 | 1487 | 349 | RTA00000596F.e.18.2 | M00001678D:A12 |
| 350 | May 14, 1998 | 1487 | 350 | RTA00000606F.g.18.1 | M00003846B:H02 |
| 351 | May 14, 1998 | 1487 | 351 | RTA00000597F.c.07.4 | M00003773B:G08 |
| 352 | May 14, 1998 | 1487 | 352 | RTA00000610F.e.15.1 | M00004117B:F01 |
| 353 | May 14, 1998 | 1487 | 353 | RTA00000595F.h.07.1 | M00001618C:E06 |
| 354 | May 14, 1998 | 1487 | 354 | RTA00000597F.f.17.1 | M00003786D:C06 |
| 355 | May 14, 1998 | 1487 | 355 | RTA00000606F.l.10.1 | M00003868B:C07 |
| 356 | May 14, 1998 | 1487 | 356 | RTA00000586F.g.20.1 | M00001478A:B06 |
| 357 | May 14, 1998 | 1487 | 357 | RTA00000606F.b.05.1 | M00003825B:D12 |
| 358 | May 14, 1998 | 1487 | 358 | RTA00000588F.p.09.2 | M00003972B:A11 |
| 359 | May 14, 1998 | 1487 | 359 | RTA00000595F.d.05.1 | M00001599A:H09 |
| 360 | May 14, 1998 | 1487 | 360 | RTA00000587F.n.19.1 | M00001572C:E07 |
| 361 | May 14, 1998 | 1487 | 361 | RTA00000590F.a.02.1 | M00004240D:E06 |
| 362 | May 14, 1998 | 1487 | 362 | RTA00000587F.m.18.1 | M00001569B:F04 |
| 363 | May 14, 1998 | 1487 | 363 | RTA00000583F.k.09.3 | M00001362A:C10 |
| 364 | May 14, 1998 | 1487 | 364 | RTA00000608F.a.23.1 | M00003974B:A04 |
| 365 | May 14, 1998 | 1487 | 365 | RTA00000597F.e.22.1 | M00003784C:B09 |
| 366 | May 14, 1998 | 1487 | 366 | RTA00000583F.e.21.1 | M00001348A:G04 |
| 367 | May 14, 1998 | 1487 | 367 | RTA00000607F.e.20.2 | M00003912B:G11 |
| 368 | May 14, 1998 | 1487 | 368 | RTA00000614F.b.16.1 | M00004388C:D05 |
| 369 | May 14, 1998 | 1487 | 369 | RTA00000587F.b.03.1 | M00001518D:A10 |
| 370 | May 14, 1998 | 1487 | 370 | RTA00000609F.f.02.3 | M00004060C:A11 |
| 371 | May 14, 1998 | 1487 | 371 | RTA00000587F.c.20.1 | M00001536B:B11 |
| 372 | May 14, 1998 | 1487 | 372 | RTA00000612F.h.05.3 | M00004245C:A03 |
| 373 | May 14, 1998 | 1487 | 373 | RTA00000596F.j.13.1 | M00001693D:F07 |
| 374 | May 14, 1998 | 1487 | 374 | RTA00000585F.f.01.2 | M00001426D:D09 |
| 375 | May 14, 1998 | 1487 | 375 | RTA00000611F.m.07.3 | M00004196C:G05 |
| 376 | May 14, 1998 | 1487 | 376 | RTA00000606F.b.08.1 | M00003825C:B12 |
| 377 | May 14, 1998 | 1487 | 377 | RTA00000609F.b.10.2 | M00004048D:A07 |
| 378 | May 14, 1998 | 1487 | 378 | RTA00000609F.g.13.1 | M00004067C:D08 |

TABLE 1A-continued

Priority Appln Information

| SEQ ID NO: | Filed | Dkt No. | SEQ ID NO: | Sequence Name | Clone Name |
|---|---|---|---|---|---|
| 379 | May 14, 1998 | 1487 | 379 | RTA00000587F.l.11.1 | M00001565A:A02 |
| 380 | May 14, 1998 | 1487 | 380 | RTA00000608F.h.07.2 | M00003993A:E12 |
| 381 | May 14, 1998 | 1487 | 381 | RTA00000596F.m.21.1 | M00003754C:F01 |
| 382 | May 14, 1998 | 1487 | 382 | RTA00000586F.p.11.1 | M00001506D:A11 |
| 383 | May 14, 1998 | 1487 | 383 | RTA00000610F.c.01.1 | M00004104A:H09 |
| 384 | May 14, 1998 | 1487 | 384 | RTA00000597F.n.10.1 | M00003815C:A06 |
| 385 | May 14, 1998 | 1487 | 385 | RTA00000595F.c.14.1 | M00001597A:C07 |
| 386 | May 14, 1998 | 1487 | 386 | RTA00000586F.j.09.1 | M00001488B:G12 |
| 387 | May 14, 1998 | 1487 | 387 | RTA00000608F.l.20.1 | M00004032D:D03 |
| 388 | May 14, 1998 | 1487 | 388 | RTA00000613F.g.13.1 | M00004324B:D09 |
| 389 | May 14, 1998 | 1487 | 389 | RTA00000587F.j.21.1 | M00001561B:C10 |
| 390 | May 14, 1998 | 1487 | 390 | RTA00000583F.l.16.3 | M00001365D:H09 |
| 391 | May 14, 1998 | 1487 | 391 | RTA00000614F.d.16.1 | M00004406A:H03 |
| 392 | May 14, 1998 | 1487 | 392 | RTA00000610F.j.11.1 | M00004134A:F08 |
| 393 | May 14, 1998 | 1487 | 393 | RTA00000611F.j.11.1 | M00004188A:E05 |
| 394 | May 14, 1998 | 1487 | 394 | RTA00000609F.p.14.1 | M00004093A:F03 |
| 395 | May 14, 1998 | 1487 | 395 | RTA00000597F.l.18.1 | M00003811B:E07 |
| 396 | May 14, 1998 | 1487 | 396 | RTA00000585F.h.03.2 | M00001432A:F12 |
| 397 | May 14, 1998 | 1487 | 397 | RTA00000607F.h.23.1 | M00003920D:D09 |
| 398 | May 14, 1998 | 1487 | 398 | RTA00000607F.f.23.2 | M00003915B:G07 |
| 399 | May 14, 1998 | 1487 | 399 | RTA00000607F.f.18.2 | M00003915A:D09 |
| 400 | May 14, 1998 | 1487 | 400 | RTA00000609F.i.23.2 | M00004073D:B11 |
| 401 | May 14, 1998 | 1487 | 401 | RTA00000612F.f.05.3 | M00004236D:F04 |
| 402 | May 14, 1998 | 1487 | 402 | RTA00000597F.o.07.1 | M00003818B:A01 |
| 403 | May 14, 1998 | 1487 | 403 | RTA00000611F.o.06.5 | M00004201D:C11 |
| 404 | May 14, 1998 | 1487 | 404 | RTA00000589F.e.05.2 | M00004051C:D02 |
| 405 | May 14, 1998 | 1487 | 405 | RTA00000584F.o.07.1 | M00001407D:H11 |
| 406 | May 14, 1998 | 1487 | 406 | RTA00000608F.e.06.1 | M00003983A:D02 |
| 407 | May 14, 1998 | 1487 | 407 | RTA00000595F.a.22.1 | M00001588D:H08 |
| 408 | May 14, 1998 | 1487 | 408 | RTA00000611F.c.03.2 | M00004164D:D02 |
| 409 | May 14, 1998 | 1487 | 409 | RTA00000585F.c.03.2 | M00001418A:C02 |
| 410 | May 14, 1998 | 1487 | 410 | RTA00000611F.b.07.1 | M00004161B:A12 |
| 411 | May 14, 1998 | 1487 | 411 | RTA00000587F.g.09.2 | M00001546B:H01 |
| 412 | May 14, 1998 | 1487 | 412 | RTA00000611F.c.11.2 | M00004165C:E09 |
| 413 | May 14, 1998 | 1487 | 413 | RTA00000610F.c.18.1 | M00004108A:D04 |
| 414 | May 14, 1998 | 1487 | 414 | RTA00000611F.i.21.1 | M00004186B:E05 |
| 415 | May 14, 1998 | 1487 | 415 | RTA00000597F.e.11.1 | M00003782D:F04 |
| 416 | May 14, 1998 | 1487 | 416 | RTA00000586F.m.02.1 | M00001496C:H10 |
| 417 | May 14, 1998 | 1487 | 417 | RTA00000585F.b.20.3 | M00001417C:A09 |
| 418 | May 14, 1998 | 1487 | 418 | RTA00000606F.n.15.1 | M00003881D:D09 |
| 419 | May 14, 1998 | 1487 | 419 | RTA00000611F.h.17.2 | M00004183A:D06 |
| 420 | May 14, 1998 | 1487 | 420 | RTA00000609F.c.15.1 | M00004052C:A08 |
| 421 | May 14, 1998 | 1487 | 421 | RTA00000614F.m.10.1 | M00004497C:E09 |
| 422 | May 14, 1998 | 1487 | 422 | RTA00000612F.c.08.2 | M00004218D:F12 |
| 423 | May 14, 1998 | 1487 | 423 | RTA00000613F.h.22.1 | M00004332C:E09 |
| 424 | May 14, 1998 | 1487 | 424 | RTA00000587F.f.05.1 | M00001543A:D03 |
| 425 | May 14, 1998 | 1487 | 425 | RTA00000585F.k.04.1 | M00001438A:H10 |
| 426 | May 14, 1998 | 1487 | 426 | RTA00000585F.k.15.1 | M00001439B:F10 |
| 427 | May 14, 1998 | 1487 | 427 | RTA00000609F.p.04.1 | M00004092A:D04 |
| 428 | May 14, 1998 | 1487 | 428 | RTA00000585F.j.01.1 | M00001435C:H05 |
| 429 | May 14, 1998 | 1487 | 429 | RTA00000587F.a.20.1 | M00001517D:C03 |
| 430 | May 14, 1998 | 1487 | 430 | RTA00000609F.f.04.3 | M00004060D:A07 |
| 431 | May 14, 1998 | 1487 | 431 | RTA00000611F.k.13.2 | M00004190D:A10 |
| 432 | May 14, 1998 | 1487 | 432 | RTA00000586F.f.08.2 | M00001471C:G03 |
| 433 | May 14, 1998 | 1487 | 433 | RTA00000585F.i.14.1 | M00001435A:G01 |
| 434 | May 14, 1998 | 1487 | 434 | RTA00000614F.b.08.1 | M00004385C:B11 |
| 435 | May 14, 1998 | 1487 | 435 | RTA00000609F.o.04.2 | M00004089A:G03 |
| 436 | May 14, 1998 | 1487 | 436 | RTA00000583F.n.03.1 | M00001370A:B01 |
| 437 | May 14, 1998 | 1487 | 437 | RTA00000584F.j.05.1 | M00001396C:G02 |
| 438 | May 14, 1998 | 1487 | 438 | RTA00000608F.a.16.2 | M00003973B:H06 |
| 439 | May 14, 1998 | 1487 | 439 | RTA00000583F.b.15.1 | M00001341A:A11 |
| 440 | May 14, 1998 | 1487 | 440 | RTA00000596F.a.22.1 | M00001659D:G08 |
| 441 | May 14, 1998 | 1487 | 441 | RTA00000589F.c.15.1 | M00004030A:G12 |
| 442 | May 14, 1998 | 1487 | 442 | RTA00000610F.o.03.1 | M00004149B:H12 |
| 443 | May 14, 1998 | 1487 | 443 | RTA00000596F.e.06.2 | M00001677A:A12 |
| 444 | May 14, 1998 | 1487 | 444 | RTA00000607F.p.01.2 | M00003965A:F07 |
| 445 | May 14, 1998 | 1487 | 445 | RTA00000611F.c.16.2 | M00004166A:F02 |
| 446 | May 14, 1998 | 1487 | 446 | RTA00000611F.b.01.1 | M00004159D:H07 |
| 447 | May 14, 1998 | 1487 | 447 | RTA00000612F.b.12.2 | M00004217A:A11 |
| 448 | May 14, 1998 | 1487 | 448 | RTA00000584F.h.09.1 | M00001391D:A09 |
| 449 | May 14, 1998 | 1487 | 449 | RTA00000612F.g.18.3 | M00004242C:C02 |
| 450 | May 14, 1998 | 1487 | 450 | RTA00000609F.b.18.2 | M00004049D:G04 |
| 451 | May 14, 1998 | 1487 | 451 | RTA00000608F.f.17.1 | M00003987D:F06 |

TABLE 1A-continued

Priority Appln Information

| SEQ ID NO: | Filed | Dkt No. | SEQ ID NO: | Sequence Name | Clone Name |
|---|---|---|---|---|---|
| 452 | May 14, 1998 | 1487 | 452 | RTA00000589F.e.21.2 | M00004058B:F12 |
| 453 | May 14, 1998 | 1487 | 453 | RTA00000606F.j.07.1 | M00003857C:A03 |
| 454 | May 14, 1998 | 1487 | 454 | RTA00000610F.b.21.1 | M00004103C:F11 |
| 455 | May 14, 1998 | 1487 | 455 | RTA00000611F.c.22.2 | M00004166D:G07 |
| 456 | May 14, 1998 | 1487 | 456 | RTA00000583F.d.04.1 | M00001344D:G11 |
| 457 | May 14, 1998 | 1487 | 457 | RTA00000610F.h.08.1 | M00004126B:G02 |
| 458 | May 14, 1998 | 1487 | 458 | RTA00000596F.a.06.1 | M00001658B:C07 |
| 459 | May 14, 1998 | 1487 | 459 | RTA00000612F.o.10.2 | M00004281B:B05 |
| 460 | May 14, 1998 | 1487 | 460 | RTA00000610F.l.22.1 | M00004143A:G12 |
| 461 | May 14, 1998 | 1487 | 461 | RTA00000612F.o.09.2 | M00004281B:B03 |
| 462 | May 14, 1998 | 1487 | 462 | RTA00000596F.f.09.2 | M00001681A:H09 |
| 463 | May 14, 1998 | 1487 | 463 | RTA00000607F.p.13.2 | M00003970A:G10 |
| 464 | May 14, 1998 | 1487 | 464 | RTA00000610F.e.11.1 | M00004115C:H04 |
| 465 | May 14, 1998 | 1487 | 465 | RTA00000611F.b.02.1 | M00004160A:A01 |
| 466 | May 14, 1998 | 1487 | 466 | RTA00000608F.j.24.1 | M00004027C:H01 |
| 467 | May 14, 1998 | 1487 | 467 | RTA00000614F.k.22.1 | M00004470C:A02 |
| 468 | May 14, 1998 | 1487 | 468 | RTA00000612F.h.09.3 | M00004247A:E01 |
| 469 | May 14, 1998 | 1487 | 469 | RTA00000587F.f.01.1 | M00001542C:D10 |
| 470 | May 14, 1998 | 1487 | 470 | RTA00000608F.d.04.1 | M00003980C:G10 |
| 471 | May 14, 1998 | 1487 | 471 | RTA00000585F.m.16.2 | M00001443D:C03 |
| 472 | May 14, 1998 | 1487 | 472 | RTA00000613F.c.17.1 | M00004298B:D04 |
| 473 | May 14, 1998 | 1487 | 473 | RTA00000613F.h.19.1 | M00004332B:D02 |
| 474 | May 14, 1998 | 1487 | 474 | RTA00000609F.d.07.1 | M00004054B:G02 |
| 475 | May 14, 1998 | 1487 | 475 | RTA00000606F.0.17.1 | M00003887B:C03 |
| 476 | May 14, 1998 | 1487 | 476 | RTA00000585F.n.10.1 | M00001445B:E03 |
| 477 | May 14, 1998 | 1487 | 477 | RTA00000612F.p.04.2 | M00004284B:F07 |
| 478 | May 14, 1998 | 1487 | 478 | RTA00000589F.c.02.1 | M00003997B:H04 |
| 479 | May 14, 1998 | 1487 | 479 | RTA00000608F.p.16.1 | M00004044A:F08 |
| 480 | May 14, 1998 | 1487 | 480 | RTA00000597F.n.12.1 | M00003815D:D01 |
| 481 | May 14, 1998 | 1487 | 481 | RTA00000608F.l.10.1 | M00004031A:G05 |
| 482 | May 14, 1998 | 1487 | 482 | RTA00000606F.o.05.1 | M00003884D:A12 |
| 483 | May 14, 1998 | 1487 | 483 | RTA00000587F.j.05.1 | M00001558B:A12 |
| 484 | May 14, 1998 | 1487 | 484 | RTA00000584F.d.15.1 | M00001384A:C09 |
| 485 | May 14, 1998 | 1487 | 485 | RTA00000612F.n.22.1 | M00004279D:E02 |
| 486 | May 14, 1998 | 1487 | 486 | RTA00000585F.m.13.2 | M00001443D:A01 |
| 487 | May 14, 1998 | 1487 | 487 | RTA00000586F.m.22.1 | M00001500A:D09 |
| 488 | May 14, 1998 | 1487 | 488 | RTA00000608F.i.17.1 | M00003997D:G11 |
| 489 | May 14, 1998 | 1487 | 489 | RTA00000614F.k.04.1 | M00004466A:E09 |
| 490 | May 14, 1998 | 1487 | 490 | RTA00000608F.n.15.1 | M00004037C:C05 |
| 491 | May 14, 1998 | 1487 | 491 | RTA00000610F.m.06.1 | M00004143C:F08 |
| 492 | May 14, 1998 | 1487 | 492 | RTA00000585F.d.12.2 | M00001422D:D02 |
| 493 | May 14, 1998 | 1487 | 493 | RTA00000608F.b.19.1 | M00003976D:D12 |
| 494 | May 14, 1998 | 1487 | 494 | RTA00000596F.k.06.1 | M00003745C:E03 |
| 495 | May 14, 1998 | 1487 | 495 | RTA00000609F.o.14.2 | M00004091A:E01 |
| 496 | May 14, 1998 | 1487 | 496 | RTA00000607F.m.14.1 | M00003949B:A08 |
| 497 | May 14, 1998 | 1487 | 497 | RTA00000606F.f.08.1 | M00003841B:D05 |
| 498 | May 14, 1998 | 1487 | 498 | RTA00000583F.l.14.3 | M00001365D:D12 |
| 499 | May 14, 1998 | 1487 | 499 | RTA00000614F.g.04.1 | M00004419D:G01 |
| 500 | May 14, 1998 | 1487 | 500 | RTA00000610F.m.21.1 | M00004145C:A03 |
| 501 | May 14, 1998 | 1487 | 501 | RTA00000585F.d.16.1 | M00001423C:D06 |
| 502 | May 14, 1998 | 1487 | 502 | RTA00000588F.o.05.2 | M00003918C:E07 |
| 503 | May 14, 1998 | 1487 | 503 | RTA00000585F.b.04.3 | M00001415D:E12 |
| 504 | May 14, 1998 | 1487 | 504 | RTA00000588F.d.21.1 | M00001687C:A06 |
| 505 | May 14, 1998 | 1487 | 505 | RTA00000595F.g.16.1 | M00001614C:G04 |
| 506 | May 14, 1998 | 1487 | 506 | RTA00000612F.i.18.2 | M00004253B:F06 |
| 507 | May 14, 1998 | 1487 | 507 | RTA00000612F.e.12.1 | M00004234B:G06 |
| 508 | May 14, 1998 | 1487 | 508 | RTA00000583F.p.08.1 | M00001374D:D09 |
| 509 | May 14, 1998 | 1487 | 509 | RTA00000608F.b.04.1 | M00003974C:A05 |
| 510 | May 14, 1998 | 1487 | 510 | RTA00000596F.l.07.1 | M00003749B:C08 |
| 511 | May 14, 1998 | 1487 | 511 | RTA00000597F.l.02.1 | M00003809A:H12 |
| 512 | May 14, 1998 | 1487 | 512 | RTA00000595F.j.05.1 | M00001626C:C10 |
| 513 | May 14, 1998 | 1487 | 513 | RTA00000586F.k.18.1 | M00001491D:E07 |
| 514 | May 14, 1998 | 1487 | 514 | RTA00000608F.p.07.1 | M00004041D:E06 |
| 515 | May 14, 1998 | 1487 | 515 | RTA00000596F.m.07.1 | M00003752D:D09 |
| 516 | May 14, 1998 | 1487 | 516 | RTA00000588F.l.20.2 | M00003859C:B09 |
| 517 | May 14, 1998 | 1487 | 517 | RTA00000614F.a.20.1 | M00004383A:F02 |
| 518 | May 14, 1998 | 1487 | 518 | RTA00000597F.i.20.1 | M00003799B:D02 |
| 519 | May 14, 1998 | 1487 | 519 | RTA00000611F.n.143 | M00004200A:A09 |
| 520 | May 14, 1998 | 1487 | 520 | RTA00000586F.m.10.1 | M00001499A:D01 |
| 521 | May 14, 1998 | 1487 | 521 | RTA00000607F.i.06.4 | M00003921D:C06 |
| 522 | May 14, 1998 | 1487 | 522 | RTA00000585F.p.19.2 | M00001453B:F08 |
| 523 | May 14, 1998 | 1487 | 523 | RTA00000583F.c.06.1 | M00001342C:A04 |
| 524 | May 14, 1998 | 1487 | 524 | RTA00000595F.p.20.1 | M00001656D:F11 |

TABLE 1A-continued

Priority Appln Information

| SEQ ID NO: | Filed | Dkt No. | SEQ ID NO: | Sequence Name | Clone Name |
|---|---|---|---|---|---|
| 525 | May 14, 1998 | 1487 | 525 | RTA00000606F.g.02.1 | M00003844C:D04 |
| 526 | May 14, 1998 | 1487 | 526 | RTA00000606F.d.10.1 | M00003834A:A03 |
| 527 | May 14, 1998 | 1487 | 527 | RTA00000597F.f.21.1 | M00003787B:D07 |
| 528 | May 14, 1998 | 1487 | 528 | RTA00000613F.h.17.1 | M00004331D:H08 |
| 529 | May 14, 1998 | 1487 | 529 | RTA00000612F.h.19.3 | M00004249D:G02 |
| 530 | May 14, 1998 | 1487 | 530 | RTA00000589F.h.23.1 | M00004091B:G04 |
| 531 | May 14, 1998 | 1487 | 531 | RTA00000614F.e.06.1 | M00004408D:A10 |
| 532 | May 14, 1998 | 1487 | 532 | RTA00000612F.j.20.2 | M00004262C:C01 |
| 533 | May 14, 1998 | 1487 | 533 | RTA00000597F.m.07.1 | M00003812B:F08 |
| 534 | May 14, 1998 | 1487 | 534 | RTA00000589F.j.08.1 | M00004115A:F01 |
| 535 | May 14, 1998 | 1487 | 535 | RTA00000609F.g.16.1 | M00004068A:F02 |
| 536 | May 14, 1998 | 1487 | 536 | RTA00000587F.j.18.1 | M00001556D:A11 |
| 537 | May 14, 1998 | 1487 | 537 | RTA00000610F.c.05.1 | M00004104D:C09 |
| 538 | May 14, 1998 | 1487 | 538 | RTA00000607F.o.16.2 | M00003963B:D12 |
| 539 | May 14, 1998 | 1487 | 539 | RTA00000585F.i.08.1 | M00001434C:D05 |
| 540 | May 14, 1998 | 1487 | 540 | RTA00000584F.a.15.2 | M00001377A:E01 |
| 541 | May 14, 1998 | 1487 | 541 | RTA00000611F.p.24.2 | M00004210A:B09 |
| 542 | May 14, 1998 | 1487 | 542 | RTA00000607F.a.13.3 | M00003893C:D12 |
| 543 | May 14, 1998 | 1487 | 543 | RTA00000612F.f.03.1 | M00004236D:E07 |
| 544 | May 14, 1998 | 1487 | 544 | RTA00000606F.p.14.1 | M00003890B:H07 |
| 545 | May 14, 1998 | 1487 | 545 | RTA00000612F.j.17.2 | M00004260C:E10 |
| 546 | May 14, 1998 | 1487 | 546 | RTA00000585F.c.24.2 | M00001421A:H07 |
| 547 | May 14, 1998 | 1487 | 547 | RTA00000607F.i.24.2 | M00003926B:E03 |
| 548 | May 14, 1998 | 1487 | 548 | RTA00000609F.e.15.3 | M00004058C:E08 |
| 549 | May 14, 1998 | 1487 | 549 | RTA00000584F.p.18.1 | M00001411C:G02 |
| 550 | May 14, 1998 | 1487 | 550 | RTA00000610F.i.10.1 | M00004130C:A09 |
| 551 | May 14, 1998 | 1487 | 551 | RTA00000585F.b.17.3 | M00001417B:C07 |
| 552 | May 14, 1998 | 1487 | 552 | RTA00000586F.o.12.1 | M00001504C:H11 |
| 553 | May 14, 1998 | 1487 | 553 | RTA00000608F.g.24.1 | M00003992C:G01 |
| 554 | May 14, 1998 | 1487 | 554 | RTA00000584F.e.20.1 | M00001387A:A04 |
| 555 | May 14, 1998 | 1487 | 555 | RTA00000588F.j.23.3 | M00003843A:B01 |
| 556 | May 14, 1998 | 1487 | 556 | RTA00000585F.b.21.3 | M00001417C:E02 |
| 557 | May 14, 1998 | 1487 | 557 | RTA00000584F.o.08.1 | M00001408A:B02 |
| 558 | May 14, 1998 | 1487 | 558 | RTA00000587F.k.22.1 | M00001563C:D06 |
| 559 | May 14, 1998 | 1487 | 559 | RTA00000608F.a.07.3 | M00003972C:F02 |
| 560 | May 14, 1998 | 1487 | 560 | RTA00000597F.c.04.4 | M00003773B:E09 |
| 561 | May 14, 1998 | 1487 | 561 | RTA00000596F.c.06.1 | M00001669B:A03 |
| 562 | May 14, 1998 | 1487 | 562 | RTA00000588F.o.01.2 | M00003912C:H01 |
| 563 | May 14, 1998 | 1487 | 563 | RTA00000597F.i.16.1 | M00003797D:H06 |
| 564 | May 14, 1998 | 1487 | 564 | RTA00000583F.n.07.1 | M00001370B:D04 |
| 565 | May 14, 1998 | 1487 | 565 | RTA00000597F.f.07.1 | M00003785D:E01 |
| 566 | May 14, 1998 | 1487 | 566 | RTA00000587F.f.06.1 | M00001543A:E04 |
| 567 | May 14, 1998 | 1487 | 567 | RTA00000614F.o.11.1 | M00004509A:H02 |
| 568 | May 14, 1998 | 1487 | 568 | RTA00000597F.b.16.5 | M00003771D:A10 |
| 569 | May 14, 1998 | 1487 | 569 | RTA00000608F.m.19.1 | M00004035B:H11 |
| 570 | May 14, 1998 | 1487 | 570 | RTA00000597F.k.21.1 | M00003808C:D09 |
| 571 | May 14, 1998 | 1487 | 571 | RTA00000584F.o.13.1 | M00001409C:D01 |
| 572 | May 14, 1998 | 1487 | 572 | RTA00000588F.n.10.3 | M00003895D:A03 |
| 573 | May 14, 1998 | 1487 | 573 | RTA00000589F.h.17.1 | M00004089A:F02 |
| 574 | May 14, 1998 | 1487 | 574 | RTA00000609F.h.13.1 | M00004069D:G02 |
| 575 | May 14, 1998 | 1487 | 575 | RTA00000608F.p.15.1 | M00004043D:C10 |
| 576 | May 14, 1998 | 1487 | 576 | RTA00000595F.l.16.1 | M00001640A:F02 |
| 577 | May 14, 1998 | 1487 | 577 | RTA00000585F.j.21.1 | M00001437B:B05 |
| 578 | May 14, 1998 | 1487 | 578 | RTA00000595F.o.01.2 | M00001649B:E08 |
| 579 | May 14, 1998 | 1487 | 579 | RTA00000606F.c.03.1 | M00003829A:B08 |
| 580 | May 14, 1998 | 1487 | 580 | RTA00000583F.n.04.1 | M00001370A:G09 |
| 581 | May 14, 1998 | 1487 | 581 | RTA00000596F.p.20.1 | M00003766B:G04 |
| 582 | May 14, 1998 | 1487 | 582 | RTA00000611F.c.20.2 | M00004166C:A03 |
| 583 | May 14, 1998 | 1487 | 583 | RTA00000584F.l.19.1 | M00001399D:F09 |
| 584 | May 14, 1998 | 1487 | 584 | RTA00000589F.p.23.1 | M00004239C:A07 |
| 585 | May 14, 1998 | 1487 | 585 | RTA00000607F.c.09.2 | M00003903C:H03 |
| 586 | May 14, 1998 | 1487 | 586 | RTA00000585F.p.23.2 | M00001453D:F09 |
| 587 | May 14, 1998 | 1487 | 587 | RTA00000596F.j.13.1 | M00003741A:E01 |
| 588 | May 14, 1998 | 1487 | 588 | RTA00000584F.m.03.1 | M00001400D:B08 |
| 589 | May 14, 1998 | 1487 | 589 | RTA00000595F.o.03.2 | M00001649D:H05 |
| 590 | May 14, 1998 | 1487 | 590 | RTA00000589F.j.03.1 | M00004109B:A01 |
| 591 | May 14, 1998 | 1487 | 591 | RTA00000610F.c.14.1 | M00004107C:A01 |
| 592 | May 14, 1998 | 1487 | 592 | RTA00000614F.f.02.1 | M00004412B:E03 |
| 593 | May 14, 1998 | 1487 | 593 | RTA00000608F.b.23.1 | M00003977C:A08 |
| 594 | May 14, 1998 | 1487 | 594 | RTA00000597F.i.06.1 | M00003796B:C07 |
| 595 | May 14, 1998 | 1487 | 595 | RTA00000609F.n.20.1 | M00004087C:F05 |
| 596 | May 14, 1998 | 1487 | 596 | RTA00000597F.c.08.2 | M00003773C:G06 |
| 597 | May 14, 1998 | 1487 | 597 | RTA00000612F.c.05.2 | M00004218C:G10 |

TABLE 1A-continued

Priority Appln Information

| SEQ ID NO: | Filed | Dkt No. | SEQ ID NO: | Sequence Name | Clone Name |
|---|---|---|---|---|---|
| 598 | May 14, 1998 | 1487 | 598 | RTA00000589F.o.14.1 | M00004202B:A02 |
| 599 | May 14, 1998 | 1487 | 599 | RTA00000609F.h.15.1 | M00004071A:H03 |
| 600 | May 14, 1998 | 1487 | 600 | RTA00000596F.p.15.1 | M00003765D:E02 |
| 601 | May 14, 1998 | 1487 | 601 | RTA00000597F.k.22.1 | M00003809A:A12 |
| 602 | May 14, 1998 | 1487 | 602 | RTA00000608F.k.09.1 | M00004028C:D01 |
| 603 | May 14, 1998 | 1487 | 603 | RTA00000612F.p.23.2 | M00004287C:B06 |
| 604 | May 14, 1998 | 1487 | 604 | RTA00000610F.n.02.1 | M00004146D:A07 |
| 605 | May 14, 1998 | 1487 | 605 | RTA00000587F.h.19.2 | M00001551D:C12 |
| 606 | May 14, 1998 | 1487 | 606 | RTA00000607F.k.18.1 | M00003934D:F01 |
| 607 | May 14, 1998 | 1487 | 607 | RTA00000588F.m.10.3 | M00003868D:F07 |
| 608 | May 14, 1998 | 1487 | 608 | RTA00000612F.p.21.1 | M00004287B:B12 |
| 609 | May 14, 1998 | 1487 | 609 | RTA00000585F.m.08.1 | M00001443A:E02 |
| 610 | May 14, 1998 | 1487 | 610 | RTA00000612F.d.01.1 | M00004225D:F01 |
| 611 | May 14, 1998 | 1487 | 611 | RTA00000596F.d.20.1 | M00001675C:B03 |
| 612 | May 14, 1998 | 1487 | 612 | RTA00000611F.k.12.2 | M00004190C:G07 |
| 613 | May 14, 1998 | 1487 | 613 | RTA00000612F.j.11.2 | M00004257C:A08 |
| 614 | May 14, 1998 | 1487 | 614 | RTA00000614F.j.16.1 | M00004463C:F11 |
| 615 | May 14, 1998 | 1487 | 615 | RTA00000611F.k.15.3 | M00004190D:G12 |
| 616 | May 14, 1998 | 1487 | 616 | RTA00000612F.j.01.2 | M00004253D:F09 |
| 617 | May 14, 1998 | 1487 | 617 | RTA00000606F.o.23.1 | M00003888B:A10 |
| 618 | May 14, 1998 | 1487 | 618 | RTA00000606F.i.13.1 | M00003852D:D03 |
| 619 | May 14, 1998 | 1487 | 619 | RTA00000588F.i.22.3 | M00003833D:D06 |
| 620 | May 14, 1998 | 1487 | 620 | RTA00000585F.j.03.1 | M00001435D:A06 |
| 621 | May 14, 1998 | 1487 | 621 | RTA00000608F.i.21.1 | M00003998A:G12 |
| 622 | May 14, 1998 | 1487 | 622 | RTA00000584F.o.02.1 | M00001406D:B06 |
| 623 | May 14, 1998 | 1487 | 623 | RTA00000608F.m.17.1 | M00004035B:F05 |
| 624 | May 14, 1998 | 1487 | 624 | RTA00000612F.k.08.2 | M00004263D:F06 |
| 625 | May 14, 1998 | 1487 | 625 | RTA00000608F.p.20.1 | M00004045A:B12 |
| 626 | May 14, 1998 | 1487 | 626 | RTA00000610F.n.07.1 | M00004147A:G03 |
| 627 | May 14, 1998 | 1487 | 627 | RTA00000608F.j.17.1 | M00004027A:B10 |
| 628 | May 14, 1998 | 1487 | 628 | RTA00000596F.n.23.1 | M00003759A:E10 |
| 629 | May 14, 1998 | 1487 | 629 | RTA00000612F.a.17.2 | M00004214A:D03 |
| 630 | May 14, 1998 | 1487 | 630 | RTA00000612F.i.17.2 | M00004253B:A10 |
| 631 | May 14, 1998 | 1487 | 631 | RTA00000585F.p.15.2 | M00001452D:E05 |
| 632 | May 14, 1998 | 1487 | 632 | RTA00000614F.m.15.1 | M00004498B:E01 |
| 633 | May 14, 1998 | 1487 | 633 | RTA00000607F.a.08.3 | M00003892D:D04 |
| 634 | May 14, 1998 | 1487 | 634 | RTA00000606F.p.16.1 | M00003890D:C03 |
| 635 | May 14, 1998 | 1487 | 635 | RTA00000610F.j.12.1 | M00004134A:H04 |
| 636 | May 14, 1998 | 1487 | 636 | RTA00000608F.o.16.1 | M00004040C:G12 |
| 637 | May 14, 1998 | 1487 | 637 | RTA00000588F.o.20.2 | M00003958C:C10 |
| 638 | May 14, 1998 | 1487 | 638 | RTA00000585F.p.06.2 | M00001451B:H11 |
| 639 | May 14, 1998 | 1487 | 639 | RTA00000610F.j.05.1 | M00004133D:A01 |
| 640 | May 14, 1998 | 1487 | 640 | RTA00000606F.e.17.1 | M00003839C:B05 |
| 641 | May 14, 1998 | 1487 | 641 | RTA00000609F.n.05.1 | M00004086A:A03 |
| 642 | May 14, 1998 | 1487 | 642 | RTA00000614F.p.22.1 | M00004609C:C11 |
| 643 | May 14, 1998 | 1487 | 643 | RTA00000585F.h.16.2 | M00001433A:F04 |
| 644 | May 14, 1998 | 1487 | 644 | RTA00000611F.n.02.3 | M00004198D:H04 |
| 645 | May 14, 1998 | 1487 | 645 | RTA00000614F.p.06.1 | M00004605C:A09 |
| 646 | May 14, 1998 | 1487 | 646 | RTA00000584F.l.17.1 | M00001399D:F01 |
| 647 | May 14, 1998 | 1487 | 647 | RTA00000584F.p.17.1 | M00001411C:F02 |
| 648 | May 14, 1998 | 1487 | 648 | RTA00000595F.l.17.1 | M00001640A:F04 |
| 649 | May 14, 1998 | 1487 | 649 | RTA00000583F.h.07.1 | M00001353B:D11 |
| 650 | May 14, 1998 | 1487 | 650 | RTA00000585F.l.19.1 | M00001442A:D08 |
| 651 | May 14, 1998 | 1487 | 651 | RTA00000610F.i.13.1 | M00004130D:E04 |
| 652 | May 14, 1998 | 1487 | 652 | RTA00000608F.n.05.1 | M00004036B:F09 |
| 653 | May 14, 1998 | 1487 | 653 | RTA00000612F.m.19.1 | M00004276C:E12 |
| 654 | May 14, 1998 | 1487 | 654 | RTA00000595F.h.22.1 | M00001621C:A04 |
| 655 | May 14, 1998 | 1487 | 655 | RTA00000608F.j.12.1 | M00003999C:C12 |
| 656 | May 14, 1998 | 1487 | 656 | RTA00000608F.k.07.2 | M00004028C:B04 |
| 657 | May 14, 1998 | 1487 | 657 | RTA00000608F.o.12.1 | M00004040B:B09 |
| 658 | May 14, 1998 | 1487 | 658 | RTA00000597F.a.08.5 | M00003767C:F04 |
| 659 | May 14, 1998 | 1487 | 659 | RTA00000585F.i.23.1 | M00001435C:G08 |
| 660 | May 14, 1998 | 1487 | 660 | RTA00000586F.j.06.1 | M00001487D:G03 |
| 661 | May 14, 1998 | 1487 | 661 | RTA00000608F.b.15.1 | M00003976C:C05 |
| 662 | May 14, 1998 | 1487 | 662 | RTA00000609F.h.06.1 | M00004069B:B01 |
| 663 | May 14, 1998 | 1487 | 663 | RTA00000612F.h.13.3 | M00004248A:G08 |
| 664 | May 14, 1998 | 1487 | 664 | RTA00000611F.j.08.1 | M00004187C:H09 |
| 665 | May 14, 1998 | 1487 | 665 | RTA00000609F.j.18.1 | M00004076A:E02 |
| 666 | May 14, 1998 | 1487 | 666 | RTA00000608F.p.01.1 | M00004041B:F01 |
| 667 | May 14, 1998 | 1487 | 667 | RTA00000584F.m.16.1 | M00001402D:H03 |
| 668 | May 14, 1998 | 1487 | 668 | RTA00000589F.d.04.1 | M00004036C:D01 |
| 669 | May 14, 1998 | 1487 | 669 | RTA00000612F.p.12.2 | M00004285B:E01 |
| 670 | May 14, 1998 | 1487 | 670 | RTA00000589F.e.09.1 | M00004052C:B05 |

TABLE 1A-continued

Priority Appln Information

| SEQ ID NO: | Filed | Dkt No. | SEQ ID NO: | Sequence Name | Clone Name |
|---|---|---|---|---|---|
| 671 | May 14, 1998 | 1487 | 671 | RTA00000584F.m.11.1 | M00001402C:E09 |
| 672 | May 14, 1998 | 1487 | 672 | RTA00000595F.i.18.1 | M00001624A:A09 |
| 673 | May 14, 1998 | 1487 | 673 | RTA00000609F.k.04.2 | M00004078A:F03 |
| 674 | May 14, 1998 | 1487 | 674 | RTA00000611F.n.17.2 | M00004200B:B04 |
| 675 | May 14, 1998 | 1487 | 675 | RTA00000595F.j.03.1 | M00001626B:H05 |
| 676 | May 14, 1998 | 1487 | 676 | RTA00000611F.o.11.3 | M00004202B:F04 |
| 677 | May 14, 1998 | 1487 | 677 | RTA00000597F.e.16.1 | M00003783C:A06 |
| 678 | May 14, 1998 | 1487 | 678 | RTA00000583F.d.16.1 | M00001346A:B09 |
| 679 | May 14, 1998 | 1487 | 679 | RTA00000589F.l.24.1 | M00004159D:C04 |
| 680 | May 14, 1998 | 1487 | 680 | RTA00000597F.a.17.2 | M00003769B:A04 |
| 681 | May 14, 1998 | 1487 | 681 | RTA00000584F.p.22.1 | M00001412A:A11 |
| 682 | May 14, 1998 | 1487 | 682 | RTA00000587F.i.23.1 | M00001557B:D10 |
| 683 | May 14, 1998 | 1487 | 683 | RTA00000612F.l.16.2 | M00004269D:E08 |
| 684 | May 14, 1998 | 1487 | 684 | RTA00000584F.c.01.1 | M00001380C:D10 |
| 685 | May 14, 1998 | 1487 | 685 | RTA00000606F.g.21.1 | M00003846D:C12 |
| 686 | May 14, 1998 | 1487 | 686 | RTA00000611F.j.12.1 | M00004188A:E10 |
| 687 | May 14, 1998 | 1487 | 687 | RTA00000585F.h.10.2 | M00001432C:G01 |
| 688 | May 14, 1998 | 1487 | 688 | RTA00000585F.h.10.1 | M00001432C:G01 |
| 689 | May 14, 1998 | 1487 | 689 | RTA00000587F.j.15.1 | M00001560C:C01 |
| 690 | May 14, 1998 | 1487 | 690 | RTA00000608F.o.06.1 | M00004039D:D03 |
| 691 | May 14, 1998 | 1487 | 691 | RTA00000596F.e.05.2 | M00001677A:A06 |
| 692 | May 14, 1998 | 1487 | 692 | RTA00000584F.p.07.1 | M00001411A:D01 |
| 693 | May 14, 1998 | 1487 | 693 | RTA00000612F.i.13.2 | M00004252D:H08 |
| 694 | May 14, 1998 | 1487 | 694 | RTA00000607F.i.14.4 | M00003923A:H07 |
| 695 | May 14, 1998 | 1487 | 695 | RTA00000595F.m.17.2 | M00001645B:C09 |
| 696 | May 14, 1998 | 1487 | 696 | RTA00000595F.i.02.1 | M00001621D:B09 |
| 697 | May 14, 1998 | 1487 | 697 | RTA00000585F.p.12.2 | M00001452B:F09 |
| 698 | May 14, 1998 | 1487 | 698 | RTA00000589F.m.02.1 | M00004160A:D07 |
| 699 | May 14, 1998 | 1487 | 699 | RTA00000595F.p.11.1 | M00001655A:F07 |
| 700 | May 14, 1998 | 1487 | 700 | RTA00000589F.o.15.1 | M00004202B:G09 |
| 701 | May 14, 1998 | 1487 | 701 | RTA00000609F.e.12.3 | M00004058B:C11 |
| 702 | May 14, 1998 | 1487 | 702 | RTA00000588F.l.13.2 | M00003858A:D01 |
| 703 | May 14, 1998 | 1487 | 703 | RTA00000608F.f.22.2 | M00003988B:C10 |
| 704 | May 14, 1998 | 1487 | 704 | RTA00000612F.i.11.2 | M00004252D:A07 |
| 705 | May 14, 1998 | 1487 | 705 | RTA00000590F.b.13.1 | M00004277D:C08 |
| 706 | May 14, 1998 | 1487 | 706 | RTA00000609F.a.21.2 | M00004047B:G09 |
| 707 | May 14, 1998 | 1487 | 707 | RTA00000586F.e.12.1 | M00001468D:D11 |
| 708 | May 14, 1998 | 1487 | 708 | RTA00000595F.k.10.1 | M00001634C:E12 |
| 709 | May 14, 1998 | 1487 | 709 | RTA00000583F.e.02.1 | M00001346C:B07 |
| 710 | May 14, 1998 | 1487 | 710 | RTA00000589F.d.01.1 | M00004035D:C05 |
| 711 | May 14, 1998 | 1487 | 711 | RTA00000584F.n.14.1 | M00001406A:G12 |
| 712 | May 14, 1998 | 1487 | 712 | RTA00000612F.k.21.2 | M00004266B:H06 |
| 713 | May 14, 1998 | 1487 | 713 | RTA00000612F.m.05.1 | M00004272D:D02 |
| 714 | May 14, 1998 | 1487 | 714 | RTA00000584F.a.20.2 | M00001377C:B08 |
| 715 | May 14, 1998 | 1487 | 715 | RTA00000612F.b.11.2 | M00004217A:A05 |
| 716 | May 14, 1998 | 1487 | 716 | RTA00000610F.h.13.1 | M00004126D:B11 |
| 717 | May 14, 1998 | 1487 | 717 | RTA00000611F.d.04.1 | M00004167C:F10 |
| 718 | May 14, 1998 | 1487 | 718 | RTA00000607F.f.12.2 | M00003914C:E03 |
| 719 | May 14, 1998 | 1487 | 719 | RTA00000586F.j.10.1 | M00001488B:H02 |
| 720 | May 14, 1998 | 1487 | 720 | RTA00000584F.p.20.1 | M00001411D:C01 |
| 721 | May 14, 1998 | 1487 | 721 | RTA00000612F.i.19.2 | M00004253C:E10 |
| 722 | May 14, 1998 | 1487 | 722 | RTA00000608F.i.09.1 | M00003996D:C04 |
| 723 | May 14, 1998 | 1487 | 723 | RTA00000584F.g.09.1 | M00001390A:H01 |
| 724 | May 14, 1998 | 1487 | 724 | RTA00000584F.n.12.1 | M00001405D:F05 |
| 725 | May 14, 1998 | 1487 | 725 | RTA00000584F.j.12.1 | M00001397B:H11 |
| 726 | May 14, 1998 | 1487 | 726 | RTA00000611F.h.21.2 | M00004183D:B07 |
| 727 | May 14, 1998 | 1487 | 727 | RTA00000606F.l.23.1 | M00003871A:E09 |
| 728 | May 14, 1998 | 1487 | 728 | RTA00000585F.b.01.3 | M00001415D:A05 |
| 729 | May 14, 1998 | 1487 | 729 | RTA00000595F.i.13.1 | M00001623B:B01 |
| 730 | May 14, 1998 | 1487 | 730 | RTA00000589F.l.22.1 | M00004158C:F03 |
| 731 | May 14, 1998 | 1487 | 731 | RTA00000608F.l.14.1 | M00004031D:G02 |
| 732 | May 14, 1998 | 1487 | 732 | RTA00000614F.k.18.1 | M00004469A:C12 |
| 733 | May 14, 1998 | 1487 | 733 | RTA00000609F.g.19.1 | M00004068B:D04 |
| 734 | May 14, 1998 | 1487 | 734 | RTA00000606F.g.05.1 | M00003845A:A05 |
| 735 | May 14, 1998 | 1487 | 735 | RTA00000585F.i.03.1 | M00001434A:A01 |
| 736 | May 14, 1998 | 1487 | 736 | RTA00000590F.a.15.1 | M00004247B:C11 |
| 737 | May 14, 1998 | 1487 | 737 | RTA00000612F.j.15.2 | M00004260C:A12 |
| 738 | May 14, 1998 | 1487 | 738 | RTA00000612F.g.13.3 | M00004241B:B01 |
| 739 | May 14, 1998 | 1487 | 739 | RTA00000606F.d.21.1 | M00003835D:H05 |
| 740 | May 14, 1998 | 1487 | 740 | RTA00000584F.b.06.1 | M00001378B:F06 |
| 741 | May 14, 1998 | 1487 | 741 | RTA00000614F.e.17.1 | M00004410A:E03 |
| 742 | May 14, 1998 | 1487 | 742 | RTA00000612F.a.13.2 | M00004213A:H12 |
| 743 | May 14, 1998 | 1487 | 743 | RTA00000585F.o.10.2 | M00001448A:D05 |

TABLE 1A-continued

Priority Appln Information

| SEQ ID NO: | Filed | Dkt No. | SEQ ID NO: | Sequence Name | Clone Name |
|---|---|---|---|---|---|
| 744 | May 14, 1998 | 1487 | 744 | RTA00000588F.i.14.3 | M00003830A:A10 |
| 745 | May 14, 1998 | 1487 | 745 | RTA00000595F.e.10.1 | M00001605D:G01 |
| 746 | May 14, 1998 | 1487 | 746 | RTA00000584F.b.06.2 | M00001378B:F06 |
| 747 | May 14, 1998 | 1487 | 747 | RTA00000608F.j.05.1 | M00003998C:H10 |
| 748 | May 14, 1998 | 1487 | 748 | RTA00000611F.j.24.2 | M00004190A:C12 |
| 749 | May 14, 1998 | 1487 | 749 | RTA00000606F.h.12.1 | M00003850B:D11 |
| 750 | May 14, 1998 | 1487 | 750 | RTA00000608F.c.22.1 | M00003980B:F12 |
| 751 | May 14, 1998 | 1487 | 751 | RTA00000588F.b.03.1 | M00001618B:F02 |
| 752 | May 15, 1998 | 1488 | 1 | RTA00000623F.c.23.1 | M00007118C:G2 |
| 753 | May 15, 1998 | 1488 | 2 | RTA00000592F.e.05.1 | M00005799C:C12 |
| 754 | May 15, 1998 | 1488 | 3 | RTA00000590F.p.04.1 | M00005390B:G10 |
| 755 | May 15, 1998 | 1488 | 4 | RTA00000621F.m.13.1 | M00006986C:G11 |
| 756 | May 15, 1998 | 1488 | 5 | RTA00000625F.n.12.1 | M00006604C:H10 |
| 757 | May 15, 1998 | 1488 | 6 | RTA00000624F.b.01.1 | M00005539D:G7 |
| 758 | May 15, 1998 | 1488 | 7 | RTA00000618F.h.12.1 | M00006698B:E6 |
| 759 | May 15, 1998 | 1488 | 8 | RTA00000615F.h.16.1 | M00005015D:D11 |
| 760 | May 15, 1998 | 1488 | 9 | RTA00000618F.l.23.1 | M00006721C:G7 |
| 761 | May 15, 1998 | 1488 | 10 | RTA00000619F.n.10.3 | M00006820A:G5 |
| 762 | May 15, 1998 | 1488 | 11 | RTA00000621F.o.06.1 | M00006992C:G2 |
| 763 | May 15, 1998 | 1488 | 12 | RTA00000619F.c.17.1 | M00006756D:E10 |
| 764 | May 15, 1998 | 1488 | 13 | RTA00000615F.i.14.1 | M00005294D:H2 |
| 765 | May 15, 1998 | 1488 | 14 | RTA00000617F.k.23.1 | M00005496D:A10 |
| 766 | May 15, 1998 | 1488 | 15 | RTA00000623F.e.05.1 | M00007125D:E3 |
| 767 | May 15, 1998 | 1488 | 16 | RTA00000617F.c.04.1 | M00005456B:B7 |
| 768 | May 15, 1998 | 1488 | 17 | RTA00000623F.a.23.1 | M00007107A:D11 |
| 769 | May 15, 1998 | 1488 | 18 | RTA00000619F.f.15.1 | M00006770B:C5 |
| 770 | May 15, 1998 | 1488 | 19 | RTA00000626F.f.07.1 | M00006650A:A10 |
| 771 | May 15, 1998 | 1488 | 20 | R1A00000624F.h.14.1 | M00005621D:F1 |
| 772 | May 15, 1998 | 1488 | 21 | RTA00000617F.f.09.2 | M00005469D:C11 |
| 773 | May 15, 1998 | 1488 | 22 | RTA00000620F.b.02.1 | M00006835B:F4 |
| 774 | May 15, 1998 | 1488 | 23 | RTA00000616F.k.05.1 | M00005415D:G2 |
| 775 | May 15, 1998 | 1488 | 24 | RTA00000617F.a.01.1 | M00005447B:D2 |
| 776 | May 15, 1998 | 1488 | 25 | RTA00000592F.f.23.1 | M00006587A:H8 |
| 777 | May 15, 1998 | 1488 | 26 | RTA00000623F.h.17.1 | M00007150A:C9 |
| 778 | May 15, 1998 | 1488 | 27 | RTA00000622F.b.02.1 | M00007010B:H1 |
| 779 | May 15, 1998 | 1488 | 28 | RTA00000621F.p.05.1 | M00006995C:A2 |
| 780 | May 15, 1998 | 1488 | 29 | RTA00000620F.j.05.1 | M00006884D:D6 |
| 781 | May 15, 1998 | 1488 | 30 | RTA00000623F.h.20.1 | M00007150A:H6 |
| 782 | May 15, 1998 | 1488 | 31 | RTA00000590F.p.21.1 | M00005399A:D1 |
| 783 | May 15, 1998 | 1488 | 32 | RTA00000622F.c.03.1 | M00007013B:F2 |
| 784 | May 15, 1998 | 1488 | 33 | RTA00000623F.f.06.1 | M00007132B:B11 |
| 785 | May 15, 1998 | 1488 | 34 | RTA00000617F.e.23.2 | M00005468A:D8 |
| 786 | May 15, 1998 | 1488 | 35 | RTA00000623F.n.17.1 | M00007204C:F9 |
| 787 | May 15, 1998 | 1488 | 36 | RTA00000619F.a.12.1 | M00006743B:G12 |
| 788 | May 15, 1998 | 1488 | 37 | RTA00000621F.n.06.1 | M00006989B:C11 |
| 789 | May 15, 1998 | 1488 | 38 | RTA00000623F.a.18.1 | M00007105D:C7 |
| 790 | May 15, 1998 | 1488 | 39 | RTA00000624F.a.15.1 | M00005534B:H10 |
| 791 | May 15, 1998 | 1488 | 40 | RTA00000625F.h.04.1 | M00005810C:D4 |
| 792 | May 15, 1998 | 1488 | 41 | RTA00000591F.g.05.1 | M00005460B:D2 |
| 793 | May 15, 1998 | 1488 | 42 | RTA00000620F.i.14.1 | M00006882A:D1 |
| 794 | May 15, 1998 | 1488 | 43 | RTA00000624F.a.14.1 | M00005534A:G6 |
| 795 | May 15, 1998 | 1488 | 44 | RTA00000621F.h.14.1 | M00006960D:E6 |
| 796 | May 15, 1998 | 1488 | 45 | RTA00000617F.k.19.1 | M00005494D:F11 |
| 797 | May 15, 1998 | 1488 | 46 | RTA00000625F.d.17.1 | M00005763B:H9 |
| 798 | May 15, 1998 | 1488 | 47 | RTA00000620F.l.13.1 | M00006901D:A11 |
| 799 | May 15, 1998 | 1488 | 48 | RTA00000623F.g.04.1 | M00007140A:F11 |
| 800 | May 15, 1998 | 1488 | 49 | RTA00000622F.b.03.1 | M00007010B:H3 |
| 801 | May 15, 1998 | 1488 | 50 | RTA00000615F.k.17.1 | M00005342A:C4 |
| 802 | May 15, 1998 | 1488 | 51 | RTA00000618F.m.11.1 | M00006725A:A3 |
| 803 | May 15, 1998 | 1488 | 52 | RTA00000618F.e.06.1 | M00006686A:G12 |
| 804 | May 15, 1998 | 1488 | 53 | RTA00000619F.k.08.1 | M00006805B:C4 |
| 805 | May 15, 1998 | 1488 | 54 | RTA00000590F.h.23.2 | M00004840C:F2 |
| 806 | May 15, 1998 | 1488 | 55 | RTA00000622F.c.09.1 | M00007014C:B7 |
| 807 | May 15, 1998 | 1488 | 56 | RTA00000619F.h.17.1 | M00006785B:F9 |
| 808 | May 15, 1998 | 1488 | 57 | RTA00000617F.d.01.1 | M00005460A:B10 |
| 809 | May 15, 1998 | 1488 | 58 | RTA00000620F.b.17.1 | M00006837C:G6 |
| 810 | May 15, 1998 | 1488 | 59 | RTA00000616F.c.13.1 | M00005383D:D6 |
| 811 | May 15, 1998 | 1488 | 60 | RTA00000619F.g.16.1 | M00006779B:A11 |
| 812 | May 15, 1998 | 1488 | 61 | RTA00000591F.i.12.1 | M00005480A:H12 |
| 813 | May 15, 1998 | 1488 | 62 | RTA00000615F.b.20.1 | M00004846A:D2 |
| 814 | May 15, 1998 | 1488 | 63 | RTA00000615F.l.18.1 | M00005352C:G9 |
| 815 | May 15, 1998 | 1488 | 64 | RTA00000591F.m.19.1 | M00005519B:H4 |
| 816 | May 15, 1998 | 1488 | 65 | RTA00000620F.i.10.1 | M00006879A:H11 |

TABLE 1A-continued

Priority Appln Information

| SEQ ID NO: | Filed | Dkt No. | SEQ ID NO: | Sequence Name | Clone Name |
|---|---|---|---|---|---|
| 817 | May 15, 1998 | 1488 | 66 | RTA00000618F.o.02.1 | M00006733D:G12 |
| 818 | May 15, 1998 | 1488 | 67 | RTA00000620F.c.18.1 | M00006846A:B1 |
| 819 | May 15, 1998 | 1488 | 68 | RTA00000624F.a.07.1 | M00005530B:D3 |
| 820 | May 15, 1998 | 1488 | 69 | RTA00000592F.c.10.1 | M00005704A:B11 |
| 821 | May 15, 1998 | 1488 | 70 | RTA00000618F.c.04.1 | M00006676B:F11 |
| 822 | May 15, 1998 | 1488 | 71 | RTA00000591F.f.04.1 | M00005452C:A2 |
| 823 | May 15, 1998 | 1488 | 72 | RTA00000617F.k.22.1 | M00005496C:A1 |
| 824 | May 15, 1998 | 1488 | 73 | RTA00000626F.e.02.1 | M00006644A:B11 |
| 825 | May 15, 1998 | 1488 | 74 | RTA00000592F.d.09.1 | M00005765C:C4 |
| 826 | May 15, 1998 | 1488 | 75 | RTA00000615F.n.23.1 | M00005359D:H8 |
| 827 | May 15, 1998 | 1488 | 76 | RTA00000591F.i.15.1 | M00005480C:B12 |
| 828 | May 15, 1998 | 1488 | 77 | RTA00000624F.a.11.1 | M00005531B:A3 |
| 829 | May 15, 1998 | 1488 | 78 | RTA00000590F.i.01.1 | M00004841C:B9 |
| 830 | May 15, 1998 | 1488 | 79 | RTA00000626F.d.05.1 | M00006640A:B1 |
| 831 | May 15, 1998 | 1488 | 80 | RTA00000591F.e.19.1 | M00005450A:B10 |
| 832 | May 15, 1998 | 1488 | 81 | RTA00000625F.m.06.1 | M00006594A:E8 |
| 833 | May 15, 1998 | 1488 | 82 | RTA00000615F.k.22.1 | M00005342B:G10 |
| 834 | May 15, 1998 | 1488 | 83 | RTA00000615F.m.11.1 | M00005354C:E2 |
| 835 | May 15, 1998 | 1488 | 84 | RTA00000624F.j.16.1 | M00005631A:A11 |
| 836 | May 15, 1998 | 1488 | 85 | RTA00000626F.d.07.1 | M00006640B:F5 |
| 837 | May 15, 1998 | 1488 | 86 | RTA00000620F.p.19.1 | M00006923C:B1 |
| 838 | May 15, 1998 | 1488 | 87 | RTA00000615F.f.10.1 | M00004999A:F1 |
| 839 | May 15, 1998 | 1488 | 88 | RTA00000615F.b.19.1 | M00004845D:E11 |
| 840 | May 15, 1998 | 1488 | 89 | RTA00000626F.a.07.1 | M00006626A:G11 |
| 841 | May 15, 1998 | 1488 | 90 | RTA00000592F.b.20.1 | M00005685B:D8 |
| 842 | May 15, 1998 | 1488 | 91 | RTA00000622F.p.16.1 | M00007100C:D1 |
| 843 | May 15, 1998 | 1488 | 92 | RTA00000620F.a.16.1 | M00006834A:C8 |
| 844 | May 15, 1998 | 1488 | 93 | RTA00000623F.e.21.1 | M00007130B:B3 |
| 845 | May 15, 1998 | 1488 | 94 | RTA00000619F.k.05.1 | M00006805A:E11 |
| 846 | May 15, 1998 | 1488 | 95 | RTA00000626F.c.10.1 | M00006636D:A5 |
| 847 | May 15, 1998 | 1488 | 96 | RTA00000619F.i.13.1 | M00006791B:B8 |
| 848 | May 15, 1998 | 1488 | 97 | RTA00000620F.k.22.1 | M00006895D:E10 |
| 849 | May 15, 1998 | 1488 | 98 | RTA00000617F.a.17.1 | M00005450D:D2 |
| 850 | May 15, 1998 | 1488 | 99 | RTA00000617F.c.18.1 | M00005457D:C8 |
| 851 | May 15, 1998 | 1488 | 100 | RTA00000626F.g.12.1 | M00006664B:B4 |
| 852 | May 15, 1998 | 1488 | 101 | RTA00000617F.j.11.1 | M00005489A:F6 |
| 853 | May 15, 1998 | 1488 | 102 | RTA00000621F.c.11.1 | M00006936B:E9 |
| 854 | May 15, 1998 | 1488 | 103 | RTA00000623F.f.12.1 | M00007134B:G7 |
| 855 | May 15, 1998 | 1488 | 104 | RTA00000626F.g.17.1 | M00006665A:F7 |
| 856 | May 15, 1998 | 1488 | 105 | RTA00000619F.o.06.4 | M00006823D:D12 |
| 857 | May 15, 1998 | 1488 | 106 | RTA00000625F.j.10.1 | M00005837A:D12 |
| 858 | May 15, 1998 | 1488 | 107 | RTA00000620F.k.12.1 | M00006893C:F2 |
| 859 | May 15, 1998 | 1488 | 108 | RTA00000625F.j.06.1 | M00005828D:C9 |
| 860 | May 15, 1998 | 1488 | 109 | RTA00000616F.b.12.1 | M00005378A:A8 |
| 861 | May 15, 1998 | 1488 | 110 | RTA00000620F.d.04.1 | M00006850C:G7 |
| 862 | May 15, 1998 | 1488 | 111 | RTA00000624F.n.20.1 | M00005655D:C4 |
| 863 | May 15, 1998 | 1488 | 112 | RTA00000620F.m.14.1 | M00006907C:D3 |
| 864 | May 15, 1998 | 1488 | 113 | RTA00000625F.m.15.1 | M00006596D:H4 |
| 865 | May 15, 1998 | 1488 | 114 | RTA00000619F.g.19.1 | M00006779D:D3 |
| 866 | May 15, 1998 | 1488 | 115 | RTA00000626F.b.10.1 | M00006633D:A6 |
| 867 | May 15, 1998 | 1488 | 116 | RTA00000618F.c.23.1 | M00006679C:D7 |
| 868 | May 15, 1998 | 1488 | 117 | RTA00000591F.o.17.1 | M00005616B:D5 |
| 869 | May 15, 1998 | 1488 | 118 | RTA00000615F.b.23.1 | M00004846D:H9 |
| 870 | May 15, 1998 | 1488 | 119 | RTA00000616F.e.20.1 | M00005394A:G7 |
| 871 | May 15, 1998 | 1488 | 120 | RTA00000625F.b.23.1 | M00005720B:D9 |
| 872 | May 15, 1998 | 1488 | 121 | RTA00000616F.i.13.4 | M00005409D:C2 |
| 873 | May 15, 1998 | 1488 | 122 | RTA00000624F.l.02.1 | M00005637D:C5 |
| 874 | May 15, 1998 | 1488 | 123 | RTA00000619F.b.06.1 | M00006745D:E8 |
| 875 | May 15, 1998 | 1488 | 124 | RTA00000626F.b.23.1 | M00006636A:E6 |
| 876 | May 15, 1998 | 1488 | 125 | RTA00000615F.k.24.1 | M00005342D:F3 |
| 877 | May 15, 1998 | 1488 | 126 | RTA00000621F.h.22.1 | M00006963A:H11 |
| 878 | May 15, 1998 | 1488 | 127 | RTA00000626F.b.05.1 | M00006631D:C4 |
| 879 | May 15, 1998 | 1488 | 128 | RTA00000621F.i.20.2 | M00006966D:G3 |
| 880 | May 15, 1998 | 1488 | 129 | RTA00000624F.m.10.1 | M00005646D:B3 |
| 881 | May 15, 1998 | 1488 | 130 | RTA00000623F.m.19.1 | M00007198C:A10 |
| 882 | May 15, 1998 | 1488 | 131 | RTA00000622F.c.12.1 | M00007014D:D4 |
| 883 | May 15, 1998 | 1488 | 132 | RTA00000617F.i.08.1 | M00005483D:A2 |
| 884 | May 15, 1998 | 1488 | 133 | RTA00000625F.b.07.1 | M00005710A:C8 |
| 885 | May 15, 1998 | 1488 | 134 | RTA00000620F.f.23.1 | M00006867C:E7 |
| 886 | May 15, 1998 | 1488 | 135 | RTA00000620F.f.15.1 | M00006866C:F3 |
| 887 | May 15, 1998 | 1488 | 136 | RTA00000621F.k.17.1 | M00006974B:D6 |
| 888 | May 15, 1998 | 1488 | 137 | RTA00000625F.h.18.1 | M00005813D:F6 |
| 889 | May 15, 1998 | 1488 | 138 | RTA00000622F.p.17.1 | M00007101A:A11 |

TABLE 1A-continued

Priority Appln Information

| SEQ ID NO: | Filed | Dkt No. | SEQ ID NO: | Sequence Name | Clone Name |
|---|---|---|---|---|---|
| 890 | May 15, 1998 | 1488 | 139 | RTA00000620F.d.08.1 | M00006851C:H9 |
| 891 | May 15, 1998 | 1488 | 140 | RTA00000621F.i.14.2 | M00006966B:B9 |
| 892 | May 15, 1998 | 1488 | 141 | RTA00000625F.j.19.1 | M00006576D:F11 |
| 893 | May 15, 1998 | 1488 | 142 | RTA00000618F.o.23.1 | M00006737C:A8 |
| 894 | May 15, 1998 | 1488 | 143 | RTA00000618F.m.12.1 | M00006725A:B3 |
| 895 | May 15, 1998 | 1488 | 144 | RTA00000625F.o.19.1 | M00006616D:C8 |
| 896 | May 15, 1998 | 1488 | 145 | RTA00000619F.a.18.1 | M00006744C:C6 |
| 897 | May 15, 1998 | 1488 | 146 | RTA00000624F.c.15.1 | M00005565C:A8 |
| 898 | May 15, 1998 | 1488 | 147 | RTA00000617F.e.13.2 | M00005465C:H2 |
| 899 | May 15, 1998 | 1488 | 148 | RTA00000592F.j.06.1 | M00006664D:H9 |
| 900 | May 15, 1998 | 1488 | 149 | RTA00000615F.n.18.1 | M00005359B:G1 |
| 901 | May 15, 1998 | 1488 | 150 | RTA00000624F.c.02.1 | M00005550B:D9 |
| 902 | May 15, 1998 | 1488 | 151 | RTA00000620F.j.10.1 | M00006886A:D6 |
| 903 | May 15, 1998 | 1488 | 152 | RTA00000620F.e.07.1 | M00006860B:H1 |
| 904 | May 15, 1998 | 1488 | 153 | RTA00000625F.g.07.1 | M00005798B:C11 |
| 905 | May 15, 1998 | 1488 | 154 | RTA00000617F.d.22.1 | M00005462C:B2 |
| 906 | May 15, 1998 | 1488 | 155 | RTA00000622F.a.12.1 | M00007006D:D4 |
| 907 | May 15, 1998 | 1488 | 156 | RTA00000620F.i.11.1 | M00006879D:A10 |
| 908 | May 15, 1998 | 1488 | 157 | RTA00000616F.k.03.1 | M00005415C:G8 |
| 909 | May 15, 1998 | 1488 | 158 | RTA00000624F.k.17.1 | M00005636C:D11 |
| 910 | May 15, 1998 | 1488 | 159 | RTA00000615F.f.11.1 | M00004999B:D12 |
| 911 | May 15, 1998 | 1488 | 160 | RTA00000620F.o.07.1 | M00006917C:E7 |
| 912 | May 15, 1998 | 1488 | 161 | RTA00000617F.k.11.1 | M00005493B:C8 |
| 913 | May 15, 1998 | 1488 | 162 | RTA00000622F.g.04.1 | M00007037B:D4 |
| 914 | May 15, 1998 | 1488 | 163 | RTA00000591F.n.04.1 | M00005528D:H6 |
| 915 | May 15, 1998 | 1488 | 164 | RTA00000625F.a.16.1 | M00005706D:A9 |
| 916 | May 15, 1998 | 1488 | 165 | RTA00000620F.m.18.1 | M00006908C:AS |
| 917 | May 15, 1998 | 1488 | 166 | RTA00000620F.a.04.1 | M00006832D:F10 |
| 918 | May 15, 1998 | 1488 | 167 | RTA00000624F.j.20.1 | M00005632C:D6 |
| 919 | May 15, 1998 | 1488 | 168 | RTA00000590F.n.19.1 | M00005378C:A10 |
| 920 | May 15, 1998 | 1488 | 169 | RTA00000626F.c.13.1 | M00006636D:F11 |
| 921 | May 15, 1998 | 1488 | 170 | RTA00000617F.f.01.2 | M00005468B:D4 |
| 922 | May 15, 1998 | 1488 | 171 | RTA00000621F.i.18.2 | M00006966C:B7 |
| 923 | May 15, 1998 | 1488 | 172 | RTA00000617F.a.13.1 | M00005450A:A2 |
| 924 | May 15, 1998 | 1488 | 173 | RTA00000591F.m.06.1 | M00005513A:D8 |
| 925 | May 15, 1998 | 1488 | 174 | RTA00000615F.g.07.1 | M00005004B:C11 |
| 926 | May 15, 1998 | 1488 | 175 | RTA00000616F.o.24.1 | M00005442D:C5 |
| 927 | May 15, 1998 | 1488 | 176 | RTA00000617F.a.20.1 | M00005451A:E3 |
| 928 | May 15, 1998 | 1488 | 177 | RTA00000626F.a.18.1 | M00006629D:D4 |
| 929 | May 15, 1998 | 1488 | 178 | RTA00000616F.c.23.1 | M00005385C:D8 |
| 930 | May 15, 1998 | 1488 | 179 | RTA00000623F.m.07.1 | M00007193D:A4 |
| 931 | May 15, 1998 | 1488 | 180 | RTA00000620F.h.18.1 | M00006875D:D10 |
| 932 | May 15, 1998 | 1488 | 181 | RTA00000615F.l.16.1 | M00005352B:D2 |
| 933 | May 15, 1998 | 1488 | 182 | RTA00000592F.c.17.1 | M00005708D:B3 |
| 934 | May 15, 1998 | 1488 | 183 | RTA00000616F.c.24.1 | M00005385C:G5 |
| 935 | May 15, 1998 | 1488 | 184 | RTA00000619F.l.16.1 | M00006813A:C4 |
| 936 | May 15, 1998 | 1488 | 185 | RTA00000622F.c.18.1 | M00007015C:G5 |
| 937 | May 15, 1998 | 1488 | 186 | RTA00000620F.p.09.1 | M00006921B:E3 |
| 938 | May 15, 1998 | 1488 | 187 | RTA00000626F.f.08.1 | M00006650A:B11 |
| 939 | May 15, 1998 | 1488 | 188 | RTA00000621F.h.08.1 | M00006960A:G11 |
| 940 | May 15, 1998 | 1488 | 189 | RTA00000591F.g.19.1 | M00005466A:F12 |
| 941 | May 15, 1998 | 1488 | 190 | RTA00000623F.m.10.1 | M00007195B:B2 |
| 942 | May 15, 1998 | 1488 | 191 | RTA00000619F.j.13.1 | M00006796A:H10 |
| 943 | May 15, 1998 | 1488 | 192 | RTA00000619F.f.22.1 | M00006771A:H7 |
| 944 | May 15, 1998 | 1488 | 193 | RTA00000622F.m.06.1 | M00007075C:D8 |
| 945 | May 15, 1998 | 1488 | 194 | RTA00000623F.i.03.1 | M00007154A:E4 |
| 946 | May 15, 1998 | 1488 | 195 | RTA00000625F.k.08.1 | M00006581D:H8 |
| 947 | May 15, 1998 | 1488 | 196 | RTA00000615F.c.13.1 | M00004854A:C9 |
| 948 | May 15, 1998 | 1488 | 197 | RTA00000619F.j.11.1 | M00006796A:C3 |
| 949 | May 15, 1998 | 1488 | 198 | RTA00000619F.o.01.1 | M00006822D:F7 |
| 950 | May 15, 1998 | 1488 | 199 | RTA00000590F.h.12.2 | M00004826A:E9 |
| 951 | May 15, 1998 | 1488 | 200 | RTA00000623F.d.07.1 | M00007121C:H1 |
| 952 | May 15, 1998 | 1488 | 201 | RTA00000616F.f.24.1 | M00005397C:B3 |
| 953 | May 15, 1998 | 1488 | 202 | RTA00000625F.o.03.1 | M00006609A:G10 |
| 954 | May 15, 1998 | 1488 | 203 | RTA00000619F.k.20.1 | M00006807D:D8 |
| 955 | May 15, 1998 | 1488 | 204 | RTA00000625F.n.22.1 | M00006607B:F4 |
| 956 | May 15, 1998 | 1488 | 205 | RTA00000625F.n.03.1 | M00006601D:F4 |
| 957 | May 15, 1998 | 1488 | 206 | RTA00000619F.c.13.1 | M00006756B:B8 |
| 958 | May 15, 1998 | 1488 | 207 | RTA00000625F.g.21.1 | M00005805D:E6 |
| 959 | May 15, 1998 | 1488 | 208 | RTA00000620F.g.06.1 | M00006868D:E2 |
| 960 | May 15, 1998 | 1488 | 209 | RTA00000622F.l.04.1 | M00007065B:B12 |
| 961 | May 15, 1998 | 1488 | 210 | RTA00000624F.d.21.1 | M00005587B:H2 |
| 962 | May 15, 1998 | 1488 | 211 | RTA00000622F.f.20.1 | M00007036A:D2 |

TABLE 1A-continued

Priority Appln Information

| SEQ ID NO: | Filed | Dkt No. | SEQ ID NO: | Sequence Name | Clone Name |
|---|---|---|---|---|---|
| 963 | May 15, 1998 | 1488 | 212 | RTA00000616F.d.09.1 | M00005388A:F7 |
| 964 | May 15, 1998 | 1488 | 213 | RTA00000620F.n.05.1 | M00006912B:E1 |
| 965 | May 15, 1998 | 1488 | 214 | RTA00000624F.k.22.1 | M00005637B:D12 |
| 966 | May 15, 1998 | 1488 | 215 | RTA00000618F.p.11.1 | M00006739B:B12 |
| 967 | May 15, 1998 | 1488 | 216 | RTA00000615F.g.09.1 | M00005005C:E6 |
| 968 | May 15, 1998 | 1488 | 217 | RTA00000618F.j.23.1 | M00006712B:H10 |
| 969 | May 15, 1998 | 1488 | 218 | RTA00000617F.l.02.1 | M00005497B:H7 |
| 970 | May 15, 1998 | 1488 | 219 | RTA00000617F.l.09.1 | M00005498B:F8 |
| 971 | May 15, 1998 | 1488 | 220 | RTA00000625F.n.21.1 | M00006607B:E3 |
| 972 | May 15, 1998 | 1488 | 221 | RTA00000623F.c.20.1 | M00007118B:B4 |
| 973 | May 15, 1998 | 1488 | 222 | RTA00000603F.d.13.1 | M00007019A:B1 |
| 974 | May 15, 1998 | 1488 | 223 | RTA00000625F.k.06.1 | M00006581C:D2 |
| 975 | May 15, 1998 | 1488 | 224 | RTA00000624F.b.23.1 | M00005548B:E3 |
| 976 | May 15, 1998 | 1488 | 225 | RTA00000626F.d.11.1 | M00006640D:H8 |
| 977 | May 15, 1998 | 1488 | 226 | RTA00000620F.g.14.1 | M00006870C:H6 |
| 978 | May 15, 1998 | 1488 | 227 | RTA00000621F.l.17.1 | M00006980A:F2 |
| 979 | May 15, 1998 | 1488 | 228 | RTA00000624F.o.13.1 | M00005685A:A4 |
| 980 | May 15, 1998 | 1488 | 229 | RTA00000621F.k.18.1 | M00006974B:F6 |
| 981 | May 15, 1998 | 1488 | 230 | RTA00000591F.a.23.1 | M00005411D:A3 |
| 982 | May 15, 1998 | 1488 | 231 | RTA00000592F.i.01.1 | M00006641C:H2 |
| 983 | May 15, 1998 | 1488 | 232 | RTA00000625F.p.10.1 | M00006619B:C11 |
| 984 | May 15, 1998 | 1488 | 233 | RTA00000622F.h.04.1 | M00007041B:C5 |
| 985 | May 15, 1998 | 1488 | 234 | RTA00000591F.e.08.1 | M00005446A:G1 |
| 986 | May 15, 1998 | 1488 | 235 | RTA00000619F.d.13.1 | M00006758D:C4 |
| 987 | May 15, 1998 | 1488 | 236 | RTA00000622F.p.10.1 | M00007099A:F9 |
| 988 | May 15, 1998 | 1488 | 237 | RTA00000623F.m.04.1 | M00007192C:H8 |
| 989 | May 15, 1998 | 1488 | 238 | RTA00000617F.i.06.1 | M00005483A:F5 |
| 990 | May 15, 1998 | 1488 | 239 | RTA00000624F.d.24.1 | M00005589C:B3 |
| 991 | May 15, 1998 | 1488 | 240 | RTA00000616F.p.08.1 | M00005444B:E11 |
| 992 | May 15, 1998 | 1488 | 241 | RTA00000615F.j.18.1 | M00005326B:F3 |
| 993 | May 15, 1998 | 1488 | 242 | RTA00000625F.p.19.1 | M00006621A:G10 |
| 994 | May 15, 1998 | 1488 | 243 | RTA00000624F.h.09.1 | M00005620C:C5 |
| 995 | May 15, 1998 | 1488 | 244 | RTA00000619F.d.23.1 | M00006760D:G12 |
| 996 | May 15, 1998 | 1488 | 245 | RTA00000618F.f.24.1 | M00006692B:E4 |
| 997 | May 15, 1998 | 1488 | 246 | RTA00000617F.l.12.1 | M00005498C:G5 |
| 998 | May 15, 1998 | 1488 | 247 | RTA00000621F.o.09.1 | M00006993B:B9 |
| 999 | May 15, 1998 | 1488 | 248 | RTA00000616F.p.04.1 | M00005443D:C12 |
| 1000 | May 15, 1998 | 1488 | 249 | RTA00000620F.c.08.1 | M00006841D:A8 |
| 1001 | May 15, 1998 | 1488 | 250 | RTA00000625F.n.01.1 | M00006601C:A7 |
| 1002 | May 15, 1998 | 1488 | 251 | RTA00000617F.k.10.1 | M00005493B:A12 |
| 1003 | May 15, 1998 | 1488 | 252 | RTA00000624F.l.11.1 | M00005641B:E2 |
| 1004 | May 15, 1998 | 1488 | 253 | RTA00000624F.h.06.1 | M00005619C:H10 |
| 1005 | May 15, 1998 | 1488 | 254 | RTA00000624F.h.11.1 | M00005621A:G10 |
| 1006 | May 15, 1998 | 1488 | 255 | RTA00000590F.h.07.2 | M00004824C:G9 |
| 1007 | May 15, 1998 | 1488 | 256 | RTA00000590F.o.09.1 | M00005384A:A1 |
| 1008 | May 15, 1998 | 1488 | 257 | RTA00000620F.e.16.1 | M00006863B:E6 |
| 1009 | May 15, 1998 | 1488 | 258 | RTA00000620F.k.11.1 | M00006893C:B2 |
| 1010 | May 15, 1998 | 1488 | 259 | RTA00000619F.o.18.4 | M00006825C:D6 |
| 1011 | May 15, 1998 | 1488 | 260 | RTA00000621F.k.03.1 | M00006972A:F10 |
| 1012 | May 15, 1998 | 1488 | 261 | RTA00000625F.c.11.1 | M00005722D:G3 |
| 1013 | May 15, 1998 | 1488 | 262 | RTA00000618F.n.05.1 | M00006727B:G8 |
| 1014 | May 15, 1998 | 1488 | 263 | RTA00000623F.d.02.1 | M00007119B:H10 |
| 1015 | May 15, 1998 | 1488 | 264 | RTA00000615F.k.05.1 | M00005330C:F9 |
| 1016 | May 15, 1998 | 1488 | 265 | RTA00000623F.f.09.1 | M00007132D:G8 |
| 1017 | May 15, 1998 | 1488 | 266 | RTA00000622F.d.01.1 | M00007016C:E6 |
| 1018 | May 15, 1998 | 1488 | 267 | RTA00000618F.p.10.1 | M00006739B:B10 |
| 1019 | May 15, 1998 | 1488 | 268 | RTA00000624F.l.23.1 | M00005645D:F8 |
| 1020 | May 15, 1998 | 1488 | 269 | RTA00000619F.e.19.1 | M00006764B:D5 |
| 1021 | May 15, 1998 | 1488 | 270 | RTA00000622F.h.12.1 | M00007043A:B5 |
| 1022 | May 15, 1998 | 1488 | 271 | RTA00000622F.i.23.1 | M00007051D:D9 |
| 1023 | May 15, 1998 | 1488 | 272 | RTA00000624F.l.13.1 | M00005642B:C3 |
| 1024 | May 15, 1998 | 1488 | 273 | RTA00000624F.a.04.1 | M00005528D:A10 |
| 1025 | May 15, 1998 | 1488 | 274 | RTA00000622F.e.17.1 | M00007031C:D1 |
| 1026 | May 15, 1998 | 1488 | 275 | RTA00000590F.l.12.1 | M00005353B:B9 |
| 1027 | May 15, 1998 | 1488 | 276 | RTA00000626F.f.01.1 | M00006648C:E4 |
| 1028 | May 15, 1998 | 1488 | 277 | RTA00000620F.a.05.1 | M00006832D:F11 |
| 1029 | May 15, 1998 | 1488 | 278 | RTA00000623F.d.04.1 | M00007121A:A5 |
| 1030 | May 15, 1998 | 1488 | 279 | RTA00000618F.p.15.1 | M00006739C:H7 |
| 1031 | May 15, 1998 | 1488 | 280 | RTA00000618F.o.03.1 | M00006734A:H12 |
| 1032 | May 15, 1998 | 1488 | 281 | RTA00000640F.b.02.1 | M00006927C:F12 |
| 1033 | May 15, 1998 | 1488 | 282 | RTA00000619F.g.20.1 | M00006780A:H12 |
| 1034 | May 15, 1998 | 1488 | 283 | RTA00000618F.n.09.1 | M00006728C:B6 |
| 1035 | May 15, 1998 | 1488 | 284 | RTA00000621F.d.09.1 | M00006939B:E5 |

TABLE 1A-continued

Priority Appln Information

| SEQ ID NO: | Filed | Dkt No. | SEQ ID NO: | Sequence Name | Clone Name |
|---|---|---|---|---|---|
| 1036 | May 15, 1998 | 1488 | 285 | RTA00000619F.n.23.4 | M00006822D:D5 |
| 1037 | May 15, 1998 | 1488 | 286 | RTA00000616F.k.16.1 | M00005417A:E10 |
| 1038 | May 15, 1998 | 1488 | 287 | RTA00000625F.f.21.1 | M00005783A:C5 |
| 1039 | May 15, 1998 | 1488 | 288 | RTA00000619F.b.17.1 | M00006751B:B11 |
| 1040 | May 15, 1998 | 1488 | 289 | RTA00000622F.h.11.1 | M00007042A:E7 |
| 1041 | May 15, 1998 | 1488 | 290 | RTA00000621F.k.12.1 | M00006973D:E11 |
| 1042 | May 15, 1998 | 1488 | 291 | RTA00000620F.p.08.1 | M00006921B:E1 |
| 1043 | May 15, 1998 | 1488 | 292 | RTA00000625F.d.13.1 | M00005762D:A1 |
| 1044 | May 15, 1998 | 1488 | 293 | RTA00000592F.g.18.1 | M00006618C:G8 |
| 1045 | May 15, 1998 | 1488 | 294 | RTA00000622F.b.17.1 | M00007012B:D7 |
| 1046 | May 15, 1998 | 1488 | 295 | RTA00000624F.i.07.1 | M00005625D:C3 |
| 1047 | May 15, 1998 | 1488 | 296 | RTA00000619F.c.01.1 | M00006754B:D5 |
| 1048 | May 15, 1998 | 1488 | 297 | RTA00000621F.a.07.1 | M00006926A:H11 |
| 1049 | May 15, 1998 | 1488 | 298 | RTA00000620F.d.21.1 | M00006855C:H2 |
| 1050 | May 15, 1998 | 1488 | 299 | RTA00000616F.c.15.1 | M00005383D:E7 |
| 1051 | May 15, 1998 | 1488 | 300 | RTA00000619F.n.19.4 | M00006822A:D7 |
| 1052 | May 15, 1998 | 1488 | 301 | RTA00000615F.l.09.1 | M00005349B:G1 |
| 1053 | May 15, 1998 | 1488 | 302 | RTA00000626F.b.04.1 | M00006631D:B2 |
| 1054 | May 15, 1998 | 1488 | 303 | RTA00000617F.j.23.1 | M00005491B:C3 |
| 1055 | May 15, 1998 | 1488 | 304 | RTA00000615F.k.14.1 | M00005333C:C8 |
| 1056 | May 15, 1998 | 1488 | 305 | RTA00000616F.l.07.1 | M00005419A:D5 |
| 1057 | May 15, 1998 | 1488 | 306 | RTA00000619F.d.04.1 | M00006758A:B12 |
| 1058 | May 15, 1998 | 1488 | 307 | RTA00000622F.o.15.1 | M00007093A:F9 |
| 1059 | May 15, 1998 | 1488 | 308 | RTA00000625F.m.11.1 | M00006594D:F9 |
| 1060 | May 15, 1998 | 1488 | 309 | RTA00000619F.e.10.1 | M00006763B:B11 |
| 1061 | May 15, 1998 | 1488 | 310 | RTA00000617F.n.15.1 | M00005508B:B4 |
| 1062 | May 15, 1998 | 1488 | 311 | RTA00000615F.n.22.1 | M00005359D:G7 |
| 1063 | May 15, 1998 | 1488 | 312 | RTA00000622F.j.21.1 | M00007058A:C2 |
| 1064 | May 15, 1998 | 1488 | 313 | RTA00000625F.c.09.1 | M00005722A:E9 |
| 1065 | May 15, 1998 | 1488 | 314 | RTA00000591F.m.01.1 | M00005510B:D6 |
| 1066 | May 15, 1998 | 1488 | 315 | RTA00000617F.n.14.1 | M00005508A:H1 |
| 1067 | May 15, 1998 | 1488 | 316 | RTA00000624F.p.18.1 | M00005703A:C8 |
| 1068 | May 15, 1998 | 1488 | 317 | RTA00000623F.j.10.2 | M00007163B:A12 |
| 1069 | May 15, 1998 | 1488 | 318 | RTA00000591F.e.20.1 | M00005450B:B1 |
| 1070 | May 15, 1998 | 1488 | 319 | RTA00000615F.i.11.1 | M00005294C:G8 |
| 1071 | May 15, 1998 | 1488 | 320 | RTA00000622F.p.12.1 | M00007099C:F9 |
| 1072 | May 15, 1998 | 1488 | 321 | RTA00000619F.j.22.1 | M00006800C:G8 |
| 1073 | May 15, 1998 | 1488 | 322 | RTA00000621F.g.12.1 | M00006953D:H11 |
| 1074 | May 15, 1998 | 1488 | 323 | RTA00000617F.m.14.1 | M00005505A:C8 |
| 1075 | May 15, 1998 | 1488 | 324 | RTA00000619F.k.06.1 | M00006805A:H9 |
| 1076 | May 15, 1998 | 1488 | 325 | RTA00000616F.k.18.1 | M00005417C:E10 |
| 1077 | May 15, 1998 | 1488 | 326 | RTA00000625F.d.04.1 | M00005743B:F2 |
| 1078 | May 15, 1998 | 1488 | 327 | RTA00000626F.b.06.1 | M00006631D:E9 |
| 1079 | May 15, 1998 | 1488 | 328 | RTA00000621F.p.15.1 | M00006997B:E6 |
| 1080 | May 15, 1998 | 1488 | 329 | RTA00000618F.d.19.1 | M00006681C:G4 |
| 1081 | May 15, 1998 | 1488 | 330 | RTA00000618F.a.02.1 | M00006665B:D10 |
| 1082 | May 15, 1998 | 1488 | 331 | RTA00000592F.f.15.1 | M00006577B:H12 |
| 1083 | May 15, 1998 | 1488 | 332 | RTA00000619F.d.12.1 | M00006758D:C1 |
| 1084 | May 15, 1998 | 1488 | 333 | RTA00000624F.d.08.1 | M00005571A:E11 |
| 1085 | May 15, 1998 | 1488 | 334 | RTA00000620F.o.15.1 | M00006919B:C3 |
| 1086 | May 15, 1998 | 1488 | 335 | RTA00000620F.e.03.1 | M00006859A:F6 |
| 1087 | May 15, 1998 | 1488 | 336 | RTA00000622F.a.24.1 | M00007010B:C11 |
| 1088 | May 15, 1998 | 1488 | 337 | RTA00000619F.n.04.2 | M00006819A:D10 |
| 1089 | May 15, 1998 | 1488 | 338 | RTA00000616F.d.16.1 | M00005388D:F9 |
| 1090 | May 15, 1998 | 1488 | 339 | RTA00000622F.n.15.1 | M00007085A:B7 |
| 1091 | May 15, 1998 | 1488 | 340 | RTA00000619F.i.04.1 | M00006789C:F4 |
| 1092 | May 15, 1998 | 1488 | 341 | RTA00000617F.i.13.1 | M00005484A:D9 |
| 1093 | May 15, 1998 | 1488 | 342 | RTA00000616F.l.11.1 | M00005419C:D9 |
| 1094 | May 15, 1998 | 1488 | 343 | RTA00000617F.b.18.1 | M00005454C:H12 |
| 1095 | May 15, 1998 | 1488 | 344 | RTA00000618F.j.01.1 | M00006705B:D2 |
| 1096 | May 15, 1998 | 1488 | 345 | RTA00000618F.k.24.1 | M00006717A:D4 |
| 1097 | May 15, 1998 | 1488 | 346 | RTA00000618F.c.05.1 | M00006676D:D11 |
| 1098 | May 15, 1998 | 1488 | 347 | RTA00000619F.g.08.1 | M00006777B:D10 |
| 1099 | May 15, 1998 | 1488 | 348 | RTA00000618F.n.04.1 | M00006727B:E9 |
| 1100 | May 15, 1998 | 1488 | 349 | RTA00000617F.i.09.1 | M00005483D:A12 |
| 1101 | May 15, 1998 | 1488 | 350 | RTA00000617F.l.04.1 | M00005497C:C7 |
| 1102 | May 15, 1998 | 1488 | 351 | RTA00000619F.n.17.4 | M00006821C:C10 |
| 1103 | May 15, 1998 | 1488 | 352 | RTA00000622F.l.09.1 | M00007065D:C1 |
| 1104 | May 15, 1998 | 1488 | 353 | RTA00000623F.j.03.2 | M00007161A:H3 |
| 1105 | May 15, 1998 | 1488 | 354 | RTA00000615F.m.17.1 | M00005356A:D9 |
| 1106 | May 15, 1998 | 1488 | 355 | RTA00000616F.g.13.1 | M00005400A:D2 |
| 1107 | May 15, 1998 | 1488 | 356 | RTA00000615F.f.15.1 | M00004999D:E1 |
| 1108 | May 15, 1998 | 1488 | 357 | RTA00000591F.f.15.1 | M00005455A:D1 |

TABLE 1A-continued

Priority Appln Information

| SEQ ID NO: | Filed | Dkt No. | SEQ ID NO: | Sequence Name | Clone Name |
|---|---|---|---|---|---|
| 1109 | May 15, 1998 | 1488 | 358 | RTA00000592F.g.07.1 | M00006596A:F7 |
| 1110 | May 15, 1998 | 1488 | 359 | RTA00000625F.o.16.1 | M00006615D:F4 |
| 1111 | May 15, 1998 | 1488 | 360 | RTA00000622F.f.13.1 | M00007033D:F4 |
| 1112 | May 15, 1998 | 1488 | 361 | RTA00000619F.p.02.3 | M00006826B:H3 |
| 1113 | May 15, 1998 | 1488 | 362 | RTA00000625F.h.11.1 | M00005812C:F10 |
| 1114 | May 15, 1998 | 1488 | 363 | RTA00000591F.i.05.1 | M00005477C:D8 |
| 1115 | May 15, 1998 | 1488 | 364 | RTA00000622F.j.07.1 | M00007053B:C7 |
| 1116 | May 15, 1998 | 1488 | 365 | RTA00000619F.k.01.1 | M00006801A:G5 |
| 1117 | May 15, 1998 | 1488 | 366 | RTA00000619F.b.24.1 | M00006754B:D5 |
| 1118 | May 15, 1998 | 1488 | 367 | RTA00000619F.b.16.1 | M00006751A:F3 |
| 1119 | May 15, 1998 | 1488 | 368 | RTA00000618F.p.04.1 | M00006738A:E5 |
| 1120 | May 15, 1998 | 1488 | 369 | RTA00000615F.k.18.1 | M00005342A:D4 |
| 1121 | May 15, 1998 | 1488 | 370 | RTA00000618F.g.23.1 | M00006695B:F8 |
| 1122 | May 15, 1998 | 1488 | 371 | RTA00000618F.n.14.1 | M00006728D:G10 |
| 1123 | May 15, 1998 | 1488 | 372 | RTA00000619F.e.23.1 | M00006765B:H6 |
| 1124 | May 15, 1998 | 1488 | 373 | RTA00000617F.j.06.1 | M00005487A:H1 |
| 1125 | May 15, 1998 | 1488 | 374 | RTA00000622F.f.06.1 | M00007033A:H5 |
| 1126 | May 15, 1998 | 1488 | 375 | RTA00000622F.e.09.1 | M00007030C:F8 |
| 1127 | May 15, 1998 | 1488 | 376 | RTA00000624F.k.11.1 | M00005635C:F11 |
| 1128 | May 15, 1998 | 1488 | 377 | RTA00000619F.a.24.1 | M00006745A:A1 |
| 1129 | May 15, 1998 | 1488 | 378 | RTA00000625F.i.03.1 | M00005818C:G1 |
| 1130 | May 15, 1998 | 1488 | 379 | RTA00000590F.l.10.1 | M00005352D:E6 |
| 1131 | May 15, 1998 | 1488 | 380 | RTA00000623F.d.12.1 | M00007122B:A11 |
| 1132 | May 15, 1998 | 1488 | 381 | RTA00000622F.o.05.1 | M00007090B:A2 |
| 1133 | May 15, 1998 | 1488 | 382 | RTA00000623F.n.07.1 | M00007200B:C2 |
| 1134 | May 15, 1998 | 1488 | 383 | RTA00000621F.k.10.1 | M00006973C:E11 |
| 1135 | May 15, 1998 | 1488 | 384 | RTA00000616F.b.O5.1 | M00005377A:A4 |
| 1136 | May 15, 1998 | 1488 | 385 | RTA00000619F.p.11.4 | M00006828D:C12 |
| 1137 | May 15, 1998 | 1488 | 386 | RTA00000616F.d.15.1 | M00005388D:B11 |
| 1138 | May 15, 1998 | 1488 | 387 | RTA00000615F.b.07.1 | M00004839C:B1 |
| 1139 | May 15, 1998 | 1488 | 388 | RTA00000619F.f.19.1 | M00006771A:E6 |
| 1140 | May 15, 1998 | 1488 | 389 | RTA00000621F.l.06.1 | M00006976C:E9 |
| 1141 | May 15, 1998 | 1488 | 390 | RTA00000624F.m.08.1 | M00005646C:B9 |
| 1142 | May 15, 1998 | 1488 | 391 | RTA00000617F.k.13.1 | M00005493B:E1 |
| 1143 | May 15, 1998 | 1488 | 392 | RTA00000592F.h.07.1 | M00006630B:H6 |
| 1144 | May 15, 1998 | 1488 | 393 | RTA00000619F.f.24.1 | M00006771B:F3 |
| 1145 | May 15, 1998 | 1488 | 394 | RTA00000622F.e.20.1 | M00007032A:F11 |
| 1146 | May 15, 1998 | 1488 | 395 | RTA00000623F.h.23.1 | M00007152A:B4 |
| 1147 | May 15, 1998 | 1488 | 396 | RTA00000626F.b.20.1 | M00006635C:B10 |
| 1148 | May 15, 1998 | 1488 | 397 | RTA00000623F.n.03.1 | M00007199D:B7 |
| 1149 | May 15, 1998 | 1488 | 398 | RTA00000625F.i.02.1 | M00005818C:E8 |
| 1150 | May 15, 1998 | 1488 | 399 | RTA00000622F.i.08.1 | M00007047B:D1 |
| 1151 | May 15, 1998 | 1488 | 400 | RTA00000621F.c.23.1 | M00006937B:G9 |
| 1152 | May 15, 1998 | 1488 | 401 | RTA00000619F.f.11.1 | M00006769D:A4 |
| 1153 | May 15, 1998 | 1488 | 402 | RTA00000621F.b.14.1 | M00006934A:G2 |
| 1154 | May 15, 1998 | 1488 | 403 | RTA00000621F.g.10.1 | M00006953B:H10 |
| 1155 | May 15, 1998 | 1488 | 404 | RTA00000619F.p.22.3 | M00006832A:F5 |
| 1156 | May 15, 1998 | 1488 | 405 | RTA00000590F.p.23.1 | M00005399D:B2 |
| 1157 | May 15, 1998 | 1488 | 406 | RTA00000621F.m.23.1 | M00006987B:F4 |
| 1158 | May 15, 1998 | 1488 | 407 | RTA00000592F.d.20.1 | M00005772A:F3 |
| 1159 | May 15, 1998 | 1488 | 408 | RTA00000624F.m.14.1 | M00005647D:D9 |
| 1160 | May 15, 1998 | 1488 | 409 | RTA00000617F.a.08.1 | M00005448D:E8 |
| 1161 | May 15, 1998 | 1488 | 410 | RTA00000620F.i.04.1 | M00006877B:E5 |
| 1162 | May 15, 1998 | 1488 | 411 | RTA00000623F.l.12.1 | M00007188A:D3 |
| 1163 | May 15, 1998 | 1488 | 412 | RTA00000591F.b.02.1 | M00005411D:E5 |
| 1164 | May 15, 1998 | 1488 | 413 | RTA00000623F.h.07.1 | M00007146D:G1 |
| 1165 | May 15, 1998 | 1488 | 414 | RTA00000624F.p.21.1 | M00005703C:B1 |
| 1166 | May 15, 1998 | 1488 | 415 | RTA00000623F.j.09.2 | M00007163A:F11 |
| 1167 | May 15, 1998 | 1488 | 416 | RTA00000623F.l.17.1 | M00007189D:A9 |
| 1168 | May 15, 1998 | 1488 | 417 | RTA00000619F.p.18.3 | M00006831B:B4 |
| 1169 | May 15, 1998 | 1488 | 418 | RTA00000622F.h.06.1 | M00007041B:G1 |
| 1170 | May 15, 1998 | 1488 | 419 | RTA00000591F.m.20.1 | M00005519C:F8 |
| 1171 | May 15, 1998 | 1488 | 420 | RTA00000623F.h.10.1 | M00007148B:C6 |
| 1172 | May 15, 1998 | 1488 | 421 | RTA00000619F.i.10.1 | M00006790D:A5 |
| 1173 | May 15, 1998 | 1488 | 422 | RTA00000625F.b.13.1 | M00005711A:H1 |
| 1174 | May 15, 1998 | 1488 | 423 | RTA00000623F.e.16.1 | M00007129A:E4 |
| 1175 | May 15, 1998 | 1488 | 424 | RTA00000625F.k.12.1 | M00006582D:E5 |
| 1176 | May 15, 1998 | 1488 | 425 | RTA00000624F.i.09.1 | M00005626A:B11 |
| 1177 | May 15, 1998 | 1488 | 426 | RTA00000625F.k.09.1 | M00006582A:B9 |
| 1178 | May 15, 1998 | 1488 | 427 | RTA00000622F.k.10.1 | M00007062A:D3 |
| 1179 | May 15, 1998 | 1488 | 428 | RTA00000616F.h.12.1 | M00005403D:E11 |
| 1180 | May 15, 1998 | 1488 | 429 | RTA00000623F.k.07.1 | M00007170D:A10 |
| 1181 | May 15, 1998 | 1488 | 430 | RTA00000620F.p.18.1 | M00006923B:H8 |

TABLE 1A-continued

Priority Appln Information

| SEQ ID NO: | Filed | Dkt No. | SEQ ID NO: | Sequence Name | Clone Name |
| --- | --- | --- | --- | --- | --- |
| 1182 | May 15, 1998 | 1488 | 431 | RTA00000620F.e.01.1 | M00006855D:H2 |
| 1183 | May 15, 1998 | 1488 | 432 | RTA00000616F.b.10.1 | M00005377D:F11 |
| 1184 | May 15, 1998 | 1488 | 433 | RTA00000615F.d.06.1 | M00004858D:E6 |
| 1185 | May 15, 1998 | 1488 | 434 | RTA00000592F.h.23.1 | M00006640B:H9 |
| 1186 | May 15, 1998 | 1488 | 435 | RTA00000622F.e.07.1 | M00007030A:G1 |
| 1187 | May 15, 1998 | 1488 | 436 | RTA00000617F.f.23.2 | M00005473D:E10 |
| 1188 | May 15, 1998 | 1488 | 437 | RTA00000620F.h.10.1 | M00006875A:A2 |
| 1189 | May 15, 1998 | 1488 | 438 | RTA00000615F.g.19.1 | M00005009B:A2 |
| 1190 | May 15, 1998 | 1488 | 439 | RTA00000626F.b.09.1 | M00006633C:E11 |
| 1191 | May 15, 1998 | 1488 | 440 | RTA00000626F.e.10.1 | M00006644D:C2 |
| 1192 | May 15, 1998 | 1488 | 441 | RTA00000591F.a.08.1 | M00005404C:F2 |
| 1193 | May 15, 1998 | 1488 | 442 | RTA00000622F.j.09.1 | M00007053B:H3 |
| 1194 | May 15, 1998 | 1488 | 443 | RTA00000591F.n.01.1 | M00005524C:B1 |
| 1195 | May 15, 1998 | 1488 | 444 | RTA00000623F.e.12.1 | M00007127B:A4 |
| 1196 | May 15, 1998 | 1488 | 445 | RTA00000625F.p.01.1 | M00006617B:D9 |
| 1197 | May 15, 1998 | 1488 | 446 | RTA00000623F.f.13.1 | M00007134C:F7 |
| 1198 | May 15, 1998 | 1488 | 447 | RTA00000620F.c.24.1 | M00006850C:D9 |
| 1199 | May 15, 1998 | 1488 | 448 | RTA00000618F.i.21.1 | M00006704D:D3 |
| 1200 | May 15, 1998 | 1488 | 449 | RTA00000617F.l.08.1 | M00005497C:E3 |
| 1201 | May 15, 1998 | 1488 | 450 | RTA00000619F.l.07.1 | M00006810D:A5 |
| 1202 | May 15, 1998 | 1488 | 451 | RTA00000624F.n.16.1 | M00005655B:C2 |
| 1203 | May 15, 1998 | 1488 | 452 | RTA00000621F.n.24.1 | M00006991D:G7 |
| 1204 | May 15, 1998 | 1488 | 453 | RTA00000621F.c.20.1 | M00006937B:F7 |
| 1205 | May 15, 1998 | 1488 | 454 | RTA00000623F.g.07.1 | M00007140D:C12 |
| 1206 | May 15, 1998 | 1488 | 455 | RTA00000591F.i.17.1 | M00005481C:A5 |
| 1207 | May 15, 1998 | 1488 | 456 | RTA00000626F.b.22.1 | M00006636A:B8 |
| 1208 | May 15, 1998 | 1488 | 457 | RTA00000620F.i.16.1 | M00006882D:F3 |
| 1209 | May 15, 1998 | 1488 | 458 | RTA00000623F.f.21.1 | M00007137D:C10 |
| 1210 | May 15, 1998 | 1488 | 459 | RTA00000591F.f.18.1 | M00005455A:G3 |
| 1211 | May 15, 1998 | 1488 | 460 | RTA00000616F.e.10.1 | M00005392C:C4 |
| 1212 | May 15, 1998 | 1488 | 461 | RTA00000619F.l.22.1 | M00006814A:F7 |
| 1213 | May 15, 1998 | 1488 | 462 | RTA00000591F.a.20.1 | M00005411A:C7 |
| 1214 | May 15, 1998 | 1488 | 463 | RTA00000623F.b.23.1 | M00007112B:C6 |
| 1215 | May 15, 1998 | 1488 | 464 | RTA00000621F.n.15.1 | M00006990B:H9 |
| 1216 | May 15, 1998 | 1488 | 465 | RTA00000620F.m.15.1 | M00006907D:C7 |
| 1217 | May 15, 1998 | 1488 | 466 | RTA00000591F.a.15.1 | M00005406D:B8 |
| 1218 | May 15, 1998 | 1488 | 467 | RTA00000620F.p.05.1 | M00006921B:C2 |
| 1219 | May 15, 1998 | 1488 | 468 | RTA00000620F.h.04.1 | M00006873B:G11 |
| 1220 | May 15, 1998 | 1488 | 469 | RTA00000592F.g.15.1 | M00006615B:F5 |
| 1221 | May 15, 1998 | 1488 | 470 | RTA00000625F.b.21.1 | M00005720A:D3 |
| 1222 | May 15, 1998 | 1488 | 471 | RTA00000621F.n.18.1 | M00006991A:E7 |
| 1223 | May 15, 1998 | 1488 | 472 | RTA00000591F.h.08.1 | M00005470B:E1 |
| 1224 | May 15, 1998 | 1488 | 473 | RTA00000591F.j.13.1 | M00005486C:B3 |
| 1225 | May 15, 1998 | 1488 | 474 | RTA00000626F.e.08.1 | M00006644C:E9 |
| 1226 | May 15, 1998 | 1488 | 475 | RTA00000623F.d.23.1 | M00007124C:A11 |
| 1227 | May 15, 1998 | 1488 | 476 | RTA00000592F.g.04.1 | M00006592A:D3 |
| 1228 | May 15, 1998 | 1488 | 477 | RTA00000590F.p.22.1 | M00005399B:F2 |
| 1229 | May 15, 1998 | 1488 | 478 | RTA00000590F.n.10.1 | M00005377A:D5 |
| 1230 | May 15, 1998 | 1488 | 479 | RTA00000623F.j.16.2 | M00007166B:E6 |
| 1231 | May 15, 1998 | 1488 | 480 | RTA00000619F.j.19.1 | M00006797B:D12 |
| 1232 | May 15, 1998 | 1488 | 481 | RTA00000621F.c.12.1 | M00006936B:F10 |
| 1233 | May 15, 1998 | 1488 | 482 | RTA00000618F.b.17.1 | M00006674B:F4 |
| 1234 | May 15, 1998 | 1488 | 483 | RTA00000621F.p.08.1 | M00006995D:A3 |
| 1235 | May 15, 1998 | 1488 | 484 | RTA00000626F.b.13.1 | M00006634B:C2 |
| 1236 | May 15, 1998 | 1488 | 485 | RTA00000623F.e.18.1 | M00007129A:G10 |
| 1237 | May 15, 1998 | 1488 | 486 | RTA00000625F.j.01.1 | M00005827B:H8 |
| 1238 | May 15, 1998 | 1488 | 487 | RTA00000625F.o.18.1 | M00006616C:H9 |
| 1239 | May 15, 1998 | 1488 | 488 | RTA00000623F.k.13.1 | M00007172D:C8 |
| 1240 | May 15, 1998 | 1488 | 489 | RTA00000623F.k.10.1 | M00007172A:A5 |
| 1241 | May 15, 1998 | 1488 | 490 | RTA00000626F.d.12.1 | M00006641A:B3 |
| 1242 | May 15, 1998 | 1488 | 491 | RTA00000626F.d.23.1 | M00006643A:E10 |
| 1243 | May 15, 1998 | 1488 | 492 | RTA00000623F.j.02.1 | M00007160C:B8 |
| 1244 | May 15, 1998 | 1488 | 493 | RTA00000618F.o.07.1 | M00006735A:H2 |
| 1245 | May 15, 1998 | 1488 | 494 | RTA00000620F.a.08.1 | M00006833B:E11 |
| 1246 | May 15, 1998 | 1488 | 495 | RTA00000623F.d.11.1 | M00007122A:G11 |
| 1247 | May 15, 1998 | 1488 | 496 | RTA00000623F.h.16.1 | M00007149D:G6 |
| 1248 | May 15, 1998 | 1488 | 497 | RTA00000624F.a.17.1 | M00005535B:F6 |
| 1249 | May 15, 1998 | 1488 | 498 | RTA00000621F.n.17.1 | M00006990D:D6 |
| 1250 | May 15, 1998 | 1488 | 499 | RTA00000625F.n.02.1 | M00006601C:E6 |
| 1251 | May 15, 1998 | 1488 | 500 | RTA00000591F.n.05.1 | M00005530B:E4 |
| 1252 | May 15, 1998 | 1488 | 501 | RTA00000622F.n.09.1 | M00007084B:A5 |
| 1253 | May 15, 1998 | 1488 | 502 | RTA00000617F.l.05.1 | M00005497C:C10 |
| 1254 | May 15, 1998 | 1488 | 503 | RTA00000623F.j.08.2 | M00007163A:B10 |

TABLE 1A-continued

Priority Appln Information

| SEQ ID NO: | Filed | Dkt No. | SEQ ID NO: | Sequence Name | Clone Name |
|---|---|---|---|---|---|
| 1255 | May 15, 1998 | 1488 | 504 | RTA00000626F.g.02.1 | M00006656C:C10 |
| 1256 | May 15, 1998 | 1488 | 505 | RTA00000617F.l.06.1 | M00005497C:C12 |
| 1257 | May 15, 1998 | 1488 | 506 | RTA00000592F.a.06.1 | M00005635B:A6 |
| 1258 | May 15, 1998 | 1488 | 507 | RTA00000591F.j.11.1 | M00005485C:A3 |
| 1259 | May 15, 1998 | 1488 | 508 | RTA00000622F.h.21.1 | M00007046A:D2 |
| 1260 | May 15, 1998 | 1488 | 509 | RTA00000591F.h.03.1 | M00005468D:F4 |
| 1261 | May 15, 1998 | 1488 | 510 | RTA00000620F.g.22.1 | M00006872B:G1 |
| 1262 | May 15, 1998 | 1488 | 511 | RTA00000617F.c.05.1 | M00005456B:E3 |
| 1263 | May 15, 1998 | 1488 | 512 | RTA00000616F.e.15.3 | M00005393A:E11 |
| 1264 | May 15, 1998 | 1488 | 513 | RTA00000616F.f.15.3 | M00005396B:C4 |
| 1265 | May 15, 1998 | 1488 | 514 | RTA00000622F.c.11.1 | M00007014D:C5 |
| 1266 | May 15, 1998 | 1488 | 515 | RTA00000621F.f.12.1 | M00006949B:F3 |
| 1267 | May 15, 1998 | 1488 | 516 | RTA00000603F.c.23.1 | M00006720C:C11 |
| 1268 | May 15, 1998 | 1488 | 517 | RTA00000640F.a.23.1 | M00005817D:E12 |
| 1269 | May 15, 1998 | 1488 | 518 | RTA00000618F.h.15.1 | M00006699B:C7 |
| 1270 | May 15, 1998 | 1488 | 519 | RTA00000616F.p.22.1 | M00005446C:D12 |
| 1271 | May 15, 1998 | 1488 | 520 | RTA00000621F.p.18.1 | M00006997D:B3 |
| 1272 | May 15, 1998 | 1488 | 521 | RTA00000615F.b.10.1 | M00004840C:H5 |
| 1273 | May 15, 1998 | 1488 | 522 | RTA00000590F.l.05.1 | M00005332A:H10 |
| 1274 | May 15, 1998 | 1488 | 523 | RTA00000619F.g.06.1 | M00006774D:C1 |
| 1275 | May 15, 1998 | 1488 | 524 | RTA00000619F.c.24.1 | M00006757D:E4 |
| 1276 | May 15, 1998 | 1488 | 525 | RTA00000619F.f.23.1 | M00006771B:A9 |
| 1277 | May 15, 1998 | 1489 | 1 | RTA00000639F.e.11.1 | M00023011A:A6 |
| 1278 | May 15, 1998 | 1489 | 2 | RTA00000631F.e.20.1 | M00022386B:D11 |
| 1279 | May 15, 1998 | 1489 | 3 | RTA00000631F.e.15.1 | M00022386A:A7 |
| 1280 | May 15, 1998 | 1489 | 4 | RTA00000639F.d.02.1 | M00022993A:F2 |
| 1281 | May 15, 1998 | 1489 | 5 | RTA00000639F.f.10.1 | M00023021A:H8 |
| 1282 | May 15, 1998 | 1489 | 6 | RTA00000628F.e.17.1 | M00021862D:F1 |
| 1283 | May 15, 1998 | 1489 | 7 | RTA00000627F.p.18.1 | M00021670B:G11 |
| 1284 | May 15, 1998 | 1489 | 8 | RTA00000633F.o.22.1 | M00022901D:C9 |
| 1285 | May 15, 1998 | 1489 | 9 | RTA00000632F.b.04.1 | M00022493C:B7 |
| 1286 | May 15, 1998 | 1489 | 10 | RTA00000639F.g.14.1 | M00023034C:E5 |
| 1287 | May 15, 1998 | 1489 | 11 | RTA00000631F.p.10.1 | M00022474A:H9 |
| 1288 | May 15, 1998 | 1489 | 12 | RTA00000628F.c.20.1 | M00021828A:C8 |
| 1289 | May 15, 1998 | 1489 | 13 | RTA00000630F.o.20.1 | M00022289A:D5 |
| 1290 | May 15, 1998 | 1489 | 14 | RTA00000630F.e.18.1 | M00022202C:F11 |
| 1291 | May 15, 1998 | 1489 | 15 | RTA00000628F.b.18.1 | M00021690C:B7 |
| 1292 | May 15, 1998 | 1489 | 16 | RTA00000590F.j.07.1 | M00004873C:C10 |
| 1293 | May 15, 1998 | 1489 | 17 | RTA00000630F.a.19.1 | M00022169C:C2 |
| 1294 | May 15, 1998 | 1489 | 18 | RTA00000630F.i.02.1 | M00022226D:A7 |
| 1295 | May 15, 1998 | 1489 | 19 | RTA00000631F.a.22.1 | M00022364C:G12 |
| 1296 | May 15, 1998 | 1489 | 20 | RTA00000630F.l.19.1 | M00022255D:E3 |
| 1297 | May 15, 1998 | 1489 | 21 | RTA00000633F.a.15.1 | M00022661D:H1 |
| 1298 | May 15, 1998 | 1489 | 22 | RTA00000639F.c.06.1 | M00022972D:C10 |
| 1299 | May 15, 1998 | 1489 | 23 | RTA00000630F.p.23.1 | M00022305C:A1 |
| 1300 | May 15, 1998 | 1489 | 24 | RTA00000629F.o.19.2 | M00022150D:D11 |
| 1301 | May 15, 1998 | 1489 | 25 | RTA00000632F.j.18.1 | M00022599D:E7 |
| 1302 | May 15, 1998 | 1489 | 26 | RTA00000630F.o.21.1 | M00022289D:B6 |
| 1303 | May 15, 1998 | 1489 | 27 | RTA00000629F.l.02.1 | M00022117C:G7 |
| 1304 | May 15, 1998 | 1489 | 28 | RTA00000628F.e.13.1 | M00021861C:A2 |
| 1305 | May 15, 1998 | 1489 | 29 | RTA00000632F.j.02.1 | M00022587C:G4 |
| 1306 | May 15, 1998 | 1489 | 30 | RTA00000639F.e.01.1 | M00023003C:A3 |
| 1307 | May 15, 1998 | 1489 | 31 | RTA00000631F.f.01.1 | M00022386C:D7 |
| 1308 | May 15, 1998 | 1489 | 32 | RTA00000630F.p.22.1 | M00022305A:H11 |
| 1309 | May 15, 1998 | 1489 | 33 | RTA00000628F.l.05.1 | M00021946D:C11 |
| 1310 | May 15, 1998 | 1489 | 34 | RTA00000629F.b.06.1 | M00022049A:A2 |
| 1311 | May 15, 1998 | 1489 | 35 | RTA00000628F.g.20.1 | M00021892B:H3 |
| 1312 | May 15, 1998 | 1489 | 36 | RTA00000628F.n.11.1 | M00021982C:F8 |
| 1313 | May 15, 1998 | 1489 | 37 | RTA00000593F.e.21.1 | M00022074D:F11 |
| 1314 | May 15, 1998 | 1489 | 38 | RTA00000633F.c.07.1 | M00022674D:G4 |
| 1315 | May 15, 1998 | 1489 | 39 | RTA00000629F.k.17.1 | M00022110A:E4 |
| 1316 | May 15, 1998 | 1489 | 40 | RTA00000633F.a.11.1 | M00022661B:E11 |
| 1317 | May 15, 1998 | 1489 | 41 | RTA00000629F.e.16.1 | M00022068D:D12 |
| 1318 | May 15, 1998 | 1489 | 42 | RTA00000631F.c.01.1 | M00022372B:D3 |
| 1319 | May 15, 1998 | 1489 | 43 | RTA00000630F.n.22.1 | M00022278C:E3 |
| 1320 | May 15, 1998 | 1489 | 44 | RTA00000628F.j.14.1 | M00021927B:F1 |
| 1321 | May 15, 1998 | 1489 | 45 | RTA00000631F.l.14.1 | M00022449D:F6 |
| 1322 | May 15, 1998 | 1489 | 46 | RTA00000631F.j.06.1 | M00022423B:D3 |
| 1323 | May 15, 1998 | 1489 | 47 | RTA00000630F.b.17.1 | M00022175A:A11 |
| 1324 | May 15, 1998 | 1489 | 48 | RTA00000593F.i.08.2 | M00022218C:B6 |
| 1325 | May 15, 1998 | 1489 | 49 | RTA00000631F.l.12.1 | M00022449C:B1 |
| 1326 | May 15, 1998 | 1489 | 50 | RTA00000628F.m.20.1 | M00021978A:F8 |
| 1327 | May 15, 1998 | 1489 | 51 | RTA00000632F.c.02.1 | M00022504B:E3 |

TABLE 1A-continued

Priority Appln Information

| SEQ ID NO: | Filed | Dkt No. | SEQ ID NO: | Sequence Name | Clone Name |
|---|---|---|---|---|---|
| 1328 | May 15, 1998 | 1489 | 52 | RTA00000632F.h.03.1 | M00022565C:H2 |
| 1329 | May 15, 1998 | 1489 | 53 | RTA00000592F.l.16.1 | M00007977C:E8 |
| 1330 | May 15, 1998 | 1489 | 54 | RTA00000630F.c.01.1 | M00022176A:E8 |
| 1331 | May 15, 1998 | 1489 | 55 | RTA00000593F.e.19.1 | M00022071C:D9 |
| 1332 | May 15, 1998 | 1489 | 56 | RTA00000632F.a.10.1 | M00022490C:C1 |
| 1333 | May 15, 1998 | 1489 | 57 | RTA00000632F.f.12.1 | M00022536B:B4 |
| 1334 | May 15, 1998 | 1489 | 58 | RTA00000630F.m.06.1 | M00022259B:G2 |
| 1335 | May 15, 1998 | 1489 | 59 | RTA00000629F.e.07.1 | M00022067D:C5 |
| 1336 | May 15, 1998 | 1489 | 60 | RTA00000627F.k.19.1 | M00021618D:D7 |
| 1337 | May 15, 1998 | 1489 | 61 | RTA00000629F.o.15.2 | M00022149B:D5 |
| 1338 | May 15, 1998 | 1489 | 62 | RTA00000592F.o.02.1 | M00008015D:E9 |
| 1339 | May 15, 1998 | 1489 | 63 | RTA00000628F.h.18.1 | M00021906C:G11 |
| 1340 | May 15, 1998 | 1489 | 64 | RTA00000632F.h.23.1 | M00022578D:A8 |
| 1341 | May 15, 1998 | 1489 | 65 | RTA00000639F.h.18.1 | M00023103A:E11 |
| 1342 | May 15, 1998 | 1489 | 66 | RTA00000630F.p.11.1 | M00022296B:C11 |
| 1343 | May 15, 1998 | 1489 | 67 | RTA00000632F.o.18.1 | M00022651D:C6 |
| 1344 | May 15, 1998 | 1489 | 68 | RTA00000629F.a.24.1 | M00022032A:E7 |
| 1345 | May 15, 1998 | 1489 | 69 | RTA00000633F.f.19.1 | M00022708D:G10 |
| 1346 | May 15, 1998 | 1489 | 70 | RTA00000627F.n.04.1 | M00021640A:G3 |
| 1347 | May 15, 1998 | 1489 | 71 | RTA00000630F.p.04.1 | M00022294A:D11 |
| 1348 | May 15, 1998 | 1489 | 72 | RTA00000633F.h.21.1 | M00022730A:E4 |
| 1349 | May 15, 1998 | 1489 | 73 | RTA00000632F.d.12.1 | M00022515D:C4 |
| 1350 | May 15, 1998 | 1489 | 74 | RTA00000627F.o.23.1 | M00021660C:G4 |
| 1351 | May 15, 1998 | 1489 | 75 | RTA00000628F.j.12.1 | M00021927A:C11 |
| 1352 | May 15, 1998 | 1489 | 76 | RTA00000632F.f.03.1 | M00022531B:D7 |
| 1353 | May 15, 1998 | 1489 | 77 | RTA00000593F.o.03.1 | M00022549B:G7 |
| 1354 | May 15, 1998 | 1489 | 78 | RTA00000631F.b.06.1 | M00022366B:E9 |
| 1355 | May 15, 1998 | 1489 | 79 | RTA00000633F.g.15.1 | M00022716D:D8 |
| 1356 | May 15, 1998 | 1489 | 80 | RTA00000594F.b.04.1 | M00022828C:E4 |
| 1357 | May 15, 1998 | 1489 | 81 | RTA00000623F.o.14.1 | M00007929B:H10 |
| 1358 | May 15, 1998 | 1489 | 82 | RTA00000632F.g.02.1 | M00022551A:G3 |
| 1359 | May 15, 1998 | 1489 | 83 | RTA00000629F.h.11.1 | M00022084B:F4 |
| 1360 | May 15, 1998 | 1489 | 84 | RTA00000632F.b.17.1 | M00022498C:C8 |
| 1361 | May 15, 1998 | 1489 | 85 | RTA00000631F.m.04.1 | M00022452C:B3 |
| 1362 | May 15, 1998 | 1489 | 86 | RTA00000627F.k.02.1 | M00021614B:G12 |
| 1363 | May 15, 1998 | 1489 | 87 | RTA00000631F.n.06.1 | M00022457C:B1 |
| 1364 | May 15, 1998 | 1489 | 88 | RTA00000633F.i.15.1 | M00022737A:C8 |
| 1365 | May 15, 1998 | 1489 | 89 | RTA00000639F.f.11.1 | M00023023A:B12 |
| 1366 | May 15, 1998 | 1489 | 90 | RTA00000630F.j.04.1 | M00022236D:A3 |
| 1367 | May 15, 1998 | 1489 | 91 | RTA00000630F.j.14.1 | M00022239D:A7 |
| 1368 | May 15, 1998 | 1489 | 92 | RTA00000627F.k.24.1 | M00021619B:G10 |
| 1369 | May 15, 1998 | 1489 | 93 | RTA00000630F.j.13.1 | M00022239B:B7 |
| 1370 | May 15, 1998 | 1489 | 94 | RTA00000629F.j.07.1 | M00022094B:G10 |
| 1371 | May 15, 1998 | 1489 | 95 | RTA00000628F.m.02.1 | M00021964A:C4 |
| 1372 | May 15, 1998 | 1489 | 96 | RTA00000639F.g.08.1 | M00023033A:E10 |
| 1373 | May 15, 1998 | 1489 | 97 | RTA00000628F.i.05.1 | M00021910A:C10 |
| 1374 | May 15, 1998 | 1489 | 98 | RTA00000639F.a.16.1 | M00022953B:C7 |
| 1375 | May 15, 1998 | 1489 | 99 | RTA00000633F.c.21.1 | M00022682A:F12 |
| 1376 | May 15, 1998 | 1489 | 100 | RTA00000639F.b.03.1 | M00022960D:E8 |
| 1377 | May 15, 1998 | 1489 | 101 | RTA00000633F.b.05.1 | M00022666C:H11 |
| 1378 | May 15, 1998 | 1489 | 102 | RTA00000631F.h.05.2 | M00022412A:C8 |
| 1379 | May 15, 1998 | 1489 | 103 | RTA00000628F.h.14.1 | M00021905B:A1 |
| 1380 | May 15, 1998 | 1489 | 104 | RTA00000633F.b.03.1 | M00022666B:E12 |
| 1381 | May 15, 1998 | 1489 | 105 | RTA00000632F.g.08.1 | M00022556B:G2 |
| 1382 | May 15, 1998 | 1489 | 106 | RTA00000593F.g.18.1 | M00022171D:B8 |
| 1383 | May 15, 1998 | 1489 | 107 | RTA00000592F.p.10.1 | M00008061A:F2 |
| 1384 | May 15, 1998 | 1489 | 108 | RTA00000639F.f.19.1 | M00023028A:A2 |
| 1385 | May 15, 1998 | 1489 | 109 | RTA00000630F.f.04.1 | M00022206B:G6 |
| 1386 | May 15, 1998 | 1489 | 110 | RTA00000633F.o.02.1 | M00022893C:H11 |
| 1387 | May 15, 1998 | 1489 | 111 | RTA00000632F.b.12.1 | M00022495C:G5 |
| 1388 | May 15, 1998 | 1489 | 112 | RTA00000632F.g.20.1 | M00022562C:H10 |
| 1389 | May 15, 1998 | 1489 | 113 | RTA00000593F.f.12.1 | M00022109B:A11 |
| 1390 | May 15, 1998 | 1489 | 114 | RTA00000633F.c.19.1 | M00022681C:H2 |
| 1391 | May 15, 1998 | 1489 | 115 | RTA00000629F.e.12.1 | M00022068B:H11 |
| 1392 | May 15, 1998 | 1489 | 116 | RTA00000629F.j.01.1 | M00022093A:A5 |
| 1393 | May 15, 1998 | 1489 | 117 | RTA00000627F.m.07.1 | M00021625A:C7 |
| 1394 | May 15, 1998 | 1489 | 118 | RTA00000633F.n.12.1 | M00022856C:B11 |
| 1395 | May 15, 1998 | 1489 | 119 | RTA00000632F.e.15.1 | M00022527D:B3 |
| 1396 | May 15, 1998 | 1489 | 120 | RTA00000632F.a.09.1 | M00022490C:A8 |
| 1397 | May 15, 1998 | 1489 | 121 | RTA00000631F.k.12.1 | M00022439A:E7 |
| 1398 | May 15, 1998 | 1489 | 122 | RTA00000628F.c.02.1 | M00021694B:A7 |
| 1399 | May 15, 1998 | 1489 | 123 | RTA00000632F.f.10.1 | M00022535D:B11 |
| 1400 | May 15, 1998 | 1489 | 124 | RTA00000631F.f.11.1 | M00022389B:H4 |

TABLE 1A-continued

Priority Appln Information

| SEQ ID NO: | Filed | Dkt No. | SEQ ID NO: | Sequence Name | Clone Name |
|---|---|---|---|---|---|
| 1401 | May 15, 1998 | 1489 | 125 | RTA00000633F.n.06.1 | M00022854D:H7 |
| 1402 | May 15, 1998 | 1489 | 126 | RTA00000628F.l.14.1 | M00021954A:A3 |
| 1403 | May 15, 1998 | 1489 | 127 | RTA00000632F.k.10.1 | M00022607B:A4 |
| 1404 | May 15, 1998 | 1489 | 128 | RTA00000629F.b.08.1 | M00022049A:D6 |
| 1405 | May 15, 1998 | 1489 | 129 | RTA00000629F.l.10.1 | M00022122D:D6 |
| 1406 | May 15, 1998 | 1489 | 130 | RTA00000632F.c.04.1 | M00022505D:A12 |
| 1407 | May 15, 1998 | 1489 | 131 | RTA00000630F.h.22.1 | M00022221D:E8 |
| 1408 | May 15, 1998 | 1489 | 132 | RTA00000593F.e.18.1 | M00022070B:C10 |
| 1409 | May 15, 1998 | 1489 | 133 | RTA00000630F.l.02.1 | M00022252C:E6 |
| 1410 | May 15, 1998 | 1489 | 134 | RTA00000632F.k.20.1 | M00022613D:C4 |
| 1411 | May 15, 1998 | 1489 | 135 | RTA00000628F.p.01.1 | M00022005C:G3 |
| 1412 | May 15, 1998 | 1489 | 136 | RTA00000631F.l.01.1 | M00022444A:A11 |
| 1413 | May 15, 1998 | 1489 | 137 | RTA00000628F.a.16.1 | M00021678A:B8 |
| 1414 | May 15, 1998 | 1489 | 138 | RTA00000632F.j.14.1 | M00022598A:F11 |
| 1415 | May 15, 1998 | 1489 | 139 | RTA00000628F.e.06.1 | M00021859A:D4 |
| 1416 | May 15, 1998 | 1489 | 140 | RTA00000631F.n.08.1 | M00022458B:E6 |
| 1417 | May 15, 1998 | 1489 | 141 | RTA00000630F.g.18.1 | M00022216D:C1 |
| 1418 | May 15, 1998 | 1489 | 142 | RTA00000628F.m.08.1 | M00021967D:E8 |
| 1419 | May 15, 1998 | 1489 | 143 | RTA00000592F.k.12.1 | M00007961A:B1 |
| 1420 | May 15, 1998 | 1489 | 144 | RTA00000631F.e.22.1 | M00022386C:A4 |
| 1421 | May 15, 1998 | 1489 | 145 | RTA00000628F.b.21.1 | M00021692A:E3 |
| 1422 | May 15, 1998 | 1489 | 146 | RTA00000631F.d.13.1 | M00022381C:C12 |
| 1423 | May 15, 1998 | 1489 | 147 | RTA00000629F.p.04.2 | M00022153D:D11 |
| 1424 | May 15, 1998 | 1489 | 148 | RTA00000628F.b.01.1 | M00021680B:C1 |
| 1425 | May 15, 1998 | 1489 | 149 | RTA00000630F.c.19.1 | M00022183A:G3 |
| 1426 | May 15, 1998 | 1489 | 150 | RTA00000593F.l.06.1 | M00022404D:G5 |
| 1427 | May 15, 1998 | 1489 | 151 | RTA00000628F.c.11.1 | M00021698B:B12 |
| 1428 | May 15, 1998 | 1489 | 152 | RTA00000630F.l.05.1 | M00022253B:E6 |
| 1429 | May 15, 1998 | 1489 | 153 | RTA00000628F.b.22.1 | M00021692C:E6 |
| 1430 | May 15, 1998 | 1489 | 154 | RTA00000633F.g.19.1 | M00022718D:G5 |
| 1431 | May 15, 1998 | 1489 | 155 | RTA00000629F.p.10.2 | M00022157B:A10 |
| 1432 | May 15, 1998 | 1489 | 156 | RTA00000628F.b.17.1 | M00021690B:B6 |
| 1433 | May 15, 1998 | 1489 | 157 | RTA00000627F.j.18.1 | M00021611D:H3 |
| 1434 | May 15, 1998 | 1489 | 158 | RTA00000627F.p.10.1 | M00021665A:D4 |
| 1435 | May 15, 1998 | 1489 | 159 | RTA00000628F.e.15.1 | M00021862A:A4 |
| 1436 | May 15, 1998 | 1489 | 160 | RTA00000630F.h.12.1 | M00022218D:B12 |
| 1437 | May 15, 1998 | 1489 | 161 | RTA00000628F.i.08.1 | M00021912B:H11 |
| 1438 | May 15, 1998 | 1489 | 162 | RTA00000630F.c.09.1 | M00022178D:H1 |
| 1439 | May 15, 1998 | 1489 | 163 | RTA00000633F.o.08.1 | M00022897A:F4 |
| 1440 | May 15, 1998 | 1489 | 164 | RTA00000628F.l.07.1 | M00021947A:C1 |
| 1441 | May 15, 1998 | 1489 | 165 | RTA00000628F.n.18.1 | M00021983D:B10 |
| 1442 | May 15, 1998 | 1489 | 166 | RTA00000630F.l.10.1 | M00022254C:D8 |
| 1443 | May 15, 1998 | 1489 | 167 | RTA00000632F.i.01.1 | M00022578D:F3 |
| 1444 | May 15, 1998 | 1489 | 168 | RTA00000629F.j.04.1 | M00022093D:B10 |
| 1445 | May 15, 1998 | 1489 | 169 | RTA00000627F.j.16.1 | M00021611D:D5 |
| 1446 | May 15, 1998 | 1489 | 170 | RTA00000629F.e.20.1 | M00022069D:G2 |
| 1447 | May 15, 1998 | 1489 | 171 | RTA00000632F.h.21.1 | M00022578C:B7 |
| 1448 | May 15, 1998 | 1489 | 172 | RTA00000629F.p.09.2 | M00022157A:F12 |
| 1449 | May 15, 1998 | 1489 | 173 | RTA00000631F.d.22.1 | M00022382D:H11 |
| 1450 | May 15, 1998 | 1489 | 174 | RTA00000630F.l.14.1 | M00022255A:C8 |
| 1451 | May 15, 1998 | 1489 | 175 | RTA00000633F.h.12.1 | M00022725C:E9 |
| 1452 | May 15, 1998 | 1489 | 176 | RTA00000630F.i.11.1 | M00022231C:A4 |
| 1453 | May 15, 1998 | 1489 | 177 | RTA00000632F.a.05.1 | M00022489C:A8 |
| 1454 | May 15, 1998 | 1489 | 178 | RTA00000629F.g.21.1 | M00022081C:G11 |
| 1455 | May 15, 1998 | 1489 | 179 | RTA00000632F.e.12.1 | M00022527A:E5 |
| 1456 | May 15, 1998 | 1489 | 180 | RTA00000632F.g.11.1 | M00022557B:A8 |
| 1457 | May 15, 1998 | 1489 | 181 | RTA00000629F.f.22.1 | M00022075D:F5 |
| 1458 | May 15, 1998 | 1489 | 182 | RTA00000630F.j.12.1 | M00022239A:A10 |
| 1459 | May 15, 1998 | 1489 | 183 | RTA00000629F.h.16.1 | M00022085C:C4 |
| 1460 | May 15, 1998 | 1489 | 184 | RTA00000633F.j.13.1 | M00022745A:B4 |
| 1461 | May 15, 1998 | 1489 | 185 | RTA00000633F.h.10.1 | M00022725C:B3 |
| 1462 | May 15, 1998 | 1489 | 186 | RTA00000632F.b.05.1 | M00022493C:C6 |
| 1463 | May 15, 1998 | 1489 | 187 | RTA00000633F.h.18.1 | M00022727B:C5 |
| 1464 | May 15, 1998 | 1489 | 188 | RTA00000633F.h.13.1 | M00022726A:A6 |
| 1465 | May 15, 1998 | 1489 | 189 | RTA00000630F.i.09.1 | M00022231A:F12 |
| 1466 | May 15, 1998 | 1489 | 190 | RTA00000593F.h.03.1 | M00022176C:A8 |
| 1467 | May 15, 1998 | 1489 | 191 | RTA00000632F.c.18.1 | M00022509D:F6 |
| 1468 | May 15, 1998 | 1489 | 192 | RTA00000593F.f.03.1 | M00022081C:B11 |
| 1469 | May 15, 1998 | 1489 | 193 | RTA00000627F.n.21.1 | M00021653A:G7 |
| 1470 | May 15, 1998 | 1489 | 194 | RTA00000631F.g.18.2 | M00022407C:H11 |
| 1471 | May 15, 1998 | 1489 | 195 | RTA00000639F.c.14.1 | M00022980B:E11 |
| 1472 | May 15, 1998 | 1489 | 196 | RTA00000633F.m.08.1 | M00022824C:H11 |
| 1473 | May 15, 1998 | 1489 | 197 | RTA00000627F.m.10.1 | M00021629D:D5 |

TABLE 1A-continued

Priority Appln Information

| SEQ ID NO: | Filed | Dkt No. | SEQ ID NO: | Sequence Name | Clone Name |
|---|---|---|---|---|---|
| 1474 | May 15, 1998 | 1489 | 198 | RTA00000632F.h.20.1 | M00022578B:G5 |
| 1475 | May 15, 1998 | 1489 | 199 | RTA00000627F.o.09.1 | M00021657B:C8 |
| 1476 | May 15, 1998 | 1489 | 200 | RTA00000632F.j.06.1 | M00022594B:H12 |
| 1477 | May 15, 1998 | 1489 | 201 | RTA00000632F.d.07.1 | M00022514A:D4 |
| 1478 | May 15, 1998 | 1489 | 202 | RTA00000629F.d.23.1 | M00022064C:H7 |
| 1479 | May 15, 1998 | 1489 | 203 | RTA00000629F.m.05.1 | M00022128A:D4 |
| 1480 | May 15, 1998 | 1489 | 204 | RTA00000639F.b.08.1 | M00022963A:D11 |
| 1481 | May 15, 1998 | 1489 | 205 | RTA00000627F.l.21.1 | M00021624A:D7 |
| 1482 | May 15, 1998 | 1489 | 206 | RTA00000628F.j.16.1 | M00021927D:D12 |
| 1483 | May 15, 1998 | 1489 | 207 | RTA00000628F.b.08.1 | M00021681C:B10 |
| 1484 | May 15, 1998 | 1489 | 208 | RTA00000630F.e.10.1 | M00022199C:F3 |
| 1485 | May 15, 1998 | 1489 | 209 | RTA00000639F.b.21.1 | M00022968A:F2 |
| 1486 | May 15, 1998 | 1489 | 210 | RTA00000631F.h.04.1 | M00022411D:G9 |
| 1487 | May 15, 1998 | 1489 | 211 | RTA00000639F.c.15.1 | M00022980C:A9 |
| 1488 | May 15, 1998 | 1489 | 212 | RTA00000631F.d.11.1 | M00022381A:F5 |
| 1489 | May 15, 1998 | 1489 | 213 | RTA00000633F.e.18.1 | M00022698C:E6 |
| 1490 | May 15, 1998 | 1489 | 214 | RTA00000615F.e.19.1 | M00004875A:G9 |
| 1491 | May 15, 1998 | 1489 | 215 | RTA00000629F.n.11.2 | M00022139A:C1 |
| 1492 | May 15, 1998 | 1489 | 216 | RTA0000063LF.g.11.2 | M00022404B:H5 |
| 1493 | May 15, 1998 | 1489 | 217 | RTA00000630F.o.18.1 | M00022288C:D4 |
| 1494 | May 15, 1998 | 1489 | 218 | RTA00000633F.h.22.1 | M00022730D:E10 |
| 1495 | May 15, 1998 | 1489 | 219 | RTA00000633F.e.24.1 | M00022701B:B12 |
| 1496 | May 15, 1998 | 1489 | 220 | RTA00000633F.o.19.1 | M00022900D:E8 |
| 1497 | May 15, 1998 | 1489 | 221 | RTA00000630F.e.04.1 | M00022198A:C12 |
| 1498 | May 15, 1998 | 1489 | 222 | RTA00000627F.o.01.1 | M00021654C:A2 |
| 1499 | May 15, 1998 | 1489 | 223 | RTA00000629F.k.21.1 | M00022114C:B2 |
| 1500 | May 15, 1998 | 1489 | 224 | RTA00000631F.g.04.1 | M00022399C:A10 |
| 1501 | May 15, 1998 | 1489 | 225 | RTA00000630F.m.03.1 | M00022258C:F6 |
| 1502 | May 15, 1998 | 1489 | 226 | RTA00000629F.i.08.1 | M00022090A:G8 |
| 1503 | May 15, 1998 | 1489 | 227 | RTA00000593F.d.02.2 | M00021682B:D12 |
| 1504 | May 15, 1998 | 1489 | 228 | RTA00000631F.a.24.1 | M00022365A:A1 |
| 1505 | May 15, 1998 | 1489 | 229 | RTA00000629F.p.06.2 | M00022154A:C1 |
| 1506 | May 15, 1998 | 1489 | 230 | RTA00000633F.n.09.1 | M00022856B:D7 |
| 1507 | May 15, 1998 | 1489 | 231 | RTA00000633F.f.14.1 | M00022708A:C8 |
| 1508 | May 15, 1998 | 1489 | 232 | RTA00000629F.k.11.1 | M00022106C:F4 |
| 1509 | May 15, 1998 | 1489 | 233 | RTA00000630F.b.02.1 | M00022170D:H9 |
| 1510 | May 15, 1998 | 1489 | 234 | RTA00000633F.p.04.1 | M00022902D:D3 |
| 1511 | May 15, 1998 | 1489 | 235 | RTA00000633F.n.08.1 | M00022856A:D2 |
| 1512 | May 15, 1998 | 1489 | 236 | RTA00000628F.h.06.1 | M00021897B:A6 |
| 1513 | May 15, 1998 | 1489 | 237 | RTA00000628F.d.05.1 | M00021841C:D7 |
| 1514 | May 15, 1998 | 1489 | 238 | RTA00000627F.l.22.1 | M00021624B:A3 |
| 1515 | May 15, 1998 | 1489 | 239 | RTA00000630F.f.19.1 | M00022212C:C2 |
| 1516 | May 15, 1998 | 1489 | 240 | RTA00000630F.h.17.1 | M00022220C:F8 |
| 1517 | May 15, 1998 | 1489 | 241 | RTA00000632F.i.15.1 | M00022583B:E5 |
| 1518 | May 15, 1998 | 1489 | 242 | RTA00000633F.j.15.1 | M00022745B:G2 |
| 1519 | May 15, 1998 | 1489 | 243 | RTA00000628F.k.05.1 | M00021932C:G10 |
| 1520 | May 15, 1998 | 1489 | 244 | RTA00000633F.d.04.1 | M00022685A:F11 |
| 1521 | May 15, 1998 | 1489 | 245 | RTA00000639F.h.10.1 | M00023094A:C4 |
| 1522 | May 15, 1998 | 1489 | 246 | RTA00000632F.f.11.1 | M00022535D:C4 |
| 1523 | May 15, 1998 | 1489 | 247 | RTA00000631F.p.20.1 | M00022480B:E7 |
| 1524 | May 15, 1998 | 1489 | 248 | RTA00000629F.o.17.2 | M00022150A:H6 |
| 1525 | May 15, 1998 | 1489 | 249 | RTA00000592F.l.23.1 | M00007986C:C5 |
| 1526 | May 15, 1998 | 1489 | 250 | RTA00000630F.d.10.1 | M00022189A:A1 |
| 1527 | May 15, 1998 | 1489 | 251 | RTA00000632F.j.19.1 | M00022600C:A6 |
| 1528 | May 15, 1998 | 1489 | 252 | RTA00000633F.n.10.1 | M00022856B:F4 |
| 1529 | May 15, 1998 | 1489 | 253 | RTA00000628F.h.13.1 | M00021905A:G5 |
| 1530 | May 15, 1998 | 1489 | 254 | RTA00000633F.k.05.1 | M00022763A:E10 |
| 1531 | May 15, 1998 | 1489 | 255 | RTA00000633F.i.11.1 | M00022735B:B1 |
| 1532 | May 15, 1998 | 1489 | 256 | RTA00000633F.o.20.1 | M00022900D:G3 |
| 1533 | May 15, 1998 | 1489 | 257 | RTA00000628F.b.19.1 | M00021690D:E5 |
| 1534 | May 15, 1998 | 1489 | 258 | RTA00000627F.p.14.1 | M00021667D:E3 |
| 1535 | May 15, 1998 | 1489 | 259 | RTA00000628F.n.15.1 | M00021983B:B3 |
| 1536 | May 15, 1998 | 1489 | 260 | RTA00000592F.p.22.1 | M00008074D:C1 |
| 1537 | May 15, 1998 | 1489 | 261 | RTA00000628F.m.19.1 | M00021977D:E2 |
| 1538 | May 15, 1998 | 1489 | 262 | RTA00000593F.a.05.1 | M00008078C:C6 |
| 1539 | May 15, 1998 | 1489 | 263 | RTA00000639F.g.17.1 | M00023036D:C4 |
| 1540 | May 15, 1998 | 1489 | 264 | RTA00000632F.j.15.1 | M00022599A:C3 |
| 1541 | May 15, 1998 | 1489 | 265 | RTA00000592F.l.04.1 | M00007971A:B4 |
| 1542 | May 15, 1998 | 1489 | 266 | RTA00000629F.c.07.1 | M00022054D:C5 |
| 1543 | May 15, 1998 | 1489 | 267 | RTA00000592F.l.21.1 | M00007985A:B9 |
| 1544 | May 15, 1998 | 1489 | 268 | RTA00000629F.h.15.1 | M00022085C:A7 |
| 1545 | May 15, 1998 | 1489 | 269 | RTA00000633F.n.02.1 | M00022835C:E6 |
| 1546 | May 15, 1998 | 1489 | 270 | RTA00000630F.n.24.1 | M00022278D:F10 |

TABLE 1A-continued

Priority Appln Information

| SEQ ID NO: | Filed | Dkt No. | SEQ ID NO: | Sequence Name | Clone Name |
|---|---|---|---|---|---|
| 1547 | May 15, 1998 | 1489 | 271 | RTA00000592F.k.09.1 | M00007953B:B3 |
| 1548 | May 15, 1998 | 1489 | 272 | RTA00000592F.l.10.1 | M00007974B:C11 |
| 1549 | May 15, 1998 | 1489 | 273 | RTA00000628F.k.04.1 | M00021932C:C5 |
| 1550 | May 15, 1998 | 1489 | 274 | RTA00000630F.h.24.1 | M00022226C:B6 |
| 1551 | May 15, 1998 | 1489 | 275 | RTA00000629F.i.13.1 | M00022091B:B7 |
| 1552 | May 15, 1998 | 1489 | 276 | RTA00000630F.b.01.1 | M00022170D:H7 |
| 1553 | May 15, 1998 | 1489 | 277 | RTA00000628F.g.13.1 | M00021886D:E4 |
| 1554 | May 15, 1998 | 1489 | 278 | RTA00000592F.m.13.1 | M00007995D:E6 |
| 1555 | May 15, 1998 | 1489 | 279 | RTA00000633F.h.20.1 | M00022728A:A9 |
| 1556 | May 15, 1998 | 1489 | 280 | RTA00000593F.d.08.2 | M00021860B:G6 |
| 1557 | May 15, 1998 | 1489 | 281 | RTA00000629F.f.01.1 | M00022071B:D5 |
| 1558 | May 15, 1998 | 1489 | 282 | RTA00000632F.i.11.1 | M00022582C:E12 |
| 1559 | May 15, 1998 | 1489 | 283 | RTA00000632F.j.24.1 | M00022604B:C11 |
| 1560 | May 15, 1998 | 1489 | 284 | RTA00000629F.f.03.1 | M00022071C:C9 |
| 1561 | May 15, 1998 | 1489 | 285 | RTA00000593F.b.04.1 | M00008094A:E10 |
| 1562 | May 15, 1998 | 1489 | 286 | RTA00000628F.l.12.1 | M00021952B:F11 |
| 1563 | May 15, 1998 | 1489 | 287 | RTA00000632F.j.12.1 | M00022597B:F11 |
| 1564 | May 15, 1998 | 1489 | 288 | RTA00000592F.k.23.1 | M00007964B:D10 |
| 1565 | May 15, 1998 | 1489 | 289 | RTA00000632F.g.07.1 | M00022556B:C4 |

TABLE 1B

| SEQ ID NO: | Sample Name | Overlap | Clone Name |
|---|---|---|---|
| 1566 | 803.F11.sp6:165002 | VO | M00004236D:E07 |
| 1567 | 180.B11.sp6:135937 | VO | M00001453B:F08 |
| 1568 | 1033.D01.sp6:188349 | VO | M00001455A:E09 |
| 1569 | 1164.H10.sp6:186952 | VO | M00001455A:E09 |
| 1570 | 80.E12.sp6:130267 | VNO | |
| 1571 | 121.C2.sp6:131906 | VNO | |
| 1572 | 1035.D01.sp6:188733 | VO | M00003939A:A02 |
| 1573 | 1034.G03.sp6:188579 | VNO | |
| 1574 | 020.C1.sp6:128615 | VO | M00003820C:A09 |
| 1575 | 019.B1.sp6:128411 | VO | M00003820C:A09 |
| 1576 | 803.F4.sp6:164995 | VO | M00004052C:B05 |
| 1577 | 1033.C06.sp6:188342 | VO | M00001654D:F06 |
| 1578 | 1035.H07.sp6:188787 | VO | M00004034C:F05 |
| 1579 | 396.C9.sp6:149508 | VO | M00004034C:F05 |
| 1580 | 396.D9.sp6:149520 | VO | M00004035B:F05 |
| 1581 | 1035.B08.sp6:188716 | VO | M00004035B:F05 |
| 1582 | 396.H9.sp6:149568 | VNO | |
| 1583 | 1035.D09.sp6:188741 | VO | M00004037C:D07 |
| 1584 | 1036.B05.sp6:188905 | VO | M00004115C:H04 |
| 1585 | 404.G2.sp6:162929 | VNO | |
| 1586 | 1035.D07.sp6:188739 | VO | M00004031D:G02 |
| 1587 | 1034.A05.sp6:188509 | VO | M00003829A:B08 |
| 1588 | 395.B5.sp6:149300 | VO | M00003829A:B08 |
| 1589 | 1034.F07.sp6:188571 | VO | M00003852D:D03 |
| 1590 | 1035.E04.sp6:188748 | VO | M00003982A:G03 |
| 1591 | 396.F3.sp6:149538 | VO | M00003982A:G03 |
| 1592 | 396.H3.sp6:149562 | VO | M00003982B:C10 |
| 1593 | 1035.F04.sp6:188760 | VNO | |
| 1594 | 396.D4.sp6:149515 | VO | M00003983A:D02 |
| 1595 | 1035.G04.sp6:188772 | VO | M00003983A:D02 |
| 1596 | 396.D5.sp6:149516 | VO | M00003985A:C01 |
| 1597 | 1035.B05.sp6:188713 | VO | M00003985A:C01 |
| 1598 | 1035.C06.sp6:188726 | VO | M00004028C:D01 |
| 1599 | 396.A7.sp6:149482 | VNO | |
| 1600 | 1035.E06.sp6:188750 | VO | M00004029C:B03 |
| 1601 | 801.E1.sp6:164692 | VO | M00001344D:G11 |
| 1602 | 801.F1.sp6:164704 | VO | M00001345A:A12 |
| 1603 | 801.A2.sp6:164645 | VNO | |
| 1604 | 801.B2.sp6:164657 | VNO | |
| 1605 | 801.C2.sp6:164669 | VO | M00001347A:G06 |
| 1606 | 801.D2.sp6:164681 | VO | M00001347B:H01 |
| 1607 | 801.E2.sp6:164693 | VNO | |
| 1608 | 801.F2.sp6:164705 | VNO | |
| 1609 | 801.A3.sp6:164646 | VO | M00001355B:A01 |
| 1610 | 801.B3.sp6:164658 | VO | M00001358D:D09 |
| 1611 | 801.C3.sp6:164670 | VO | M00001359A:B07 |
| 1612 | 801.D3.sp6:164682 | VO | M00001362A:C10 |
| 1613 | 801.E3.sp6:164694 | VO | M00001362B:A09 |
| 1614 | 801.G3.sp6:164718 | VO | M00001365D:D12 |
| 1615 | 801.H3.sp6:164730 | VO | M00001365D:H09 |
| 1616 | 801.A4.sp6:164647 | VNO | |
| 1617 | 801.B4.sp6:164659 | VO | M00001370A:G09 |
| 1618 | 801.C4.sp6:164671 | VO | M00001370B:B04 |
| 1619 | 801.D4.sp6:164683 | VO | M00001370B:B12 |
| 1620 | 801.E4.sp6:164695 | VNO | |
| 1621 | 801.G4.sp6:164719 | VO | M00001374D:D09 |
| 1622 | 801.D5.sp6:164684 | VO | M00001377C:B08 |
| 1623 | 801.F5.sp6:164707 | VNO | |
| 1624 | 801.G5.sp6:164720 | VNO | |
| 1625 | 801.H5.sp6:164732 | VNO | |
| 1626 | 801.A6.sp6:164649 | VO | M00001384A:C09 |
| 1627 | 801.B6.sp6:164661 | VO | M00001387A:A04 |
| 1628 | 801.D6.sp6:164685 | VO | M00001389B:B06 |
| 1629 | 801.E6.sp6:164697 | VO | M00001390A:C06 |
| 1630 | 801.F6.sp6:164709 | VO | M00001390A:H01 |
| 1631 | 801.D7.sp6:164686 | VNO | |
| 1632 | 801.E7.sp6:164698 | VO | M00001399C:E10 |
| 1633 | 1033.A01.sp6:188313 | VO | M00001399D:F09 |
| 1634 | 801.G7.sp6:164722 | VNO | |
| 1635 | 801.H7.sp6:164734 | VO | M00001401D:D04 |
| 1636 | 801.A8.sp6:164651 | VNO | |
| 1637 | 801.B8.sp6:164663 | VO | M00001402C:C07 |
| 1638 | 801.C8.sp6:164675 | VO | M00001402D:H03 |
| 1639 | 801.D8.sp6:164687 | VO | M00001403B:A01 |
| 1640 | 801.E8.sp6:164699 | VO | M00001405D:F05 |
| 1641 | 801.G8.sp6:164723 | VO | M00001406C:A11 |
| 1642 | 801.B9.sp6:164664 | VO | M00001407B:A08 |
| 1643 | 801.C9.sp6:164676 | VO | M00001407D:H11 |
| 1644 | 801.D9.sp6:164688 | VNO | |
| 1645 | 801.E9.sp6:164700 | VNO | |
| 1646 | 801.F9.sp6:164712 | VO | M00001411A:D01 |
| 1647 | 801.G9.sp6:164724 | VNO | |
| 1648 | 801.H9.sp6:164736 | VO | M00001411C:G02 |
| 1649 | 801.B10.sp6:164665 | VO | M00001412A:A11 |
| 1650 | 801.C10.sp6:164677 | VNO | |
| 1651 | 801.D10.sp6:164689 | VNO | |
| 1652 | 801.E10.sp6:164701 | VO | M00001415D:E12 |
| 1653 | 801.F10.sp6:164713 | VNO | |
| 1654 | 801.G10.sp6:164725 | VO | M00001417B:E01 |
| 1655 | 020.A6.sp6:128596 | VO | M00001417B:E01 |

TABLE 1B-continued

| SEQ ID NO: | Sample Name | Overlap | Clone Name |
|---|---|---|---|
| 1656 | 801.H10.sp6:164737 | VNO | |
| 1657 | 801.A11.sp6:164654 | VO | M00001417C:E02 |
| 1658 | 801.B11.sp6:164666 | VNO | |
| 1659 | 801.C11.sp6:164678 | VO | M00001421A:H07 |
| 1660 | 801.F11.sp6:164714 | VO | M00001423C:D06 |
| 1661 | 801.G11.sp6:164726 | VO | M00001424A:H09 |
| 1662 | 801.H11.sp6:164738 | VO | M00001425C:E10 |
| 1663 | 801.B12.sp6:164667 | VO | M00001426A:F09 |
| 1664 | 801.C12.sp6:164679 | VO | M00001426D:D09 |
| 1665 | 801.E12.sp6:164703 | VO | M00001431A:C10 |
| 1666 | 801.F12.sp6:164715 | VO | M00001431A:E05 |
| 1667 | 801.G12.sp6:164727 | VO | M00001432A:F12 |
| 1668 | 801.H12.sp6:164739 | VO | M00001432B:H08 |
| 1669 | 802.A1.sp6:164740 | VO | M00001432C:G01 |
| 1670 | 802.B1.sp6:164752 | VO | M00001433A:C07 |
| 1671 | 802.C1.sp6:164764 | VNO | |
| 1672 | 802.D1.sp6:164776 | VO | M00001434A:A01 |
| 1673 | 802.E1.sp6:164788 | VNO | |
| 1674 | 802.F1.sp6:164800 | VO | M00001435A:F03 |
| 1675 | 802.G1.sp6:164812 | VO | M00001435A:G01 |
| 1676 | 802.H1.sp6:164824 | VO | M00001435B:G10 |
| 1677 | 802.A2.sp6:164741 | VO | M00001435C:G08 |
| 1678 | 802.B2.sp6:164753 | VNO | |
| 1679 | 802.C2.sp6:164765 | VO | M00001435D:A06 |
| 1680 | 802.D2.sp6:164777 | VO | M00001436D:C10 |
| 1681 | 802.E2.sp6:164789 | VO | M00001437B:B05 |
| 1682 | 802.G2.sp6:164813 | VNO | |
| 1683 | 802.H2.sp6:164825 | VO | M00001438C:H05 |
| 1684 | 802.A3.sp6:164742 | VNO | |
| 1685 | 802.B3.sp6:164754 | VO | M00001439B:F10 |
| 1686 | 802.C3.sp6:164766 | VO | M00001439C:A01 |
| 1687 | 802.D3.sp6:164778 | VO | M00001439C:G06 |
| 1688 | 802.E3.sp6:164790 | VO | M00001441D:H05 |
| 1689 | 802.F3.sp6:164802 | VO | M00001442A:D08 |
| 1690 | 802.G3.sp6:164814 | VNO | |
| 1691 | 802.H3.sp6:164826 | VO | M00001443D:A01 |
| 1692 | 802.A4.sp6:164743 | VNO | |
| 1693 | 802.B4.sp6:164755 | VO | M00001444A:A09 |
| 1694 | 802.C4.sp6:164767 | VNO | |
| 1695 | 802.D4.sp6:164779 | VNO | |
| 1696 | 802.E4.sp6:164791 | VO | M00001446D:B10 |
| 1697 | 1033.B01.sp6:188325 | VO | M00001448A:D05 |
| 1698 | 802.F4.sp6:164803 | VO | M00001451B:H11 |
| 1699 | 802.G4.sp6:164815 | VNO | |
| 1700 | 802.H4.sp6:164827 | VO | M00001452B:H06 |
| 1701 | 802.A5.sp6:164744 | VO | M00001452D:E05 |
| 1702 | 802.C5.sp6:164768 | VO | M00001453D:F09 |
| 1703 | 1033.C01.sp6:188337 | VO | M00001455A:C03 |
| 1704 | 1033.E01.sp6:188361 | VO | M00001456C:F02 |
| 1705 | 1033.F01.sp6:188373 | VO | M00001458B:F06 |
| 1706 | 802.D5.sp6:164780 | VO | M00001463C:A01 |
| 1707 | 802.E5.sp6:164792 | VO | M00001466C:F02 |
| 1708 | 802.F5.sp6:164804 | VNO | |
| 1709 | 802.G5.sp6:164816 | VO | M00001471C:G03 |
| 1710 | 1033.G01.sp6:188385 | VO | M00001478A:B06 |
| 1711 | 1033.H01.sp6:188397 | VO | M00001487D:D11 |
| 1712 | 802.H5.sp6:164828 | VO | M00001488B:G12 |
| 1713 | 802.B6.sp6:164757 | VO | M00001489B:F08 |
| 1714 | 802.C6.sp6:164769 | VO | M00001489D:C08 |
| 1715 | 802.D6.sp6:164781 | VO | M00001490B:G04 |
| 1716 | 802.E6.sp6:164793 | VO | M00001491C:C01 |
| 1717 | 802.F6.sp6:164805 | VNO | |
| 1718 | 802.G6.sp6:164817 | VO | M00001496A:B03 |
| 1719 | 802.H6.sp6:164829 | VNO | |
| 1720 | 802.A7.sp6:164746 | VO | M00001496D:D02 |
| 1721 | 802.B7.sp6:164758 | VNO | |
| 1722 | 802.D7.sp6:164782 | VNO | |
| 1723 | 802.E7.sp6:164794 | VO | M00001500A:D09 |
| 1724 | 802.F7.sp6:164806 | VNO | |
| 1725 | 802.G7.sp6:164818 | VNO | |
| 1726 | 802.H7.sp6:164830 | VO | M00001504D:D09 |
| 1727 | 802.A8.sp6:164747 | VO | M00001505A:E09 |
| 1728 | 802.B8.sp6:164759 | VO | M00001506A:F01 |
| 1729 | 802.D8.sp6:164783 | VO | M00001517D:C03 |
| 1730 | 802.E8.sp6:164795 | VO | M00001518D:A10 |
| 1731 | 1033.A02.sp6:188314 | VO | M00001530A:D11 |
| 1732 | 802.F8.sp6:164807 | VO | M00001536B:B11 |
| 1733 | 802.G8.sp6:164819 | VO | M00001537B:C12 |
| 1734 | 1033.B02.sp6:188326 | VO | M00001539B:B01 |
| 1735 | 802.H8.sp6:164831 | VO | M00001542C:D10 |
| 1736 | 802.A9.sp6:164748 | VO | M00001542C:F06 |
| 1737 | 802.B9.sp6:164760 | VNO | |
| 1738 | 802.C9.sp6:164772 | VO | M00001543A:E04 |
| 1739 | 802.E9.sp6:164796 | VO | M00001546B:H01 |
| 1740 | 802.G9.sp6:164820 | VO | M00001551D:C12 |
| 1741 | 802.H9.sp6:164832 | VO | M00001552B:D01 |
| 1742 | 802.A10.sp6:164749 | VO | M00001553D:B06 |
| 1743 | 802.B10.sp6:164761 | VNO | |
| 1744 | 802.C10.sp6:164773 | VO | M00001556D:A11 |
| 1745 | 802.D10.sp6:164785 | VNO | |
| 1746 | 802.E10.sp6:164797 | VO | M00001557C:B08 |
| 1747 | 802.F10.sp6:164809 | VO | M00001558B:A12 |
| 1748 | 802.G10.sp6:164821 | VO | M00001560C:C01 |
| 1749 | 802.H10.sp6:164833 | VO | M00001561B:C10 |
| 1750 | 1033.C02.sp6:188338 | VO | M00001563C:D06 |
| 1751 | 1033.D02.sp6:188350 | VO | M00001564C:D04 |
| 1752 | 1033.E02.sp6:188362 | VO | M00001565A:A02 |
| 1753 | 1033.F02.sp6:188374 | VO | M00001569B:F04 |
| 1754 | 1033.G02.sp6:188386 | VO | M00001572C:E07 |
| 1755 | 1033.H02.sp6:188398 | VO | M00001575A:H02 |
| 1756 | 1033.A03.sp6:188315 | VO | M00001582B:B10 |
| 1757 | 1033.B03.sp6:188327 | VO | M00001584C:A03 |
| 1758 | 1033.E04.sp6:188364 | VO | M00001618B:F02 |
| 1759 | 1033.B08.sp6:188332 | VO | M00001687C:A06 |
| 1760 | 1033.H12.sp6:188408 | VNO | |
| 1761 | 1034.C05.sp6:188533 | VO | M00003830A:A10 |
| 1762 | 1034.F05.sp6:188569 | VO | M00003833D:D06 |
| 1763 | 1034.D06.sp6:188546 | VO | M00003839D:G06 |
| 1764 | 1034.G06.sp6:188582 | VO | M00003843A:B01 |
| 1765 | 1034.H07.sp6:188595 | VO | M00003858A:D01 |
| 1766 | 1034.A08.sp6:188512 | VO | M00003859C:B09 |
| 1767 | 1034.E08.sp6:188560 | VO | M00003868D:F07 |
| 1768 | 1034.C10.sp6:188538 | VO | M00003895D:A03 |
| 1769 | 1034.B11.sp6:188527 | VO | M00003906C:H12 |
| 1770 | 1034.G11.sp6:188587 | VNO | |
| 1771 | 1034.D12.sp6:188552 | VO | M00003918C:E07 |
| 1772 | 1035.H01.sp6:188781 | VNO | |
| 1773 | 1035.G02.sp6:188770 | VNO | |
| 1774 | 325.D3.sp6:145862 | VNO | |
| 1775 | 1035.A05.sp6:188701 | VO | |
| 1776 | 1035.F05.sp6:188761 | VNO | |
| 1777 | 803.H1.sp6:165016 | VNO | |
| 1778 | 803.F2.sp6:164993 | VNO | |
| 1779 | 1035.G06.sp6:188774 | VO | M00004030A:G12 |
| 1780 | 1035.A07.sp6:188703 | VO | M00004030B:C05 |
| 1781 | 1035.B07.sp6:188715 | VNO | |
| 1782 | 1035.D08.sp6:188740 | VO | M00004035D:C05 |
| 1783 | 1035.G08.sp6:188776 | VO | M00004036C:D01 |
| 1784 | 1035.A09.sp6:188705 | VNO | |
| 1785 | 1035.B09.sp6:188717 | VO | M00004037B:B05 |
| 1786 | 1035.G09.sp6:188777 | VO | M00004038C:D12 |
| 1787 | 803.C4.sp6:164959 | VO | M00004051C:D02 |
| 1788 | 803.A5.sp6:164936 | VNO | |
| 1789 | 774.E2.sp6:162484 | VO | M00004054D:D02 |
| 1790 | 803.D5.sp6:164972 | VNO | |
| 1791 | 803.C6.sp6:164961 | VNO | |
| 1792 | 803.D6.sp6:164973 | VNO | |
| 1793 | 1035.A12.sp6:188708 | VNO | |
| 1794 | 1035.C12.sp6:188732 | VO | M00004076D:B03 |
| 1795 | 774.E4.sp6:162500 | VO | M00004081B:C11 |
| 1796 | 1035.G12.sp6:188780 | VO | M00004081B:C11 |
| 1797 | 1036.H01.sp6:188973 | VO | M00004089A:F02 |
| 1798 | 1036.D02.sp6:188926 | VO | M00004091B:G04 |
| 1799 | 1036.G03.sp6:188963 | VO | M00004103B:C07 |
| 1800 | 1036.F04.sp6:188952 | VNO | |
| 1801 | 1036.H04.sp6:188976 | VO | M00004115A:F01 |
| 1802 | 1036.A05.sp6:188893 | VO | M00004115A:G09 |
| 1803 | 1036.B06.sp6:188906 | VNO | |
| 1804 | 803.A7.sp6:164938 | VNO | |
| 1805 | 803.E8.sp6:164987 | VNO | |
| 1806 | 803.F8.sp6:164999 | VO | M00004159D:C04 |
| 1807 | 803.A9.sp6:164940 | VO | M00004160A:D07 |
| 1808 | 1036.D06.sp6:188930 | VO | M00004178B:F06 |
| 1809 | 1036.F06.sp6:188954 | VNO | |

TABLE 1B-continued

| SEQ ID NO: | Sample Name | Overlap | Clone Name |
|---|---|---|---|
| 1810 | 1036.H06.sp6:188978 | VO | M00004184B:F11 |
| 1811 | 1036.D09.sp6:188933 | VO | M00004202B:A02 |
| 1812 | 1036.F09.sp6:188957 | VO | M00004202B:G09 |
| 1813 | 803.H10.sp6:165025 | VNO | |
| 1814 | 803.H11.sp6:165026 | VNO | |
| 1815 | 803.C12.sp6:164967 | VNO | |
| 1816 | 804.D1.sp6:165160 | VNO | |
| 1817 | 983.D01.sp6:186199 | VO | M00004247B:C11 |
| 1818 | 1036.D11.sp6:188935 | VO | M00004249C:E12 |
| 1819 | 804.B3.sp6:165138 | VNO | |
| 1820 | 983.B03.sp6:186181 | VO | M00004277D:C08 |
| 1821 | 804.F5.sp6:165188 | VNO | |
| 1822 | 983.F05.sp6:186221 | VO | M00004337D:G08 |
| 1823 | 983.G05.sp6:186230 | VO | M00004345A:H06 |
| 1824 | 804.G5.sp6:165200 | VNO | |
| 1825 | 983.A06.sp6:186174 | VO | M00004350B:F06 |
| 1826 | 804.A6.sp6:165129 | VNO | |
| 1827 | 774.D12.sp6:162563 | VO | M00004350B:F06 |
| 1828 | 804.F7.sp6:165190 | VNO | |
| 1829 | 983.F07.sp6:186223 | VO | M00004446A:G01 |
| 1830 | 992.E01.sp6:186367 | VO | M00005332A:H10 |
| 1831 | 992.G02.sp6:186392 | VNO | |
| 1832 | 992.A04.sp6:186322 | VO | M00005378C:A10 |
| 1833 | 992.D04.sp6:186358 | VO | M00005384A:A01 |
| 1834 | 992.B05.sp6:186335 | VO | M00005390B:G10 |
| 1835 | 992.H05.sp6:186407 | VO | M00005399A:D01 |
| 1836 | 992.A06.sp6:186324 | VNO | |
| 1837 | 992.B06.sp6:186336 | VO | M00005399D:B02 |
| 1838 | 020.G4.sp6:128666 | VO | M00005404C:F02 |
| 1839 | 020.G8.sp6:128670 | VO | M00005411A:C07 |
| 1840 | 992.H06.sp6:186408 | VNO | |
| 1841 | 953.F01.sp6:185185 | VO | M00005411D:A03 |
| 1842 | 992.A07.sp6:186325 | VO | M00005411D:A03 |
| 1843 | 992.D08.sp6:186362 | VO | M00005446A:G01 |
| 1844 | 992.B09.sp6:186339 | VO | M00005450B:B01 |
| 1845 | 953.A07.sp6:185131 | VO | M00005450B:B01 |
| 1846 | 953.E07.sp6:185179 | VO | M00005452C:A02 |
| 1847 | 992.E09.sp6:186375 | VO | M00005452C:A02 |
| 1848 | 992.G09.sp6:186399 | VO | M00005455A:D01 |
| 1849 | 992.H09.sp6:186411 | VO | M00005455A:G03 |
| 1850 | 992.D11.sp6:186365 | VNO | |
| 1851 | 953.H10.sp6:185218 | VO | M00005477C:D08 |
| 1852 | 992.F11.sp6:186389 | VO | M00005477C:D08 |
| 1853 | 953.D11.sp6:185171 | VO | M00005480A:H12 |
| 1854 | 992.H11.sp6:186413 | VO | M00005480C:B12 |
| 1855 | 992.A12.sp6:186330 | VO | M00005481C:A05 |
| 1856 | 953.E11.sp6:185183 | VO | M00005481C:A05 |
| 1857 | 953.C12.sp6:185160 | VO | M00005485C:A03 |
| 1858 | 992.F12.sp6:186390 | VO | M00005485C:A03 |
| 1859 | 953.E12.sp6:185184 | VO | M00005486C:B03 |
| 1860 | 993.C03.sp6:186537 | VO | M00005510B:D06 |
| 1861 | 993.D03.sp6:186549 | VO | M00005513A:D08 |
| 1862 | 993.E03.sp6:186561 | VO | M00005524C:B01 |
| 1863 | 993.G03.sp6:186585 | VO | M00005528D:H06 |
| 1864 | 993.A04.sp6:186514 | VO | M00005530B:E04 |
| 1865 | 993.B05.sp6:186527 | VO | M00005616B:D05 |
| 1866 | 993.C06.sp6:186540 | VNO | |
| 1867 | 993.B08.sp6:186530 | VO | M00005704A:B11 |
| 1868 | 993.C08.sp6:186542 | VO | M00005708D:B03 |
| 1869 | 993.D09.sp6:186555 | VO | M00005765C:C04 |
| 1870 | 993.E09.sp6:186567 | VO | M00005772A:F03 |
| 1871 | 993.F10.sp6:186580 | VO | M00006577B:H12 |
| 1872 | 993.C11.sp6:186545 | VO | M00006587A:H08 |
| 1873 | 993.D11.sp6:186557 | VNO | |
| 1874 | 993.G11.sp6:186593 | VNO | |
| 1875 | 993.H12.sp6:186606 | VO | M00006615B:F05 |
| 1876 | 626.B2.sp6:157417 | VO | M00007953B:B03 |
| 1877 | 627.E6.sp6:157649 | VO | M00007985A:B09 |
| 1878 | 633.C4.sp6:156098 | VO | M00008061A:F02 |
| 1879 | 636.F10.sp6:158241 | VO | M00022070B:C10 |
| 1880 | 641.G8.GZ42:158428 | VO | M00022109B:A11 |
| 1881 | 642.B7.sp6:156281 | VO | M00022176C:A08 |
| 1882 | 1010.F02.sp6:189986 | VNO | |
| 1883 | 1010.A09.sp6:189945 | VO | M00022828C:E04 |
| 1884 | 1033.C03.sp6:188339 | VO | M0000 1586A:F09 |
| 1885 | 1033.D03.sp6:188351 | VO | M00001588D:H08 |
| 1886 | 1033.E03.sp6:188363 | VO | M00001589C:D12 |
| 1887 | 1033.F03.sp6:188375 | VO | M00001589D:G10 |
| 1888 | 1033.G03.sp6:188387 | VO | M00001590D:A07 |
| 1889 | 802.A11.sp6:164750 | VNO | |
| 1890 | 802.B11.sp6:164762 | VO | M00001597C:B03 |
| 1891 | 1033.H03.sp6:188399 | VO | M00001598C:D10 |
| 1892 | 1033.A04.sp6:188316 | VO | M00001599A:H09 |
| 1893 | 1033.B04.sp6:188328 | VNO | |
| 1894 | 1033.C04.sp6:188340 | VO | M00001610B:A01 |
| 1895 | 1033.D04.sp6:188352 | VO | M00001614C:G04 |
| 1896 | 1033.F04.sp6:188376 | VO | M00001618C:E06 |
| 1897 | 1033.G04.sp6:188388 | VO | M00001621C:A04 |
| 1898 | 802.E11.sp6:164798 | VNO | |
| 1899 | 802.G11.sp6:164822 | VO | M00001623B:B01 |
| 1900 | 802.H11.sp6:164834 | VO | M00001623D:A09 |
| 1901 | 1033.H04.sp6:188400 | VO | M00001626B:H05 |
| 1902 | 1033.A05.sp6:188317 | VNO | |
| 1903 | 1033.B05.sp6:188329 | VO | M00001634C:E12 |
| 1904 | 1033.C05.sp6:188341 | VO | M00001639A:A04 |
| 1905 | 1033.D05.sp6:188353 | VNO | |
| 1906 | 1033.E05.sp6:188365 | VO | M00001640A:F04 |
| 1907 | 1033.F05.sp6:188377 | VO | M00001641B:G05 |
| 1908 | 802.C12.sp6:164775 | VO | M00001644D:F09 |
| 1909 | 1033.G05.sp6:188389 | VO | M00001647C:C07 |
| 1910 | 1033.H05.sp6:188401 | VO | M00001648C:F06 |
| 1911 | 1033.A06.sp6:188318 | VNO | |
| 1912 | 1033.B06.sp6:188330 | VO | M00001649D:H05 |
| 1913 | 1033.D06.sp6:188354 | VO | M00001655A:F07 |
| 1914 | 1033.E06.sp6:188366 | VO | M00001656D:F11 |
| 1915 | 1033.F06.sp6:188378 | VNO | |
| 1916 | 1033.G06.sp6:188390 | VNO | |
| 1917 | 1033.H06.sp6:188402 | VO | M00001660A:F10 |
| 1918 | 1033.A07.sp6:188319 | VO | M00001663C:C03 |
| 1919 | 1033.B07.sp6:188331 | VO | M00001669A:H11 |
| 1920 | 1033.C07.sp6:188343 | VO | M00001669B:A03 |
| 1921 | 1033.D07.sp6:188355 | VO | M00001675C:B03 |
| 1922 | 1033.E07.sp6:188367 | VO | M00001677A:A06 |
| 1923 | 1033.F07.sp6:188379 | VO | M00001677A:A12 |
| 1924 | 1033.G07.sp6:188391 | VO | M00001678D:A12 |
| 1925 | 1033.H07.sp6:188403 | VO | |
| 1926 | 1033.A08.sp6:188320 | VNO | |
| 1927 | 1033.C08.sp6:188344 | VO | M00001693D:F07 |
| 1928 | 1033.D08.sp6:188356 | VO | M00003741A:E01 |
| 1929 | 1033.E08.sp6:188368 | VO | M00003745C:E03 |
| 1930 | 1033.F08.sp6:188380 | VO | M00003746A:E01 |
| 1931 | 1033.G08.sp6:188392 | VNO | |
| 1932 | 1033.H08.sp6:188404 | VO | M00003748B:B06 |
| 1933 | 1033.A09.sp6:188321 | VO | M00003749B:C08 |
| 1934 | 1033.B09.sp6:188333 | VO | M00003749D:G07 |
| 1935 | 1033.C09.sp6:188345 | VO | M00003752A:B06 |
| 1936 | 1033.D09.sp6:188357 | VO | M00003752D:D09 |
| 1937 | 1033.E09.sp6:188369 | VO | M00003753C:B01 |
| 1938 | 1033.F09.sp6:188381 | VO | M00003754C:F01 |
| 1939 | 1033.G09.sp6:188393 | VO | M00003756C:C08 |
| 1940 | 1033.H09.sp6:188405 | VO | M00003759A:E10 |
| 1941 | 1033.A10.sp6:188322 | VO | M00003762A:D11 |
| 1942 | 1033.B10.sp6:188334 | VO | M00003763B:D03 |
| 1943 | 1033.C10.sp6:188346 | VO | M00003763D:F06 |
| 1944 | 1033.D10.sp6:188358 | VO | M00003765D:E02 |
| 1945 | 1033.E10.sp6:188370 | VO | M00003766A:G09 |
| 1946 | 1033.F10.sp6:188382 | VO | M00003766B:G04 |
| 1947 | 1033.G10.sp6:188394 | VO | M00003767C:F04 |
| 1948 | 1033.H10.sp6:188406 | VO | M00003769B:A04 |
| 1949 | 1033.A11.sp6:188323 | VO | M00003769D:G12 |
| 1950 | 1033.B11.sp6:188335 | VO | M00003770D:F08 |
| 1951 | 1033.C11.sp6:188347 | VO | M00003771A:G09 |
| 1952 | 1033.D11.sp6:188359 | VO | M00003771D:A10 |
| 1953 | 1033.E11.sp6:188371 | VO | M00003773A:C09 |
| 1954 | 1033.F11.sp6:188383 | VO | M00003773B:E09 |
| 1955 | 1033.G11.sp6:188395 | VO | M00003773B:G08 |
| 1956 | 1033.H11.sp6:188407 | VO | M00003773C:G06 |
| 1957 | 1033.A12.sp6:188324 | VO | M00003773D:C02 |
| 1958 | 802.E12.sp6:164799 | VNO | |
| 1959 | 802.F12.sp6:164811 | VNO | |
| 1960 | 802.G12.sp6:164823 | VO | M00003784C:B09 |
| 1961 | 802.H12.sp6.164835 | VO | M00003785D:E01 |
| 1962 | 803.A1.sp6:164932 | VNO | |
| 1963 | 803.B1.sp6:164944 | VNO | |

TABLE 1B-continued

| SEQ ID NO: | Sample Name | Overlap | Clone Name |
|---|---|---|---|
| 1964 | 803.C1.sp6:164956 | VNO | |
| 1965 | 1033.B12.sp6:188336 | VO | M00003789C:E03 |
| 1966 | 1033.C12.sp6:188348 | VO | M00003790B:F12 |
| 1967 | 1033.D12.sp6:188360 | VO | M00003793C:D11 |
| 1968 | 1033.F12.sp6:188384 | VO | M00003796B:C07 |
| 1969 | 1033.G12.sp6:188396 | VO | M00003796C:H03 |
| 1970 | 1034.A01.sp6:188505 | VO | M00003797D:H06 |
| 1971 | 1034.B01.sp6:188517 | VNO | |
| 1972 | 1034.C01.sp6:188529 | VO | M00003801D:F05 |
| 1973 | 1034.D01.sp6:188541 | VO | M00003805A:G05 |
| 1974 | 1034.E01.sp6:188553 | VO | M00003808C:D09 |
| 1975 | 1034.F01.sp6:188565 | VO | M00003809A:A12 |
| 1976 | 1034.G01.sp6:188577 | VO | M00003809A:H12 |
| 1977 | 1034.H01.sp6:188589 | VO | M00003809B:D08 |
| 1978 | 1034.A02.sp6:188506 | VO | M00003811B:E07 |
| 1979 | 1034.B02.sp6:188518 | VO | M00003812B:F08 |
| 1980 | 1034.C02.sp6:188530 | VO | M00003812D:E08 |
| 1981 | 1034.D02.sp6:188542 | VO | M00003813D:A06 |
| 1982 | 1034.E02.sp6:188554 | VO | M00003815C:A06 |
| 1983 | 1034.F02.sp6:188566 | VNO | |
| 1984 | 1034.G02.sp6:188578 | VNO | |
| 1985 | 1034.H02.sp6:188590 | VO | M00003818A:F09 |
| 1986 | 1034.A03.sp6:188507 | VO | M00003818B:A01 |
| 1987 | 1034.B03.sp6:188519 | VO | M00003818C:E09 |
| 1988 | 1034.C03.sp6:188531 | VNO | |
| 1989 | 1034.D03.sp6:188543 | VO | M00003819C:E04 |
| 1990 | 1034.E03.sp6:188555 | VO | M00003819D:G09 |
| 1991 | 1034.F03.sp6:188567 | VO | M00003820A:H04 |
| 1992 | 1034.H03.sp6:188591 | VO | M00003820D:E02 |
| 1993 | 1034.A04.sp6:188508 | VO | M00003821C:E04 |
| 1994 | 1034.B04.sp6:188520 | VO | M00003822A:G05 |
| 1995 | 803.E12.sp6:164991 | VNO | |
| 1996 | 020.E2.sp6:128640 | VO | M00004242C:C01 |
| 1997 | 019.F9.sp6:128467 | VO | M00006720C:C11 |
| 1998 | 019.G10.sp6:128480 | VO | M00007019A:B01 |
| 1999 | 1034.C04.sp6:188532 | VNO | |
| 2000 | 1034.D04.sp6:188544 | VO | M00003825B:A05 |
| 2001 | 1034.E04.sp6:188556 | VNO | |
| 2002 | 1034.F04.sp6:188568 | VO | M00003825C:B02 |
| 2003 | 1034.G04.sp6:188580 | VO | M00003825C:B12 |
| 2004 | 1034.B05.sp6:188521 | VO | M00003829A:E02 |
| 2005 | 1034.D05.sp6:188545 | VO | M00003832B:G03 |
| 2006 | 1034.E05.sp6:188557 | VO | M00003833B:A11 |
| 2007 | 1034.G05.sp6:188581 | VO | M00003834A:A03 |
| 2008 | 1034.A06.sp6:188510 | VO | M00003835D:H05 |
| 2009 | 1034.B06.sp6:188522 | VO | M00003837C:F05 |
| 2010 | 1034.C06.sp6:188534 | VNO | |
| 2011 | 1034.E06.sp6:188558 | VO | M00003841A:E09 |
| 2012 | 1034.F06.sp6:188570 | VO | M00003841B:D05 |
| 2013 | 1034.H06.sp6:188594 | VO | M00003844C:D04 |
| 2014 | 1034.A07.sp6:188511 | VO | M00003844C:H05 |
| 2015 | 1034.B07.sp6:188523 | VO | M00003845A:A05 |
| 2016 | 1034.C07.sp6:188535 | VO | M00003846B:H02 |
| 2017 | 1034.D07.sp6:188547 | VO | M00003846D:C12 |
| 2018 | 1034.E07.sp6:188559 | VO | M00003850B:D11 |
| 2019 | 1034.G07.sp6:188583 | VNO | |
| 2020 | 1034.B08.sp6:188524 | VO | M00003860B:A07 |
| 2021 | 803.D1.sp6:164968 | VO | M00003862C:H10 |
| 2022 | 803.E1.sp6:164980 | VO | M00003864B:A04 |
| 2023 | 803.F1.sp6:164992 | VNO | |
| 2024 | 803.G1.sp6:165004 | VO | M00003864D:G05 |
| 2025 | 1034.C08.sp6:188536 | VNO | |
| 2026 | 1034.D08.sp6:188548 | VO | M00003868D:F02 |
| 2027 | 1034.F08.sp6:188572 | VO | M00003871A:E09 |
| 2028 | 1034.G08.sp6:188584 | VNO | |
| 2029 | 1034.H08.sp6:188596 | VNO | |
| 2030 | 1034.A09.sp6:188513 | VNO | |
| 2031 | 1034.B09.sp6:188525 | VO | M00003884D:A12 |
| 2032 | 1034.C09.sp6:188537 | VNO | |
| 2033 | 1034.D09.sp6:188549 | VO | M00003887B:C03 |
| 2034 | 1034.E09.sp6:188561 | VO | M00003888B:A10 |
| 2035 | 1034.F09.sp6:188573 | VO | M00003888C:E01 |
| 2036 | 1034.G09.sp6:188585 | VO | M00003890B:H07 |
| 2037 | 1034.H09.sp6:188597 | VO | M00003890D:C03 |
| 2038 | 1034.A10.sp6:188514 | VO | M00003892D:D04 |
| 2039 | 1034.B10.sp6:188526 | VO | M00003893C:D12 |
| 2040 | 1034.D10.sp6:188550 | VO | M00003896B:F08 |
| 2041 | 1034.E10.sp6:188562 | VO | M00003896D:B01 |
| 2042 | 1034.F10.sp6:188574 | VNO | |
| 2043 | 1034.G10.sp6:188586 | VO | M00003903C:H03 |
| 2044 | 1034.H10.sp6:188598 | VO | M00003905C:B01 |
| 2045 | 1034.A11.sp6:188515 | VO | M00003905C:E10 |
| 2046 | 1034.C11.sp6:188539 | VO | M00003909D:G01 |
| 2047 | 1034.D11.sp6:188551 | VO | M00003911C:G05 |
| 2048 | 1034.E11.sp6:188563 | VO | M00003912B:G11 |
| 2049 | 1034.F11.sp6:188575 | VO | M00003912C:C11 |
| 2050 | 1034.H11.sp6:188599 | VO | M00003914C:E03 |
| 2051 | 1034.A12.sp6:188516 | VO | M00003915A:D09 |
| 2052 | 1034.B12.sp6:188528 | VNO | |
| 2053 | 1034.C12.sp6:188540 | VO | M00003915C:G01 |
| 2054 | 1034.E12.sp6:188564 | VO | M00003920B:A10 |
| 2055 | 1034.F12.sp6:188576 | VNO | |
| 2056 | 1034.G12.sp6:188588 | VO | M00003921D:C06 |
| 2057 | 1034.H12.sp6:188600 | VO | M00003923A:H07 |
| 2058 | 1035.A01.sp6:188697 | VNO | |
| 2059 | 1035.B01.sp6:188709 | VNO | |
| 2060 | 1035.C01.sp6:188721 | VO | M00003936C:F10 |
| 2061 | 1035.E01.sp6:188745 | VO | M00003948B:B03 |
| 2062 | 1035.F01.sp6:188757 | VO | M00003949B:A08 |
| 2063 | 1035.G01.sp6:188769 | VO | M00003949B:D05 |
| 2064 | 1035.A02.sp6:188698 | VO | M00003961B:A12 |
| 2065 | 1035.B02.sp6:188710 | VO | M00003961C:G02 |
| 2066 | 1035.C02.sp6:188722 | VO | M00003962B:B09 |
| 2067 | 1035.D02.sp6:188734 | VO | M00003963B:D12 |
| 2068 | 1035.E02.sp6:188746 | VO | M00003965A:F07 |
| 2069 | 1035.F02.sp6:188758 | VNO | |
| 2070 | 1035.H02.sp6:188782 | VNO | |
| 2071 | 1035.A03.sp6:188699 | VO | M00003973A:C05 |
| 2072 | 1035.B03.sp6:188711 | VO | M00003973B:H06 |
| 2073 | 1035.C03.sp6:188723 | VO | M00003974B:A04 |
| 2074 | 1035.D03.sp6:188735 | VNO | |
| 2075 | 1035.E03.sp6:188747 | VNO | |
| 2076 | 1035.F03.sp6:188759 | VNO | |
| 2077 | 1035.G03.sp6:188771 | VO | M00003976D:D12 |
| 2078 | 1035.H03.sp6:188783 | VO | M00003977C:A08 |
| 2079 | 1035.A04.sp6:188700 | VO | M00003980B:F12 |
| 2080 | 1035.B04.sp6:188712 | VO | M00003980C:A11 |
| 2081 | 1035.C04.sp6:188724 | VO | M00003980C:G10 |
| 2082 | 1035.D04.sp6:188736 | VO | M00003981C:E04 |
| 2083 | 1035.H04.sp6:188784 | VO | M00003983C:E07 |
| 2084 | 1035.C05.sp6:188725 | VNO | |
| 2085 | 1035.D05.sp6:188737 | VO | M00003987D:F06 |
| 2086 | 1035.E05.sp6:188749 | VO | M00003988B:C10 |
| 2087 | 1035.G05.sp6:188773 | VNO | |
| 2088 | 803.A2.sp6:164933 | VO | M00003992C:G01 |
| 2089 | 803.B2.sp6:164945 | VO | M00003992D:G01 |
| 2090 | 803.C2.sp6:164957 | VNO | |
| 2091 | 803.D2.sp6:164969 | VO | M00003994C:C11 |
| 2092 | 803.E2.sp6:164981 | VO | M00003996D:C04 |
| 2093 | 803.G2.sp6:165005 | VO | M00003997D:D07 |
| 2094 | 803.H2.sp6:165017 | VNO | |
| 2095 | 803.A3.sp6:164934 | VO | M00003998A:D03 |
| 2096 | 803.B3.sp6:164946 | VO | M00003998A:G12 |
| 2097 | 803.C3.sp6:164958 | VO | M00003998C:H10 |
| 2098 | 803.D3.sp6:164970 | VO | M00003999C:C12 |
| 2099 | 1035.H05.sp6:188785 | VO | M00004027A:B10 |
| 2100 | 1035.A06.sp6:188702 | VO | M00004027C:H01 |
| 2101 | 1035.B06.sp6:188714 | VO | M00004028C:B04 |
| 2102 | 1035.D06.sp6:188738 | VO | M00004029A:E01 |
| 2103 | 1035.F06.sp6:188762 | VNO | |
| 2104 | 1035.H06.sp6:188786 | VO | M00004030B:B02 |
| 2105 | 1035.C07.sp6:188727 | VO | M00004031A:G05 |
| 2106 | 1035.E07.sp6:188751 | VO | M00004032D:D03 |
| 2107 | 1035.F07.sp6:188763 | VNO | |
| 2108 | 1035.G07.sp6:188775 | VO | |
| 2109 | 1035.A08.sp6:188704 | VNO | |
| 2110 | 1035.C08.sp6:188728 | VO | M00004035B:H11 |
| 2111 | 1035.E08.sp6:188752 | VO | M00004035D:E04 |
| 2112 | 1035.F08.sp6:188764 | VO | M00004036B:F09 |
| 2113 | 1035.H08.sp6:188788 | VO | M00004037A:A07 |
| 2114 | 1035.C09.sp6:188729 | VO | M00004037C:C05 |
| 2115 | 1035.E09.sp6:188753 | VO | M00004037D:B05 |
| 2116 | 1035.F09.sp6:188765 | VO | M00004038C:C05 |
| 2117 | 1035.H09.sp6:188789 | VO | M00004039D:D03 |

TABLE 1B-continued

| SEQ ID NO: | Sample Name | Overlap | Clone Name |
|---|---|---|---|
| 2118 | 1035.A10.sp6:188706 | VO | M00004040B:B09 |
| 2119 | 1035.B10.sp6:188718 | VO | M00004040C:G12 |
| 2120 | 1035.C10.sp6:188730 | VO | M00004040D:B05 |
| 2121 | 1035.D10.sp6:188742 | VO | M00004041B:F01 |
| 2122 | 1035.E10.sp6:188754 | VO | M00004041D:E06 |
| 2123 | 1035.F10.sp6:188766 | VO | M00004043D:C10 |
| 2124 | 1035.G10.sp6:188778 | VNO | |
| 2125 | 803.E3.sp6:164982 | VO | M00004045A:B12 |
| 2126 | 803.F3.sp6:164994 | VO | M00004046A:F04 |
| 2127 | 803.G3.sp6:165006 | VNO | |
| 2128 | 803.H3.sp6:165018 | VNO | |
| 2129 | 803.A4.sp6:164935 | VNO | |
| 2130 | 803.B4.sp6:164947 | VNO | |
| 2131 | 803.D4.sp6:164971 | VNO | |
| 2132 | 803.E4.sp6:164983 | VO | M00004052C:A08 |
| 2133 | 803.G4.sp6:165007 | VO | M00004054B:G02 |
| 2134 | 803.H4.sp6:165019 | VO | M00004054D:A03 |
| 2135 | 803.B5.sp6:164948 | VO | M00004055B:F06 |
| 2136 | 803.C5.sp6:164960 | VO | M00004058B:C11 |
| 2137 | 803.E5.sp6:164984 | VO | M00004058C:E08 |
| 2138 | 803.F5.sp6:164996 | VO | M00004059A:G09 |
| 2139 | 803.G5.sp6:165008 | VO | M00004060C:A02 |
| 2140 | 803.H5.sp6:165020 | VNO | |
| 2141 | 803.A6.sp6:164937 | VO | M00004060D:A07 |
| 2142 | 803.B6.sp6:164949 | VO | M00004063C:B11 |
| 2143 | 803.E6.sp6:164985 | VNO | |
| 2144 | 1035.H10.sp6:188790 | VO | M00004068A:F02 |
| 2145 | 1035.A11.sp6:188707 | VO | M00004068B:D04 |
| 2146 | 1035.B11.sp6:188719 | VNO | |
| 2147 | 1035.C11.sp6:188731 | VO | M00004069B:B01 |
| 2148 | 1035.D11.sp6:188743 | VO | M00004069D:G02 |
| 2149 | 1035.E11.sp6:188755 | VO | M00004071A:H03 |
| 2150 | 1035.F11.sp6:188767 | VO | M00004073D:B11 |
| 2151 | 1035.G11.sp6:188779 | VNO | |
| 2152 | 1035.H11.sp6:188791 | VNO | |
| 2153 | 1035.B12.sp6:188720 | VNO | |
| 2154 | 1035.D12.sp6:188744 | VNO | |
| 2155 | 1035.E12.sp6:188756 | VNO | |
| 2156 | 1035.F12.sp6:188768 | VO | M00004078C:A08 |
| 2157 | 1035.H12.sp6:188792 | VO | M00004081A:A01 |
| 2158 | 1036.A10.sp6:188889 | VO | M00004084A:D11 |
| 2159 | 1036.B01.sp6:188901 | VO | M00004084C:G04 |
| 2160 | 1036.C01.sp6:188913 | VO | M00004085B:G06 |
| 2161 | 1036.D01.sp6:188925 | VO | M00004086A:A03 |
| 2162 | 1036.E01.sp6:188937 | VO | M00004086D:A07 |
| 2163 | 1036.F01.sp6:188949 | VO | M00004087C:F05 |
| 2164 | 1036.G01.sp6:188961 | VO | M00004088A:F12 |
| 2165 | 1036.A02.sp6:188890 | VO | M00004089A:G03 |
| 2166 | 1036.B02.sp6:188902 | VO | M00004091A:E01 |
| 2167 | 1036.C02.sp6:188914 | VO | M00004091B:C12 |
| 2168 | 1036.E02.sp6:188938 | VO | M00004091C:F04 |
| 2169 | 1036.F02.sp6:188950 | VO | M00004091D:D09 |
| 2170 | 1036.G02.sp6:188962 | VO | M00004092A:C03 |
| 2171 | 1036.H02.sp6:188974 | VO | M00004092A:D04 |
| 2172 | 1036.A03.sp6:188891 | VO | M00004093A:F03 |
| 2173 | 1036.B03.sp6:188903 | VO | M00004093D:D09 |
| 2174 | 1036.C03.sp6:188915 | VNO | |
| 2175 | 1036.D03.sp6:188927 | VO | M00004101D:A03 |
| 2176 | 1036.E03.sp6:188939 | VO | M00004102B:B04 |
| 2177 | 1036.F03.sp6:188951 | VO | M00004102C:F07 |
| 2178 | 1036.H03.sp6:188975 | VNO | |
| 2179 | 1036.A04.sp6:188892 | VNO | |
| 2180 | 1036.B04.sp6:188904 | VNO | |
| 2181 | 1036.C04.sp6:188916 | VNO | |
| 2182 | 1036.D04.sp6:188928 | VO | M00004107C:A01 |
| 2183 | 1036.E04.sp6:188940 | VNO | |
| 2184 | 1036.G04.sp6:188964 | VO | M00004114C:F02 |
| 2185 | 1036.C05.sp6:188917 | VO | M00004117B:F01 |
| 2186 | 1036.D05.sp6:188929 | VO | M00004120A:C02 |
| 2187 | 1036.E05.sp6:188941 | VO | M00004126B:G02 |
| 2188 | 1036.F05.sp6:188953 | VNO | |
| 2189 | 1036.G05.sp6:188965 | VO | M00004129A:H08 |
| 2190 | 1036.H05.sp6:188977 | VO | M00004130C:A09 |
| 2191 | 1036.A06.sp6:188894 | VO | M00004130D:E04 |
| 2192 | 1036.C06.sp6:188918 | VO | M00004133D:A01 |
| 2193 | 803.F6.sp6:164997 | VNO | |
| 2194 | 803.G6.sp6:165009 | VNO | |
| 2195 | 803.H6.sp6:165021 | VNO | |
| 2196 | 803.B7.sp6:164950 | VO | M00004143A:G12 |
| 2197 | 803.C7.sp6:164962 | VO | M00004143A:H07 |
| 2198 | 803.D7.sp6:164974 | VNO | |
| 2199 | 803.E7.sp6:164986 | VNO | |
| 2200 | 803.F7.sp6:164998 | VO | M00004145C:A03 |
| 2201 | 803.G7.sp6:165010 | VO | M00004146D:A07 |
| 2202 | 803.H7.sp6:165022 | VO | M00004147A:G03 |
| 2203 | 803.A8.sp6:164939 | VO | M00004149B:H12 |
| 2204 | 803.B8.sp6:164951 | VNO | |
| 2205 | 803.C8.sp6:164963 | VO | M00004153D:E06 |
| 2206 | 803.D8.sp6:164975 | VO | M00004154D:F11 |
| 2207 | 803.G8.sp6:165011 | VNO | |
| 2208 | 803.H8.sp6:165023 | VNO | |
| 2209 | 803.B9.sp6:164952 | VNO | |
| 2210 | 803.C9.sp6:164964 | VNO | |
| 2211 | 803.D9.sp6:164976 | VNO | |
| 2212 | 803.E9.sp6:164988 | VNO | |
| 2213 | 803.F9.sp6:165000 | VNO | |
| 2214 | 803.G9.sp6:165012 | VO | M00004166B:E10 |
| 2215 | 803.H9.sp6:165024 | VO | M00004166C:A03 |
| 2216 | 803.A10.sp6:164941 | VO | M00004166D:G07 |
| 2217 | 803.B10.sp6:164953 | VNO | |
| 2218 | 803.C10.sp6:164965 | VNO | |
| 2219 | 1036.E06.sp6:188942 | VO | M00004180B:F04 |
| 2220 | 1036.G06.sp6:188966 | VNO | |
| 2221 | 803.D10.sp6:164977 | VNO | |
| 2222 | 1036.A07.sp6:188895 | VNO | |
| 2223 | 1036.B07.sp6:188907 | VNO | |
| 2224 | 1036.C07.sp6:188919 | VNO | |
| 2225 | 1036.D07.sp6:188931 | VO | M00004188A:E10 |
| 2226 | 1036.F07.sp6:188955 | VNO | |
| 2227 | 1036.G07.sp6:188967 | VO | M00004190C:G07 |
| 2228 | 1036.H07.sp6:188979 | VO | M00004190D:A10 |
| 2229 | 1036.A08.sp6:188896 | VNO | |
| 2230 | 1036.B08.sp6:188908 | VO | M00004191B:G01 |
| 2231 | 1036.C08.sp6:188920 | VO | M00004193A:C07 |
| 2232 | 1036.D08.sp6:188932 | VO | M00004193C:H01 |
| 2233 | 803.E10.sp6:164989 | VO | M00004196C:G05 |
| 2234 | 1036.E08.sp6:188944 | VO | M00004198D:H04 |
| 2235 | 1036.F08.sp6:188956 | VO | M00004199D:C02 |
| 2236 | 1036.G08.sp6:188968 | VO | M00004200A:A09 |
| 2237 | 1036.H08.sp6:188980 | VO | M00004200A:G06 |
| 2238 | 803.F10.sp6:165001 | VNO | |
| 2239 | 1036.A09.sp6:188897 | VO | M00004200D:A07 |
| 2240 | 1036.B09.sp6:188909 | VO | M00004201D:C11 |
| 2241 | 1036.C09.sp6:188921 | VO | M00004201D:E12 |
| 2242 | 1036.E09.sp6:188945 | VNO | |
| 2243 | 1036.G09.sp6:188969 | VO | M00004204A:D04 |
| 2244 | 1036.H09.sp6:188981 | VO | M00004204A:D10 |
| 2245 | 1036.A10.sp6:188898 | VO | M00004204B:A04 |
| 2246 | 1036.B10.sp6:188910 | VNO | |
| 2247 | 1036.C10.sp6:188922 | VO | M00004210A:B09 |
| 2248 | 1036.D10.sp6:188934 | VO | M00004213A:H12 |
| 2249 | 1036.E10.sp6:188946 | VO | M00004214A:D03 |
| 2250 | 1036.F10.sp6:188958 | VO | M00004216D:E10 |
| 2251 | 1036.G10.sp6:188970 | VO | M00004217A:A05 |
| 2252 | 1036.H10.sp6:188982 | VO | M00004217A:A11 |
| 2253 | 1036.A11.sp6:188899 | VO | M00004217D:G10 |
| 2254 | 1036.B11.sp6:188911 | VO | M00004218C:G10 |
| 2255 | 1036.C11.sp6:188923 | VNO | |
| 2256 | 803.G10.sp6:165013 | VNO | |
| 2257 | 803.A11.sp6:164942 | VNO | |
| 2258 | 803.B11.sp6:164954 | VNO | |
| 2259 | 803.C11.sp6:164966 | VNO | |
| 2260 | 803.D11.sp6:164978 | VO | M00004234B:E03 |
| 2261 | 803.E11.sp6:164990 | VO | M00004234B:G06 |
| 2262 | 803.G11.sp6:165014 | VO | M00004236D:F04 |
| 2263 | 803.A12.sp6:164943 | VNO | |
| 2264 | 803.B12.sp6:164955 | VO | M00004240D:A07 |
| 2265 | 803.D12.sp6:164979 | VNO | |
| 2266 | 803.F12.sp6:165003 | VO | M00004242C:C02 |
| 2267 | 803.G12.sp6:165015 | VNO | |
| 2268 | 803.H12.sp6:165027 | VO | M00004244B:A02 |
| 2269 | 804.A1.sp6:165124 | VNO | |
| 2270 | 983.A01.sp6:186169 | VO | M00004245A:G09 |
| 2271 | 983.B01.sp6:186179 | VO | M00004245C:A03 |

TABLE 1B-continued

| SEQ ID NO: | Sample Name | Overlap | Clone Name |
|---|---|---|---|
| 2272 | 804.C1.sp6:165148 | VNO | |
| 2273 | 983.C01.sp6:186189 | VO | M00004247A:E01 |
| 2274 | 983.E01.sp6:186208 | VO | M00004248A:G08 |
| 2275 | 804.E1.sp6:165172 | VNO | |
| 2276 | 1036.E11.sp6:188947 | VNO | |
| 2277 | 1036.F11.sp6:188959 | VO | M00004252D:A07 |
| 2278 | 1036.G11.sp6:188971 | VO | M00004252D:H08 |
| 2279 | 1036.H11.sp6:188983 | VO | M00004253B:A10 |
| 2280 | 1036.A12.sp6:188900 | VO | M00004253B:F06 |
| 2281 | 1036.B12.sp6:188912 | VO | M00004253C:E10 |
| 2282 | 1036.C12.sp6:188924 | VO | M00004253D:F09 |
| 2283 | 1036.D12.sp6:188936 | VO | M00004257C:A08 |
| 2284 | 1036.E12.sp6:188948 | VO | M00004260A:B07 |
| 2285 | 1036.F12.sp6:188960 | VO | M00004260C:A12 |
| 2286 | 1036.G12.sp6:188972 | VO | M00004260C:E10 |
| 2287 | 1036.H12.sp6:188984 | VO | M00004262C:C01 |
| 2288 | 804.F1.sp6:165184 | VNO | |
| 2289 | 983.F01.sp6:186217 | VO | M00004263D:F06 |
| 2290 | 983.G01.sp6:186226 | VNO | |
| 2291 | 983.H01.sp6:186235 | VO | M00004266B:H06 |
| 2292 | 804.H1.sp6:165208 | VNO | |
| 2293 | 983.A02.sp6:186170 | VO | M00004268C:F08 |
| 2294 | 983.B02.sp6:186180 | VO | M00004268D:G07 |
| 2295 | 804.B2.sp6:165137 | VNO | |
| 2296 | 983.C02.sp6:186190 | VO | M00004269A:B11 |
| 2297 | 804.D2.sp6:165161 | VNO | |
| 2298 | 983.D02.sp6:186200 | VO | M00004269D:E08 |
| 2299 | 983.E02.sp6:186209 | VO | M00004272D:D02 |
| 2300 | 804.E2.sp6:165173 | VNO | |
| 2301 | 804.F2.sp6:165185 | VNO | |
| 2302 | 983.F02.sp6:186218 | VO | M00004273D:E11 |
| 2303 | 804.G2.sp6:165197 | VNO | |
| 2304 | 983.G02.sp6:186227 | VO | M00004276C:E12 |
| 2305 | 804.H2.sp6:165209 | VNO | |
| 2306 | 983.H02.sp6:186236 | VNO | |
| 2307 | 983.A03.sp6:186171 | VO | M00004277C:H11 |
| 2308 | 804.A3.sp6:165126 | VNO | |
| 2309 | 804.C3.sp6:165150 | VNO | |
| 2310 | 983.C03.sp6:186191 | VO | M00004279D:E02 |
| 2311 | 983.D03.sp6:186201 | VNO | |
| 2312 | 804.D3.sp6:165162 | VNO | |
| 2313 | 983.E03.sp6:186210 | VO | M00004281B:B05 |
| 2314 | 804.E3.sp6:165174 | VNO | |
| 2315 | 804.F3.sp6:165186 | VNO | |
| 2316 | 983.F03.sp6:186219 | VO | M00004283C:D03 |
| 2317 | 983.G03.sp6:186228 | VNO | |
| 2318 | 804.G3.sp6:165198 | VNO | |
| 2319 | 804.H3.sp6:165210 | VNO | |
| 2320 | 983.H03.sp6:186237 | VO | M00004285B:E01 |
| 2321 | 804.A4.sp6:165127 | VNO | |
| 2322 | 983.A04.sp6:186172 | VNO | |
| 2323 | 804.B4.sp6:165139 | VNO | |
| 2324 | 983.B04.sp6:186182 | VNO | |
| 2325 | 804.C4.sp6:165151 | VNO | |
| 2326 | 983.C04.sp6:186192 | VNO | |
| 2327 | 983.D04.sp6:186202 | VO | M00004297D:E08 |
| 2328 | 804.D4.sp6:165163 | VNO | |
| 2329 | 804.E4.sp6:165175 | VNO | |
| 2330 | 983.E04.sp6:186211 | VO | M00004298B:D04 |
| 2331 | 804.F4.sp6:165187 | VNO | |
| 2332 | 983.F04.sp6:186220 | VO | M00004308A:E06 |
| 2333 | 804.G4.sp6:165199 | VNO | |
| 2334 | 983.G04.sp6:186229 | VO | M00004324B:D09 |
| 2335 | 983.H04.sp6:186238 | VO | M00004328A:H06 |
| 2336 | 804.H4.sp6:165211 | VNO | |
| 2337 | 804.A5.sp6:165128 | VNO | |
| 2338 | 983.A05.sp6:186173 | VO | M00004329C:F11 |
| 2339 | 804.B5.sp6:165140 | VNO | |
| 2340 | 983.B05.sp6:186183 | VO | M00004331D:H08 |
| 2341 | 983.C05.sp6:186193 | VNO | |
| 2342 | 804.C5.sp6:165152 | VNO | |
| 2343 | 983.D05.sp6:186203 | VO | M00004332B:E11 |
| 2344 | 804.D5.sp6:165164 | VNO | |
| 2345 | 983.E05.sp6:186212 | VO | M00004332C:E09 |
| 2346 | 804.E5.sp6:165176 | VNO | |
| 2347 | 983.H05.sp6:186239 | VNO | |
| 2348 | 804.H5.sp6:165212 | VNO | |
| 2349 | 804.B6.sp6:165141 | VNO | |
| 2350 | 983.B06.sp6:186184 | VO | M00004383A:F02 |
| 2351 | 983.C06.sp6:186194 | VO | M00004385C:B11 |
| 2352 | 804.C6.sp6:165153 | VNO | |
| 2353 | 983.D06.sp6:186204 | VO | M00004388C:D05 |
| 2354 | 804.D6.sp6:165165 | VNO | |
| 2355 | 804.E6.sp6:165177 | VNO | |
| 2356 | 983.E06.sp6:186213 | VO | M00004389C:E01 |
| 2357 | 983.F06.sp6:186222 | VNO | |
| 2358 | 804.F6.sp6:165189 | VNO | |
| 2359 | 983.G06.sp6:186231 | VO | M00004406A:H03 |
| 2360 | 804.G6.sp6:165201 | VNO | |
| 2361 | 983.H06.sp6:186240 | VNO | |
| 2362 | 804.H6.sp6:165213 | VNO | |
| 2363 | 804.A7.sp6:165130 | VO | M00004408D:A10 |
| 2364 | 983.A07.sp6:186175 | VO | M00004408D:A10 |
| 2365 | 983.B07.sp6:186185 | VO | M00004410A:E03 |
| 2366 | 983.C07.sp6:186195 | VO | M00004412B:E03 |
| 2367 | 983.D07.sp6:186205 | VO | M00004419D:G01 |
| 2368 | 804.E7.sp6:165178 | VNO | |
| 2369 | 983.E07.sp6:186214 | VO | M00004421A:G04 |
| 2370 | 804.G7.sp6:165202 | VNO | |
| 2371 | 983.G07.sp6:186232 | VO | M00004447D:D10 |
| 2372 | 804.H7.sp6:165214 | VNO | |
| 2373 | 983.H07.sp6:186241 | VO | M00004449D:H01 |
| 2374 | 983.A08.sp6:186176 | VO | M00004460B:H09 |
| 2375 | 804.A8.sp6:165131 | VNO | |
| 2376 | 804.B8.sp6:165143 | VNO | |
| 2377 | 983.B08.sp6:186186 | VNO | |
| 2378 | 983.C08.sp6:186196 | VO | M00004465C:B10 |
| 2379 | 804.C8.sp6:165155 | VNO | |
| 2380 | 983.D08.sp6:186206 | VO | M00004465C:B12 |
| 2381 | 804.D8.sp6:165167 | VNO | |
| 2382 | 983.E08.sp6:186215 | VNO | |
| 2383 | 804.E5.sp6:165179 | VNO | |
| 2384 | 983.F08.sp6:186224 | VO | M00004467A:F09 |
| 2385 | 804.F8.sp6:165191 | VNO | |
| 2386 | 804.G8.sp6:165203 | VNO | |
| 2387 | 983.G08.sp6:186233 | VO | M00004467D:F09 |
| 2388 | 804.H8.sp6:165215 | VNO | |
| 2389 | 983.H08.sp6:186242 | VO | M00004469A:C12 |
| 2390 | 804.A9.sp6:165132 | VNO | |
| 2391 | 983.A09.sp6:186177 | VNO | |
| 2392 | 983.B09.sp6:186187 | VO | M00004491D:D07 |
| 2393 | 804.B9.sp6:165144 | VNO | |
| 2394 | 804.C9.sp6:165156 | VNO | |
| 2395 | 983.C09.sp6:186197 | VO | M00004497C:E09 |
| 2396 | 983.D09.sp6:186207 | VO | M00004498B:E01 |
| 2397 | 804.D9.sp6:165168 | VNO | |
| 2398 | 804.E9.sp6:165180 | VNO | |
| 2399 | 983.E09.sp6:186216 | VO | M00004501A:G06 |
| 2400 | 983.F09.sp6:186225 | VO | M00004506C:H10 |
| 2401 | 804.G9.sp6:165204 | VNO | |
| 2402 | 983.G09.sp6:186234 | VO | M00004508A:G12 |
| 2403 | 804.H9.sp6:165216 | VNO | |
| 2404 | 983.H09.sp6:186243 | VO | M00004508B:G02 |
| 2405 | 804.A10.sp6:165133 | VNO | |
| 2406 | 983.A10.sp6:186178 | VO | M00004509A:H02 |
| 2407 | 983.B10.sp6:186188 | VNO | |
| 2408 | 804.B10.sp6:165145 | VNO | |
| 2409 | 983.C10.sp6:186198 | VO | M00004609C:C11 |
| 2410 | 992.B01.sp6:186331 | VO | M00005294D:H02 |
| 2411 | 992.C01.sp6:186343 | VO | M00005326B:F03 |
| 2412 | 992.G01.sp6:186391 | VO | M00005342A:C04 |
| 2413 | 992.H01.sp6:186403 | VO | M00005342A:D04 |
| 2414 | 992.A02.sp6:186320 | VO | M00005342B:G10 |
| 2415 | 992.B02.sp6:186332 | VO | M00005342D:F03 |
| 2416 | 992.C02.sp6:186344 | VO | M00005349B:G01 |
| 2417 | 992.D02.sp6:186356 | VO | M00005352B:D02 |
| 2418 | 992.H02.sp6:186404 | VO | M00005354C:E02 |
| 2419 | 992.A03.sp6:186321 | VO | M00005356A:D09 |
| 2420 | 992.C03.sp6:186345 | VO | M00005359D:G07 |
| 2421 | 992.E03.sp6:186369 | VO | M00005377A:A04 |
| 2422 | 992.H03.sp6:186405 | VO | M00005378A:A08 |
| 2423 | 992.B04.sp6:186334 | VO | M00005383D:D06 |
| 2424 | 992.C04.sp6:186346 | VO | M00005383D:E07 |
| 2425 | 992.E04.sp6:186370 | VNO | |

TABLE 1B-continued

| SEQ ID NO: | Sample Name | Overlap | Clone Name |
|---|---|---|---|
| 2426 | 992.F04.sp6:186382 | VO | M00005385C:G05 |
| 2427 | 992.G04.sp6:186394 | VNO | |
| 2428 | 992.A05.sp6:186323 | VO | M00005388D:F09 |
| 2429 | 992.D05.sp6:186359 | VO | M00005393A:E11 |
| 2430 | 992.E05.sp6:186371 | VO | M00005394A:G07 |
| 2431 | 992.G05.sp6:186395 | VO | M00005397C:B03 |
| 2432 | 992.D06.sp6:186360 | VNO | |
| 2433 | 992.G06.sp6:186396 | VO | M00005409D:C02 |
| 2434 | 992.C07.sp6:186349 | VO | M00005415C:G08 |
| 2435 | 992.E07.sp6:186373 | VO | M00005417A:E10 |
| 2436 | 992.F07.sp6:186385 | VNO | |
| 2437 | 992.A08.sp6:186326 | VO | M00005442D:C05 |
| 2438 | 992.B08.sp6:186338 | VNO | |
| 2439 | 992.C08.sp6:186350 | VO | M00005444B:E11 |
| 2440 | 992.E08.sp6:186374 | VO | M00005446C:D12 |
| 2441 | 992.F08.sp6:186386 | VNO | |
| 2442 | 992.G08.sp6:186398 | VNO | |
| 2443 | 992.H08.sp6:186410 | VNO | |
| 2444 | 992.D09.sp6:186363 | VNO | |
| 2445 | 992.F09.sp6:186387 | VO | M00005454C:H12 |
| 2446 | 992.E10.sp6:186376 | VO | M00005462C:B02 |
| 2447 | 992.H10.sp6:186412 | VO | M00005468A:D08 |
| 2448 | 953.H09.sp6:185217 | VO | M00005468A:D08 |
| 2449 | 992.C11.sp6:186353 | VO | M00005469D:C11 |
| 2450 | 992.D12.sp6:186366 | VO | M00005483D:A12 |
| 2451 | 992.E12.sp6:186378 | VO | M00005484A:D09 |
| 2452 | 992.H12.sp6:186414 | VNO | |
| 2453 | 993.A01.sp6:186511 | VNO | |
| 2454 | 993.B01.sp6:186523 | VO | M00005491B:C03 |
| 2455 | 993.C01.sp6:186535 | VO | M00005493B:A12 |
| 2456 | 993.D01.sp6:186547 | VO | M00005493B:C08 |
| 2457 | 993.E01.sp6:186559 | VO | M00005493B:E01 |
| 2458 | 993.F01.sp6:186571 | VO | M00005494D:F11 |
| 2459 | 993.G01.sp6:186583 | VO | M00005496C:A01 |
| 2460 | 993.H01.sp6:186595 | VO | M00005496D:A10 |
| 2461 | 993.A02.sp6:186512 | VO | M00005497B:H07 |
| 2462 | 993.B02.sp6:186524 | VO | M00005497C:C07 |
| 2463 | 993.C02.sp6:186536 | VNO | |
| 2464 | 993.D02.sp6:186548 | VO | M00005497C:C12 |
| 2465 | 993.E02.sp6:186560 | VO | M00005497C:E03 |
| 2466 | 993.F02.sp6:186572 | VO | M00005498B:F08 |
| 2467 | 993.G02.sp6:186584 | VO | M00005498C:G05 |
| 2468 | 993.H02.sp6:186596 | VO | M00005505A:C08 |
| 2469 | 993.A03.sp6:186513 | VO | M00005508A:H01 |
| 2470 | 993.B03.sp6:186525 | VO | M00005508B:B04 |
| 2471 | 993.F03.sp6:186573 | VO | M00005528D:A10 |
| 2472 | 993.H03.sp6:186597 | VO | M00005530B:D03 |
| 2473 | 993.B04.sp6:186526 | VO | M00005534A:G06 |
| 2474 | 993.C04.sp6:186538 | VO | M00005534B:H10 |
| 2475 | 993.D04.sp6:186550 | VO | M00005539D:G07 |
| 2476 | 993.E04.sp6:186562 | VO | M00005548B:E03 |
| 2477 | 993.F04.sp6:186574 | VO | M00005550B:D09 |
| 2478 | 993.G04.sp6:186586 | VO | M00005565C:A08 |
| 2479 | 993.H04.sp6:186598 | VO | M00005571A:E11 |
| 2480 | 993.A05.sp6:186515 | VO | M00005589C:B03 |
| 2481 | 993.C05.sp6:186539 | VNO | |
| 2482 | 993.D05.sp6:186551 | VO | M00005620C:C05 |
| 2483 | 993.E05.sp6:186563 | VO | M00005621A:G10 |
| 2484 | 993.F05.sp6:186575 | VO | M00005621D:F01 |
| 2485 | 993.G05.sp6:186587 | VNO | |
| 2486 | 993.H05.sp6:186599 | VO | M00005626A:B11 |
| 2487 | 993.A06.sp6:186516 | VO | M00005631A:A11 |
| 2488 | 993.B06.sp6:186528 | VO | M00005632C:D06 |
| 2489 | 993.D06.sp6:186552 | VNO | |
| 2490 | 993.E06.sp6:186564 | VO | M00005636C:D11 |
| 2491 | 993.F06.sp6:186576 | VO | M00005637B:D12 |
| 2492 | 993.G06.sp6:186588 | VNO | |
| 2493 | 993.H06.sp6:186600 | VNO | |
| 2494 | 993.A07.sp6:186517 | VO | M00005642B:C03 |
| 2495 | 993.B07.sp6:186529 | VO | M00005645D:F08 |
| 2496 | 993.C07.sp6:186541 | VNO | |
| 2497 | 993.D07.sp6:186553 | VNO | |
| 2498 | 993.E07.sp6:186565 | VO | M00005647D:D09 |
| 2499 | 993.F07.sp6:186577 | VO | M00005655B:C02 |
| 2500 | 993.G07.sp6:186589 | VNO | |
| 2501 | 993.H07.sp6:186601 | VO | M00005703A:C08 |
| 2502 | 993.A08.sp6:186518 | VNO | |
| 2503 | 993.D08.sp6:186554 | VO | M00005710A:C08 |
| 2504 | 993.E08.sp6:186566 | VO | M00005720A:D03 |
| 2505 | 993.F08.sp6:186578 | VO | M00005720B:D09 |
| 2506 | 993.G08.sp6:186590 | VNO | |
| 2507 | 993.H08.sp6:186602 | VO | M00005722D:G03 |
| 2508 | 993.A09.sp6:186519 | VO | M00005743B:F02 |
| 2509 | 993.B09.sp6:186531 | VO | M00005762D:A01 |
| 2510 | 993.C09.sp6:186543 | VO | M00005763B:H09 |
| 2511 | 993.F09.sp6:186579 | VO | M00005783A:C05 |
| 2512 | 993.G09.sp6:186591 | VO | M00005810C:D04 |
| 2513 | 993.H09.sp6:186603 | VO | M00005812C:F10 |
| 2514 | 993.A10.sp6:186520 | VO | M00005813D:F06 |
| 2515 | 993.C10.sp6:186544 | VO | M00005818C:E08 |
| 2516 | 993.D10.sp6:186556 | VO | M00005818C:G01 |
| 2517 | 993.E10.sp6:186568 | VO | M00006576D:F11 |
| 2518 | 993.G10.sp6:186592 | VO | M00006581C:D02 |
| 2519 | 993.H10.sp6:186604 | VO | M00006581D:H08 |
| 2520 | 993.A11.sp6:186521 | VNO | |
| 2521 | 993.B11.sp6:186533 | VO | M00006582D:E05 |
| 2522 | 993.E11.sp6:186569 | VO | M00006594A:E08 |
| 2523 | 993.F11.sp6:186581 | VO | M00006594D:F09 |
| 2524 | 993.H11.sp6:186605 | VO | M00006596C:H04 |
| 2525 | 993.A12.sp6:186522 | VO | M00006601C:A07 |
| 2526 | 993.B12.sp6:186534 | VO | M00006601C:E06 |
| 2527 | 993.C12.sp6:186546 | VO | M00006601D:F04 |
| 2528 | 993.D12.sp6:186558 | VO | M00006604C:H10 |
| 2529 | 993.E12.sp6:186570 | VO | M00006607B:E03 |
| 2530 | 993.F12.sp6:186582 | VO | M00006607B:F04 |
| 2531 | 993.G12.sp6:186594 | VO | M00006609A:G10 |
| 2532 | 1010.A01.sp6:189937 | VO | M00022495C:G05 |
| 2533 | 1010.B01.sp6:189947 | VO | M00022498C:C08 |
| 2534 | 1010.C01.sp6:189957 | VO | M00022504B:E03 |
| 2535 | 1010.D01.sp6:189967 | VO | M00022505D:A12 |
| 2536 | 1010.E01.sp6:189976 | VO | M00022509D:F06 |
| 2537 | 1010.F01.sp6:189985 | VNO | |
| 2538 | 1010.G01.sp6:189994 | VO | M00022515D:C04 |
| 2539 | 1010.H01.sp6:190003 | VO | M00022527A:E05 |
| 2540 | 1010.A02.sp6:189938 | VO | M00022527D:B03 |
| 2541 | 1010.B02.sp6:189948 | VO | M00022531D:B11 |
| 2542 | 1010.C02.sp6:189958 | VO | M00022535D:B11 |
| 2543 | 1010.D02.sp6:189968 | VO | M00022535D:C04 |
| 2544 | 1010.E02.sp6:189977 | VO | M00022536B:B04 |
| 2545 | 1010.G02.sp6:189995 | VO | M00022551A:G03 |
| 2546 | 1010.H02.sp6:190004 | VO | M00022556B:C04 |
| 2547 | 1010.A03.sp6:189939 | VO | M00022556B:G02 |
| 2548 | 1010.B03.sp6:189949 | VNO | |
| 2549 | 1010.C03.sp6:189959 | VO | M00022562C:H10 |
| 2550 | 1010.D03.sp6:189969 | VNO | |
| 2551 | 1010.E03.sp6:189978 | VO | M00022578B:G05 |
| 2552 | 1010.F03.sp6:189987 | VO | M00022578C:B07 |
| 2553 | 1010.G03.sp6:189996 | VO | M00022578D:A08 |
| 2554 | 1010.H03.sp6:190005 | VO | M00022578D:F03 |
| 2555 | 1010.A04.sp6:189940 | VNO | |
| 2556 | 1010.B04.sp6:189950 | VO | M00022583B:E05 |
| 2557 | 1010.C04.sp6:189960 | VO | M00022587C:G04 |
| 2558 | 1010.D04.sp6:189970 | VO | M00022594B:H12 |
| 2559 | 1010.E04.sp6:189979 | VO | M00022597B:F11 |
| 2560 | 1010.F04.sp6:189988 | VO | M00022598A:F11 |
| 2561 | 1010.G04.sp6:189997 | VNO | |
| 2562 | 1010.H04.sp6:190006 | VO | M00022599D:E07 |
| 2563 | 1010.A05.sp6:189941 | VO | M00022600C:A06 |
| 2564 | 1010.B05.sp6:189951 | VO | M00022604B:C11 |
| 2565 | 1010.C05.sp6:189961 | VO | M00022607B:A04 |
| 2566 | 1010.D05.sp6:189971 | VO | M00022613D:C04 |
| 2567 | 1010.E05.sp6:189980 | VO | M00022651D:C06 |
| 2568 | 1010.F05.sp6:189989 | VNO | |
| 2569 | 1010.G05.sp6:189998 | VNO | |
| 2570 | 1010.H05.sp6:190007 | VO | M00022666B:E12 |
| 2571 | 1010.A06.sp6:189942 | VO | M00022666C:H11 |
| 2572 | 1010.B06.sp6:189952 | VNO | |
| 2573 | 1010.C06.sp6:189962 | VO | M00022681B:H02 |
| 2574 | 1010.D06.sp6:189972 | VO | M00022682A:F12 |
| 2575 | 1010.E06.sp6:189981 | VO | M00022685A:F11 |
| 2576 | 1010.F06.sp6:189990 | VO | M00022698C:E06 |
| 2577 | 1010.G06.sp6:189999 | VO | M00022701B:B12 |
| 2578 | 1010.H06.sp6:190008 | VO | M00022708A:C08 |
| 2579 | 1010.A07.sp6:189943 | VO | M00022708D:G10 |

TABLE 1B-continued

| SEQ ID NO: | Sample Name | Overlap | Clone Name |
|---|---|---|---|
| 2580 | 1010.B07.sp6:189953 | VO | M00022716D:D08 |
| 2581 | 1010.C07.sp6:189963 | VNO | |
| 2582 | 1010.D07.sp6:189973 | VO | M00022725C:B03 |
| 2583 | 1010.E07.sp6:189982 | VO | M00022725C:E09 |
| 2584 | 1010.F07.sp6:189991 | VO | M00022726A:A06 |
| 2585 | 1010.G07.sp6:190000 | VNO | |
| 2586 | 1010.H07.sp6:190009 | VNO | |
| 2587 | 1010.A08.sp6:189944 | VO | M00022730A:E04 |
| 2588 | 1010.B08.sp6:189954 | VNO | |
| 2589 | 1010.C08.sp6:189964 | VO | M00022735B:B01 |
| 2590 | 1010.D08.sp6:189974 | VO | M00022737A:C08 |
| 2591 | 1010.E08.sp6:189983 | VNO | |
| 2592 | 1010.F08.sp6:189992 | VO | M00022745B:G02 |
| 2593 | 1010.G08.sp6:190001 | VO | M00022763A:E10 |
| 2594 | 1010.H08.sp6:190010 | VO | M00022824C:H11 |
| 2595 | 1010.B09.sp6:189955 | VO | M00022835C:E06 |
| 2596 | 1010.C09.sp6:189965 | VO | M00022854D:H07 |
| 2597 | 1010.D09.sp6:189975 | VO | M00022856A:D02 |
| 2598 | 1010.E09.sp6:189984 | VNO | |
| 2599 | 1010.F09.sp6:189993 | VO | M00022856B:F04 |
| 2600 | 1010.G09.sp6:190002 | VO | M00022856C:B11 |
| 2601 | 1010.H09.sp6:190011 | VO | M00022893C:H11 |
| 2602 | 1010.A10.sp6:189946 | VO | M00022897A:F04 |
| 2603 | 1010.B10.sp6:189956 | VO | M00022900D:E08 |
| 2604 | 1010.C10.sp6:189966 | VO | M00022900D:G03 |
| 2605 | 019.C4.sp6:128426 | VO | M00004190A:A09 |
| 2606 | 774.C8.sp6:162530 | VO | M00004190A:A09 |
| 2607 | 1036.E07.sp6:188943 | VO | M00004190A:A09 |
| 2608 | 019.E11.sp6:128457 | VO | M00005817D:E12 |
| 2609 | 993.B10.sp6:186532 | VO | M00005817D:E12 |
| 2610 | 019.G5.sp6:128475 | VO | M00006927C:F12 |

TABLE 1C

| SEQ ID NO: | Sequence Name | THC Accession No. |
|---|---|---|
| 2611 | RTA00000587F.p.24.1.Seq | THC226834 |
| 2612 | RTA00000629F.l.02.1.Seq | THC210324 |
| 2613 | RTA00000623F.n.17.1.Seq | THC208388 |
| 2614 | RTA00000593F.i.08.2.Seq | H91190 |
| 2615 | RTA00000622F.b.03.1.Seq | AA554045 |
| 2616 | RTA00000618F.e.06.1.Seq | THC226692 |
| 2617 | RTA00000592F.o.02.1.Seq | AA099789 |
| 2618 | RTA00000618F.c.04.1.Seq | THC222808 |
| 2619 | RTA00000590F.i.01.1.Seq | THC173163 |
| 2620 | RTA00000606F.o.14.1.Seq | THC223717 |
| 2621 | RTA00000626F.d.07.1.Seq | THC234888 |
| 2622 | RTA00000587F.1.08.1.Seq | THC104384 |
| 2623 | RTA00000586F.a.13.1.Seq | THC140691 |
| 2624 | RTA00000617F.a.17.1.Seq | THC221850 |
| 2625 | RTA00000615F.b.23.1.Seq | THC205191 |
| 2626 | RTA00000632F.f.10.1.Seq | N39216 |
| 2627 | RTA00000607F.o.13.2.Seq | THC233619 |
| 2628 | RTA00000622F.c.12.1.Seq | THC118482 |
| 2629 | RTA00000625F.b.07.1.Seq | THC223154 |
| 2630 | RTA00000587F.j.01.1.Seq | H63018 |
| 2631 | RTA00000608F.i.15.1.Seq | THC216448 |
| 2632 | RTA00000592F.j.06.1.Seq | THC148215 |
| 2633 | RTA00000589F.b.14.1.Seq | THC158020 |
| 2634 | RTA00000633F.g.19.1.Seq | THC202541 |
| 2635 | RTA00000620F.o.07.1.Seq | THC155200 |
| 2636 | RTA00000586F.p.01.1.Seq | AA558590 |
| 2637 | RTA00000630F.1.10.1.Seq | THC204748 |
| 2638 | RTA00000626F.c.13.1.Seq | AA159259 |
| 2639 | RTA00000591F.m.06.1.Seq | THC227858 |
| 2640 | RTA00000630F.i.11.1.Seq | THC228806 |
| 2641 | RTA00000621F.h.08.1.Seq | THC163604 |
| 2642 | RTA00000589F.d.10.1.Seq | THC177076 |
| 2643 | RTA00000597F.p.01.1.Seq | THC210746 |
| 2644 | RTA00000619F.c.13.1.Seq | R57955 |
| 2645 | RTA00000607F.c.07.2.Seq | THC208762 |
| 2646 | RTA00000595F.b.02.1.Seq | THC233682 |
| 2647 | RTA00000631F.h.04.1.Seq | THC223281 |
| 2648 | RTA00000596F.p.18.1.Seq | THC197103 |
| 2649 | RTA00000586F.o.13.1.Seq | THC222729 |
| 2650 | RTA00000610F.p.17.1.Seq | EST19015 |
| 2651 | RTA00000596F.c.05.1.Seq | E5T72617 |
| 2652 | RTA00000632F.j.19.1.Seq | THC90741 |
| 2653 | RTA00000607F.e.23.2.Seq | AA639216 |
| 2654 | RTA00000628F.b.19.1.Seq | THC118075 |
| 2655 | RTA00000609F.d.13.1.Seq | THC195579 |
| 2656 | RTA00000621F.k.03.1.Seq | EST70278 |
| 2657 | RTA00000592F.1.04.1.Seq | THC91941 |
| 2658 | RTA00000592F.k.09.1.Seq | THC229803 |
| 2659 | RTA00000622F.e.17.1.Seq | R57425 |
| 2660 | RTA00000628F.g.13.1.Seq | THC176706 |
| 2661 | RTA00000592F.k.23.1.Seq | THC232202 |
| 2662 | RTA00000609F.m.04.2.Seq | AA507611 |
| 2663 | RTA00000626F.b.04.1.Seq | EST69420 |
| 2664 | RTA00000591F.m.01.1.Seq | H41850 |
| 2665 | RTA00000608F.n.23.1.Seq | THC214886 |
| 2666 | RTA00000583F.d.19.1.Seq | THC229251 |
| 2667 | RTA00000621F.p.15.1.Seq | THC212450 |
| 2668 | RTA00000583F.n.05.1.Seq | AA252468 |
| 2669 | RTA00000597F.f.17.1.Seq | THC219322 |
| 2670 | RTA00000606F.1.10.1.Seq | THC225232 |
| 2671 | RTA00000618F.n.14.1.Seq | THC216591 |
| 2672 | RTA00000612F.h.05.3.Seq | THC158250 |
| 2673 | RTA00000619F.a.24.1.Seq | AA437370 |
| 2674 | RTA00000617F.k.13.1.Seq | AA244445 |
| 2675 | RTA00000623F.h.07.1.Seq | THC212330 |
| 2676 | RTA00000620F.e.01.1.Seq | THC167493 |
| 2677 | RTA00000620F.h.10.1.Seq | THC232456 |
| 2678 | RTA00000589F.e.21.2.Seq | THC208239 |
| 2679 | RTA00000626F.b.22.1.Seq | THC225644 |
| 2680 | RTA00000620F.i.16.1.Seq | AA536090 |
| 2681 | RTA00000613F.c.17.1.Seq | THC92470 |
| 2682 | RTA00000621F.c.12.1.Seq | THC156244 |
| 2683 | RTA00000618F.b.17.1.Seq | THC209838 |
| 2684 | RTA00000585F.d.16.1.Seq | THC211870 |
| 2685 | RTA00000592F.a.06.1.Seq | THC233200 |
| 2686 | RTA00000583F.p.08.1.Seq | THC196844 |
| 2687 | RTA00000622F.h.21.1.Seq | EST12698 |
| 2688 | RTA00000591F.h.03.1.Seq | THC213771 |
| 2689 | RTA00000620F.g.22.1.Seq | THC224063 |
| 2690 | RTA00000588F.1.20.2.Seq | R84876 |
| 2691 | RTA00000614F.a.20.1.Seq | R84876 |
| 2692 | RTA00000611F.n.14.3.Seq | THC200742 |
| 2693 | RTA00000619F.f.23.1.Seq | THC227573 |
| 2694 | RTA00000608F.g.24.1.Seq | T93977 |
| 2695 | RTA00000595F.o.01.2.Seq | EST61392 |
| 2696 | RTA00000608F.b.23.1.Seq | THC161665 |
| 2697 | RTA00000606F.o.23.1.Seq | AA464645 |
| 2698 | RTA00000588F.i.22.3.Seq | THC162216 |
| 2699 | RTA00000610F.i.13.1.Seq | AA595068 |
| 2700 | RTA00000608F.b.15.1.Seq | EST11866 |
| 2701 | RTA00000597F.e.16.1.Seq | N88730 |
| 2702 | RTA00000610F.h.13.1.Seq | THC195895 |
| 2703 | RTA00000611F.h.21.2.Seq | EST46722 |
| 2704 | RTA00000584F.b.06.1.Seq | EST02998 |
| 2705 | RTA00000584F.b.06.2.Seq | EST02998 |
| 2706 | RTA00000608F.j.05.1.Seq | EST60433 |
| 2707 | RTA00000588F.b.03.1.Seq | THC164651 |

TABLE 2A

Nearest Neighbor (BlastN vs. Genbank)

| SEQ ID | ACC'N | DESCRIP. | P VALUE |
|---|---|---|---|
| 571 | L17043 | *Homo sapiens* pregnancy-specific beta-1-glycoprotein-11 gene. | 1.00E-12 |
| 578 | M18864 | Rat bone protein I (BP-I) mRNA, partial cds. | 7.00E-30 |
| 609 | L13838 | Human genomic sequence from chromosome 13, clone ch13lambdacDNA17–18. | 4.00E-36 |
| 618 | U09646 | Human carnitine palmitoyltransferase II precursor | 1.00E-34 |
| 627 | U72621 | Human LOT1 mRNA, complete cds | 1.00E-43 |
| 629 | M20910 | Human 7S L gene, complete. | 1.00E-35 |
| 636 | Z48950 | *H.sapiens* hH3.3B gene for histone H3.3 | 4.00E-36 |
| 639 | X00247 | Human translocated c-myc gene in Raji Burkitt lymphoma cells | 3.00E-44 |
| 643 | D80007 | Human mRNA for KIAA0185 gene, partial cds | 7.00E-52 |
| 646 | U14967 | Human ribosomal protein L21 mRNA, complete cds. | 2.00E-42 |
| 649 | M13934 | Human ribosomal protein S14 gene, complete cds. | 4.00E-45 |
| 652 | NM_003902.1 | *Homo sapiens* far upstream element binding protein (FUBP) mRNA > :: gb|U05040|HSU05040 Human FUSE binding protein mRNA, complete cds. | 1.00E-54 |
| 657 | L41142 | *Homo sapiens* signal transducer and activator of transcription (STAT5) mRNA, complete cds. | 2.00E-62 |
| 665 | Z12112 | pWE15A cosmid vector DNA | 2.00E-52 |
| 667 | Z54386 | *H.sapiens* CpG island DNA genomic Mse1 fragment, clone 10g3, forward read cpg10g3.ft1a | 7.00E-48 |
| 668 | X80333 | *M.musculus* rab18 mRNA | 2.00E-52 |
| 669 | X52126 | Human alternatively spliced c-myb mRNA | 1.00E-64 |
| 671 | L26247 | *Homo sapiens* suiliso1 mRNA, complete cds. | 3.00E-54 |
| 676 | NM_001736.1 | *Homo sapiens* complement component 5 receptor 1 C5a anaphylatoxin receptor mRNA, complete cds. | 4.00E-56 |
| 677 | Z50798 | *G.gallus* mRNA for p52 | 4.00E-55 |
| 679 | AB002368 | Human mRNA for KIAA0370 gene, partial cds | 2.00E-58 |
| 681 | M26697 | Human nucleolar protein (B23) mRNA, complete cds. | 4.00E-48 |
| 683 | D42087 | Human mRNA for KIAA0118 gene, partial cds | 4.00E-56 |
| 693 | D50734 | Rat mRNA of antizyme inhibitor, complete cds | 2.00E-50 |
| 697 | X02344 | *Homo sapiens* beta 2 gene | 1.00E-67 |
| 698 | NM_001067.1 | *Homo sapiens* topoisomerase (DNA) II alpha topoisomerase II (top2) mRNA, complete cds. | 7.00E-63 |
| 701 | U36309 | *Gallus gallus* rhoGap protein mRNA, complete cds | 3.00E-62 |
| 703 | NM_002842.1 | *Homo sapiens* protein tyrosine phosphatase, receptor type, H (PTPRH) mRNA > :: dbj|D15049|HUMSAP1C Human mRNA for protein tyrosine phosphatase | 2.00E-81 |
| 707 | U47322 | Cloning vector DNA, complete sequence. | 1.00E-63 |
| 714 | NM_001190.1 | *Homo sapiens* branched chain aminotransferase 2. mitochondrial (BCAT2) mRNA > :: gb|U68418|HSU68418 Human branched chain aminotransferase precursor (BCATm) mRNA, nuclear gene encoding mitochondrial protein, complete cds | 4.00E-67 |
| 718 | S62077 | HP1Hs alpha = 25 kda chromosomal autoantigen [human, mRNA, 876 nt] | 5.00E-68 |
| 719 | U34991 | Human endogenous retrovirus clone c18.4, HERV-H/HERV-E hybrid multiply spliced protease/integrase mRNA, complete cds, and envelope protein mRNA, partial cds | 2.00E-61 |
| 722 | U18671 | Human Stat2 gene, complete cds. | 4.00E-77 |
| 723 | L18964 | Human protein kinase C iota isoform (PRKCI) mRNA, complete cds. | 4.00E-68 |
| 724 | D29956 | Human mRNA for KIAA0055 gene, complete cds | 6.00E-70 |
| 725 | M77140 | *H.sapiens* pro-galanin mRNA, 3' end. | 2.00E-72 |
| 728 | U51432 | *Homo sapiens* nuclear protein Skip mRNA, complete cds | 1.00E-75 |
| 729 | M84334 | *Macacca mulatta* hnRNP A1-gamma isoform mRNA, complete cds. | 5.00E-50 |
| 730 | NM_002592.1 | *Homo sapiens* proliferating cell nuclear antigen (PCNA) mRNA >:: gb|M15796|HUMCYL Human cyclin protein gene, complete cds. | 1.00E-74 |
| 731 | M88458 | Human ELP-1 mRNA sequence. | 4.00E-76 |
| 732 | U44940 | *Mus musculus* quaking type I (QKI) mRNA, complete cds | 2.00E-69 |
| 733 | D17577 | Mouse mRNA for kinesin-like protein (Kif1b), complete cds | 2.00E-71 |
| 734 | U18920 | Human chromosome 17q12-21 mRNA, clone pOV-3, partial cds. | 2.00E-72 |
| 736 | M21188 | Human insulin-degrading enzyme (IDE) mRNA, complete cds. | 7.00E-82 |
| 737 | U49058 | *Rattus norvegicus* CTD-binding SR-like protein rA4 mRNA, partial cds | 1.00E-67 |
| 739 | D10630 | *Mus musculus* mRNA for zinc finger protein, complete cds, clone:CTfin51 | 4.00E-76 |
| 740 | U29156 | *Mus musculus* eps15R mRNA, complete cds. | 3.00E-84 |
| 741 | Y08135 | *M.musculus* mRNA for ASM-like phosphodiesterase 3a | 1.00E-86 |
| 742 | Y90567 | *Gallus gallus* glutamine rich protein mRNA, partial cds | 5.00E-58 |
| 743 | U58280 | *Mus musculus* second largest subunit of RNA polymerase I (RPA2) mRNA, complete cds | 4.00E-77 |
| 744 | S79539 | Pat-12 = Pat-12 product [mice, embryonic stem ES cells, mRNA, 2781 nt] | 9.00E-84 |

TABLE 2A-continued

Nearest Neighbor (BlastN vs. Genbank)

| SEQ ID | ACC'N | DESCRIP. | P VALUE |
|---|---|---|---|
| 745 | D30666 | Rat mRNA for brain acyl-CoA synthetase II, complete cds | 2.00E−89 |
| 746 | U29156 | *Mus musculus* eps15R mRNA, complete cds. | 2.00E−92 |
| 748 | U36909 | *Bos taurus* Rho-associated kinase mRNA, complete cds | e−104 |
| 749 | L36315 | *Mus musculus* (clone pMLZ-1) zinc finger protein | e−105 |
| 750 | X80169 | *M.musculus* mRNA for 200 kD protein | e−106 |
| 751 | X83577 | *M.musculus* mRNA for K-glypican | e−107 |
| 1060 | Z95437 | Human DNA sequence from cosmid A1 on chromosome 6 contains ESTs. HERV like retroviral sequence | 8.00E−21 |
| 1112 | X69907 | *H.sapiens* gene for mitochondrial ATP synthase c subunit (P1 form) | 6.00E−07 |
| 1125 | M19390 | Bovine interstitial retinol binding protein | 8.00E−31 |
| 1156 | U19247 | *Homo sapiens* interferon-gamma receptor alpha chain gene, exon 7 and complete cds | 7.00E−41 |
| 1170 | U20239 | *Mus musculus* fibrosin mRNA, partial cds | 5.00E−38 |
| 1171 | D26361 | Human mRNA for KIAA0042 gene, complete cds | 2.00E−41 |
| 1195 | NM_000694.1 | *Homo sapiens* aldehyde dehydrogenase 7 (ALDH7) mRNA > :: gb|U10868|HSU10868 Human aldehyde dehydrogenase ALDH7 mRNA, complete cds. | 1.00E−37 |
| 1196 | U84404 | Human E6-associated protein E6-AP/ubiquitin-protein ligase (UBE3A) mRNA, alternatively spliced, complete cds | 1.00E−46 |
| 1203 | U51714 | Human GPI protein p137 mRNA, partial sequence, 3'-UTR. | 9.00E−53 |
| 1204 | U58884 | *Mus musculus* SH3-containing protein SH3P7 mRNA, complete cds. similar to Human Drebrin | 2.00E−49 |
| 1210 | X79067 | *H.sapiens* ERF-1 mRNA 3' end | 2.00E−72 |
| 1212 | U00946 | Human clone A9A2BRB5 (CAC)n/(GTG)n repeat-containing mRNA | 3.00E−54 |
| 1217 | D11078 | *Homo sapiens* RGH2 gene, retrovirus-like element | 6.00E−49 |
| 1219 | U05989 | *Rattus norvegicus* clone par-4 induced by effectors of apoptosis mRNA, complete cds. | 3.00E−64 |
| 1220 | U13185 | Cloning vector pbetagal-Enhancer, complete sequence. | 3.00E−52 |
| 1222 | D87443 | Human mRNA for KIAA0254 gene, complete cds | 8.00E−63 |
| 1225 | U19867 | Cloning vector pSPL3, exon splicing vector, complete sequence, HIV envelope protein gp160 and beta-lactamase, complete cds. | 7.00E−72 |
| 1227 | U04817 | Human protein kinase PITSLRE alpha 2–3 mRNA, complete cds. | 4.00E−57 |
| 1230 | U03687 | *Photinus pyralis* modified luciferase gene, complete cds, and pUC18 derived vector. | 3.00E−62 |
| 1231 | U27196 | *Gallus gallus* zinc finger protein (Fzf-1) mRNA, complete cds. | 1.00E−66 |
| 1235 | X53586 | Human mRNA for integrin alpha 6 | 2.00E−71 |
| 1236 | J05016 | Human (clone pA3) protein disulfide isomerase related protein (ERp72) mRNA, complete cds. | 3.00E−67 |
| 1237 | M86752 | Human transformation-sensitive protein (IEF SSP 3521) mRNA, complete cds. | 1.00E−66 |
| 1239 | L19437 | Human transaldolase mRNA containing transposable element, complete cds | 5.00E−70 |
| 1241 | X90857 | *H.sapiens* mRNA for −14 gene, containing globin regulatory element | 1.00E−74 |
| 1242 | NM_003980.1 | *Homo sapiens* microtubule associated protein 7 mRNA | 9.00E−76 |
| 1245 | U17901 | *Rattus norvegicus* phospholipase A-2-activating protein (plap) mRNA, complete cds. | 3.00E−75 |
| 1246 | S80632 | threonine, tyrosine phosphatase [human, brain, mRNA Partial, 1236 nt] | 2.00E−69 |
| 1247 | M76541 | Human DNA-binding protein (NF-E1) mRNA, complete cds. | 2.00E−80 |
| 1248 | S55305 | 14-3-3 protein gamma subtype = putative protein kinase C regulatory protein [rats, brain, mRNA, 3410 nt] > :: dbj|D17447|D17447 *Rattus norvegicus* mRNA for 14-3-3 protein gamma-subtype, complete cds | 7.00E−93 |
| 1249 | NM_002350.1 | *Homo sapiens* v-yes-1 Yamaguchi sarcoma viral related oncogene homolog (LYN) mRNA > :: gb|M16038|HUMLYN Human lyn mRNA encoding a tyrosine kinase. | 3.00E−86 |
| 1250 | Y10725 | *M.musculus* mRNA for protein kinase KIS | 4.00E−68 |
| 1251 | U89931 | Cloning vector pTRE, complete sequence | 3.00E−65 |
| 1252 | Z46386 | Bovine herpesvirus type 4 DNA for nonconserved region F (DN599 like strain) | 3.00E−73 |
| 1253 | L77599 | *Homo sapiens* (clone SEL214) 17q YAC (303G8) RNA. | 2.00E−69 |
| 1255 | Y10746 | *H.sapiens* mRNA for protein containing MBD 1 | 2.00E−79 |
| 1256 | L77599 | *Homo sapiens* (clone SEL214) 17q YAC (303G8) RNA. | 2.00E−71 |
| 1257 | Z57619 | *H.sapiens* CpG island DNA genomic Mse1 fragment, clone 187a6, forward read cpg187a6.ft1b | 7.00E−72 |
| 1258 | U48807 | Human MAP kinase phosphatase (MKP-2) mRNA, complete cds | 3.00E−76 |
| 1260 | M27444 | *Bos taurus* (clone pTKD7) dopamine and cyclic AMP-regulated neuronal phosphoprotein (DARPP-32) mRNA, complete cds. | 4.00E−76 |
| 1261 | U37150 | *Bos taurus* peptide methionine sulfoxide reductase (msrA) mRNA, complete cds | 5.00E−78 |

TABLE 2A-continued

Nearest Neighbor (BlastN vs. Genbank)

| SEQ ID | ACC'N | DESCRIP. | P VALUE |
|---|---|---|---|
| 1262 | U02435 | Cloning vector pSVbeta, complete sequence | 1.00E−77 |
| 1263 | U09662 | Cloning vector pSEAP-Enhancer, complete sequence | 4.00E−79 |
| 1264 | M99566 | sCos cloning vector SfiI containing bacteriophage promoters and flanking restriction sites in sCos vectors. | 1.00E−79 |
| 1266 | Z12112 | pWE15A cosmid vector DNA | 4.00E−80 |
| 1267 | U55387 | *Cricetulus griseus* SL15 mRNA, complete cds | 2.00E−82 |
| 1269 | L14684 | *Rattus norvegicus* nuclear-encoded mitochondrial elongation factor G mRNA, complete cds. | 2.00E−91 |
| 1270 | U49057 | *Rattus norvegicus* CTD-binding SR-like protein rA9 mRNA, complete cds | 7.00E−93 |
| 1271 | U57368 | *Mus musculus* EGF repeat transmembrane protein mRNA, complete cds. | 4.00E−97 |
| 1272 | AF000938 | *Mus musculus* RNA polymerase I largest subunit | 8.00E−94 |
| 1274 | X80169 | *M.musculus* mRNA for 200 kD protein | e−102 |
| 1275 | U09874 | *Mus musculus* SKD3 mRNA, complete cds. | e−105 |
| 1276 | D78020 | Rat mRNA for NFI-A4, partial cds | e−108 |
| 1515 | Z73360 | Human DNA sequence from cosmid 92M18, BRCA2 gene region chromosome 13q12-13 | 9.00E−22 |
| 1522 | X62078 | *H.sapiens* mRNA for GM2 activator protein | 7.00E−72 |
| 1523 | X85750 | *H.sapiens* mRNA for transcript associated with monocyte to macrophage differentiation | 2.00E−50 |
| 1525 | X03473 | Human gene for histone H1(0) | 1.00E−67 |
| 1535 | X64411 | *R.norvegicus* mRNA for 100 kDa protein | 1.00E−54 |
| 1538 | X13345 | Human gene for plasminogen activator inhibitor 1 | 2.00E−59 |
| 1542 | D86971 | Human mRNA for KIAA0217 gene, partial cds | 7.00E−83 |
| 1543 | NM_001859.1 | *Homo sapiens* solute carrier family 31 gb|U83460|HSU83460 Human high-affinity copper uptake protein (hCTR1) mRNA, complete cds | 7.00E−72 |
| 1544 | X68194 | *H.sapiens* h-Sp1 mRNA | 5.00E−57 |
| 1545 | AB002326 | Human mRNA for KIAA0328 gene, partial cds | 3.00E−74 |
| 1548 | D31762 | Human mRNA for KIAA0057 gene, complete cds | 3.00E−85 |
| 1550 | X58472 | Mouse KIN17 mRNA for kin17 protein | 2.00E−57 |
| 1551 | U13185 | Cloning vector pbetagal-Enhancer, complete sequence. | 2.00E−79 |
| 1552 | U55939 | Expression vector pVP-Nco, complete sequence. | 1.00E−76 |
| 1553 | D87671 | *Rattus norvegicus* mRNA for TIP120, complete cds | 1.00E−87 |
| 1554 | U25691 | *Mus musculus* lymphocyte specific helicase mRNA, complete cds | 4.00E−86 |
| 1555 | U55939 | Expression vector pVP-Nco, complete sequence. | 5.00E−79 |
| 1556 | Z12112 | pWE15A cosmid vector DNA | 2.00E−79 |
| 1557 | U13185 | Cloning vector pbetagal-Enhancer, complete sequence. | 2.00E−79 |
| 1558 | U13185 | Cloning vector pbetagal-Enhancer, complete sequence. | 6.00E−80 |
| 1559 | Z12112 | pWE15A cosmid vector DNA | 6.00E−80 |
| 1560 | U09661 | Cloning vector pSEAP-Control, complete sequence | 6.00E−80 |
| 1561 | U36909 | *Bos taurus* Rho-associated kinase mRNA, complete cds | 2.00E−90 |
| 1562 | L36610 | *Mus musculus* protein synthesis initiation factor 4A (eIF-4A) gene, exons 5, 6, 7, 8, and 9. | 2.00E−71 |
| 1563 | S79463 | M-Sema F = a factor in neural network development | 1.00E−85 |
| 1564 | U35312 | *Mus musculus* nuclear receptor co-repressor mRNA, complete cds | 1.00E−98 |
| 1571 | L32977 | *Homo sapiens* (clone f17252) ubiquinol cytochrome c reductase Rieske iron-sulphur protein (UQCRFS1) gene, exon 2 | 0 |
| 1576 | S78454 | *Mus musculus* metal response element DNA-binding protein M96 mRNA, complete cds | 0 |
| 1586 | M88458 | Human ELP-1 mRNA sequence. | 0 |
| 1622 | S77512 | LAMB2 = laminin beta 2 chain [human, placenta, mRNA, 5642 nt] | e−131 |
| 1624 | X53305 | *H.sapiens* mRNA for statlimin | 0 |
| 1625 | J03591 | Human ADP/ATP translocase mRNA, 3' end, clone pHAT3. | 0 |
| 1630 | L18964 | Human protein kinase C iota isoform (PRKCI) mRNA, complete cds. | 2E−67 |
| 1640 | D29956 | Human mRNA for KIAA0055 gene, complete cds | 0 |
| 1649 | M26697 | Human nucleolar protein (B23) mRNA, complete cds. | e−149 |
| 1669 | U47322 | Cloning vector DNA, complete sequence. | 4E−65 |
| 1689 | NM_002079.1 | *Homo sapiens* glutamic-oxaloacetic transaminase 1, soluble (aspartate aminotransferase 1) aspartate aminotransferase mRNA, complete cds. | 0 |
| 1693 | U55939 | Expression vector pVP-Nco, complete sequence. | 2E−70 |
| 1694 | D80007 | Human mRNA for KIAA0185 gene, partial cds | 0 |
| 1695 | NM_001904.1 | *Homo sapiens* catenin (cadherin-associated protein), beta 1 (88kD) (CTNNB1) mRNA > :: emb|X87838|HSRNABECA *H.sapiens* mRNA for beta-catenin | e−108 |
| 1701 | U19867 | Cloning vector pSPL3, exon splicing vector, complete sequence, HIV envelope protein gp160 and beta-lactamase, complete cds. | 1E−44 |
| 1702 | M31061 | Human ornithine decarboxylase gene, complete cds. | 0 |

TABLE 2A-continued

Nearest Neighbor (BlastN vs. Genbank)

| SEQ ID | ACC'N | DESCRIP. | P VALUE |
|---|---|---|---|
| 1721 | Z96177 | *H.sapiens* telomeric DNA sequence, clone 10QTEL040, read 10QTELOO040.seq | 2E−70 |
| 1722 | NM_001904.1 | *Homo sapiens* catenin (cadherin-associated protein), beta 1 (88 kD) (CTNNB1) mRNA > :: emb|X87838|HSRNABECA *H.sapiens* mRNA for beta-catenin | e−176 |
| 1758 | X83577 | *M.musculus* mRNA for K-glypican | 0 |
| 1761 | S79539 | Pat-12 = Pat-12 product [mice, embryonic stem ES cells, mRNA, 2781 nt] | e−176 |
| 1773 | L38951 | *Homo sapiens* importin beta subunit mRNA, complete cds | 1E−78 |
| 1776 | NM_003902.1 | *Homo sapiens* far upstream element binding protein (FUBP) mRNA > :: gb|U05040|HSU05040 Human FUSE binding protein mRNA, complete cds. | 0 |
| 1791 | L08783 | BlueScribe M13 Plus cloning vector. | 0 |
| 1809 | U86751 | Human nucleolar fibrillar center protein (ASE-1) mRNA, complete cds | 8E−95 |
| 1817 | M21188 | Human insulin-degrading enzyme (IDE) mRNA, complete cds. | e−134 |
| 1831 | NM_001614.1 | *Homo sapiens* actin, gamma 1 (ACTG1) mRNA > :: emb|X04098|HSACTCGR Human mRNA for cytoskeletal gamma-actin | 0.00E+00 |
| 1836 | U12404 | Human Csa-19 mRNA, complete cds. | 0 |
| 1837 | X79236 | *H.sapiens* rps26 gene | e−145 |
| 1838 | NM_003313.1 | *Homo sapiens* tissue specific transplantation antigen P35B (TSTA3) mRNA > :: gb|U58766|HSU58766 Human FX protein mRNA, complete cds | 0 |
| 1839 | M27436 | Human tissue factor gene, complete cds, with a Alu repetitive sequence in the 3' untranslated region. > :: gb|I05724| Sequence 12 from Patent EP 0278776 | e−121 |
| 1849 | X79067 | *H.sapiens* ERF-1 mRNA 3' end | 0 |
| 1850 | NM_003017 | *Homo sapiens* splicing factor, arginine/serine-rich 3 (SFRS3) mRNA > :: gb|L10838|HUMSRP20 *Homo sapiens* SR protein family, pre-mRNA splicing factor (SRp20) mRNA, complete cds. | e−135 |
| 1857 | U48807 | Human MAP kinase phosphatase (MKP-2) mRNA, complete cds | 0.00E+00 |
| 1858 | U48807 | Human MAP kinase phosphatase (MKP-2) mRNA, complete cds | 0.00E+00 |
| 1873 | U04817 | Human protein kinase PITSLRE alpha 2–3 mRNA, complete cds. | 8.00E−53 |
| 1876 | U18297 | Human MST1 (MST1) mRNA, complete cds. | 0.00E+00 |
| 1877 | NM_001859.1 | *Homo sapiens* solute carrier family 31 gb|U83460|HSU83460 Human high-affinity copper uptake protein (hCTR1) mRNA, complete cds | 0 |
| 1889 | X70272 | single stranded replicative centromeric *Saccharomyces cerevisiae*/*E. coli* shuttle vector | 3.00E−76 |
| 1897 | L26050 | Human mitochondrial 2,4-dienoyl-CoA reductase mRNA, complete cds. | 0.00E+00 |
| 1899 | X06747 | Human hnRNP core protein A1 | e−157 |
| 1901 | M64571 | Human microtubule-associated protein 4 mRNA, complete cds. | 0.00E+00 |
| 1908 | X65322.1 | Cloning vector pCAT-Basic | 9.00E−53 |
| 1913 | NM_002654.1 | *Homo sapiens* pyruvate kinase, muscle (PKM2) mRNA > :: gb|M23725|HUMPKM2L Human M2-type pyruvate kinase mRNA, complete cds. | e−159 |
| 1916 | U49352 | Human liver 2,4-dienoyl-CoA reductase mRNA, complete cds | 2.00E−71 |
| 1926 | D31889 | Human mRNA for KIAA0072 gene, partial cds > :: gb|G27027|G27027 human STS SHGC-31585. | e−167 |
| 1941 | U43944 | Human breast cancer cytosolic NADP(+)-dependent malic enzyme mRNA, partial cds | 1.00E−89 |
| 1971 | U83659 | Human multidrug resistance-associated protein homolog (MRP3) mRNA, partial cds | 3.00E−85 |
| 1996 | M33519 | Human HLA-B-associated transcript 3 (BAT3) mRNA, complete cds. | 3.00E−84 |
| 1997 | U55387 | *Cricetulus griseus* SL15 mRNA, complete cds | e−150 |
| 2018 | L36315 | *Mus musculus* (clone pMLZ-1) zinc finger protein | e−162 |
| 2025 | NM_003902.1 | *Homo sapiens* far upstream element binding protein (FUBP) mRNA > :: gb|U05040|HSU05040 Human FUSE binding protein mRNA, complete cds. | e−175 |
| 2032 | X56932 | *H.sapiens* mRNA for 23 kD highly basic protein | 0.00E+00 |
| 2039 | X98654 | *H.sapiens* mRNA for DRES9 protein | 9.00E−97 |
| 2050 | S62077 | HP1Hs alpha = 25 kda chromosomal autoantigen [human, mRNA, 876 nt] | 4.00E−68 |
| 2057 | M23619 | Human HMG-I protein isoform mRNA (HMGI gene), clone 6A. | e−117 |
| 2077 | NM_003217.1 | *Homo sapiens* testis enhanced gene transcript | 4E−99 |
| 2092 | U18671 | Human Stat2 gene, complete cds. | 0.00E+00 |
| 2096 | D43636 | Human mRNA for KIAA0096 gene, partial cds | 0 |

TABLE 2A-continued

Nearest Neighbor (BlastN vs. Genbank)

| SEQ ID | ACC'N | DESCRIP. | P VALUE |
|---|---|---|---|
| 2098 | NM_002734.1 | *Homo sapiens* protein kinase, cAMP-dependent, regulatory, type I, alpha (tissue specific extinguisher 1) (PRKAR1A) mRNA > :: gb|M33336|HUMCAMPPK Human cAMP-dependent protein kinase type 1-alpha subunit | 0 |
| 2099 | U72621 | Human LOT1 mRNA, complete cds | 0.00E+00 |
| 2112 | NM_003902.1 | *Homo sapiens* far upstream element binding protein (FUBP) mRNA > :: gb|U05040|HSU05040 Human FUSE binding protein mRNA, complete cds. | 0.00E+00 |
| 2118 | L41142 | *Homo sapiens* signal transducer and activator of transcription (STAT5) mRNA, complete cds. | 0.00E+00 |
| 2119 | Z48950 | *H.sapiens* hH3.3B gene for histone H3.3 | 0.00E+00 |
| 2153 | L09260 | Human (chromosome 3p25) membrane protein mRNA. | e-100 |
| 2158 | X65304.1 | Cloning vector pGEM-3Z | e-173 |
| 2163 | NM_003358.1 | *Homo sapiens* UDP-glucose ceramide glucosyltransferase (UGCG) mRNA > :: dbj|D50840|HUMCGA *Homo sapiens* mRNA for ceramide glucosyltransferase, complete cds > :: dbj|E12454|E12454 cDNA encoding human ceramide glucosyltransferase | e-141 |
| 2179 | M95605 | *Bos taurus* S-adenosylmethionine decarboxylase | e-175 |
| 2180 | M12623 | Human non-histone chromosomal protein HMG-17 mRNA, complete cds. | 0.00E+00 |
| 2181 | U79143 | Human phosphoinositide 3'-hydroxykinase p110-alpha subunit mRNA, complete cds | 0.00E+00 |
| 2192 | K01906 | Human fetal liver c-myc proto-oncogene, exon 3 and flanks. | e-165 |
| 2194 | X74870 | *H.sapiens* gene for RNA pol II largest subunit, exons 23–29 | e-161 |
| 2235 | L16991 | Human thymidylate kinase (CDC8) mRNA, complete cds. | 0.00E+00 |
| 2257 | L08783 | BlueScribe M13 Plus cloning vector. | 0.00E+00 |
| 2276 | NM_002245.1 | *Homo sapiens* potassium inwardly-rectifying channel, subfamily K, member 1 (KCNK1) mRNA > :: gb|U33632|HSU33632 Human two P-domain K+ channel TWIK-1 mRNA, complete cds. | 0 |
| 2278 | D50734 | Rat mRNA of antizyme inhibitor, complete cds | e-157 |
| 2279 | U26401 | Human galactokinase (galK) mRNA, complete cds. > | 0.00E+00 |
| 2285 | U49058 | *Rattus norvegicus* CTD-binding SR-like protein rA4 mRNA, partial cds | e-138 |
| 2287 | X65306.1 | Cloning vector pGEM-3Zf(+) | e-116 |
| 2299 | NM_001172.1 | *Homo sapiens* arginase, type II (ARG2) mRNA > :: gb|U82256|HSU82256 *Homo sapiens* arginase type II mRNA, complete cds | e-127 |
| 2309 | M25160 | Human Na,K-ATPase beta subunit (ATP1B) gene, exons 3 through 6. | 0.00E+00 |
| 2315 | Y08736 | *H.sapiens* vegf gene, 3'UTR | 1.00E-78 |
| 2320 | U13737 | Human cysteine protease CPP32 isoform alpha mRNA, complete cds. | 0.00E+00 |
| 2323 | Y08135 | *M.musculus* mRNA for ASM-like phosphodiesterase 3a | e-148 |
| 2324 | Y08135 | *M.musculus* mRNA for ASM-like phosphodiesterase 3a | 0 |
| 2328 | NM_001677.1 | *Homo sapiens* ATPase, Na+/K+ transporting, beta 1 polypeptide (ATP1B1) mRNA > :: emb|X03747|HSATPBR Human mRNA for Na/K-ATPase beta subunit | 1E-77 |
| 2337 | Y08135 | *M.musculus* mRNA for ASM-like phosphodiesterase 3a | e-168 |
| 2364 | U54778 | Human 14-3-3 epsilon mRNA, complete cds | 1E-67 |
| 2365 | Y08135 | *M.musculus* mRNA for ASM-like phosphodiesterase 3a | 0 |
| 2368 | NM_001172.1 | *Homo sapiens* arginase, type II (ARG2) mRNA > :: gb|U82256|HSU82256 *Homo sapiens* arginase type II mRNA, complete cds | e-127 |
| 2385 | AB002293 | Human mRNA for KIAA0295 gene, partial cds | 0 |
| 2394 | M21188 | Human insulin-degrading enzyme (IDE) mRNA, complete cds. | 2E-81 |
| 2425 | D87466 | Human mRNA for KIAA0276 gene, partial cds | 1E-97 |
| 2429 | U58884 | *Mus musculus* SH3-containing protein SH3P7 mRNA, complete cds. similar to Human Drebrin | 4E-96 |
| 2441 | AB005216 | *Homo sapiens* mRNA for Nck, Ash and phospholipase C gamma-binding protein NAP4, partial cds | 0 |
| 2442 | NM_001960.1 | *Homo sapiens* eukaryotic translation elongation factor 1 delta (guanine nucleotide exchange protein) (EEF1D) mRNA > :: emb|Z21507|HSEF1DELA *H.sapiens* EF-1delta gene encoding human elongation factor-1-delta | 0.00E+00 |
| 2444 | M92449 | Human LTR mRNA, 3' end of coding region and 3' flank. | e-143 |
| 2452 | NM_003350.1 | *Homo sapiens* ubiquitin-conjugating enzyme E2 variant 2 (UBE2V2) mRNA > :: emb|X98091|HSVITDITR *H.sapiens* mRNA for protein induced by vitamin D | 0 |
| 2456 | U44975 | *Homo sapiens* DNA-binding protein CPBP (CPBP) mRNA, partial cds | 5.00E-69 |
| 2459 | Z84510 | *H.sapiens* flow-sorted chromosome 6 HindIII fragment, SC6pA28B7 | 4.00E-66 |

TABLE 2A-continued

Nearest Neighbor (BlastN vs. Genbank)

| SEQ ID | ACC'N | DESCRIP. | P VALUE |
|---|---|---|---|
| 2463 | Z48042 | *H.sapiens* mRNA encoding GPI-anchored protein p137 | e-172 |
| 2497 | U32986 | Human xeroderma pigmentosum group E UV-damaged DNA binding factor mRNA, complete cds. | 0 |
| 2515 | NM_003419 .1 | *Homo sapiens* zinc finger protein 10 (KOX 1) for zinc finger protein | e-129 |
| 2520 | Y00711 | Human mRNA for lactate dehydrogenase B (LDH-B) | 0.00E+00 |
| 2526 | Y10725 | *M.musculus* mRNA for protein kinase KIS | 0.00E+00 |
| 2543 | X62078 | *H.sapiens* mRNA for GM2 activator protein | e-164 |
| 2548 | NM_001009 .1 | *Homo sapiens* ribosomal protein S5 (RPS5) mRNA complete cds. | 0.00E+00 |
| 2556 | U97188 | *Homo sapiens* putative RNA binding protein KOC | 1E-86 |
| 2575 | NM_002852 .1 | *Homo sapiens* pentaxin-related gene, rapidly induced by IL-1 beta (PTX3) mRNA > :: emb|X63613|HSPTX3R *H.sapiens* mRNA for pentaxin (PTX3) | 0.00E+00 |
| 2578 | X67155 | *H.sapiens* mRNA for mitotic kinesin-like protein-1 | 0.00E+00 |
| 2588 | M54968 | Human K-ras oncogene protein mRNA, complete cds > | e-123 |
| 2591 | D88687 | *Homo sapiens* mRNA for KM-102-derived reductase-like factor, complete cds | 0 |
| 2593 | NM_001436 .1 | *Homo sapiens* fibrillarin (FBL) mRNA > :: gb|M59849|HUMFIBAA Human fibrillarin (Hfib1) mRNA, complete cds. | e-103 |
| 2595 | AB002326 | Human mRNA for KIAA0328 gene, partial cds | 0.00E+00 |
| 2598 | M11948 | Human promyelocytic leukemia cell mRNA, clones pHH58 and pHH81. | 9.00E-84 |

TABLE 2B

Nearest Neighbor (BlastX vs. Non-Redundant Proteins)

| SEQ ID | ACC'N | DESCRIP. | P VALUE |
|---|---|---|---|
| 37 | 4239895 | (AB016816) MASL1 [*Homo sapiens*] | 9.00E-54 |
| 66 | 4514653 | (AB024057) vascular Rab-GAP/TBC-containing protein [*Homo sapiens*] | 6.00E-55 |
| 78 | 4454524 | (AC004841) similar to insulin receptor substrate BAP2; similar to PID:g4126477 [*Homo sapiens*] | 6.00E-22 |
| 79 | 4545264 | (AF118240) peroxisomal biogenesis factor 16 [*Homo sapiens*] | 1.00E-45 |
| 112 | 3413938 | (AB007963) KIAA0494 protein [*Homo sapiens*] | 3.00E-44 |
| 122 | 4239895 | (AB016816) MASL1 [*Homo sapiens*] | 1.00E-47 |
| 139 | 4502371 | breast cancer antiestrogen resistance 3 > gi|3237306 (U92715) breast cancer antiestrogen resistance 3 protein [*Homo sapiens*] | 2.00E-44 |
| 154 | 4586880 | (AB017114) AD 3 [*Homo sapiens*] | 4.00E-48 |
| 157 | 3327170 | (AB014578) KIAA0678 protein [*Homo sapiens*] | 2.00E-51 |
| 168 | 3153241 | (AF053004) class I cytokine receptor [*Homo sapiens*] | 2.00E-17 |
| 171 | 4138233 | (AJ007780) parp-2 gene [*Mus musculus*] | 2.00E-32 |
| 174 | 3287173 | (AJ006266) AND-1 protein [*Homo sapiens*] | 2.00E-42 |
| 187 | 4507145 | UNKNOWN > gi|3873216 (AF065485) sorting nexin 4 [*Homo sapiens*] | 8.00E-46 |
| 207 | 4153860 | (AC005074) similar to U47321 (PID:g1245146) [*Homo sapiens*] | 4.00E-15 |
| 224 | 3236430 | (AF067379) ubiquitin-protein ligase E3-alpha [*Mus musculus*] | 3.00E-35 |
| 253 | 3043696 | (AB011158) KIAA0586 protein [*Homo sapiens*] | 1.00E-44 |
| 260 | 4519623 | (AB017616) homologous to the yeast YGR163 gene [*Mus musculus*] | 2.00E-54 |
| 280 | 4455035 | (AF116238) pseudouridine synthase 1 [*Homo sapiens*] | 4.00E-48 |
| 304 | 3075377 | (AC004602) F23487_2 [*Homo sapiens*] | 2.00E-21 |
| 306 | 4505611 | poly(A)-specific ribonuclease | 7.00E-41 |
| 373 | 1825606 | (U88169) similar to molybdoterin biosynthesis MOEB proteins [*Caenorhabditis elegans*] | 2.00E-37 |
| 382 | 4586287 | (AB004794) DUF140 [*Xenopus laevis*] | 7.00E-45 |
| 396 | 3941342 | (AF043250) mitochondrial outer membrane protein [*Homo sapiens*] > gi|3941347 (AF043253) mitochondrial outer membrane protein [*Homo sapiens*] > gi|4105703|gb|AAD02504| | 5.00E-40 |
| 414 | 4586844 | (AB015633) type II membrane protein | 2.00E-46 |
| 422 | 3327078 | (AB014532) KIAA0632 protein [*Homo sapiens*] | 6.00E-36 |
| 433 | 3327230 | (AB014608) KIAA0708 protein [*Homo sapiens*] | 5.00E-52 |
| 472 | 3372677 | (AF061749) tumorous imaginal discs protein Tid56 homolog | 7.00E-35 |
| 502 | 4050034 | (AF098482) transcriptional coactivator p52 [*Homo sapiens*] | 1.00E-36 |
| 504 | 4406632 | (AF131801) Unknown [*Homo sapiens*] | 3.00E-21 |
| 512 | 3114828 | (AJ005897) JM5 [*Homo sapiens*] | 3.00E-44 |

TABLE 2B-continued

Nearest Neighbor (BlastX vs. Non-Redundant Proteins)

| SEQ ID | ACC'N | DESCRIP. | P VALUE |
|---|---|---|---|
| 530 | 3766209 | (AF071777) IRE1 [*Mus musculus*] | 2.00E−29 |
| 561 | 3043644 | (AB011132) KIAA0560 protein [*Homo sapiens*] | 3.00E−43 |
| 572 | 3088575 | (AF059531) protein arginine N-methyltransferase 3 [*Homo sapiens*] | 4.00E−46 |
| 578 | 4505891 | UNKNOWN > gi|3153235 (AF046889) lysyl hydroxylase isoform 3 [*Homo sapiens*] > gi|3551836 | 3.00E−30 |
| 590 | 3114828 | (AJ005897) JM5 [*Homo sapiens*] | 1.00E−24 |
| 592 | 3242214 | (AJ006778) DRIM protein [*Homo sapiens*] | 2.00E−36 |
| 598 | 4200236 | (AL035308) hypothetical protein [*Homo sapiens*] | 8.00E−09 |
| 600 | 3413892 | (AB007934) KIAA0465 protein [*Homo sapiens*] | 2.00E−51 |
| 635 | 3043626 | (AB011123) KIAA0551 protein [*Homo sapiens*] | 3.00E−31 |
| 643 | 2498864 | RRP5 PROTEIN HOMOLOG (KIAA0185) hypothetical protein YM9959.11C of S.cerevisiae. [*Homo sapiens*] | 3.00E−13 |
| 670 | 3402197 | (AJ010014) M96A protein [*Homo sapiens*] | 1.00E−21 |
| 677 | 2217964 | (Z50798) p52 [*Gallus gallus*] | 7.00E−14 |
| 686 | 3043626 | (AB011123) KIAA0551 protein [*Homo sapiens*] | 1.00E−40 |
| 697 | 135470 | TUBULIN BETA-5 CHAIN sapiens] | 3.00E−21 |
| 701 | 3327056 | (AB014521) KIAA0621 protein [*Homo sapiens*] | 2.00E−29 |
| 704 | 4506787 | UNKNOWN GTPASE-ACTIVATING-LIKE PROTEIN IQGAP1 (P195) (KIAA0051) protein-human > gi|473931|dbj|BAA06123| (D29640) KIAA0051 [*Homo sapiens*] > gi|536844 (L33075) ras GTPase-activating-like protein [*Homo sapiens*] | 4.00E−41 |
| 709 | 1350762 | 60S RIBOSOMAL PROTEIN L6 sapiens] | 2.00E−22 |
| 713 | 2687400 | (AF035824) vesicle soluble NSF attachment protein receptor [*Homo sapiens*] | 1.00E−23 |
| 730 | 2914385 | Chain C, Human Pcna > gi|2914387|pdb|1AXC|E Chain E, Human Pcna | 2.00E−27 |
| 731 | 284076 | ERD-2-like protein, ELP-1-human | 1.00E−26 |
| 733 | 2497524 | KINESIN-LIKE PROTEIN KIF1B mouse > gi|407339|dbj|BAA04503| (D17577) Kif1b [*Mus musculus*] | 9.00E−33 |
| 735 | 3327056 | (AB014521) KIAA0621 protein [*Homo sapiens*] | 1.00E−13 |
| 736 | 279567 | insulinase (EC 3.4.99.45)-human | 2.00E−26 |
| 738 | 487416 | (L20302) actin filament protein [*Gallus gallus*] | 3.00E−45 |
| 739 | 1731428 | ZINC FINGER PROTEIN ZFP-38 | 7.00E−35 |
| 740 | 968973 | (U29156) involved in signaling by the epidermal growth factor receptor; Method: conceptual translation supplied by author. [*Mus musculus*] | 1.00E−22 |
| 741 | 1552350 | (Y08135) acid sphingomyelinase-like phosphodiesterase [*Mus musculus*] | 2.00E−35 |
| 742 | 3327098 | (AB014542) KIAA0642 protein [*Homo sapiens*] | 3.00E−15 |
| 743 | 3914801 | DNA-DIRECTED RNA POLYMERASE I 135 KD POLYPEPTIDE (RNA POLYMERASE I SUBUNIT 2) (RPA135) (RNA POLYMERASE I 127 KD SUBUNIT) > gi|2739048 (AF025424) RNA polymerase I 127 kDa subunit [*Rattus norvegicus*] | 2.00E−45 |
| 745 | 4165018 | (D89053) Acyl-CoA synthetase 3 [*Homo sapiens*] | 2.00E−53 |
| 746 | 968973 | (U29156) involved in signaling by the epidermal growth factor receptor; Method: conceptual translation supplied by author. [*Mus musculus*] | 3.00E−40 |
| 747 | 4519883 | (AB017970) dipeptidyl peptidase III | 4.00E−50 |
| 748 | 3327052 | (AB014519) KIAA0619 protein [*Homo sapiens*] | 7.00E−30 |
| 749 | 538413 | (L36315) zinc finger protein [*Mus musculus*] | 6.00E−55 |
| 750 | 1717793 | PROTEIN TSG24 (MEIOTIC CHECK POINT REGULATOR) > gi|1083553|pir||A55117 tsg24 protein-mouse | 1.00E−50 |
| 751 | 3420277 | (AF064826) glypican 4 [*Homo sapiens*] | 3.00E−54 |
| 808 | 4580645 | (AF118855) trans-prenyltransferase [*Mus musculus*] | 2.00E−48 |
| 829 | 3882171 | (AB018268) KIAA0725 protein [*Homo sapiens*] | 3.00E−24 |
| 833 | 4104976 | (AF043117) ubiquitin-fusion degradation protein 2 [*Homo sapiens*] | 2.00E−41 |
| 841 | 3242214 | (AJ006778) DRIM protein [*Homo sapiens*] | 4.00E−34 |
| 914 | 4191810 | (AB006532) DNA helicase [*Homo sapiens*] | 5.00E−41 |
| 959 | 3043714 | (AB011167) KIAA0595 protein [*Homo sapiens*] | 5.00E−20 |
| 982 | 4379097 | (Y17999) Dyrk1B protein kinase [*Homo sapiens*] | 3.00E−21 |
| 1028 | 3043712 | (AB011166) KIAA0594 protein [*Homo sapiens*] | 2.00E−49 |
| 1079 | 4240227 | (AB020676) KIAA0869 protein [*Homo sapiens*] | 4.00E−35 |
| 1091 | 4235226 | (AF061025) leucine zipper-EF-hand containing transmembrane protein 1 [*Homo sapiens*] | 6.00E−34 |
| 1134 | 3426268 | (AF044201) neural membrane protein 35; NMP35 [*Rattus norvegicus*] | 1.00E−29 |
| 1152 | 4507367 | threonyl-tRNA synthetase SYNTHETASE, CYTOPLASMIC (THREONINE--TRNA LIGASE) (THRRS) 6.1.1.3)-human > gi|1464742 (M63180) threonyl-tRNA synthetase [*Homo sapiens*] | 3.00E−26 |

TABLE 2B-continued

Nearest Neighbor (BlastX vs. Non-Redundant Proteins)

| SEQ ID | ACC'N | DESCRIP. | P VALUE |
|---|---|---|---|
| 1153 | 2072294 | (U95097) mitotic phosphoprotein 43 [Xenopus laevis] | 1.00E−19 |
| 1163 | 543222 | glutamine (Q)-rich factor 1, QRF-1-mouse factor 1, QRF-1 [mice, B-cell leukemia, BCL1, Peptide Partial, 84 aa] | 1.00E−39 |
| 1164 | 3335569 | (AF072759) fatty acid transport protein 4; FATP4 [Mus musculus] | 7.00E−39 |
| 1168 | 2996194 | (AF053232) SIK similar protein [Mus musculus] | 1.00E−31 |
| 1172 | 2935597 | (AC004262) R29368_2 [Homo sapiens] | 6.00E−49 |
| 1201 | 2645205 | (U63648) p160 myb-binding protein [Mus musculus] | 1.00E−21 |
| 1204 | 1407655 | (U58884) SH3P7 [Mus musculus] | 8.00E−21 |
| 1214 | 2134381 | polybromo 1 protein-chicken | 8.00E−29 |
| 1219 | 4505613 | PRKC, apoptosis, WT1, regulator par-4 [Homo sapiens] | 6.00E−34 |
| 1229 | 3757892 | (AF079765) enhancer of polycomb [Mus musculus] | 3.00E−41 |
| 1231 | 2134436 | zinc finger protein-chicken (fragment) | 4.00E−37 |
| 1232 | 2393722 | (U90313) glutathione-S-transferase homolog [Homo sapiens] | 6.00E−34 |
| 1234 | 459002 | (U00036) R151.6 gene product [Caenorhabditis elegans] | 7.00E−10 |
| 1236 | 119530 | PROTEIN DISULFIDE ISOMERASE-RELATED PROTEIN PRECURSOR (ERP72) > gi\|87320\|pir\|\|A23723 protein disulfide-isomerase (EC 5.3.4.1) ERp72 precursor-human protein [Homo sapiens] | 3.00E−23 |
| 1239 | 2073541 | (L19437) transaldolase [Homo sapiens] > gi\|2612879 | 2.00E−24 |
| 1241 | 984125 | (X90857)-14 [Homo sapiens] | 2.00E−23 |
| 1245 | 4106818 | (AF083395) phospholipase A2-activating protein [Homo sapiens] | 4.00E−36 |
| 1247 | 4507955 | YY1 transcription factor REPRESSOR PROTEIN YY1 (YIN AND YANG 1) (YY-1) (DELTA TRANSCRIPTION FACTOR) (NF-E1) > gi\|38011\|emb\|CAA78455\| | 4.00E−27 |
| 1250 | 1698779 | (U70372) PAM COOH-terminal interactor protein 2 [Rattus norvegicus] | 6.00E−35 |
| 1252 | 4204684 | (AF102542) beta-1,6-N-acetylglucosaminyltransferase core 2/core 4 beta-1,6-N-acetylglucosaminyltransferase; core 2/4-GnT [Homo sapiens] | 9.00E−43 |
| 1255 | 2239126 | (Y10746) methyl-CpG binding protein [Homo sapiens] | 4.00E−16 |
| 1259 | 1747519 | (U76759) nuclear protein NIP45 [Mus musculus] | 2.00E−29 |
| 1260 | 545790 | DARPP-32 = dopamine and cAMP-regulated phosphoprotein [human, brain, Peptide, 204 aa] sapiens] | 1.00E−29 |
| 1261 | 1709689 | PEPTIDE METHIONINE SULFOXIDE REDUCTASE (PEPTIDE MET(O) REDUCTASE) > gi\|1205993 taurus] | 1.00E−37 |
| 1265 | 2736151 | (AF021935) myotonic dystrophy kinase-related Cdc42-binding kinase [Rattus norvegicus] | 1.00E−41 |
| 1267 | 3329392 | (AF038961) SL15 protein [Homo sapiens] | 8.00E−36 |
| 1268 | 4097712 | (U67322) HBV associated factor [Homo sapiens] | 7.00E−56 |
| 1269 | 585084 | ELONGATION FACTOR G, MITOCHONDRIAL PRECURSOR (MEF-G) > gi\|543383\|pir\|\|S40780 translation elongation factor G, mitochondrial-rat > gi\|310102 | 7.00E−49 |
| 1270 | 1438534 | (U49057) rA9 [Rattus norvegicus] | 3.00E−45 |
| 1271 | 1336628 | (U57368) EGF repeat transmembrane protein [Mus musculus] | 7.00E−47 |
| 1272 | 3914802 | DNA-DIRECTED RNA POLYMERASE I LARGEST SUBUNIT (RNA POLYMERASE I 194 KD SUBUNIT) (RPA194) | 1.00E−37 |
| 1273 | 3387977 | (AF070598) ABC transporter [Homo sapiens] | 5.00E−50 |
| 1274 | 1717793 | PROTEIN TSG24 (MEIOTIC CHECK POINT REGULATOR) > gi\|1083553\|pir\|\|A55117 tsg24 protein-mouse | 2.00E−48 |
| 1275 | 2493735 | SKD3 PROTEIN SKD3 [Mus musculus] | 7.00E−43 |
| 1276 | 1041038 | (D78020) NFI-A4 [Rattus norvegicus] | 3.00E−26 |
| 1284 | 4455118 | (AF125158) zinc finger DNA binding protein 99 | 9.00E−41 |
| 1322 | 4049922 | (AF072810) transcription factor WSTF [Homo sapiens] | 4.00E−48 |
| 1338 | 4586287 | (AB004794) DUF140 [Xenopus laevis] | 3.00E−45 |
| 1345 | 3435244 | (AF083322) centriole associated protein CEP110 [Homo sapiens] | 2.00E−40 |
| 1370 | 3413886 | (AB007931) KIAA0462 protein [Homo sapiens] | 2.00E−35 |
| 1462 | 3882311 | (AB018338) KIAA0795 protein [Homo sapiens] | 4.00E−47 |
| 1497 | 4240167 | (AB020646) KIAA0839 protein [Homo sapiens] | 2.00E−46 |
| 1517 | 4191610 | (AF117107) IGF-II mRNA-binding protein 2 [Homo sapiens] | 3.00E−49 |
| 1519 | 3135669 | (AF064084) prenylcysteine carboxyl methyltransferase | 1.00E−39 |
| 1529 | 3043548 | (AB011084) KIAA0512 protein [Homo sapiens] | 2.00E−47 |
| 1531 | 3093476 | (AF008915) EVI-5 homolog [Homo sapiens] | 6.00E−19 |
| 1532 | 3834629 | (AF094519) diaphanous-related formin; p134 mDia2 [Mus musculus] | 1.00E−32 |
| 1533 | 3193226 | (AF068706) gamma2-adaptin [Homo sapiens] | 1.00E−46 |
| 1534 | 3851584 | (AF092563) chromosome-associated protein-E [Homo sapiens] | 4.00E−48 |
| 1535 | 4101695 | (AF006010) progestin induced protein [Homo sapiens] | 5.00E−30 |
| 1550 | 3850704 | (AJ005273) Kin17 [Homo sapiens] | 9.00E−24 |
| 1553 | 4240147 | (AB020636) KIAA0829 protein [Homo sapiens] | 9.00E−41 |

TABLE 2B-continued

Nearest Neighbor (BlastX vs. Non-Redundant Proteins)

| SEQ ID | ACC'N | DESCRIP. | P VALUE |
|---|---|---|---|
| 1554 | 2137490 | lymphocyte specific helicase-mouse *musculus*] | 5.00E−35 |
| 1561 | 3327052 | (AB014519) KIAA0619 protein [*Homo sapiens*] | 1.00E−41 |
| 1563 | 2137494 | M-sema F protein precusor-mouse F [mice, neonatal brain, Peptide, 834 aa] [*Mus* sp.] nuclear receptor co-repressor N-CoR-mouse *musculus*] | 7.00E−34 |
| 1564 | 2137603 | > gi|1583865|prf||12121436A thyroid hormone receptor co-repressor [*Mus musculus*] | 9.00E−41 |
| 1565 | 2674107 | (AF023451) guanine nucleotide-exchange protein [*Bos taurus*] | 3.00E−48 |
| 1587 | 3659505 | (AC005084) similar to mouse mCASK-A; similar to e1288039 | 1.00E−57 |
| 1649 | 114762 | NUCLEOPHOSMIN (NPM) (NUCLEOLAR PHOSPHOPROTEIN B23) (NUMATRIN) (NUCLEOLAR PROTEIN NO38) *sapiens*] | 6.00E−35 |
| 1651 | 3327056 | (AB014521) KIAA0621 protein [*Homo sapiens*] | 8.00E−40 |
| 1688 | 4545264 | (AF118240) peroxisomal biogenesis factor 16 [*Homo sapiens*] | 2.00E−65 |
| 1694 | 2498864 | RRP5 PROTEIN HOMOLOG (KIAA0185) hypothetical protein YM9959.11C of S.cerevisiae. [*Homo sapiens*] | 7.00E−77 |
| 1758 | 3420277 | (AF064826) glypican 4 [*Homo sapiens*] | 4.00E−76 |
| 1768 | 3088575 | (AF059531) protein arginine N-methyltransferase 3 [*Homo sapiens*] | 7.00E−97 |
| 1771 | 4050034 | (AF098482) transcriptional coactivator p52 [*Homo sapiens*] | 2.00E−58 |
| 1811 | 4506357 | UNKNOWN; PZR > gi|3851145 *sapiens*] | 2.00E−60 |
| 1830 | 3387977 | (AF070598) ABC transporter [*Homo sapiens*] | e-113 |
| 1836 | 1709974 | 60S RIBOSOMAL PROTEIN L10A protein L10a [*Rattus norvegicus*] Ribosomal Protein RPL10A) [*Homo sapiens*] | e-111 |
| 1838 | 4507709 | tissue specific transplantation antigen P35B > gi|1381179 (U58766) FX [*Homo sapiens*] | 9.00E−90 |
| 1876 | 1117791 | (U18297) MST1 [*Homo sapiens*] | 4E-85 |
| 1877 | 4507015 | copper transporter 1 | 3.00E−72 |
| 1897 | 4503301 | 2,4-dienoyl CoA reductase REDUCTASE, MITOCHONDRIAL PRECURSOR (2,4-DIENOYL-COA REDUCTASE (NADPH)) (4-ENOYL-COA REDUCTASE (NADPH)) precursor, mitochondrial-human > gi|602703 (L26050) 2,4-dienoyl-CoA reductase [*Homo sapiens*] > gi|2673979 precursor [*Homo sapiens*] > gi|4126313 (AF049895) 2,4-dienoyl-CoA reductase [*Homo sapiens*] | 6E-94 |
| 1901 | 126743 | MICROTUBULE-ASSOCIATED PROTEIN 4 human > gi|187383 (M64571) microtubule-associated protein 4 [*Homo sapiens*] | 6E-84 |
| 1914 | 4505987 | PTPRF interacting protein, binding protein 1 (liprin beta 1) > gi|3309539 (AF034802) liprin-beta1 [*Homo sapiens*] | 4E-89 |
| 1920 | 3043644 | (AB011132) KIAA0560 protein [*Homo sapiens*] | e-108 |
| 1944 | 3413892 | (AB007934) KIAA0465 protein [*Homo sapiens*] | 7.00E−87 |
| 1956 | 4185796 | (AF103796) placenta-specific ATP-binding cassette transporter [*Homo sapiens*] | 2E-68 |
| 1973 | 4507145 | UNKNOWN > gi|3873216 (AF065485) sorting nexin 4 [*Homo sapiens*] | 1.00E−73 |
| 2008 | 1083566 | zinc finger protein/transactivator Zfp-38-mouse > gi|55477 |emb| CAA45280| (X63747) Zfp-38 [*Mus musculus*] | 2E-64 |
| 2018 | 1806134 | (Z67747) zinc finger protein [*Mus musculus*] | 7.00E−78 |
| 2032 | 730451 | 60S RIBOSOMAL PROTEIN L13A (23 KD HIGHLY BASIC PROTEIN) > gi|345897|pir||S29539 basic protein, 23K-human > gi|23691|emb|CAA40254| (X56932) 23 kD highly basic protein [*Homo sapiens*] | 4.00E−87 |
| 2285 | 4102967 | (AF023142) pre-mRNA splicing SR protein rA4 [*Homo sapiens*] | 1.00E−33 |
| 2317 | 3108093 | (AF061258) LIM protein [*Homo sapiens*] | 6.00E−82 |
| 2318 | 3170887 | (AF061555) ubiquitin-protein ligase E3-alpha [*Mus musculus*] | e-104 |
| 2324 | 1552350 | (Y08135) acid sphingomyelinase-like phosphodiesterase [*Mus musculus*] | 6.00E−91 |
| 2365 | 1552350 | (Y08135) acid sphingomyelinase-like phosphodiesterase [*Mus musculus*] | e-106 |
| 2366 | 3242214 | (AJ006778) DRIM protein [*Homo sapiens*] | e-114 |
| 2387 | 4514653 | (AB024057) vascular Rab-GAP/TBC-containing protein [*Homo sapiens*] | e-121 |
| 2441 | 2443367 | (AB005216) Nck, Ash and phospholipase C gamma-binding protein NAP4 [*Homo sapiens*] | e-120 |
| 2475 | 119110 | EBNA-1 NUCLEAR PROTEIN herpesvirus 4 (strain B95-8) > gi|1334880|emb|CAA24816.1| gene. [Human herpesvirus 4] | 2.00E−38 |
| 2479 | 121640 | GLYCINE-RICH CELL WALL STRUCTURAL PROTEIN PRECURSOR > gi|72320|pir||KNMU glycine-rich cell wall protein precursor-*Arabidopsis thaliana* | 8.00E−31 |
| 2495 | 1362077 | glycin-rich protein-cowpea (fragment) | 2E-40 |

TABLE 2B-continued

Nearest Neighbor (BlastX vs. Non-Redundant Proteins)

| SEQ ID | ACC'N | DESCRIP. | P VALUE |
|---|---|---|---|
| 2519 | 121640 | GLYCINE-RICH CELL WALL STRUCTURAL PROTEIN PRECURSOR > gi|72320|pir||KNMU glycine-rich cell wall protein precursor-*Arabidopsis thaliana* | 9.00E−27 |
| 2546 | 2674107 | (AF023451) guanine nucleotide-exchange protein [*Bos taurus*] | 5E−89 |
| 2548 | 3717978 | (Y12431) 5S ribosomal protein [*Mus musculus*] | 5E−94 |
| 2556 | 4191610 | (AF117107) IGF-II mRNA-binding protein 2 [*Homo sapiens*] | e−111 |
| 2578 | 2119281 | CHO1 antigen-Chinese hamster | e−101 |
| 2579 | 3435244 | (AF083322) centriole associated protein CEP110 [*Homo sapiens*] | 2E−70 |
| 2591 | 1843434 | (D88687) KM-102-derived reductase-like factor [*Homo sapiens*] | 4.00E−91 |
| 2604 | 3834629 | (AF094519) diaphanous-related formin; p134 mDia2 [*Mus musculus*] | 1E−49 |

TABLE 3A

Profile Hits

| SEQ ID NO: | Description | Start | Stop | Dir |
|---|---|---|---|---|
| 1967 | 14_3_3 proteins | 166 | 845 | for |
| 2366 | 3'5'-cyclic nucleotide phosphodiesterases | 64 | 573 | for |
| 1579 | 4 transmembrane integral membrane proteins | 300 | 924 | rev |
| 1978 | 4 transmembrane integral membrane proteins | 340 | 941 | rev |
| 1652 | 7 transmembrane receptor (rhodopsin family) | 109 | 647 | rev |
| 1927 | 7 transmembrane receptor (rhodopsin family) | 84 | 947 | rev |
| 2068 | 7 transmembrane receptor (rhodopsin family) | 305 | 975 | for |
| 1598 | 7 transmembrane receptor (Secretin family) | 50 | 1269 | for |
| 1719 | 7 transmembrane receptor (Secretin family) | 63 | 1160 | rev |
| 1911 | 7 transmembrane receptor (Secretin family) | 38 | 869 | rev |
| 1927 | 7 transmembrane receptor (Secretin family) | 237 | 930 | rev |
| 2068 | 7 transmembrane receptor (Secretin family) | 188 | 975 | for |
| 2341 | 7 transmembrane receptor (Secretin family) | 377 | 1524 | rev |
| 1671 | ATPases Associated with Various Cellular Activities | 136 | 718 | for |
| 1672 | ATPases Associated with Various Cellular Activities | 271 | 765 | for |
| 1688 | ATPases Associated with Various Cellular Activities | 206 | 709 | rev |
| 1796 | ATPases Associated with Various Cellular Activities | 139 | 783 | for |
| 1830 | ATPases Associated with Various Cellular Activities | 265 | 713 | for |
| 1872 | ATPases Associated with Various Cellular Activities | 152 | 616 | rev |
| 1913 | ATPases Associated with Various Cellular Activities | 12 | 510 | for |
| 1922 | ATPases Associated with Various Cellular Activities | 125 | 658 | for |
| 1964 | ATPases Associated with Various Cellular Activities | 97 | 752 | for |
| 1997 | ATPases Associated with Various Cellular Activities | 185 | 664 | for |
| 2032 | ATPases Associated with Various Cellular Activities | 69 | 485 | for |
| 2170 | ATPases Associated with Various Cellular Activities | 73 | 550 | for |
| 2177 | ATPases Associated with Various Cellular Activities | 340 | 928 | for |
| 2290 | ATPases Associated with Various Cellular Activities | 872 | 1390 | rev |
| 2343 | ATPases Associated with Various Cellular Activities | 122 | 635 | for |
| 2358 | ATPases Associated with Various Cellular Activities | 84 | 492 | rev |
| 2390 | ATPases Associated with Various Cellular Activities | 31 | 434 | rev |
| 2414 | ATPases Associated with Various Cellular Activities | 953 | 1358 | rev |
| 2461 | ATPases Associated with Various Cellular Activities | 192 | 690 | rev |
| 2476 | ATPases Associated with Various Cellular Activities | 51 | 593 | for |
| 2482 | ATPases Associated with Various Cellular Activities | 135 | 615 | rev |
| 2578 | ATPases Associated with Various Cellular Activities | 0 | 673 | for |
| 1623 | Basic region plus leucine zipper transcription factors | 81 | 277 | for |
| 1715 | C2 domain (prot. kinase C like) | 403 | 582 | for |
| 2426 | C2 domain (prot. kinase C like) | 493 | 637 | for |
| 2238 | Cysteine proteases | 359 | 984 | for |
| 1630 | DEAD and DEAH box helicases | 34 | 690 | rev |
| 1865 | DEAD and DEAH box helicases | 43 | 753 | for |
| 2517 | DEAD and DEAH box helicases | 426 | 719 | for |
| 1714 | Dual specificity phosphatase, catalytic domain | 365 | 696 | rev |
| 1728 | Dual specificity phosphatase, catalytic domain | 243 | 597 | for |
| 2087 | Dual specificity phosphatase, catalytic domain | 786 | 1566 | for |
| 1595 | EF-hand | 556 | 630 | for |
| 1671 | Eukaryotic aspartyl proteases | 116 | 763 | for |
| 1778 | Eukaryotic aspartyl proteases | 92 | 1008 | for |
| 1903 | Eukaryotic aspartyl proteases | 73 | 603 | rev |
| 1945 | Eukaryotic aspartyl proteases | 147 | 694 | rev |
| 1963 | Eukaryotic aspartyl proteases | 38 | 740 | rev |
| 1991 | Eukaryotic aspartyl proteases | 404 | 1113 | rev |
| 2130 | Eukaryotic aspartyl proteases | 237 | 829 | rev |
| 2138 | Eukaryotic aspartyl proteases | 117 | 729 | rev |
| 2193 | Eukaryotic aspartyl proteases | 217 | 1397 | rev |
| 2290 | Eukaryotic aspartyl proteases | 413 | 1366 | rev |
| 2291 | Eukaryotic aspartyl proteases | 8 | 710 | rev |
| 2348 | Eukaryotic aspartyl proteases | 291 | 1146 | rev |
| 2430 | Eukaryotic aspartyl proteases | 216 | 1158 | rev |
| 2496 | Eukaryotic aspartyl proteases | 228 | 659 | for |
| 2523 | Eukaryotic aspartyl proteases | 276 | 1291 | rev |
| 2589 | Eukaryotic aspartyl proteases | 525 | 1431 | for |
| 1968 | Fibronectin type II domain | 455 | 565 | rev |
| 1779 | G-protein alpha subunit | 24 | 583 | rev |
| 1621 | Helicases conserved C-terminal domain | 160 | 309 | for |
| 1652 | Helicases conserved C-terminal domain | 363 | 560 | rev |
| 2192 | Helix-loop-helix DNA binding domain | 224 | 382 | for |
| 2181 | kinase domain of tors | 474 | 713 | for |
| 1825 | mkk like kinases | 17 | 626 | rev |
| 1876 | mkk like kinases | 35 | 719 | for |
| 2039 | mkk like kinases | 114 | 527 | for |
| 2526 | mkk like kinases | 9 | 463 | for |
| 1782 | Neurotransmitter-gated ion-channel | 267 | 1411 | for |
| 1922 | Neurotransmitter-gated ion-channel | 367 | 1168 | for |
| 2068 | Neurotransmitter-gated ion-channel | 222 | 1024 | for |

TABLE 3A-continued

Profile Hits

| SEQ ID NO: | Description | Start | Stop | Dir |
|---|---|---|---|---|
| 2102 | Neurotransmitter-gated ion-channel | 352 | 1273 | for |
| 2154 | Neurotransmitter-gated ion-channel | 377 | 1159 | for |
| 2538 | Neurotransmitter-gated ion-channel | 112 | 1120 | for |
| 1621 | protein kinase | 153 | 743 | for |
| 1630 | protein kinase | 123 | 904 | for |
| 1705 | protein kinase | 471 | 1072 | for |
| 1706 | protein kinase | 190 | 609 | for |
| 1710 | protein kinase | 235 | 641 | for |
| 1744 | protein kinase | 8 | 711 | rev |
| 1767 | protein kinase | 90 | 537 | for |
| 1776 | protein kinase | 200 | 524 | rev |
| 1782 | protein kinase | 706 | 1331 | for |
| 1822 | protein kinase | 24 | 666 | for |
| 1825 | protein kinase | 56 | 593 | rev |
| 1844 | protein kinase | 263 | 824 | for |
| 1850 | protein kinase | 217 | 779 | for |
| 1876 | protein kinase | 290 | 711 | for |
| 1977 | protein kinase | 38 | 776 | for |
| 2051 | protein kinase | 14 | 657 | for |
| 2112 | protein kinase | 202 | 644 | rev |
| 2169 | protein kinase | 1 | 656 | for |
| 2205 | protein kinase | 57 | 689 | for |
| 2242 | protein kinase | 33 | 646 | for |
| 2291 | protein kinase | 630 | 1148 | rev |
| 2454 | protein kinase | 49 | 761 | rev |
| 2526 | protein kinase | 0 | 463 | for |
| 2558 | protein kinase | 77 | 590 | for |
| 1719 | Protein Tyrosine Phosphatase | 82 | 482 | rev |
| 1769 | Protein Tyrosine Phosphatase | 71 | 461 | rev |
| 2062 | Protein Tyrosine Phosphatase | 270 | 704 | for |
| 2197 | Protein Tyrosine Phosphatase | 359 | 851 | for |
| 2275 | Protein Tyrosine Phosphatase | 56 | 680 | for |
| 1850 | RNA recognition motif. (aka RRM, RBD, or RNP domain) | 165 | 365 | for |
| 2194 | RNA recognition motif. (aka RRM, RBD, or RNP domain) | 37 | 174 | for |
| 2441 | SH2 Domain | 201 | 362 | for |
| 1618 | Thioredoxins | 253 | 554 | for |
| 1579 | Trypsin | 252 | 1007 | rev |
| 2290 | Trypsin | 350 | 1164 | rev |
| 2341 | Trypsin | 447 | 1211 | rev |
| 2421 | Trypsin | 14 | 765 | rev |
| 2430 | Trypsin | 700 | 1556 | rev |
| 2438 | Trypsin | 47 | 670 | rev |
| 2281 | WD domain, G-beta repeats | 70 | 161 | for |
| 1579 | wnt family of developmental signaling proteins | 282 | 1017 | rev |
| 1653 | wnt family of developmental signaling proteins | 154 | 978 | rev |
| 1778 | wnt family of developmental signaling proteins | 38 | 858 | rev |
| 1826 | wnt family of developmental signaling proteins | 574 | 1318 | rev |
| 1875 | wnt family of developmental signaling proteins | 578 | 1313 | rev |
| 1904 | wnt family of developmental signaling proteins | 205 | 1068 | rev |
| 1992 | wnt family of developmental signaling proteins | 2 | 824 | rev |
| 2004 | wnt family of developmental signaling proteins | 621 | 1420 | rev |
| 2129 | wnt family of developmental signaling proteins | 394 | 1343 | rev |
| 2145 | wnt family of developmental signaling proteins | 162 | 1027 | rev |
| 2204 | wnt family of developmental signaling proteins | 274 | 1405 | rev |
| 2238 | wnt family of developmental signaling proteins | 560 | 1195 | rev |
| 2290 | wnt family of developmental signaling proteins | 250 | 1273 | rev |
| 2291 | wnt family of developmental signaling proteins | 523 | 1409 | rev |
| 2294 | wnt family of developmental signaling proteins | 297 | 1237 | rev |
| 2341 | wnt family of developmental signaling proteins | 51 | 1002 | rev |
| 2343 | wnt family of developmental signaling proteins | 28 | 1180 | rev |
| 2348 | wnt family of developmental signaling proteins | 638 | 1614 | rev |
| 2373 | wnt family of developmental signaling proteins | 30 | 1078 | rev |
| 2409 | wnt family of developmental signaling proteins | 4 | 1074 | rev |
| 2410 | wnt family of developmental signaling proteins | 208 | 1107 | rev |
| 2414 | wnt family of developmental signaling proteins | 242 | 1068 | rev |
| 2421 | wnt family of developmental signaling proteins | 159 | 1057 | rev |
| 2430 | wnt family of developmental signaling proteins | 844 | 1691 | rev |
| 2436 | wnt family of developmental signaling proteins | 107 | 784 | rev |
| 2438 | wnt family of developmental signaling proteins | 127 | 1226 | rev |
| 2463 | wnt family of developmental signaling proteins | 5 | 704 | rev |
| 2473 | wnt family of developmental signaling proteins | 328 | 1193 | rev |
| 2511 | wnt family of developmental signaling proteins | 341 | 1222 | rev |
| 2523 | wnt family of developmental signaling proteins | 820 | 1617 | rev |
| 2528 | wnt family of developmental signaling proteins | 461 | 1283 | rev |
| 1735 | Zinc finger, C2H2 type | 495 | 557 | for |
| 1942 | Zinc finger, C2H2 type | 500 | 562 | for |
| 2018 | Zinc finger, C2H2 type | 279 | 341 | for |
| 2254 | Zinc finger, C2H2 type | 148 | 210 | for |
| 2515 | Zinc finger, C2H2 type | 422 | 484 | for |

TABLE 3B

Profile Hits for Contigs

| SEQ ID NO: | Description | Start | Stop | Dir |
|---|---|---|---|---|
| 2641 | ATPases Associated with Various Cellular Activities | 118 | 661 | for |
| 2655 | ATPases Associated with Various Cellular Activities | 135 | 536 | for |
| 2685 | ATPases Associated with Various Cellular Activities | 142 | 574 | for |
| 2648 | DEAD and DEAH box helicases | 66 | 931 | rev |
| 2686 | Helicases conserved C-terminal domain | 51 | 242 | for |
| 2661 | Neurotransmitter-gated ion-channel | 169 | 738 | rev |
| 2640 | Protein phosphatase 2A regulatory subunit PR55 | 275 | 1510 | for |
| 2655 | Protein phosphatase 2A regulatory subunit PR55 | 55 | 1087 | for |
| 2670 | Protein phosphatase 2A regulatory subunit PR55 | 13 | 1183 | for |
| 2684 | Protein phosphatase 2A regulatory subunit PR55 | 511 | 1861 | rev |
| 2679 | Protein Tyrosine Phosphatase | 292 | 768 | for |
| 2668 | Thioredoxins | 182 | 475 | for |

TABLE 22

Deposits of Pooled Clones

| ES34 | ES35 | ES36 | ES37 |
|---|---|---|---|
| M00006992C:G02 | M00005468A:D08 | M00005452C:A02 | M00022171D:B08 |
| M00006756D:E10 | M00021892B:H03 | M00001382C:C09 | M00008061A:F02 |
| M00003984C:F04 | M00001390A:C06 | M00004841C:B09 | M00003820C:A09 |
| M00007125D:E03 | M00022074D:F11 | M00001441D:H05 | M00022109B:A11 |
| M00006650A:A10 | M00005460B:D02 | M00022716D:D08 | M00005342D:F03 |
| M00001452B:H06 | M00024423B:D03 | M00022828C:E04 | M00022070B:C10 |
| M00022972D:C10 | M00007140A:F11 | M00004350B:F06 | M00006966B:B09 |
| M00022305C:A01 | M00004081B:C11 | M00005685B:D08 | M00022381C:C12 |
| M00007010B:H01 | M00005480A:H12 | M00004190A:A09 | M00003991B:B05 |
| M00021946D:C11 | M00008015D:E09 | M00004054D:D02 | M00022404D:G05 |

| ES38 | ES39 | ES40 | ES41 |
|---|---|---|---|
| M00021912B:H11 | M00007118B:B04 | M00006993B:B09 | M00007974B:C11 |
| M00005378C:A10 | M00007019A:B01 | M00004242C:C01 | M00021860B:G06 |
| M00022578C:B07 | M00021682B:D12 | M00007986C:C05 | M00006927C:F12 |
| M00005513A:D08 | M00005411D:A03 | M00004115A:G09 | M00022582C:E12 |
| M00022176C:A08 | M00006641C:H02 | M00022600C:A06 | M00006618C:G08 |
| M00006822D:F07 | M00007041C:C05 | M00005384A:A01 | M00005450B:B01 |
| M00004031A:B04 | M00005444B:E11 | M00021667E:E03 | M00001417B:E01 |
| M00021927D:D12 | M00022745B:G02 | M00008078C:C06 | M00003825B:A05 |
| M00001553D:B06 | M00022685A:F11 | M00007985A:B09 | M00001370B:B04 |
| M00022404B:H05 | M00004446A:G01 | M00007953B:B03 | M00006727B:E09 |

| ES42 | ES43 | ES44 | ES45 |
|---|---|---|---|
| M00001478A:B06 | M00006923B:H08 | M00006615B:F05 | M00005468D:F04 |
| M00003972B:A11 | M00005377D:F11 | M00005486C:B03 | M00006720C:C11 |
| M00005477C:D08 | M00006640B:H09 | M00007124C:A11 | M00005817D:E12 |
| M00006745A:A01 | M00005404C:F02 | M00006995D:A03 | M00001669B:A03 |
| M00007090B:A02 | M00004030A:G12 | M00007149D:G06 | M00003998A:G12 |
| M00007152A:B04 | M00006704D:D03 | M00006990D:D06 | M00004045A:B12 |
| M00006953B:H10 | M00006810D:A05 | M00005530B:E04 | M00004130D:E04 |
| M00005399D:B02 | M00005481C:A05 | M00003918C:E07 | M00004160A:D07 |
| M00006987B:F04 | M00005411A:C07 | M00007163A:B10 | M00001655A:F07 |
| M00005772A:F03 | M00003970A:G10 | M00005485C:A03 | M00001468D:D11 |

| ES46 | | | |
|---|---|---|---|
| M00004217A:A05 | | | |
| M00004183D:B07 | | | |
| M00001415D:A05 | | | |
| M00004158C:F03 | | | |
| M00004031D:G02 | | | |

TABLE 23

Library Deposits

| ES47 | ES48 | ES49 | ES50 |
|---|---|---|---|
| M00001399D:F09 | M00004217D:G10 | M00004508A:G12 | M00021653A:G07 |
| M00001455A:C03 | M00004218C:G10 | M00004508B:G02 | M00021654C:A02 |
| M00001456C:F02 | M00004252D:H08 | M00001432B:H08 | M00021660C:G04 |
| M00001487D:G03 | M00004253B:A10 | M00001432C:G01 | M00021665A:D04 |
| M00001539B:B01 | M00004253C:F06 | M00003992D:G01 | M00021670B:G11 |
| M00001565A:A02 | M00004253C:E10 | M00005326B:F03 | M00021678A:B08 |
| M00001572C:E07 | M00004260A:B07 | M00005332A:H10 | M00021680B:C01 |
| M00001582D:B10 | M00004260C:A12 | M00005342A:C04 | M00021681C:B10 |
| M00001584C:A03 | M00004260C:E10 | M00005342A:D04 | M00021690D:E05 |
| M00001586A:F09 | M00001339B:A03 | M00005349B:G01 | M00021692A:E03 |
| M00001588D:H08 | M00001342C:A04 | M00005352B:D02 | M00021692C:E06 |
| M00001610B:A01 | M00001344D:G11 | M00005354C:E02 | M00021694B:A07 |
| M00001618B:F02 | M00001345A:A12 | M00005356A:D09 | M00021698B:B12 |
| M00001618C:E06 | M00001347A:G06 | M00005359D:G07 | M00021828A:C08 |
| M00001621C:A04 | M00001347B:H01 | M00005378A:A08 | M00021841C:D07 |
| M00001626B:H05 | M00001353B:D11 | M00005383D:D06 | M00021859A:D04 |
| M00001641B:G05 | M00001355A:A01 | M00005383E:E07 | M00021861C:A02 |
| M00001648C:F06 | M00001358D:D09 | M00005385C:G05 | M00021862A:A04 |
| M00001649D:H05 | M00001359A:B07 | M00005388D:F09 | M00021862D:F01 |
| M00001656D:F11 | M00001362A:C10 | M00005390B:G10 | M00021886D:E04 |
| M00001660A:F10 | M00001362B:A09 | M00005397C:B03 | M00021897B:A06 |

TABLE 23-continued

Library Deposits

| ES47 | ES48 | ES49 | ES50 |
|---|---|---|---|
| M00001669A:H11 | M00001365D:D12 | M00005399A:D01 | M00021905A:G05 |
| M00003741A:E01 | M00001365D:H09 | M00005409D:C02 | M00021905B:A01 |
| M00003745C:E03 | M00001370A:G09 | M00005415C:G08 | M00021906C:G11 |
| M00003746A:E01 | M00001370B:B12 | M00005417A:E10 | M00021910A:C10 |
| M00003748B:B06 | M00001374D:D09 | M00005442D:C05 | M00021927A:C11 |
| M00003749B:C08 | M00001376B:C11 | M00005446A:G01 | M00021927B:F01 |
| M00003749D:G07 | M00001377A:D03 | M00005446C:D12 | M00021932C:C05 |
| M00003752A:B06 | M00001377A:E01 | M00005454C:H12 | M00021932C:G10 |
| M00003752D:D09 | M00001377C:B08 | M00005455A:D01 | M00021947A:C01 |
| M00003753C:B01 | M00001387A:A04 | M00005455A:G03 | M00021952B:F11 |
| M00003754C:F01 | M00001387D:C07 | M00005462C:B02 | M00021954A:A03 |
| M00003756C:C08 | M00001389B:B06 | M00005469D:C11 | M00021964A:C04 |
| M00003759A:E10 | M00001390A:H01 | M00005480C:B12 | M00021967D:E08 |
| M00003762A:D11 | M00001399C:E10 | M00005483D:A12 | M00021977D:E02 |
| M00003763B:D03 | M00001401D:D04 | M00005484A:D09 | M00021978A:F08 |
| M00003763D:F06 | M00001402D:C07 | M00005491B:C03 | M00021982C:F08 |
| M00003765D:E02 | M00001402D:H03 | M00005493B:C08 | M00021983B:B03 |
| M00003766B:G04 | M00001403B:A01 | M00005494D:F11 | M00021983D:B10 |
| M00003767C:F04 | M00001405D:F05 | M00005496C:A01 | M00022005C:G03 |
| M00003769B:A04 | M00001406C:A11 | M00005496D:A10 | M00022032A:E07 |
| M00003769D:G12 | M00001406D:H01 | M00005497B:H07 | M00022049A:A02 |
| M00003770D:C07 | M00001407B:A08 | M00005497C:C07 | M00022049A:D06 |
| M00003771A:G09 | M00001407D:H11 | M00005497C:C12 | M00022054D:C05 |
| M00003771D:A10 | M00001411A:D01 | M00005497C:E03 | M00022064C:H07 |
| M00003773A:C09 | M00001411C:G02 | M00005498B:F08 | M00022067D:C05 |
| M00003773B:E09 | M00001412A:A11 | M00005498C:G05 | M00022068B:H11 |
| M00003773B:G08 | M00001415D:E12 | M00005508B:B04 | M00022068D:D12 |
| M00003773C:G06 | M00001417C:E02 | M00005524C:B01 | M00022069D:G02 |
| M00003773D:C02 | M00001421A:H07 | M00005528C:A10 | M00022071B:D05 |
| M00003789C:E03 | M00001422D:D02 | M00005530B:D03 | M00022071C:D09 |
| M00003790B:F12 | M00001423C:D06 | M00005534B:H10 | M00022075D:F05 |
| M00003793C:D11 | M00001424A:H09 | M00005548B:E03 | M00022081C:G11 |
| M00003796B:C07 | M00001425C:E10 | M00005550B:D09 | M00022084B:F04 |
| M00003797D:H06 | M00001426A:F09 | M00005565C:A08 | M00022085C:C04 |
| M00003801D:F05 | M00001426D:D09 | M00005589C:B03 | M00022090A:G08 |
| M00003805A:G05 | M00001431A:C10 | M00005616B:D05 | M00022093A:A05 |
| M00003808C:D09 | M00001431A:E05 | M00005620C:C05 | M00022093D:B10 |
| M00003809A:A12 | M00001432A:F12 | M00005621A:G10 | M00022094B:G10 |
| M00003809A:H12 | M00001432B:H08 | M00005621D:F01 | M00022106C:F04 |
| M00003813D:A06 | M00001432C:G01 | M00005631A:A11 | M00022110A:E04 |
| M00003818A:F09 | M00001433A:C07 | M00005632C:D06 | M00022114C:B02 |
| M00003818B:A01 | M00001434A:A01 | M00005637B:D12 | M00022117C:G07 |
| M00003819D:G09 | M00001435A:F03 | M00005642B:C03 | M00022128A:D04 |
| M00003821C:E04 | M00001435A:G01 | M00005647D:D09 | M00022139A:C01 |
| M00003822A:G05 | M00001435B:G10 | M00005655B:C02 | M00022149B:D05 |
| M00003825C:B02 | M00001435C:G08 | M00005703A:C08 | M00022150A:H06 |
| M00003825C:B12 | M00001435D:A06 | M00005704A:B11 | M00022153D:D11 |
| M00003833B:A11 | M00001436D:C10 | M00005708D:B03 | M00022157A:F12 |
| M00003834A:A03 | M00001437B:B05 | M00005710A:C08 | M00022157B:A10 |
| M00003835D:H05 | M00001438C:H05 | M00005720A:D03 | M00022169D:C02 |
| M00003839D:G06 | M00001439B:F10 | M00005722C:G03 | M00022170D:H09 |
| M00003841A:E09 | M00001439C:A01 | M00005743B:F02 | M00022175A:A11 |
| M00003841B:D05 | M00001439C:G06 | M00005763B:H09 | M00022176A:E08 |
| M00003843A:B01 | M00001442A:D08 | M00005765C:C04 | M00022178D:H01 |
| M00003844C:D04 | M00001443D:A01 | M00005810C:D04 | M00022183A:G03 |
| M00003844C:H05 | M00001444A:A09 | M00005813D:F06 | M00022189A:A01 |
| M00003846B:H02 | M00001446D:B10 | M00005818C:E08 | M00022198A:C12 |
| M00003850B:D11 | M00001452D:E05 | M00005818C:G01 | M00022199C:F03 |
| M00003852D:D03 | M00001453D:F09 | M00006576D:F11 | M00022202C:F11 |
| M00003859C:B09 | M00001463C:A01 | M00006577B:H12 | M00022206B:G06 |
| M00003868D:F02 | M00001466C:F02 | M00006587A:H08 | M00022212C:C02 |
| M00003868D:F07 | M00001471C:G03 | M00006594A:E08 | M00022216D:C01 |
| M00003871A:E09 | M00001488B:G12 | M00006596D:H04 | M00022218C:B06 |
| M00003884D:A12 | M00001489B:F08 | M00006601C:A07 | M00022218D:B12 |
| M00003887B:C03 | M00001489D:C08 | M00006601C:E06 | M00022220C:F08 |
| M00003888B:A10 | M00001490B:G04 | M00006609A:G10 | M00022221D:E08 |
| M00003888C:E01 | M00001491C:C01 | M00006633C:E11 | M00022226C:B06 |
| M00003890B:H07 | M00001496A:B03 | M00006633D:A06 | M00022226D:A07 |
| M00003890D:C03 | M00001496D:D02 | M00006634B:C02 | M00022231A:F12 |
| M00003892D:D04 | M00001500A:D09 | M00006636A:B08 | M00022231C:A04 |
| M00003893C:D12 | M00001504D:D09 | M00006644A:B11 | M00022236D:A03 |
| M00003895D:A03 | M00001505A:E09 | M00006644D:C02 | M00022239A:A10 |
| M00003896C:F08 | M00001506A:F01 | M00006686A:G12 | M00022239B:B07 |
| M00003896D:B01 | M00001517D:C03 | M00006692B:E04 | M00022239D:A07 |
| M00003903C:H03 | M00001518D:A10 | M00006728D:G10 | M00022252C:E06 |

TABLE 23-continued

Library Deposits

| ES47 | ES48 | ES49 | ES50 |
|---|---|---|---|
| M00003905C:B01 | M00001536B:B11 | M00006733D:G12 | M00022253B:E06 |
| M00003905C:E10 | M00001537B:C12 | M00006734A:H12 | M00022254C:D08 |
| M00003906C:H12 | M00001542B:D10 | M00006735A:H02 | M00022255A:C08 |
| M00003909D:G01 | M00001542C:F06 | M00006764B:D05 | M00022255D:E03 |
| M00003911C:G05 | M00001543A:E04 | M00006765B:H06 | M00022258C:F06 |
| M00003912B:G11 | M00001546B:H01 | M00006785B:F09 | M00022259B:G02 |
| M00003912C:C11 | M00001551D:C12 | M00006791B:B08 | M00022278C:E03 |
| M00003914C:E03 | M00001552B:D01 | M00006796A:C03 | M00022278D:F10 |
| M00003915A:D09 | M00001556D:A11 | M00006800C:G08 | M00022288C:D04 |
| M00003915C:G01 | M00001557C:B08 | M00006814A:F07 | M00022289A:D05 |
| M00003920B:A10 | M00001558B:A12 | M00006819A:D10 | M00022289D:B06 |
| M00003921D:C06 | M00001560C:C01 | M00006820A:G05 | M00022294A:D11 |
| M00003923A:H07 | M00001561B:C10 | M00006821C:C10 | M00022296B:C11 |
| M00003936C:F10 | M00001597C:B03 | M00006822A:D07 | M00022305A:H11 |
| M00003948B:B03 | M00001623B:B01 | M00006823B:D12 | M00022364C:G12 |
| M00003949B:A08 | M00001623D:A09 | M00006826B:H03 | M00022366B:E09 |
| M00003949B:D05 | M00001644D:F09 | M00006828D:C12 | M00022372B:D03 |
| M00003961B:A12 | M00003784C:B09 | M00006832D:F11 | M00022381A:F05 |
| M00003961C:G02 | M00003785D:E01 | M00006846A:B01 | M00022382D:H11 |
| M00003962B:B09 | M00003862C:H10 | M00006850C:D09 | M00022386A:A07 |
| M00003963B:D12 | M00003864B:A04 | M00006850C:G07 | M00022386B:D11 |
| M00003973A:C05 | M00003864D:G05 | M00006851C:H09 | M00022386C:A04 |
| M00003973B:H06 | M00003992C:G01 | M00006863B:E06 | M00022386C:D07 |
| M00003976D:D12 | M00003992D:G01 | M00006866C:F03 | M00022399C:A10 |
| M00003977C:A08 | M00003994C:C11 | M00006867C:E07 | M00022407C:H11 |
| M00003980B:F12 | M00003996C:C04 | M00006868D:E02 | M00022411D:G09 |
| M00003980C:G10 | M00003997D:D07 | M00006870C:H06 | M00022412A:C08 |
| M00003981C:E04 | M00003998A:D03 | M00006873B:G11 | M00022444A:A11 |
| M00003983C:E07 | M00003998C:H10 | M00006875A:A02 | M00022449C:B01 |
| M00003987D:F06 | M00003999C:C12 | M00006877B:E05 | M00022452C:B03 |
| M00004027A:B10 | M00004046A:F04 | M00006879A:H11 | M00022457C:B01 |
| M00004027C:H01 | M00004051C:D02 | M00006882A:D01 | M00022495C:G05 |
| M00004028C:B04 | M00004052C:A08 | M00006901D:A11 | M00022504B:E03 |
| M00004030B:B02 | M00004052C:B05 | M00006907C:D03 | M00022505D:A12 |
| M00004030B:C05 | M00004054B:G02 | M00006907C:C07 | M00022509D:F06 |
| M00004035D:E04 | M00004054D:A03 | M00006912B:E01 | M00022527A:E05 |
| M00004036B:F09 | M00004055B:F06 | M00006921B:E01 | M00022527D:B03 |
| M00004036C:D01 | M00004058B:C11 | M00006960D:E06 | M00022531B:D07 |
| M00004037A:A07 | M00004058C:E08 | M00006963A:H11 | M00022535D:B11 |
| M00004037B:B05 | M00004059A:G09 | M00006966C:B07 | M00022535D:C04 |
| M00004038C:C05 | M00004060C:A02 | M00006972A:F10 | M00022536B:B04 |
| M00004038C:D12 | M00004060D:A07 | M00006973C:E11 | M00022551A:G03 |
| M00004039D:D03 | M00004063C:B11 | M00006973D:E11 | M00022556B:C04 |
| M00004040B:B09 | M00004143A:G12 | M00006974B:F06 | M00022556B:G02 |
| M00004040C:G12 | M00004143A:H07 | M00006976C:E09 | M00022562C:H10 |
| M00004040D:B05 | M00004145C:A03 | M00007014C:B07 | M00022578B:G05 |
| M00004041B:F01 | M00004146A:A07 | M00007015C:G05 | M00022578D:F03 |
| M00004041D:E06 | M00004147A:G03 | M00007016C:E06 | M00022583B:E05 |
| M00004043D:C10 | M00004149B:H12 | M00007041B:G01 | M00022587C:G04 |
| M00004069D:G02 | M00004153D:E06 | M00007042A:E07 | M00022594B:H12 |
| M00004071A:H03 | M00004154D:F11 | M00007043A:B05 | M00022598A:F11 |
| M00004073D:B11 | M00004159A:C04 | M00007046A:D02 | M00022599D:E07 |
| M00004076D:B03 | M00004166B:E10 | M00007047B:D01 | M00022604B:C11 |
| M00004081C:A01 | M00004166C:A03 | M00007051D:D09 | M00022607B:A04 |
| M00004084C:G04 | M00004166D:G07 | M00007053B:H03 | M00022613D:C04 |
| M00004085B:G06 | M00004196C:G05 | M00007058A:C02 | M00022651C:C06 |
| M00004087C:F05 | M00004234B:E03 | M00007062A:D03 | M00022666C:H11 |
| M00004091A:E01 | M00004234B:G06 | M00007099A:F09 | M00022681C:H02 |
| M00004091B:C12 | M00004236D:E07 | M00007100C:D01 | M00022682A:F12 |
| M00004091B:G04 | M00004236D:F04 | M00007112B:C06 | M00022698C:E06 |
| M00004091C:F04 | M00004240D:A07 | M00007105D:C07 | M00022701B:B12 |
| M00004091D:D09 | M00004242C:C02 | M00007121A:A05 | M00022708C:A08 |
| M00004092A:C03 | M00004244B:A02 | M00007122B:G11 | M00022708D:G10 |
| M00004092A:D04 | M00004245A:G09 | M00007122B:A11 | M00022725C:E09 |
| M00004093D:D09 | M00004245C:A03 | M00007127B:A04 | M00022726A:A06 |
| M00004101D:A03 | M00004247A:E01 | M00007129A:G10 | M00022730A:E04 |
| M00004103B:C07 | M00004247B:C11 | M00007130B:B03 | M00022737A:C08 |
| M00004107C:A01 | M00004248A:G08 | M00007132B:G08 | M00022763A:E10 |
| M00004114C:F02 | M00004263D:F06 | M00007134C:F07 | M00022824C:H11 |
| M00004115A:F01 | M00004272D:D02 | M00007137D:C10 | M00022835C:E06 |
| M00004117B:F01 | M00004273D:E11 | M00007140D:C12 | M00022854D:H07 |
| M00004120A:C02 | M00004277D:C08 | M00007150C:C09 | M00022856A:D02 |
| M00004126B:G02 | M00004281B:B05 | M00007150A:H06 | M00022856B:F04 |
| M00004129A:H08 | M00004283C:D03 | M00007154A:E04 | M00022856C:B11 |
| M00004130C:A09 | M00004285B:E01 | M00007163A:F11 | M00022893C:H11 |

TABLE 23-continued

Library Deposits

| ES47 | ES48 | ES49 | ES50 |
|---|---|---|---|
| M00004133D:A01 | M00004297D:E08 | M00007163B:A12 | M00022897A:F04 |
| M00004178B:F06 | M00004298D:D04 | M00007166B:E06 | M00022900D:E08 |
| M00004180B:F04 | M00004308A:E06 | M00007170D:A10 | M00022900D:G03 |
| M00004184B:F11 | M00004324B:D09 | M00007172A:A05 | |
| M00004191B:G01 | M00004328A:H06 | M00007172C:C08 | |
| M00004193A:C07 | M00004329C:F11 | M00007188A:D03 | |
| M00004193C:H01 | M00004331D:H08 | M00007189D:A09 | |
| M00004199D:C02 | M00004332C:E09 | M00007193D:A04 | |
| M00004200A:A09 | M00004337D:G08 | M00007195B:B02 | |
| M00004200A:G06 | M00004345A:H06 | M00007198C:A10 | |
| M00004200D:A07 | M00004383A:F02 | M00007199D:B07 | |
| M00004201D:C11 | M00004385C:B11 | M00007204C:F09 | |
| M00004201D:E12 | M00004388C:D05 | M00007929D:H10 | |
| M00004202B:A02 | M00004406A:H03 | M00007961A:B01 | |
| M00004204A:D04 | M00004408D:A10 | M00007964B:D10 | |
| M00004204A:D10 | M00004410A:E03 | M00007971A:B04 | |
| M00004204B:A04 | M00004412B:E03 | M00007977C:E08 | |
| M00004210A:B09 | M00004421A:G04 | M00007995D:E06 | |
| M00004216D:E10 | M00004447D:D10 | M00008074D:C01 | |
| M00004217A:A11 | M00004460B:H09 | M00008094A:E10 | |
| | M00004465C:B10 | M00021611D:D05 | |
| | M00004465C:B12 | M00021611D:H03 | |
| | M00004467A:F09 | M00021614B:G12 | |
| | M00004467D:F09 | M00021618D:D07 | |
| | M00004491D:D07 | M00021624A:D07 | |
| | M00004497C:E09 | M00021624B:A03 | |
| | M00004501A:G06 | M00021625A:C07 | |
| | M00004506C:H10 | M00021629D:D05 | |

TABLE 24

Library Deposits

| ES51 | ES52 | ES53 | ES54 |
|---|---|---|---|
| M00001448A:D05 | M00001439B:E02 | M00006621A:G10 | M00021640A:G03 |
| M00001458B:F06 | M00001443A:E02 | M00006626A:G11 | M00021657B:C08 |
| M00001530A:D11 | M00001443D:C03 | M00006629D:D04 | M00021690B:B06 |
| M00001563C:D06 | M00001444A:G12 | M00006630B:H06 | M00021690C:B07 |
| M00001564C:D04 | M00001445B:E03 | M00006631B:B02 | M00022071C:C09 |
| M00001569B:F04 | M00001451B:H11 | M00006631D:C04 | M00022081C:B11 |
| M00001575A:H02 | M00001452B:F09 | M00006631D:E09 | M00022085C:A07 |
| M00001589C:D12 | M00001488B:H02 | M00006635C:B10 | M00022091B:B07 |
| M00001589D:G10 | M00001491B:E07 | M00006636A:E06 | M00022122D:D06 |
| M00001590A:A07 | M00001496C:H10 | M00006636D:A05 | M00022150D:D11 |
| M00001598C:D10 | M00001499A:D01 | M00006636D:F11 | M00022154A:C01 |
| M00001599A:H09 | M00001499A:D05 | M00006640A:B01 | M00022170D:H07 |
| M00001609A:B12 | M00001499B:H05 | M00006640A:F05 | M00022365A:A01 |
| M00001614C:G04 | M00001500B:H07 | M00006640D:H08 | M00022389B:H04 |
| M00001626C:C10 | M00001504C:H11 | M00006641A:B03 | M00022439A:E07 |
| M00001634C:E12 | M00001506D:A11 | M00006643A:E10 | M00022449D:F06 |
| M00001639A:A04 | M00001543A:D03 | M00006644C:E09 | M00022458B:E06 |
| M00001640A:F02 | M00001543A:F01 | M00006648C:E04 | M00022474A:H09 |
| M00001640A:F04 | M00001548C:A09 | M00006650A:B11 | M00022480B:E07 |
| M00001647C:C07 | M00001555D:F11 | M00006656C:C10 | M00022489C:A08 |
| M00001649B:E08 | M00001557B:D10 | M00006664B:B04 | M00022490C:A08 |
| M00001654D:F06 | M00001597A:C07 | M00006664D:H09 | M00022490C:C01 |
| M00001658B:C07 | M00001604B:D09 | M00006665A:F07 | M00022493C:B07 |
| M00001659D:G08 | M00001605D:G01 | M00006665B:D10 | M00022493C:C06 |
| M00001663C:C03 | M00001621B:B09 | M00006674B:F04 | M00022498C:C08 |
| M00001675C:B03 | M00001622C:F06 | M00006676B:F11 | M00022514A:D04 |
| M00001677A:A06 | M00001624A:A09 | M00006676D:D11 | M00022515D:C04 |
| M00001677A:A12 | M00001640D:C10 | M00006679C:D07 | M00022549B:G07 |
| M00001678D:A12 | M00001645B:C09 | M00006681C:G04 | M00022557B:A08 |
| M00001679C:F03 | M00003782D:F04 | M00006695B:F08 | M00022565C:H02 |
| M00001681A:H09 | M00003783C:A06 | M00006698B:E06 | M00022578D:A08 |
| M00001687C:A06 | M00003786D:C06 | M00006699B:C07 | M00022597B:F11 |
| M00001693D:F07 | M00003787B:B07 | M00006705B:D02 | M00022599A:C03 |
| M00003746B:E12 | M00003787D:A06 | M00006712B:H10 | M00022661B:E11 |
| M00003766A:G09 | M00003864C:D09 | M00006717A:D04 | M00022661D:H01 |
| M00003795A:B01 | M00003993D:E12 | M00006721C:G07 | M00022666B:E12 |
| M00003796C:H03 | M00003997B:H04 | M00006725A:A03 | M00022674D:G04 |

TABLE 24-continued

Library Deposits

| ES51 | ES52 | ES53 | ES54 |
|---|---|---|---|
| M00003797D:E10 | M00003997D:G11 | M00006725A:B03 | M00022718D:G05 |
| M00003799B:D02 | M00004047D:G09 | M00006727B:G08 | M00022725C:B03 |
| M00003809B:D08 | M00004048D:A07 | M00006728C:B06 | M00022727B:C05 |
| M00003811B:E07 | M00004049D:G04 | M00006737C:A08 | M00022728A:A09 |
| M00003812B:F08 | M00004050A:F02 | M00006738A:E05 | M00022730D:E10 |
| M00003812D:E08 | M00004051C:D10 | M00006739B:B10 | M00022735B:B01 |
| M00003815C:A06 | M00004058B:F12 | M00006739B:B12 | M00022745A:B04 |
| M00003815D:D01 | M00004060C:A11 | M00006739C:H07 | M00022856B:D07 |
| M00003816C:F10 | M00004064A:B12 | M00006743B:G12 | M00022901D:C09 |
| M00003818C:E09 | M00004066A:E12 | M00006744C:C06 | M00022902D:D03 |
| M00003819A:B09 | M00004067C:D08 | M00006745D:E08 | M00022953B:C07 |
| M00003819C:E04 | M00004134A:F08 | M00006751A:F03 | M00022960D:E08 |
| M00003820A:H04 | M00004134A:H04 | M00006758D:C01 | M00022963A:D11 |
| M00003820D:E02 | M00004134C:B11 | M00006760D:G12 | M00022968A:F02 |
| M00003824B:D06 | M00004140B:B01 | M00006763B:B11 | M00022980B:E11 |
| M00003825B:D12 | M00004143C:F08 | M00006769D:A04 | M00022980C:A09 |
| M00003826B:D01 | M00004144D:B06 | M00006770B:C05 | M00022993A:F02 |
| M00003829A:E02 | M00004152C:E01 | M00006771A:E06 | M00023003C:A03 |
| M00003832B:G03 | M00004159D:H07 | M00006771A:H07 | M00023011A:A06 |
| M00003833D:D06 | M00004160A:A01 | M00006771A:A09 | M00023021A:H08 |
| M00003835A:E03 | M00004161B:A12 | M00006771B:F03 | M00023023A:B12 |
| M00003837C:F05 | M00004163A:D11 | M00006774D:C01 | M00023028A:A02 |
| M00003839C:B05 | M00004164D:D02 | M00006777B:D10 | M00023033A:E10 |
| M00003845A:A05 | M00004165C:E09 | M00006779B:A11 | M00023034C:E05 |
| M00003846D:C12 | M00004166A:F02 | M00006779D:D03 | M00023036D:C04 |
| M00003857C:A03 | M00004167C:F10 | M00006780A:H12 | M00023094A:C04 |
| M00003858A:D01 | M00004169A:B11 | M00006789C:F04 | M00023103A:E11 |
| M00003860B:A07 | M00004200B:B04 | M00006790D:A05 | M00006754B:D05 |
| M00003868B:C07 | M00004222A:H10 | M00006796A:H10 | |
| M00003881D:D09 | M00004223D:D07 | M00006797B:D12 | |
| M00003883D:C03 | M00004225D:F01 | M00006801A:G05 | |
| M00003884B:E06 | M00004228C:D11 | M00006805A:E11 | |
| M00003886C:D10 | M00004229C:G11 | M00006805A:H09 | |
| M00003903C:A12 | M00004239C:A07 | M00006805B:C04 | |
| M00003912C:H01 | M00004239C:C09 | M00006807D:D08 | |
| M00003915B:G07 | M00004240D:E06 | M00006813A:C04 | |
| M00003920D:D09 | M00004241B:B01 | M00006822D:D05 | |
| M00003926B:E03 | M00004243C:E10 | M00006825C:D06 | |
| M00003934D:F01 | M00004266A:F10 | M00006831B:B04 | |
| M00003958C:C10 | M00004266B:H06 | M00006832A:F05 | |
| M00003965A:F07 | M00004268C:F08 | M00006832D:F10 | |
| M00003972C:F02 | M00004268D:G07 | M00006833B:E11 | |
| M00003974B:A04 | M00004269A:B11 | M00006872B:G01 | |
| M00003974C:A05 | M00004269D:E08 | M00006875D:D10 | |
| M00003975B:H09 | M00004276C:E12 | M00006879D:A10 | |
| M00003976C:C05 | M00004277B:C06 | M00006882D:F03 | |
| M00003980C:A11 | M00004277C:H11 | M00006884D:D06 | |
| M00003987A:C07 | M00004279D:E02 | M00006908C:A05 | |
| M00003988B:C10 | M00004281B:B03 | M00006921B:C02 | |
| M00003988C:A06 | M00004284B:F07 | M00006921B:E03 | |
| M00003989C:F01 | M00004287B:B12 | M00006949B:F03 | |
| M00004028C:D01 | M00004287C:B06 | M00006960A:G11 | |
| M00004029A:E01 | M00004297D:B08 | M00006966D:G03 | |
| M00004030A:E09 | M00004332B:D02 | M00006974B:D06 | |
| M00004031A:G05 | M00004332D:E11 | M00007013B:F02 | |
| M00004032D:D03 | M00004346D:B06 | M00007014C:C05 | |
| M00004033C:D10 | M00004389C:E01 | M00007014D:D04 | |
| M00004034A:E08 | M00004403A:B05 | M00007030A:G01 | |
| M00004035A:A10 | M00004407D:B09 | M00007030C:F08 | |
| M00004035B:H11 | M00004419D:G01 | M00007053B:C07 | |
| M00004035D:C05 | M00004449D:H01 | M00007065B:B12 | |
| M00004037B:A09 | M00004463C:F11 | M00007065D:C01 | |
| M00004037C:C05 | M00004466A:E09 | M00007075C:D08 | |
| M00004037D:B05 | M00004469A:C12 | M00007085A:B07 | |
| M00004044A:F08 | M00004470C:A02 | M00007118C:G02 | |
| M00004068A:F02 | M00004498B:E01 | M00007119B:H10 | |
| M00004068B:D04 | M00004509A:H02 | M00004824C:G09 | |
| M00004068D:B01 | M00004605C:A09 | M00004826A:E09 | |
| M00004069B:B01 | M00004609C:C11 | M00004839C:B01 | |
| M00004073D:E01 | M00001378B:F06 | M00004840C:F02 | |
| M00004075A:G10 | M00005294C:G08 | M00004840A:H05 | |
| M00004075C:C09 | M00005294D:H02 | M00004845D:E11 | |
| M00004076A:E02 | M00005330C:F09 | M00004846A:D02 | |
| M00004077D:D10 | M00005333C:C08 | M00004846D:H09 | |
| M00004078A:F03 | M00005342B:G10 | M00004854A:C09 | |

TABLE 24-continued

Library Deposits

| ES51 | ES52 | ES53 | ES54 |
|---|---|---|---|
| M00004078C:A08 | M00005352C:G09 | M00004858D:E06 | |
| M00004084A:D11 | M00005352D:E06 | M00004999A:F01 | |
| M00004086A:A03 | M00005353B:B09 | M00004999B:D12 | |
| M00004086D:A07 | M00005359B:G01 | M00004999D:E01 | |
| M00004088A:F12 | M00005359D:H08 | M00005004B:C11 | |
| M00004089A:F02 | M00005377A:A04 | M00005005C:E06 | |
| M00004089A:G03 | M00005377A:D05 | M00005009B:A02 | |
| M00004093A:F03 | M00005385C:D08 | M00005015D:D11 | |
| M00004097C:A03 | M00005388A:F07 | M00005457D:C08 | |
| M00004102B:B04 | M00005388D:B11 | M00005519B:H04 | |
| M00004102C:F07 | M00005392C:C04 | M00005519C:F08 | |
| M00004103B:C09 | M00005393A:E11 | M00005531B:A03 | |
| M00004103C:F11 | M00005394A:G07 | M00005535B:F06 | |
| M00004104A:H09 | M00005396B:C04 | M00005587B:H02 | |
| M00004104D:C09 | M00005399B:F02 | M00005685A:A04 | |
| M00004108A:D04 | M00005400A:D02 | M00005706D:A09 | |
| M00004109B:A01 | M00005403A:E11 | M00005711A:H01 | |
| M00004126D:B11 | M00005406B:B08 | M00005798B:C11 | |
| M00004133C:B02 | M00005411D:E05 | M00005799C:C12 | |
| M00004182D:H03 | M00005415D:G02 | M00005805D:E06 | |
| M00004183A:D06 | M00005417C:E10 | M00005827B:H08 | |
| M00004186B:E05 | M00005419A:D05 | M00005828D:C09 | |
| M00004187C:H09 | M00005419C:D09 | M00005837A:D12 | |
| M00004188A:E05 | M00005443D:C12 | M00006751B:B11 | |
| M00004188A:E10 | M00005447B:D02 | M00006754B:D05 | |
| M00004190A:C12 | M00005448D:E08 | M00006756B:B08 | |
| M00004190C:G07 | M00005450A:A02 | M00006757D:E04 | |
| M00004190D:A10 | M00005450A:B10 | M00006758A:B12 | |
| M00004190D:G12 | M00005450D:C04 | M00006758D:C04 | |
| M00004198D:H04 | M00005451A:E03 | M00006834A:C08 | |
| M00004202B:F04 | M00005456B:B07 | M00006835B:F04 | |
| M00004202B:G09 | M00005456B:E03 | M00006837C:G06 | |
| M00004206C:G11 | M00005460A:B10 | M00006841D:A08 | |
| M00004213A:H12 | M00005465C:H02 | M00006855C:H02 | |
| M00004214A:D03 | M00005466A:F12 | M00006855D:H02 | |
| M00004218D:F12 | M00005468B:D04 | M00006859A:F06 | |
| M00004249C:E12 | M00005470B:E01 | M00006860B:H01 | |
| M00004249D:G02 | M00005473D:E10 | M00006886A:D06 | |
| M00004252D:A07 | M00005483A:F05 | M00006893C:B02 | |
| M00004253D:F09 | M00005483D:A02 | M00006893C:F02 | |
| M00004257C:A08 | M00005487A:H01 | M00006895D:E10 | |
| M00004262C:C01 | M00005489A:F06 | M00006917C:E07 | |
| M00001339B:E05 | M00005493B:A12 | M00006919B:C03 | |
| M00001341A:A11 | M00005493B:E01 | M00006923C:B01 | |
| M00001346A:B09 | M00005497C:C10 | M00006926A:H11 | |
| M00001346B:A07 | M00005505A:C08 | M00006934A:G02 | |
| M00001346B:G03 | M00005508A:H01 | M00006936B:E09 | |
| M00001346C:B07 | M00005510B:D06 | M00006936B:F10 | |
| M00001348A:G04 | M00005528D:H06 | M00006937B:F07 | |
| M00001348D:H08 | M00005534A:G06 | M00006937B:G09 | |
| M00001352C:E01 | M00005539D:G07 | M00006939B:E05 | |
| M00001362B:H09 | M00005571A:E11 | M00006953D:H11 | |
| M00001370A:B01 | M00005619C:H10 | M00006980A:F02 | |
| M00001370B:D04 | M00005625D:C03 | M00006986C:G11 | |
| M00001374C:C09 | M00005626A:B11 | M00006989B:C11 | |
| M00001376A:H02 | M00005635B:A06 | M00006990B:H09 | |
| M00001378B:F06 | M00005635C:F11 | M00006991A:E07 | |
| M00001380C:D10 | M00005636C:D11 | M00006991D:G07 | |
| M00001383C:C07 | M00005637D:C05 | M00006995C:A02 | |
| M00001384A:C09 | M00005641B:E02 | M00006997B:E06 | |
| M00001391D:A07 | M00005645D:F08 | M00006997D:B03 | |
| M00001391D:A09 | M00005646C:B09 | M00007006D:D04 | |
| M00001396C:G02 | M00005646D:B03 | M00007010B:C11 | |
| M00001397A:F10 | M00005655D:C04 | M00007010B:H03 | |
| M00001397B:E02 | M00005703C:B01 | M00007012B:D07 | |
| M00001397B:H11 | M00005720B:D09 | M00007031C:D01 | |
| M00001399D:F01 | M00005722A:E09 | M00007032A:F11 | |
| M00001400D:B08 | M00005762D:A01 | M00007033A:H05 | |
| M00001402C:E09 | M00005783A:C05 | M00007033D:F04 | |
| M00001406A:G12 | M00005812C:F10 | M00007036A:D02 | |
| M00001406D:B06 | M00006581C:D02 | M00007037B:D04 | |
| M00001408A:B02 | M00006581D:H08 | M00007084B:A05 | |
| M00001409C:D01 | M00006582A:B09 | M00007093A:F09 | |
| M00001411C:F02 | M00006582D:E05 | M00007099C:F09 | |

TABLE 24-continued

Library Deposits

| ES51 | ES52 | ES53 | ES54 |
|---|---|---|---|
| M00001411D:C01 | M00006592A:D03 | M00007101A:A11 | |
| M00001412D:C03 | M00006594D:F09 | M00007107A:D11 | |
| M00001417B:C07 | M00006596A:F07 | M00007121C:H01 | |
| M00001417C:A09 | M00006601D:F04 | M00007129A:E04 | |
| M00001418A:C02 | M00006604C:H10 | M00007132B:B11 | |
| M00001421C:A03 | M00006607B:E03 | M00007134B:G07 | |
| M00001426A:C02 | M00006607B:F04 | M00007146D:G01 | |
| M00001427A:C05 | M00006615D:F04 | M00007148B:C06 | |
| M00001433A:F04 | M00006616C:H09 | M00007160C:B08 | |
| M00001434C:D05 | M00006616D:C08 | M00007161A:H03 | |
| M00001435C:H05 | M00006617B:D09 | M00007192C:H08 | |
| M00001438A:H10 | M00006619B:C11 | M00007200B:C02 | |
| M00001438B:H06 | | M00021619B:G10 | |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07122373B1). An electronic copy of the "Sequence Listing" will also be available from the USPTO upon request and payment of the fee set forth in 37 CFR 1.19(b)(3).

We claim:

1. An isolated polynucleotide comprising at least 150 contiguous nucleotides of a sequence selected from SEQ ID NO:972 and a complement of SEQ ID:972.

2. A vector comprising a polynucleotide of claim 1.

3. A host cell comprising the vector of claim 2.

4. An isolated polynucleotide comprising at least 200 contiguous nucleotides of SEQ ID NO:972 and which hybridizes under stringent conditions to a polynucleotide of a sequence selected from SEQ ID NO:972 and a complement of SEQ ID:972.

5. An isolated polynucleotide comprising a nucleotide sequence of an insert contained in a clone deposited as clone number M00007118B:B04 of ATCC Deposit Number PTA-60, wherein said isolated polynucleotide comprises at least 1.50 contiguous nucleotides of a sequence selected from SEQ ID NO:972 and a complement of SEQ ID NO:972.

6. An isolated polynucleotide comprising at least 150 contiguous nucleotides of SEQ ID NO:972 obtained by amplifying a fragment of cDNA using at least one polynucleotide primer comprising at least 15 contiguous nucleotides of a nucleotide sequence selected from the group consisting of: SEQ ID NO: 972 and a complement of SEQ ID NO: 972.

7. A vector comprising a polynucleotide of claim 6.

8. A host cell comprising the vector of claim 7.

* * * * *